US010392667B2

(12) United States Patent
Knudsen

(10) Patent No.: US 10,392,667 B2
(45) Date of Patent: Aug. 27, 2019

(54) METHODS AND DEVICES FOR PREDICTING TREATMENT EFFICACY OF FULVESTRANT IN CANCER PATIENTS

(71) Applicant: Medical Prognosis Institute A/S, Hørsholm (DK)

(72) Inventor: Steen Knudsen, Hørsholm (DK)

(73) Assignee: Medical Prognosis Institute A/S, Hørsholm (DK)

( * ) Notice: Subject to any disclaimer, the term of this patent is extended or adjusted under 35 U.S.C. 154(b) by 53 days.

(21) Appl. No.: 14/896,220

(22) PCT Filed: Feb. 5, 2014

(86) PCT No.: PCT/EP2014/052236
§ 371 (c)(1),
(2) Date: Dec. 4, 2015

(87) PCT Pub. No.: WO2014/195032
PCT Pub. Date: Dec. 11, 2014

(65) Prior Publication Data

US 2016/0138111 A1 May 19, 2016

(30) Foreign Application Priority Data

Jun. 7, 2013 (DK) ................................ 2013 00348

(51) Int. Cl.

| | |
|---|---|
| ***C12Q 1/68*** | (2018.01) |
| ***C12Q 1/6886*** | (2018.01) |
| ***A61K 31/138*** | (2006.01) |
| ***A61K 31/18*** | (2006.01) |
| ***A61K 31/4196*** | (2006.01) |
| ***A61K 31/4535*** | (2006.01) |
| ***A61K 31/475*** | (2006.01) |
| ***A61K 31/517*** | (2006.01) |
| ***A61K 31/5377*** | (2006.01) |
| ***A61K 31/565*** | (2006.01) |
| ***A61K 33/24*** | (2019.01) |
| ***C07K 16/22*** | (2006.01) |
| ***C07K 16/40*** | (2006.01) |

(52) U.S. Cl.
CPC .......... *C12Q 1/6886* (2013.01); *A61K 31/138* (2013.01); *A61K 31/18* (2013.01); *A61K 31/4196* (2013.01); *A61K 31/4535* (2013.01); *A61K 31/475* (2013.01); *A61K 31/517* (2013.01); *A61K 31/5377* (2013.01); *A61K 31/565* (2013.01); *A61K 33/24* (2013.01); *C07K 16/22* (2013.01); *C07K 16/40* (2013.01); *C12Q 2600/106* (2013.01); *C12Q 2600/118* (2013.01); *C12Q 2600/158* (2013.01)

(58) Field of Classification Search
CPC .................................................... C12Q 1/6886
See application file for complete search history.

(56) References Cited

U.S. PATENT DOCUMENTS

| | | | | |
|---|---|---|---|---|
| 2006/0121511 A1* | 6/2006 | Lee | C12Q 1/6886 435/6.14 |
| 2009/0239223 A1* | 9/2009 | Gehrmann | C12Q 1/6886 435/5 |
| 2010/0240043 A1* | 9/2010 | Rotter | C12Q 1/6883 435/6.14 |
| 2011/0123990 A1* | 5/2011 | Baker | C12Q 1/6886 435/6.12 |
| 2015/0353928 A1* | 12/2015 | Weiner | C12N 15/113 435/375 |

FOREIGN PATENT DOCUMENTS

| | | |
|---|---|---|
| WO | WO-2011/135459 A2 | 11/2011 |
| WO | WO-2012/109233 A2 | 8/2012 |
| WO | WO-2012/163541 A1 | 12/2012 |

OTHER PUBLICATIONS

Chow et al, Proteomic Clin Appl, 3:654-662, 2009.*
Agrawal et al., "Long-term effect of fulvestrant on hormone receptors and proliferation marker in breast cancer," EJC Supplements. 8(3):111 (2010).
International Preliminary Report on Patentability issued for International Application No. PCT/EP2015/052236, dated Dec. 8, 2015 (1 page).
International Search Report and Written Opinion for International Application No. PCT/EP2014/052236, dated Jul. 9, 2014 (21 pages).
Juncker-Jensen et al., "Insulin-like growth factor binding protein 2 is a marker for antiestrogen resistant human breast cancer cell lines but is not a major growth regulator," Growth Horm IGF Res. 16(4):224-39 (2006).
Kuter et al., "Dose-dependent change in biomarkers during neoadjuvant endocrine therapy with fulvestrant: results from NEWEST, a randomized Phase II study," Breast Cancer Res Treat. 133(1):237-46 (2012).
McCune et al., "Prognosis of hormone-dependent breast cancers: implications of the presence of dysfunctional transcriptional networks activated by insulin via the immune transcription factor T-bet," Cancer Res. 70(2):685-96 (2010).
Nikas et al., "Prognosis of treatment response (pathological complete response) in breast cancer," Biomark Insights. 7:59-70 (2012).

* cited by examiner

*Primary Examiner* — Mark Halvorson
(74) *Attorney, Agent, or Firm* — Clark & Elbing LLP

(57) ABSTRACT

The present invention features methods, devices, and kits for predicting the sensitivity of a patient to a compound or medical treatment, such as fulvestrant.

25 Claims, 9 Drawing Sheets

Specification includes a Sequence Listing.

SEQUENCE LISTING

<160> NUMBER OF SEQ ID NOS: 445

<210> SEQ ID NO 1
<211> LENGTH: 25
<212> TYPE: DNA
<213> ORGANISM: Artificial Sequence
<220> FEATURE:
<223> OTHER INFORMATION: Synthetic Construct

<400> SEQUENCE: 1
gctttgtgaa caagtccctg taatt 25

<210> SEQ ID NO 2
<211> LENGTH: 25
<212> TYPE: DNA
<213> ORGANISM: Artificial Sequence
<220> FEATURE:
<223> OTHER INFORMATION: Artificial Synthetic

<400> SEQUENCE: 2
tccctgtaat tgttgtttgt atgta 25

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
aggagctcac tgtggtgtct gtgtt 25

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
catctgtgtg cgtggctatc aggag 25

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
tgaactacga caagctgagc cgctc 25

<210> SEQ ID NO 6
<211> LENGTH: 25
<212> TYPE: DNA
<213> ORGANISM: Artificial Sequence
<220> FEATURE:
<223> OTHER INFORMATION: Synthetic Construct

<400> SEQUENCE: 6
cacggctctg cccaggttaa gggcc 25

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct

<400> SEQUENCE: 7
gacgtccctc cagaagagga gtgtg 25

<210> SEQ ID NO 8

```
<211> LENGTH: 25
<212> TYPE: DNA
<213> ORGANISM: Artificial Sequence
<220> FEATURE:
<223> OTHER INFORMATION: Synthetic Construct

<400> SEQUENCE: 8

gtccagttcc cagaaggcat atcag                                           25


<210> SEQ ID NO 9
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9

agcaatgtca gcctgtggac tgcag                                           25


<210> SEQ ID NO 10
<211> LENGTH: 25
<212> TYPE: DNA
<213> ORGANISM: Artificial Sequence
<220> FEATURE:
<223> OTHER INFORMATION: Synthetic Construct

<400> SEQUENCE: 10

actttccttg tctgtctagt taata                                           25


<210> SEQ ID NO 11
<211> LENGTH: 25
<212> TYPE: DNA
<213> ORGANISM: Artificial Sequence
<220> FEATURE:
<223> OTHER INFORMATION: Synthetic Construct

<400> SEQUENCE: 11

ctgacctcca aataccgtta agctg                                           25


<210> SEQ ID NO 12
<211> LENGTH: 25
<212> TYPE: DNA
<213> ORGANISM: Artificial Sequence
<220> FEATURE:
<223> OTHER INFORMATION: Synthetic Construct

<400> SEQUENCE: 12

ctgccgctct cagtggacag ggcat                                           25


<210> SEQ ID NO 13
<211> LENGTH: 25
<212> TYPE: DNA
<213> ORGANISM: Artificial Sequence
<220> FEATURE:
<223> OTHER INFORMATION: Synthetic Construct

<400> SEQUENCE: 13

atcgcactct ggtctacgga gggat                                           25


<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
```

ggcacggtcg tgctcagagt gagac 25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
aatgaagatc aaactccagc tccag 25

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct

<400> SEQUENCE: 16
tatatttctt gccaacacgc cagaa 25

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17
ctgacctcca aataccgtta agctg 25

<210> SEQ ID NO 18
<211> LENGTH: 25
<212> TYPE: DNA
<213> ORGANISM: Artificial Sequence
<220> FEATURE:
<223> OTHER INFORMATION: Synthetic Construct

<400> SEQUENCE: 18
agggaacata ctgattggtc ttaaa 25

<210> SEQ ID NO 19
<211> LENGTH: 25
<212> TYPE: DNA
<213> ORGANISM: Artificial Sequence
<220> FEATURE:
<223> OTHER INFORMATION: Synthetic Construct

<400> SEQUENCE: 19
tcaaggccgc ctggggtaag gtcgg 25

<210> SEQ ID NO 20
<211> LENGTH: 25
<212> TYPE: DNA
<213> ORGANISM: Artificial Sequence
<220> FEATURE:
<223> OTHER INFORMATION: Synthetic Construct

<400> SEQUENCE: 20
caacgactcc acaatcctag ataag 25

<210> SEQ ID NO 21
<211> LENGTH: 25
<212> TYPE: DNA

<213> ORGANISM: Artificial Sequence
<220> FEATURE:
<223> OTHER INFORMATION: Synthetic Construct

<400> SEQUENCE: 21
ggctttcttt ctgggtttgg gccat 25

<210> SEQ ID NO 22
<211> LENGTH: 25
<212> TYPE: DNA
<213> ORGANISM: Artificial Sequence
<220> FEATURE:
<223> OTHER INFORMATION: Synthetic Construct

<400> SEQUENCE: 22
gtgtggtcta ttttgccatc atcac 25

<210> SEQ ID NO 23
<211> LENGTH: 25
<212> TYPE: DNA
<213> ORGANISM: Artificial Sequence
<220> FEATURE:
<223> OTHER INFORMATION: Synthetic Construct

<400> SEQUENCE: 23
gtccgtatgt aaatcagatc tcccc 25

<210> SEQ ID NO 24
<211> LENGTH: 25
<212> TYPE: DNA
<213> ORGANISM: Artificial Sequence
<220> FEATURE:
<223> OTHER INFORMATION: Synthetic Construct

<400> SEQUENCE: 24
gttgccatgt tactatgcct caagc 25

<210> SEQ ID NO 25
<211> LENGTH: 25
<212> TYPE: DNA
<213> ORGANISM: Artificial Sequence
<220> FEATURE:
<223> OTHER INFORMATION: Synthetic Construct

<400> SEQUENCE: 25
tgaaagactt aaccagccat caccg 25

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
gaaggatggc atcaccgttg tggac 25

<210> SEQ ID NO 27
<211> LENGTH: 25
<212> TYPE: DNA
<213> ORGANISM: Artificial Sequence
<220> FEATURE:
<223> OTHER INFORMATION: Synthetic Construct

<400> SEQUENCE: 27
gagccacatg tttcacacaa gtgta 25

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
ccagggtgct tagttggctt tgccc 25

<210> SEQ ID NO 29
<211> LENGTH: 24
<212> TYPE: DNA
<213> ORGANISM: Artificial Sequence
<220> FEATURE:
<223> OTHER INFORMATION: Synthetic Construct

<400> SEQUENCE: 29
tgctgatcct cagggacacc aaga 24

<210> SEQ ID NO 30
<211> LENGTH: 25
<212> TYPE: DNA
<213> ORGANISM: Artificial Sequence
<220> FEATURE:
<223> OTHER INFORMATION: Synthetic Construct

<400> SEQUENCE: 30
ggctcacagg gaacaagaca cggct 25

<210> SEQ ID NO 31
<211> LENGTH: 25
<212> TYPE: DNA
<213> ORGANISM: Artificial Sequence
<220> FEATURE:
<223> OTHER INFORMATION: Synthetic Construct

<400> SEQUENCE: 31
ctggagagga tgttcctgtc cttcc 25

<210> SEQ ID NO 32
<211> LENGTH: 25
<212> TYPE: DNA
<213> ORGANISM: Artificial Sequence
<220> FEATURE:
<223> OTHER INFORMATION: Synthetic Construct

<400> SEQUENCE: 32
tgtcagcctg tgaactaggc cctgc 25

<210> SEQ ID NO 33
<211> LENGTH: 25
<212> TYPE: DNA
<213> ORGANISM: Artificial Sequence
<220> FEATURE:
<223> OTHER INFORMATION: Synthetic Construct

<400> SEQUENCE: 33
gtggaagctg tggtcacttt cgcag 25

<210> SEQ ID NO 34
<211> LENGTH: 25
<212> TYPE: DNA
<213> ORGANISM: Artificial Sequence
<220> FEATURE:

-continued

<223> OTHER INFORMATION: Synthetic Construct

<400> SEQUENCE: 34
tggaagcctt tcattttaca cgccc 25

<210> SEQ ID NO 35
<211> LENGTH: 25
<212> TYPE: DNA
<213> ORGANISM: Artificial Sequence
<220> FEATURE:
<223> OTHER INFORMATION: Synthetic Construct

<400> SEQUENCE: 35
caaggaagat ggagctcccc catcc 25

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcttctagat tctctctatg ttggc 25

<210> SEQ ID NO 37
<211> LENGTH: 25
<212> TYPE: DNA
<213> ORGANISM: Artificial Sequence
<220> FEATURE:
<223> OTHER INFORMATION: Synthetic Construct

<400> SEQUENCE: 37
gggcacagga cagagaagag gaagc 25

<210> SEQ ID NO 38
<211> LENGTH: 25
<212> TYPE: DNA
<213> ORGANISM: Artificial Sequence
<220> FEATURE:
<223> OTHER INFORMATION: Synthetic Construct

<400> SEQUENCE: 38
gttgaggttc tctattgcct cttga 25

<210> SEQ ID NO 39
<211> LENGTH: 25
<212> TYPE: DNA
<213> ORGANISM: Artificial Sequence
<220> FEATURE:
<223> OTHER INFORMATION: Synthetic Construct

<400> SEQUENCE: 39
gaatctagta tggtgttctg ttttc 25

<210> SEQ ID NO 40
<211> LENGTH: 25
<212> TYPE: DNA
<213> ORGANISM: Artificial Sequence
<220> FEATURE:
<223> OTHER INFORMATION: Synthetic Construct

<400> SEQUENCE: 40
gacacagagg aagttggcta gaggc 25

<210> SEQ ID NO 41
<211> LENGTH: 25
<212> TYPE: DNA
<213> ORGANISM: Artificial Sequence
<220> FEATURE:
<223> OTHER INFORMATION: Synthetic Construct

<400> SEQUENCE: 41
ctgtctactg caactgtgat ttccc 25

<210> SEQ ID NO 42
<211> LENGTH: 25
<212> TYPE: DNA
<213> ORGANISM: Artificial Sequence
<220> FEATURE:
<223> OTHER INFORMATION: Synthetic Construct

<400> SEQUENCE: 42
aacctcccag tgaaagggca gcctt 25

<210> SEQ ID NO 43
<211> LENGTH: 25
<212> TYPE: DNA
<213> ORGANISM: Artificial Sequence
<220> FEATURE:
<223> OTHER INFORMATION: Synthetic Construct

<400> SEQUENCE: 43
tgggtttggg ccatttcagt tctca 25

<210> SEQ ID NO 44
<211> LENGTH: 25
<212> TYPE: DNA
<213> ORGANISM: Artificial Sequence
<220> FEATURE:
<223> OTHER INFORMATION: Synthetic Construct

<400> SEQUENCE: 44
caacagtgga cttaccagtt tgcca 25

<210> SEQ ID NO 45
<211> LENGTH: 25
<212> TYPE: DNA
<213> ORGANISM: Artificial Sequence
<220> FEATURE:
<223> OTHER INFORMATION: Synthetic Construct

<400> SEQUENCE: 45
aacagagttt gatcctgcta ttgtc 25

<210> SEQ ID NO 46
<211> LENGTH: 25
<212> TYPE: DNA
<213> ORGANISM: Artificial Sequence
<220> FEATURE:
<223> OTHER INFORMATION: Synthetic Construct

<400> SEQUENCE: 46
tgcagctaag ggcatccttg gagtg 25

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47
gaagaagaga tcgaggttga ggagg 25

<210> SEQ ID NO 48
<211> LENGTH: 25
<212> TYPE: DNA
<213> ORGANISM: Artificial Sequence
<220> FEATURE:
<223> OTHER INFORMATION: Synthetic Construct

<400> SEQUENCE: 48
gctacgaccg caaggactac gtcta 25

<210> SEQ ID NO 49
<211> LENGTH: 25
<212> TYPE: DNA
<213> ORGANISM: Artificial Sequence
<220> FEATURE:
<223> OTHER INFORMATION: Synthetic Construct

<400> SEQUENCE: 49
gatgaatcac acttgagatg tttct 25

<210> SEQ ID NO 50
<211> LENGTH: 25
<212> TYPE: DNA
<213> ORGANISM: Artificial Sequence
<220> FEATURE:
<223> OTHER INFORMATION: Synthetic Construct

<400> SEQUENCE: 50
ctaagcattt tgaccacgtt gagca 25

<210> SEQ ID NO 51
<211> LENGTH: 25
<212> TYPE: DNA
<213> ORGANISM: Artificial Sequence
<220> FEATURE:
<223> OTHER INFORMATION: Synthetic Construct

<400> SEQUENCE: 51
ttgggtccct aaagatcacc tgata 25

<210> SEQ ID NO 52
<211> LENGTH: 25
<212> TYPE: DNA
<213> ORGANISM: Artificial Sequence
<220> FEATURE:
<223> OTHER INFORMATION: Synthetic Construct

<400> SEQUENCE: 52
ccaaacctcg ccagagaagc tcttc 25

<210> SEQ ID NO 53
<211> LENGTH: 25
<212> TYPE: DNA
<213> ORGANISM: Artificial Sequence
<220> FEATURE:
<223> OTHER INFORMATION: Synthetic Construct

<400> SEQUENCE: 53
gtactttgat atctctcagt gcttc 25

<210> SEQ ID NO 54
<211> LENGTH: 25

<212> TYPE: DNA
<213> ORGANISM: Artificial Sequence
<220> FEATURE:
<223> OTHER INFORMATION: Synthetic Construct

<400> SEQUENCE: 54
ttgagtcagt gtcttacatg ttaag 25

<210> SEQ ID NO 55
<211> LENGTH: 25
<212> TYPE: DNA
<213> ORGANISM: Artificial Sequence
<220> FEATURE:
<223> OTHER INFORMATION: Synthetic Construct

<400> SEQUENCE: 55
gggagctcag gtactctttt agtca 25

<210> SEQ ID NO 56
<211> LENGTH: 25
<212> TYPE: DNA
<213> ORGANISM: Artificial Sequence
<220> FEATURE:
<223> OTHER INFORMATION: Synthetic Construct

<400> SEQUENCE: 56
cccactgtct ctctacaatg aggag 25

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
aatgggctcc atgttctgta gcccc 25

<210> SEQ ID NO 58
<211> LENGTH: 25
<212> TYPE: DNA
<213> ORGANISM: Artificial Sequence
<220> FEATURE:
<223> OTHER INFORMATION: Synthetic Construct

<400> SEQUENCE: 58
ggtcacattc atcctaattc acaaa 25

<210> SEQ ID NO 59
<211> LENGTH: 25
<212> TYPE: DNA
<213> ORGANISM: Artificial Sequence
<220> FEATURE:
<223> OTHER INFORMATION: Synthetic Construct

<400> SEQUENCE: 59
aacaccagag gtagaacaag ctgtg 25

<210> SEQ ID NO 60
<211> LENGTH: 25
<212> TYPE: DNA
<213> ORGANISM: Artificial Sequence
<220> FEATURE:
<223> OTHER INFORMATION: Synthetic Construct

<400> SEQUENCE: 60
ggtcccagcc aattgtgatg atcct 25

<210> SEQ ID NO 61
<211> LENGTH: 25
<212> TYPE: DNA
<213> ORGANISM: Artificial Sequence
<220> FEATURE:
<223> OTHER INFORMATION: Synthetic Construct

<400> SEQUENCE: 61
tccagaagtc tgtggatgcc gctcc 25

<210> SEQ ID NO 62
<211> LENGTH: 25
<212> TYPE: DNA
<213> ORGANISM: Artificial Sequence
<220> FEATURE:
<223> OTHER INFORMATION: Synthetic Construct

<400> SEQUENCE: 62
caagatttct ctacatttgg ccaaa 25

<210> SEQ ID NO 63
<211> LENGTH: 25
<212> TYPE: DNA
<213> ORGANISM: Artificial Sequence
<220> FEATURE:
<223> OTHER INFORMATION: Synthetic Construct

<400> SEQUENCE: 63
catgtatacc tggatttgct tggct 25

<210> SEQ ID NO 64
<211> LENGTH: 25
<212> TYPE: DNA
<213> ORGANISM: Artificial Sequence
<220> FEATURE:
<223> OTHER INFORMATION: Synthetic Construct

<400> SEQUENCE: 64
gtcctgggac cagttgccca gcaga 25

<210> SEQ ID NO 65
<211> LENGTH: 25
<212> TYPE: DNA
<213> ORGANISM: Artificial Sequence
<220> FEATURE:
<223> OTHER INFORMATION: Synthetic Construct

<400> SEQUENCE: 65
gaggccattt ggacttcagt gtgaa 25

<210> SEQ ID NO 66
<211> LENGTH: 25
<212> TYPE: DNA
<213> ORGANISM: Artificial Sequence
<220> FEATURE:
<223> OTHER INFORMATION: Synthetic Construct

<400> SEQUENCE: 66
ggaggtgtat gaccatgcca ggagg 25

<210> SEQ ID NO 67
<211> LENGTH: 25
<212> TYPE: DNA
<213> ORGANISM: Artificial Sequence
<220> FEATURE:
<223> OTHER INFORMATION: Synthetic Construct

<400> SEQUENCE: 67
acgcatgtgt ttggcagcgg gaccc 25

<210> SEQ ID NO 68
<211> LENGTH: 25
<212> TYPE: DNA
<213> ORGANISM: Artificial Sequence
<220> FEATURE:
<223> OTHER INFORMATION: Synthetic Construct

<400> SEQUENCE: 68
acagctttcc cagtgatgaa atcca 25

<210> SEQ ID NO 69
<211> LENGTH: 25
<212> TYPE: DNA
<213> ORGANISM: Artificial Sequence
<220> FEATURE:
<223> OTHER INFORMATION: Synthetic Construct

<400> SEQUENCE: 69
caaagaccca gtgtcatttg ctcct 25

<210> SEQ ID NO 70
<211> LENGTH: 25
<212> TYPE: DNA
<213> ORGANISM: Artificial Sequence
<220> FEATURE:
<223> OTHER INFORMATION: Synthetic Construct

<400> SEQUENCE: 70
ggcgctgtga atttttgtac aagtc 25

<210> SEQ ID NO 71
<211> LENGTH: 25
<212> TYPE: DNA
<213> ORGANISM: Artificial Sequence
<220> FEATURE:
<223> OTHER INFORMATION: Synthetic Construct

<400> SEQUENCE: 71
cctgccaaca ccaaggtcat gctga 25

<210> SEQ ID NO 72
<211> LENGTH: 25
<212> TYPE: DNA
<213> ORGANISM: Artificial Sequence
<220> FEATURE:
<223> OTHER INFORMATION: Synthetic Construct

<400> SEQUENCE: 72
agaaaatgca gccggagcct cagtc 25

<210> SEQ ID NO 73
<211> LENGTH: 25
<212> TYPE: DNA
<213> ORGANISM: Artificial Sequence
<220> FEATURE:
<223> OTHER INFORMATION: Synthetic Construct

<400> SEQUENCE: 73
gccctaacgg gccataacac ttgac 25

```
<210> SEQ ID NO 74
<211> LENGTH: 25
<212> TYPE: DNA
<213> ORGANISM: Artificial Sequence
<220> FEATURE:
<223> OTHER INFORMATION: Synthetic Construct

<400> SEQUENCE: 74

tgccctgggt caccgtcaat gggaa                                            25


<210> SEQ ID NO 75
<211> LENGTH: 25
<212> TYPE: DNA
<213> ORGANISM: Artificial Sequence
<220> FEATURE:
<223> OTHER INFORMATION: Synthetic Construct

<400> SEQUENCE: 75

acagctgggg ccacaacttt ggtga                                            25


<210> SEQ ID NO 76
<211> LENGTH: 25
<212> TYPE: DNA
<213> ORGANISM: Artificial Sequence
<220> FEATURE:
<223> OTHER INFORMATION: Synthetic Construct

<400> SEQUENCE: 76

aagctgcaag tgcttgaccc tgtac                                            25


<210> SEQ ID NO 77
<211> LENGTH: 25
<212> TYPE: DNA
<213> ORGANISM: Artificial Sequence
<220> FEATURE:
<223> OTHER INFORMATION: Synthetic Construct

<400> SEQUENCE: 77

tccagggagg cccttttctg atcat                                            25


<210> SEQ ID NO 78
<211> LENGTH: 25
<212> TYPE: DNA
<213> ORGANISM: Artificial Sequence
<220> FEATURE:
<223> OTHER INFORMATION: Synthetic Construct

<400> SEQUENCE: 78

taaggcatcc actgcatttc ctttc                                            25


<210> SEQ ID NO 79
<211> LENGTH: 25
<212> TYPE: DNA
<213> ORGANISM: Artificial Sequence
<220> FEATURE:
<223> OTHER INFORMATION: Synthetic Construct

<400> SEQUENCE: 79

acacgctgca gatcgaggac tttct                                            25


<210> SEQ ID NO 80
<211> LENGTH: 25
<212> TYPE: DNA
<213> ORGANISM: Artificial Sequence
<220> FEATURE:
<223> OTHER INFORMATION: Synthetic Construct
```

<400> SEQUENCE: 80
tcatccaaag cacctgcaga gtcca 25

<210> SEQ ID NO 81
<211> LENGTH: 25
<212> TYPE: DNA
<213> ORGANISM: Artificial Sequence
<220> FEATURE:
<223> OTHER INFORMATION: Synthetic Construct

<400> SEQUENCE: 81
cgcctgaccc aagtgaagac acctg 25

<210> SEQ ID NO 82
<211> LENGTH: 25
<212> TYPE: DNA
<213> ORGANISM: Artificial Sequence
<220> FEATURE:
<223> OTHER INFORMATION: Synthetic Construct

<400> SEQUENCE: 82
gcacctttca gatttcttgg tggca 25

<210> SEQ ID NO 83
<211> LENGTH: 25
<212> TYPE: DNA
<213> ORGANISM: Artificial Sequence
<220> FEATURE:
<223> OTHER INFORMATION: Synthetic Construct

<400> SEQUENCE: 83
caatgaaacc ggcgatgagc ccttc 25

<210> SEQ ID NO 84
<211> LENGTH: 25
<212> TYPE: DNA
<213> ORGANISM: Artificial Sequence
<220> FEATURE:
<223> OTHER INFORMATION: Synthetic Construct

<400> SEQUENCE: 84
ttctacatca tctacatggc catcc 25

<210> SEQ ID NO 85
<211> LENGTH: 25
<212> TYPE: DNA
<213> ORGANISM: Artificial Sequence
<220> FEATURE:
<223> OTHER INFORMATION: Synthetic Construct

<400> SEQUENCE: 85
acattgaccc acaggacatt gtaaa 25

<210> SEQ ID NO 86
<211> LENGTH: 25
<212> TYPE: DNA
<213> ORGANISM: Artificial Sequence
<220> FEATURE:
<223> OTHER INFORMATION: Synthetic Construct

<400> SEQUENCE: 86
tggtacttat cagtgccaag cgtcc 25

<210> SEQ ID NO 87

<211> LENGTH: 25
<212> TYPE: DNA
<213> ORGANISM: Artificial Sequence
<220> FEATURE:
<223> OTHER INFORMATION: Synthetic Construct

<400> SEQUENCE: 87
gatattcaag tcacctcctt aaagg 25

<210> SEQ ID NO 88
<211> LENGTH: 24
<212> TYPE: DNA
<213> ORGANISM: Artificial Sequence
<220> FEATURE:
<223> OTHER INFORMATION: Synthetic Construct

<400> SEQUENCE: 88
caaatgagat cagctctcct tcca 24

<210> SEQ ID NO 89
<211> LENGTH: 25
<212> TYPE: DNA
<213> ORGANISM: Artificial Sequence
<220> FEATURE:
<223> OTHER INFORMATION: Synthetic Construct

<400> SEQUENCE: 89
gctcagatct tactagacat cggcg 25

<210> SEQ ID NO 90
<211> LENGTH: 25
<212> TYPE: DNA
<213> ORGANISM: Artificial Sequence
<220> FEATURE:
<223> OTHER INFORMATION: Synthetic Construct

<400> SEQUENCE: 90
gcttccttca ggttctagat tcttg 25

<210> SEQ ID NO 91
<211> LENGTH: 25
<212> TYPE: DNA
<213> ORGANISM: Artificial Sequence
<220> FEATURE:
<223> OTHER INFORMATION: Synthetic Construct

<400> SEQUENCE: 91
aagggcacgg tcatgggtac actgc 25

<210> SEQ ID NO 92
<211> LENGTH: 25
<212> TYPE: DNA
<213> ORGANISM: Artificial Sequence
<220> FEATURE:
<223> OTHER INFORMATION: Synthetic Construct

<400> SEQUENCE: 92
gtagcaccaa gcctgataga tctgt 25

<210> SEQ ID NO 93
<211> LENGTH: 25
<212> TYPE: DNA
<213> ORGANISM: Artificial Sequence
<220> FEATURE:
<223> OTHER INFORMATION: Synthetic Construct

<400> SEQUENCE: 93
gctcacctga aagaggtatg ctctc 25

<210> SEQ ID NO 94
<211> LENGTH: 25
<212> TYPE: DNA
<213> ORGANISM: Artificial Sequence
<220> FEATURE:
<223> OTHER INFORMATION: Synthetic Construct

<400> SEQUENCE: 94
gggcagtgac tcgacaaagg ccaca 25

<210> SEQ ID NO 95
<211> LENGTH: 25
<212> TYPE: DNA
<213> ORGANISM: Artificial Sequence
<220> FEATURE:
<223> OTHER INFORMATION: Synthetic Construct

<400> SEQUENCE: 95
caactctatt atcaactgtg cttat 25

<210> SEQ ID NO 96
<211> LENGTH: 25
<212> TYPE: DNA
<213> ORGANISM: Artificial Sequence
<220> FEATURE:
<223> OTHER INFORMATION: Synthetic Construct

<400> SEQUENCE: 96
acttgcatca gttggatatc ctttt 25

<210> SEQ ID NO 97
<211> LENGTH: 25
<212> TYPE: DNA
<213> ORGANISM: Artificial Sequence
<220> FEATURE:
<223> OTHER INFORMATION: Synthetic Construct

<400> SEQUENCE: 97
gaggggagtt ccaagtgtgc cctcc 25

<210> SEQ ID NO 98
<211> LENGTH: 25
<212> TYPE: DNA
<213> ORGANISM: Artificial Sequence
<220> FEATURE:
<223> OTHER INFORMATION: Synthetic Construct

<400> SEQUENCE: 98
caaacactca gccccgaaga tgttg 25

<210> SEQ ID NO 99
<211> LENGTH: 25
<212> TYPE: DNA
<213> ORGANISM: Artificial Sequence
<220> FEATURE:
<223> OTHER INFORMATION: Synthetic Construct

<400> SEQUENCE: 99
gattgagccc tacattgtgc tgcac 25

<210> SEQ ID NO 100
<211> LENGTH: 25
<212> TYPE: DNA

<213> ORGANISM: Artificial Sequence
<220> FEATURE:
<223> OTHER INFORMATION: Synthetic Construct

<400> SEQUENCE: 100
ggccttctag actgtcttct atgat 25

<210> SEQ ID NO 101
<211> LENGTH: 25
<212> TYPE: DNA
<213> ORGANISM: Artificial Sequence
<220> FEATURE:
<223> OTHER INFORMATION: Synthetic Construct

<400> SEQUENCE: 101
gagcttcaaa cagcgctctg acctc 25

<210> SEQ ID NO 102
<211> LENGTH: 25
<212> TYPE: DNA
<213> ORGANISM: Artificial Sequence
<220> FEATURE:
<223> OTHER INFORMATION: Synthetic Construct

<400> SEQUENCE: 102
gcactgccga gactgtgctc tgagc 25

<210> SEQ ID NO 103
<211> LENGTH: 25
<212> TYPE: DNA
<213> ORGANISM: Artificial Sequence
<220> FEATURE:
<223> OTHER INFORMATION: Synthetic Construct

<400> SEQUENCE: 103
aggctctcca ggacatgttt gcact 25

<210> SEQ ID NO 104
<211> LENGTH: 25
<212> TYPE: DNA
<213> ORGANISM: Artificial Sequence
<220> FEATURE:
<223> OTHER INFORMATION: Synthetic Construct

<400> SEQUENCE: 104
gctatcgtga agtgcgccac aagca 25

<210> SEQ ID NO 105
<211> LENGTH: 25
<212> TYPE: DNA
<213> ORGANISM: Artificial Sequence
<220> FEATURE:
<223> OTHER INFORMATION: Synthetic Construct

<400> SEQUENCE: 105
acatcgagcc tgacatcgaa gccct 25

<210> SEQ ID NO 106
<211> LENGTH: 25
<212> TYPE: DNA
<213> ORGANISM: Artificial Sequence
<220> FEATURE:
<223> OTHER INFORMATION: Synthetic Construct

<400> SEQUENCE: 106
taggaatgaa ctccagaggc tgggc 25

<210> SEQ ID NO 107
<211> LENGTH: 25
<212> TYPE: DNA
<213> ORGANISM: Artificial Sequence
<220> FEATURE:
<223> OTHER INFORMATION: Synthetic Construct

<400> SEQUENCE: 107
cagaaagcgc tgctgtacct gtgtg 25

<210> SEQ ID NO 108
<211> LENGTH: 25
<212> TYPE: DNA
<213> ORGANISM: Artificial Sequence
<220> FEATURE:
<223> OTHER INFORMATION: Synthetic Construct

<400> SEQUENCE: 108
accactagtg tctgtccatg gagtt 25

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
gtggtaatgc ctgttttcat ctgta 25

<210> SEQ ID NO 110
<211> LENGTH: 25
<212> TYPE: DNA
<213> ORGANISM: Artificial Sequence
<220> FEATURE:
<223> OTHER INFORMATION: Synthetic Construct

<400> SEQUENCE: 110
cagaaagcgc tgctgtacct gtgtg 25

<210> SEQ ID NO 111
<211> LENGTH: 25
<212> TYPE: DNA
<213> ORGANISM: Artificial Sequence
<220> FEATURE:
<223> OTHER INFORMATION: Synthetic Construct

<400> SEQUENCE: 111
ttcgagaccc cagtcgtgat gtgga 25

<210> SEQ ID NO 112
<211> LENGTH: 25
<212> TYPE: DNA
<213> ORGANISM: Artificial Sequence
<220> FEATURE:
<223> OTHER INFORMATION: Synthetic Construct

<400> SEQUENCE: 112
aatgtgcact gaatcgtttc atgta 25

<210> SEQ ID NO 113
<211> LENGTH: 25
<212> TYPE: DNA
<213> ORGANISM: Artificial Sequence
<220> FEATURE:

<223> OTHER INFORMATION: Synthetic Construct

<400> SEQUENCE: 113
ggttccaagc cttaggggat gccgc                                    25

<210> SEQ ID NO 114
<211> LENGTH: 25
<212> TYPE: DNA
<213> ORGANISM: Artificial Sequence
<220> FEATURE:
<223> OTHER INFORMATION: Synthetic Construct

<400> SEQUENCE: 114
cagaaagcgc tgctgtacct gtgtg                                    25

<210> SEQ ID NO 115
<211> LENGTH: 25
<212> TYPE: DNA
<213> ORGANISM: Artificial Sequence
<220> FEATURE:
<223> OTHER INFORMATION: Synthetic Construct

<400> SEQUENCE: 115
gtccagatgt gagttttttc caagc                                    25

<210> SEQ ID NO 116
<211> LENGTH: 25
<212> TYPE: DNA
<213> ORGANISM: Artificial Sequence
<220> FEATURE:
<223> OTHER INFORMATION: Synthetic Construct

<400> SEQUENCE: 116
tgacctggat aacatttcct tcccc                                    25

<210> SEQ ID NO 117
<211> LENGTH: 25
<212> TYPE: DNA
<213> ORGANISM: Artificial Sequence
<220> FEATURE:
<223> OTHER INFORMATION: Synthetic Construct

<400> SEQUENCE: 117
aaaaccacat cagatctctt gctgg                                    25

<210> SEQ ID NO 118
<211> LENGTH: 25
<212> TYPE: DNA
<213> ORGANISM: Artificial Sequence
<220> FEATURE:
<223> OTHER INFORMATION: Synthetic Construct

<400> SEQUENCE: 118
ttccaagcaa cctcactgaa accta                                    25

<210> SEQ ID NO 119
<211> LENGTH: 25
<212> TYPE: DNA
<213> ORGANISM: Artificial Sequence
<220> FEATURE:
<223> OTHER INFORMATION: Synthetic Construct

<400> SEQUENCE: 119
gattttgtag ccaacattca ttcaa                                    25

-continued

<210> SEQ ID NO 120
<211> LENGTH: 25
<212> TYPE: DNA
<213> ORGANISM: Artificial Sequence
<220> FEATURE:
<223> OTHER INFORMATION: Synthetic Construct

<400> SEQUENCE: 120
tcatacacct ataaatctct aacaa 25

<210> SEQ ID NO 121
<211> LENGTH: 25
<212> TYPE: DNA
<213> ORGANISM: Artificial Sequence
<220> FEATURE:
<223> OTHER INFORMATION: Synthetic Construct

<400> SEQUENCE: 121
agcgcttctg gtctggtaaa tatgt 25

<210> SEQ ID NO 122
<211> LENGTH: 25
<212> TYPE: DNA
<213> ORGANISM: Artificial Sequence
<220> FEATURE:
<223> OTHER INFORMATION: Synthetic Construct

<400> SEQUENCE: 122
aagcccttgt attttgctga tcagc 25

<210> SEQ ID NO 123
<211> LENGTH: 25
<212> TYPE: DNA
<213> ORGANISM: Artificial Sequence
<220> FEATURE:
<223> OTHER INFORMATION: Synthetic Construct

<400> SEQUENCE: 123
catatggtgt tggtctcctt attgc 25

<210> SEQ ID NO 124
<211> LENGTH: 25
<212> TYPE: DNA
<213> ORGANISM: Artificial Sequence
<220> FEATURE:
<223> OTHER INFORMATION: Synthetic Construct

<400> SEQUENCE: 124
gactggcatc ttcacaggat gtcag 25

<210> SEQ ID NO 125
<211> LENGTH: 25
<212> TYPE: DNA
<213> ORGANISM: Artificial Sequence
<220> FEATURE:
<223> OTHER INFORMATION: Synthetic Construct

<400> SEQUENCE: 125
ggagttacag atgttcaaat taatt 25

<210> SEQ ID NO 126
<211> LENGTH: 25
<212> TYPE: DNA
<213> ORGANISM: Artificial Sequence
<220> FEATURE:
<223> OTHER INFORMATION: Synthetic Construct

<400> SEQUENCE: 126
gggtttcaca gtgcaatctc tgccc 25

<210> SEQ ID NO 127
<211> LENGTH: 25
<212> TYPE: DNA
<213> ORGANISM: Artificial Sequence
<220> FEATURE:
<223> OTHER INFORMATION: Synthetic Construct

<400> SEQUENCE: 127
gacacacaac ccctggatat gtttc 25

<210> SEQ ID NO 128
<211> LENGTH: 25
<212> TYPE: DNA
<213> ORGANISM: Artificial Sequence
<220> FEATURE:
<223> OTHER INFORMATION: Synthetic Construct

<400> SEQUENCE: 128
gactgttgag tgtgctcttt cacag 25

<210> SEQ ID NO 129
<211> LENGTH: 25
<212> TYPE: DNA
<213> ORGANISM: Artificial Sequence
<220> FEATURE:
<223> OTHER INFORMATION: Synthetic Construct

<400> SEQUENCE: 129
gtcaccttcg tgaataccaa gacct 25

<210> SEQ ID NO 130
<211> LENGTH: 25
<212> TYPE: DNA
<213> ORGANISM: Artificial Sequence
<220> FEATURE:
<223> OTHER INFORMATION: Synthetic Construct

<400> SEQUENCE: 130
gtatacatgc cttgtttaac ttgga 25

<210> SEQ ID NO 131
<211> LENGTH: 25
<212> TYPE: DNA
<213> ORGANISM: Artificial Sequence
<220> FEATURE:
<223> OTHER INFORMATION: Synthetic Construct

<400> SEQUENCE: 131
cagtaactta cccttaggga ggctg 25

<210> SEQ ID NO 132
<211> LENGTH: 25
<212> TYPE: DNA
<213> ORGANISM: Artificial Sequence
<220> FEATURE:
<223> OTHER INFORMATION: Synthetic Construct

<400> SEQUENCE: 132
gtgtccacgg tggtttgatc aacaa 25

<210> SEQ ID NO 133
<211> LENGTH: 25

<212> TYPE: DNA
<213> ORGANISM: Artificial Sequence
<220> FEATURE:
<223> OTHER INFORMATION: Synthetic Construct

<400> SEQUENCE: 133
tggttggcgt ccttgtattt accca 25

<210> SEQ ID NO 134
<211> LENGTH: 25
<212> TYPE: DNA
<213> ORGANISM: Artificial Sequence
<220> FEATURE:
<223> OTHER INFORMATION: Synthetic Construct

<400> SEQUENCE: 134
aaagctgtgc tgtcggtgat acaga 25

<210> SEQ ID NO 135
<211> LENGTH: 25
<212> TYPE: DNA
<213> ORGANISM: Artificial Sequence
<220> FEATURE:
<223> OTHER INFORMATION: Synthetic Construct

<400> SEQUENCE: 135
tgtaacacct acaccattat cttgg 25

<210> SEQ ID NO 136
<211> LENGTH: 25
<212> TYPE: DNA
<213> ORGANISM: Artificial Sequence
<220> FEATURE:
<223> OTHER INFORMATION: Synthetic Construct

<400> SEQUENCE: 136
gtgctcatat aacacaccac actga 25

<210> SEQ ID NO 137
<211> LENGTH: 25
<212> TYPE: DNA
<213> ORGANISM: Artificial Sequence
<220> FEATURE:
<223> OTHER INFORMATION: Synthetic Construct

<400> SEQUENCE: 137
tcaccaagtc tggcggctca gatcg 25

<210> SEQ ID NO 138
<211> LENGTH: 25
<212> TYPE: DNA
<213> ORGANISM: Artificial Sequence
<220> FEATURE:
<223> OTHER INFORMATION: Synthetic Construct

<400> SEQUENCE: 138
atttagggta tgcagctcct tttgt 25

<210> SEQ ID NO 139
<211> LENGTH: 25
<212> TYPE: DNA
<213> ORGANISM: Artificial Sequence
<220> FEATURE:
<223> OTHER INFORMATION: Synthetic Construct

<400> SEQUENCE: 139
aaatcttgat atccagaagc acatg 25

<210> SEQ ID NO 140
<211> LENGTH: 25
<212> TYPE: DNA
<213> ORGANISM: Artificial Sequence
<220> FEATURE:
<223> OTHER INFORMATION: Synthetic Construct

<400> SEQUENCE: 140
atgtagctcc cacaaggtaa acttc 25

<210> SEQ ID NO 141
<211> LENGTH: 25
<212> TYPE: DNA
<213> ORGANISM: Artificial Sequence
<220> FEATURE:
<223> OTHER INFORMATION: Synthetic Construct

<400> SEQUENCE: 141
ctcatgctag cctcacgaaa ctgga 25

<210> SEQ ID NO 142
<211> LENGTH: 25
<212> TYPE: DNA
<213> ORGANISM: Artificial Sequence
<220> FEATURE:
<223> OTHER INFORMATION: Synthetic Construct

<400> SEQUENCE: 142
ttcaggtggt atttgcattc agtgc 25

<210> SEQ ID NO 143
<211> LENGTH: 25
<212> TYPE: DNA
<213> ORGANISM: Artificial Sequence
<220> FEATURE:
<223> OTHER INFORMATION: Synthetic Construct

<400> SEQUENCE: 143
ggagggcatc tgtgttagtc ctttc 25

<210> SEQ ID NO 144
<211> LENGTH: 25
<212> TYPE: DNA
<213> ORGANISM: Artificial Sequence
<220> FEATURE:
<223> OTHER INFORMATION: Synthetic Construct

<400> SEQUENCE: 144
aactgcagcg gaacatgtca tttct 25

<210> SEQ ID NO 145
<211> LENGTH: 25
<212> TYPE: DNA
<213> ORGANISM: Artificial Sequence
<220> FEATURE:
<223> OTHER INFORMATION: Synthetic Construct

<400> SEQUENCE: 145
ggacctggac cagtgtagag atggc 25

<210> SEQ ID NO 146
<211> LENGTH: 25
<212> TYPE: DNA
<213> ORGANISM: Artificial Sequence
<220> FEATURE:
<223> OTHER INFORMATION: Synthetic Construct

<400> SEQUENCE: 146
tttcttttcg actttatact ctgag 25

<210> SEQ ID NO 147
<211> LENGTH: 25
<212> TYPE: DNA
<213> ORGANISM: Artificial Sequence
<220> FEATURE:
<223> OTHER INFORMATION: Synthetic Construct

<400> SEQUENCE: 147
tgccatttcc caacgtcttt tggga 25

<210> SEQ ID NO 148
<211> LENGTH: 25
<212> TYPE: DNA
<213> ORGANISM: Artificial Sequence
<220> FEATURE:
<223> OTHER INFORMATION: Synthetic Construct

<400> SEQUENCE: 148
tgcagtctcc ttcaagcatt ctgtc 25

<210> SEQ ID NO 149
<211> LENGTH: 25
<212> TYPE: DNA
<213> ORGANISM: Artificial Sequence
<220> FEATURE:
<223> OTHER INFORMATION: Synthetic Construct

<400> SEQUENCE: 149
gatctctgag ctgcccagca tagtc 25

<210> SEQ ID NO 150
<211> LENGTH: 25
<212> TYPE: DNA
<213> ORGANISM: Artificial Sequence
<220> FEATURE:
<223> OTHER INFORMATION: Synthetic Construct

<400> SEQUENCE: 150
attcatcttg tgtcttattc aagta 25

<210> SEQ ID NO 151
<211> LENGTH: 25
<212> TYPE: DNA
<213> ORGANISM: Artificial Sequence
<220> FEATURE:
<223> OTHER INFORMATION: Synthetic Construct

<400> SEQUENCE: 151
aaatagcttg tgctcagact cctct 25

<210> SEQ ID NO 152
<211> LENGTH: 25
<212> TYPE: DNA
<213> ORGANISM: Artificial Sequence
<220> FEATURE:
<223> OTHER INFORMATION: Synthetic Construct

<400> SEQUENCE: 152
agaacaccgt gggctgttac ttgct 25

<210> SEQ ID NO 153
<211> LENGTH: 25
<212> TYPE: DNA
<213> ORGANISM: Artificial Sequence
<220> FEATURE:
<223> OTHER INFORMATION: Synthetic Construct

<400> SEQUENCE: 153
atactcttat agcctgcctt caatt 25

<210> SEQ ID NO 154
<211> LENGTH: 25
<212> TYPE: DNA
<213> ORGANISM: Artificial Sequence
<220> FEATURE:
<223> OTHER INFORMATION: Synthetic Construct

<400> SEQUENCE: 154
gctaacttcc actaatccat tatcc 25

<210> SEQ ID NO 155
<211> LENGTH: 25
<212> TYPE: DNA
<213> ORGANISM: Artificial Sequence
<220> FEATURE:
<223> OTHER INFORMATION: Synthetic Construct

<400> SEQUENCE: 155
atcccatcaa caggactaca cactt 25

<210> SEQ ID NO 156
<211> LENGTH: 25
<212> TYPE: DNA
<213> ORGANISM: Artificial Sequence
<220> FEATURE:
<223> OTHER INFORMATION: Synthetic Construct

<400> SEQUENCE: 156
aactatttgc accgaaatgt cttgt 25

<210> SEQ ID NO 157
<211> LENGTH: 25
<212> TYPE: DNA
<213> ORGANISM: Artificial Sequence
<220> FEATURE:
<223> OTHER INFORMATION: Synthetic Construct

<400> SEQUENCE: 157
gcaaaggccc tcaaataagc ccctc 25

<210> SEQ ID NO 158
<211> LENGTH: 25
<212> TYPE: DNA
<213> ORGANISM: Artificial Sequence
<220> FEATURE:
<223> OTHER INFORMATION: Synthetic Construct

<400> SEQUENCE: 158
actctccacc atgcaggaca aacat 25

<210> SEQ ID NO 159
<211> LENGTH: 25
<212> TYPE: DNA
<213> ORGANISM: Artificial Sequence
<220> FEATURE:
<223> OTHER INFORMATION: Synthetic Construct

<400> SEQUENCE: 159
attattctgc ctttggctaa ttgag 25

<210> SEQ ID NO 160
<211> LENGTH: 25
<212> TYPE: DNA
<213> ORGANISM: Artificial Sequence
<220> FEATURE:
<223> OTHER INFORMATION: Synthetic Construct

<400> SEQUENCE: 160
tatcatgttt acagtcaccc ttggg 25

<210> SEQ ID NO 161
<211> LENGTH: 25
<212> TYPE: DNA
<213> ORGANISM: Artificial Sequence
<220> FEATURE:
<223> OTHER INFORMATION: Synthetic Construct

<400> SEQUENCE: 161
acctctgaag ccttctttgt ggcct 25

<210> SEQ ID NO 162
<211> LENGTH: 25
<212> TYPE: DNA
<213> ORGANISM: Artificial Sequence
<220> FEATURE:
<223> OTHER INFORMATION: Synthetic Construct

<400> SEQUENCE: 162
cacagcctat tcagttcctt tgttt 25

<210> SEQ ID NO 163
<211> LENGTH: 25
<212> TYPE: DNA
<213> ORGANISM: Artificial Sequence
<220> FEATURE:
<223> OTHER INFORMATION: Synthetic Construct

<400> SEQUENCE: 163
tgaagaagca aactgcccgt tctcc 25

<210> SEQ ID NO 164
<211> LENGTH: 25
<212> TYPE: DNA
<213> ORGANISM: Artificial Sequence
<220> FEATURE:
<223> OTHER INFORMATION: Synthetic Construct

<400> SEQUENCE: 164
gatccttaga ggtcctctgg agccc 25

<210> SEQ ID NO 165
<211> LENGTH: 25
<212> TYPE: DNA
<213> ORGANISM: Artificial Sequence
<220> FEATURE:
<223> OTHER INFORMATION: Synthetic Construct

<400> SEQUENCE: 165
gtagtgtcag aggatactgt ggctt 25

<210> SEQ ID NO 166

<211> LENGTH: 25
<212> TYPE: DNA
<213> ORGANISM: Artificial Sequence
<220> FEATURE:
<223> OTHER INFORMATION: Synthetic Construct

<400> SEQUENCE: 166
tgccctgtca aaggtcccta tttga 25

<210> SEQ ID NO 167
<211> LENGTH: 25
<212> TYPE: DNA
<213> ORGANISM: Artificial Sequence
<220> FEATURE:
<223> OTHER INFORMATION: Synthetic Construct

<400> SEQUENCE: 167
ctctgtgact tcctggagac tcact 25

<210> SEQ ID NO 168
<211> LENGTH: 25
<212> TYPE: DNA
<213> ORGANISM: Artificial Sequence
<220> FEATURE:
<223> OTHER INFORMATION: Synthetic Construct

<400> SEQUENCE: 168
actgtatctt cctttactgt ttata 25

<210> SEQ ID NO 169
<211> LENGTH: 25
<212> TYPE: DNA
<213> ORGANISM: Artificial Sequence
<220> FEATURE:
<223> OTHER INFORMATION: Synthetic Construct

<400> SEQUENCE: 169
tatagatctg attctttctt ttcct 25

<210> SEQ ID NO 170
<211> LENGTH: 25
<212> TYPE: DNA
<213> ORGANISM: Artificial Sequence
<220> FEATURE:
<223> OTHER INFORMATION: Synthetic Construct

<400> SEQUENCE: 170
ctcatccaaa ctgtatcttc cttta 25

<210> SEQ ID NO 171
<211> LENGTH: 25
<212> TYPE: DNA
<213> ORGANISM: Artificial Sequence
<220> FEATURE:
<223> OTHER INFORMATION: Synthetic Construct

<400> SEQUENCE: 171
ggacatggcg aaccggatca gtgcc 25

<210> SEQ ID NO 172
<211> LENGTH: 25
<212> TYPE: DNA
<213> ORGANISM: Artificial Sequence
<220> FEATURE:
<223> OTHER INFORMATION: Synthetic Construct

<400> SEQUENCE: 172
aacgcctcac tgaaacatgg ctgtg 25

<210> SEQ ID NO 173
<211> LENGTH: 25
<212> TYPE: DNA
<213> ORGANISM: Artificial Sequence
<220> FEATURE:
<223> OTHER INFORMATION: Synthetic Construct

<400> SEQUENCE: 173
gcaattgagg cagttgacca tattc 25

<210> SEQ ID NO 174
<211> LENGTH: 25
<212> TYPE: DNA
<213> ORGANISM: Artificial Sequence
<220> FEATURE:
<223> OTHER INFORMATION: Synthetic Construct

<400> SEQUENCE: 174
aaccaccatt ccaacaggtc gagga 25

<210> SEQ ID NO 175
<211> LENGTH: 25
<212> TYPE: DNA
<213> ORGANISM: Artificial Sequence
<220> FEATURE:
<223> OTHER INFORMATION: Synthetic Construct

<400> SEQUENCE: 175
atttgcctct gagaacgatc tccca 25

<210> SEQ ID NO 176
<211> LENGTH: 25
<212> TYPE: DNA
<213> ORGANISM: Artificial Sequence
<220> FEATURE:
<223> OTHER INFORMATION: Synthetic Construct

<400> SEQUENCE: 176
ggttgaaaca tatctcttat cttac 25

<210> SEQ ID NO 177
<211> LENGTH: 25
<212> TYPE: DNA
<213> ORGANISM: Artificial Sequence
<220> FEATURE:
<223> OTHER INFORMATION: Synthetic Construct

<400> SEQUENCE: 177
gggggagtac acactggtgg tcaaa 25

<210> SEQ ID NO 178
<211> LENGTH: 25
<212> TYPE: DNA
<213> ORGANISM: Artificial Sequence
<220> FEATURE:
<223> OTHER INFORMATION: Synthetic Construct

<400> SEQUENCE: 178
gttgccgtca ctgtattaag tcgat 25

<210> SEQ ID NO 179
<211> LENGTH: 25
<212> TYPE: DNA

<213> ORGANISM: Artificial Sequence
<220> FEATURE:
<223> OTHER INFORMATION: Synthetic Construct

<400> SEQUENCE: 179
gagaacactt agtcttgcct gtcaa 25

<210> SEQ ID NO 180
<211> LENGTH: 25
<212> TYPE: DNA
<213> ORGANISM: Artificial Sequence
<220> FEATURE:
<223> OTHER INFORMATION: Synthetic Construct

<400> SEQUENCE: 180
gggggagtac acactggtgg tcaaa 25

<210> SEQ ID NO 181
<211> LENGTH: 25
<212> TYPE: DNA
<213> ORGANISM: Artificial Sequence
<220> FEATURE:
<223> OTHER INFORMATION: Synthetic Construct

<400> SEQUENCE: 181
gtacactgcc tctgaacatc taatt 25

<210> SEQ ID NO 182
<211> LENGTH: 25
<212> TYPE: DNA
<213> ORGANISM: Artificial Sequence
<220> FEATURE:
<223> OTHER INFORMATION: Synthetic Construct

<400> SEQUENCE: 182
tcccactctt ctctgggact tgtgg 25

<210> SEQ ID NO 183
<211> LENGTH: 25
<212> TYPE: DNA
<213> ORGANISM: Artificial Sequence
<220> FEATURE:
<223> OTHER INFORMATION: Synthetic Construct

<400> SEQUENCE: 183
gagctctact tacagaacag ccctg 25

<210> SEQ ID NO 184
<211> LENGTH: 25
<212> TYPE: DNA
<213> ORGANISM: Artificial Sequence
<220> FEATURE:
<223> OTHER INFORMATION: Synthetic Construct

<400> SEQUENCE: 184
agaatgatgt ccccgttgta tgtat 25

<210> SEQ ID NO 185
<211> LENGTH: 25
<212> TYPE: DNA
<213> ORGANISM: Artificial Sequence
<220> FEATURE:
<223> OTHER INFORMATION: Synthetic Construct

<400> SEQUENCE: 185
cggctggtga gctacttcat caaga 25

<210> SEQ ID NO 186
<211> LENGTH: 25
<212> TYPE: DNA
<213> ORGANISM: Artificial Sequence
<220> FEATURE:
<223> OTHER INFORMATION: Synthetic Construct

<400> SEQUENCE: 186
caaaggactc tttctaaacc atatt 25

<210> SEQ ID NO 187
<211> LENGTH: 25
<212> TYPE: DNA
<213> ORGANISM: Artificial Sequence
<220> FEATURE:
<223> OTHER INFORMATION: Synthetic Construct

<400> SEQUENCE: 187
ttgaatgggt ccattttgcc cttcc 25

<210> SEQ ID NO 188
<211> LENGTH: 25
<212> TYPE: DNA
<213> ORGANISM: Artificial Sequence
<220> FEATURE:
<223> OTHER INFORMATION: Synthetic Construct

<400> SEQUENCE: 188
gaatcagatg gacactcaca tggga 25

<210> SEQ ID NO 189
<211> LENGTH: 25
<212> TYPE: DNA
<213> ORGANISM: Artificial Sequence
<220> FEATURE:
<223> OTHER INFORMATION: Synthetic Construct

<400> SEQUENCE: 189
gccgtctcaa gtttaaactt acacg 25

<210> SEQ ID NO 190
<211> LENGTH: 25
<212> TYPE: DNA
<213> ORGANISM: Artificial Sequence
<220> FEATURE:
<223> OTHER INFORMATION: Synthetic Construct

<400> SEQUENCE: 190
ggaattcctt gtaactggag ctcgg 25

<210> SEQ ID NO 191
<211> LENGTH: 25
<212> TYPE: DNA
<213> ORGANISM: Artificial Sequence
<220> FEATURE:
<223> OTHER INFORMATION: Synthetic Construct

<400> SEQUENCE: 191
gactgctttt caggaagcct tggac 25

<210> SEQ ID NO 192
<211> LENGTH: 25
<212> TYPE: DNA
<213> ORGANISM: Artificial Sequence
<220> FEATURE:

<223> OTHER INFORMATION: Synthetic Construct

<400> SEQUENCE: 192
attaatattg ttgccgctgt tgtgt 25

<210> SEQ ID NO 193
<211> LENGTH: 25
<212> TYPE: DNA
<213> ORGANISM: Artificial Sequence
<220> FEATURE:
<223> OTHER INFORMATION: Synthetic Construct

<400> SEQUENCE: 193
tggagattcc aactctaatg tcaat 25

<210> SEQ ID NO 194
<211> LENGTH: 25
<212> TYPE: DNA
<213> ORGANISM: Artificial Sequence
<220> FEATURE:
<223> OTHER INFORMATION: Synthetic Construct

<400> SEQUENCE: 194
aattttttat catgcatgtc ctgta 25

<210> SEQ ID NO 195
<211> LENGTH: 25
<212> TYPE: DNA
<213> ORGANISM: Artificial Sequence
<220> FEATURE:
<223> OTHER INFORMATION: Synthetic Construct

<400> SEQUENCE: 195
gacgtggagg cagccgtcaa cagcc 25

<210> SEQ ID NO 196
<211> LENGTH: 25
<212> TYPE: DNA
<213> ORGANISM: Artificial Sequence
<220> FEATURE:
<223> OTHER INFORMATION: Synthetic Construct

<400> SEQUENCE: 196
gcttcacagt agactgcagc aaagc 25

<210> SEQ ID NO 197
<211> LENGTH: 25
<212> TYPE: DNA
<213> ORGANISM: Artificial Sequence
<220> FEATURE:
<223> OTHER INFORMATION: Synthetic Construct

<400> SEQUENCE: 197
gtcacaatca tcatgtcact gtggg 25

<210> SEQ ID NO 198
<211> LENGTH: 25
<212> TYPE: DNA
<213> ORGANISM: Artificial Sequence
<220> FEATURE:
<223> OTHER INFORMATION: Synthetic Construct

<400> SEQUENCE: 198
agctcagatg atggtatctg tgagt 25

-continued

<210> SEQ ID NO 199
<211> LENGTH: 25
<212> TYPE: DNA
<213> ORGANISM: Artificial Sequence
<220> FEATURE:
<223> OTHER INFORMATION: Synthetic Construct

<400> SEQUENCE: 199
ctgtgaccat cactcagtcc aaaca 25

<210> SEQ ID NO 200
<211> LENGTH: 25
<212> TYPE: DNA
<213> ORGANISM: Artificial Sequence
<220> FEATURE:
<223> OTHER INFORMATION: Synthetic Construct

<400> SEQUENCE: 200
agaaagggag cctcacgctg gctca 25

<210> SEQ ID NO 201
<211> LENGTH: 25
<212> TYPE: DNA
<213> ORGANISM: Artificial Sequence
<220> FEATURE:
<223> OTHER INFORMATION: Synthetic Construct

<400> SEQUENCE: 201
tcagcaaaat gattcctttc tttaa 25

<210> SEQ ID NO 202
<211> LENGTH: 25
<212> TYPE: DNA
<213> ORGANISM: Artificial Sequence
<220> FEATURE:
<223> OTHER INFORMATION: Synthetic Construct

<400> SEQUENCE: 202
gggctcccaa agcgacaaga tcgtt 25

<210> SEQ ID NO 203
<211> LENGTH: 25
<212> TYPE: DNA
<213> ORGANISM: Artificial Sequence
<220> FEATURE:
<223> OTHER INFORMATION: Synthetic Construct

<400> SEQUENCE: 203
ggttctttcc ttgaagggca gcctc 25

<210> SEQ ID NO 204
<211> LENGTH: 25
<212> TYPE: DNA
<213> ORGANISM: Artificial Sequence
<220> FEATURE:
<223> OTHER INFORMATION: Synthetic Construct

<400> SEQUENCE: 204
tgccaaaacc aagattttga aggaa 25

<210> SEQ ID NO 205
<211> LENGTH: 25
<212> TYPE: DNA
<213> ORGANISM: Artificial Sequence
<220> FEATURE:
<223> OTHER INFORMATION: Synthetic Construct

<400> SEQUENCE: 205
tggggttttt actgttacct gatca 25

<210> SEQ ID NO 206
<211> LENGTH: 25
<212> TYPE: DNA
<213> ORGANISM: Artificial Sequence
<220> FEATURE:
<223> OTHER INFORMATION: Synthetic Construct

<400> SEQUENCE: 206
ccttgcggta ggcctggatc tggca 25

<210> SEQ ID NO 207
<211> LENGTH: 25
<212> TYPE: DNA
<213> ORGANISM: Artificial Sequence
<220> FEATURE:
<223> OTHER INFORMATION: Synthetic Construct

<400> SEQUENCE: 207
agtggtcgcc ctggacaaga acttc 25

<210> SEQ ID NO 208
<211> LENGTH: 25
<212> TYPE: DNA
<213> ORGANISM: Artificial Sequence
<220> FEATURE:
<223> OTHER INFORMATION: Synthetic Construct

<400> SEQUENCE: 208
taatgtaccc atgtagacta gcaaa 25

<210> SEQ ID NO 209
<211> LENGTH: 25
<212> TYPE: DNA
<213> ORGANISM: Artificial Sequence
<220> FEATURE:
<223> OTHER INFORMATION: Synthetic Construct

<400> SEQUENCE: 209
ctgctaactc ctagctgact cagca 25

<210> SEQ ID NO 210
<211> LENGTH: 25
<212> TYPE: DNA
<213> ORGANISM: Artificial Sequence
<220> FEATURE:
<223> OTHER INFORMATION: Synthetic Construct

<400> SEQUENCE: 210
agcgaagact gctaaatgca ctgac 25

<210> SEQ ID NO 211
<211> LENGTH: 25
<212> TYPE: DNA
<213> ORGANISM: Artificial Sequence
<220> FEATURE:
<223> OTHER INFORMATION: Synthetic Construct

<400> SEQUENCE: 211
cgcagacggt ctgtgtgctg tttga 25

<210> SEQ ID NO 212
<211> LENGTH: 25

<212> TYPE: DNA
<213> ORGANISM: Artificial Sequence
<220> FEATURE:
<223> OTHER INFORMATION: Synthetic Construct

<400> SEQUENCE: 212
gtactaccag agcaactatg tgttc 25

<210> SEQ ID NO 213
<211> LENGTH: 25
<212> TYPE: DNA
<213> ORGANISM: Artificial Sequence
<220> FEATURE:
<223> OTHER INFORMATION: Synthetic Construct

<400> SEQUENCE: 213
agctgctgtg tcctctagtt gagtt 25

<210> SEQ ID NO 214
<211> LENGTH: 25
<212> TYPE: DNA
<213> ORGANISM: Artificial Sequence
<220> FEATURE:
<223> OTHER INFORMATION: Synthetic Construct

<400> SEQUENCE: 214
ctgaaatctc tggaggctgc atctg 25

<210> SEQ ID NO 215
<211> LENGTH: 25
<212> TYPE: DNA
<213> ORGANISM: Artificial Sequence
<220> FEATURE:
<223> OTHER INFORMATION: Synthetic Construct

<400> SEQUENCE: 215
aaagagtcac taagcacctg tatcc 25

<210> SEQ ID NO 216
<211> LENGTH: 25
<212> TYPE: DNA
<213> ORGANISM: Artificial Sequence
<220> FEATURE:
<223> OTHER INFORMATION: Synthetic Construct

<400> SEQUENCE: 216
agctgctgtg tcctctagtt gagtt 25

<210> SEQ ID NO 217
<211> LENGTH: 25
<212> TYPE: DNA
<213> ORGANISM: Artificial Sequence
<220> FEATURE:
<223> OTHER INFORMATION: Synthetic Construct

<400> SEQUENCE: 217
ttgcacggat ctaagttatt ctccc 25

<210> SEQ ID NO 218
<211> LENGTH: 25
<212> TYPE: DNA
<213> ORGANISM: Artificial Sequence
<220> FEATURE:
<223> OTHER INFORMATION: Synthetic Construct

<400> SEQUENCE: 218
tccttctcag ccgtcgggat aggat 25

<210> SEQ ID NO 219
<211> LENGTH: 25
<212> TYPE: DNA
<213> ORGANISM: Artificial Sequence
<220> FEATURE:
<223> OTHER INFORMATION: Synthetic Construct

<400> SEQUENCE: 219
tggtttacca ttgatgactt cgcct 25

<210> SEQ ID NO 220
<211> LENGTH: 25
<212> TYPE: DNA
<213> ORGANISM: Artificial Sequence
<220> FEATURE:
<223> OTHER INFORMATION: Synthetic Construct

<400> SEQUENCE: 220
tccatttctg gcagcagcct ggagc 25

<210> SEQ ID NO 221
<211> LENGTH: 25
<212> TYPE: DNA
<213> ORGANISM: Artificial Sequence
<220> FEATURE:
<223> OTHER INFORMATION: Synthetic Construct

<400> SEQUENCE: 221
gagagctgca actgtaaagg gcaag 25

<210> SEQ ID NO 222
<211> LENGTH: 25
<212> TYPE: DNA
<213> ORGANISM: Artificial Sequence
<220> FEATURE:
<223> OTHER INFORMATION: Synthetic Construct

<400> SEQUENCE: 222
aattggtata ttcacagact gtaga 25

<210> SEQ ID NO 223
<211> LENGTH: 25
<212> TYPE: DNA
<213> ORGANISM: Artificial Sequence
<220> FEATURE:
<223> OTHER INFORMATION: Synthetic Construct

<400> SEQUENCE: 223
gattcacaca ggtttgagga tgctg 25

<210> SEQ ID NO 224
<211> LENGTH: 25
<212> TYPE: DNA
<213> ORGANISM: Artificial Sequence
<220> FEATURE:
<223> OTHER INFORMATION: Synthetic Construct

<400> SEQUENCE: 224
gtccttgatt tcctcaattt tccga 25

<210> SEQ ID NO 225
<211> LENGTH: 25
<212> TYPE: DNA
<213> ORGANISM: Artificial Sequence
<220> FEATURE:
<223> OTHER INFORMATION: Synthetic Construct

<400> SEQUENCE: 225
tcaccattcc tcttggcttg gaaag 25

<210> SEQ ID NO 226
<211> LENGTH: 25
<212> TYPE: DNA
<213> ORGANISM: Artificial Sequence
<220> FEATURE:
<223> OTHER INFORMATION: Synthetic Construct

<400> SEQUENCE: 226
aagtaacatg acttccttat ttctg 25

<210> SEQ ID NO 227
<211> LENGTH: 24
<212> TYPE: DNA
<213> ORGANISM: Artificial Sequence
<220> FEATURE:
<223> OTHER INFORMATION: Synthetic Construct

<400> SEQUENCE: 227
atttttgctt gtgttagatc atta 24

<210> SEQ ID NO 228
<211> LENGTH: 25
<212> TYPE: DNA
<213> ORGANISM: Artificial Sequence
<220> FEATURE:
<223> OTHER INFORMATION: Synthetic Construct

<400> SEQUENCE: 228
gcccctgcta atgctcatct gaagg 25

<210> SEQ ID NO 229
<211> LENGTH: 25
<212> TYPE: DNA
<213> ORGANISM: Artificial Sequence
<220> FEATURE:
<223> OTHER INFORMATION: Synthetic Construct

<400> SEQUENCE: 229
tttcaatagc accttgccca caatg 25

<210> SEQ ID NO 230
<211> LENGTH: 25
<212> TYPE: DNA
<213> ORGANISM: Artificial Sequence
<220> FEATURE:
<223> OTHER INFORMATION: Synthetic Construct

<400> SEQUENCE: 230
ggcttctctg tttgggtagc gtaag 25

<210> SEQ ID NO 231
<211> LENGTH: 25
<212> TYPE: DNA
<213> ORGANISM: Artificial Sequence
<220> FEATURE:
<223> OTHER INFORMATION: Synthetic Construct

<400> SEQUENCE: 231
gggtgcctat tttagtcatg gatca 25

-continued

<210> SEQ ID NO 232
<211> LENGTH: 25
<212> TYPE: DNA
<213> ORGANISM: Artificial Sequence
<220> FEATURE:
<223> OTHER INFORMATION: Synthetic Construct

<400> SEQUENCE: 232
aaatttgatc gccttaacta ctgta 25

<210> SEQ ID NO 233
<211> LENGTH: 25
<212> TYPE: DNA
<213> ORGANISM: Artificial Sequence
<220> FEATURE:
<223> OTHER INFORMATION: Synthetic Construct

<400> SEQUENCE: 233
acagataatt tcactttcct cttcc 25

<210> SEQ ID NO 234
<211> LENGTH: 25
<212> TYPE: DNA
<213> ORGANISM: Artificial Sequence
<220> FEATURE:
<223> OTHER INFORMATION: Synthetic Construct

<400> SEQUENCE: 234
gtcagcagac atgttcatcc gatga 25

<210> SEQ ID NO 235
<211> LENGTH: 25
<212> TYPE: DNA
<213> ORGANISM: Artificial Sequence
<220> FEATURE:
<223> OTHER INFORMATION: Synthetic Construct

<400> SEQUENCE: 235
ccaccgctct catttcatgg agtct 25

<210> SEQ ID NO 236
<211> LENGTH: 25
<212> TYPE: DNA
<213> ORGANISM: Artificial Sequence
<220> FEATURE:
<223> OTHER INFORMATION: Synthetic Construct

<400> SEQUENCE: 236
agcaaggacc gcaagtacac tctaa 25

<210> SEQ ID NO 237
<211> LENGTH: 25
<212> TYPE: DNA
<213> ORGANISM: Artificial Sequence
<220> FEATURE:
<223> OTHER INFORMATION: Synthetic Construct

<400> SEQUENCE: 237
tgtcttatga tcacgtttgc catct 25

<210> SEQ ID NO 238
<211> LENGTH: 25
<212> TYPE: DNA
<213> ORGANISM: Artificial Sequence
<220> FEATURE:
<223> OTHER INFORMATION: Synthetic Construct

<400> SEQUENCE: 238
ttgaggtggg ctccctggta tggta 25

<210> SEQ ID NO 239
<211> LENGTH: 25
<212> TYPE: DNA
<213> ORGANISM: Artificial Sequence
<220> FEATURE:
<223> OTHER INFORMATION: Synthetic Construct

<400> SEQUENCE: 239
gaacaatacc caagtgctca tcaac 25

<210> SEQ ID NO 240
<211> LENGTH: 25
<212> TYPE: DNA
<213> ORGANISM: Artificial Sequence
<220> FEATURE:
<223> OTHER INFORMATION: Synthetic Construct

<400> SEQUENCE: 240
gcagcaatta agggtcttca tgttc 25

<210> SEQ ID NO 241
<211> LENGTH: 25
<212> TYPE: DNA
<213> ORGANISM: Artificial Sequence
<220> FEATURE:
<223> OTHER INFORMATION: Synthetic Construct

<400> SEQUENCE: 241
agtatggcct attctctgta tttat 25

<210> SEQ ID NO 242
<211> LENGTH: 24
<212> TYPE: DNA
<213> ORGANISM: Artificial Sequence
<220> FEATURE:
<223> OTHER INFORMATION: Synthetic Construct

<400> SEQUENCE: 242
aaagtgccac attcggggct attt 24

<210> SEQ ID NO 243
<211> LENGTH: 25
<212> TYPE: DNA
<213> ORGANISM: Artificial Sequence
<220> FEATURE:
<223> OTHER INFORMATION: Synthetic Construct

<400> SEQUENCE: 243
gccaatggcg agatctgcgt caacg 25

<210> SEQ ID NO 244
<211> LENGTH: 25
<212> TYPE: DNA
<213> ORGANISM: Artificial Sequence
<220> FEATURE:
<223> OTHER INFORMATION: Synthetic Construct

<400> SEQUENCE: 244
agattcctga attcccaatt gcacc 25

<210> SEQ ID NO 245

<211> LENGTH: 25
<212> TYPE: DNA
<213> ORGANISM: Artificial Sequence
<220> FEATURE:
<223> OTHER INFORMATION: Synthetic Construct

<400> SEQUENCE: 245
atactcatat gatcactttt ctttt 25

<210> SEQ ID NO 246
<211> LENGTH: 25
<212> TYPE: DNA
<213> ORGANISM: Artificial Sequence
<220> FEATURE:
<223> OTHER INFORMATION: Synthetic Construct

<400> SEQUENCE: 246
catgaacctc tgtattgctt tcctt 25

<210> SEQ ID NO 247
<211> LENGTH: 25
<212> TYPE: DNA
<213> ORGANISM: Artificial Sequence
<220> FEATURE:
<223> OTHER INFORMATION: Synthetic Construct

<400> SEQUENCE: 247
ccacctcgtg gcctcaagat ggcag 25

<210> SEQ ID NO 248
<211> LENGTH: 25
<212> TYPE: DNA
<213> ORGANISM: Artificial Sequence
<220> FEATURE:
<223> OTHER INFORMATION: Synthetic Construct

<400> SEQUENCE: 248
gaaacacatt cactgcttca gggtt 25

<210> SEQ ID NO 249
<211> LENGTH: 25
<212> TYPE: DNA
<213> ORGANISM: Artificial Sequence
<220> FEATURE:
<223> OTHER INFORMATION: Synthetic Construct

<400> SEQUENCE: 249
aatgctatgg gctatgtacg aatga 25

<210> SEQ ID NO 250
<211> LENGTH: 25
<212> TYPE: DNA
<213> ORGANISM: Artificial Sequence
<220> FEATURE:
<223> OTHER INFORMATION: Synthetic Construct

<400> SEQUENCE: 250
ctctcttcct ttagggctac tgagt 25

<210> SEQ ID NO 251
<211> LENGTH: 25
<212> TYPE: DNA
<213> ORGANISM: Artificial Sequence
<220> FEATURE:
<223> OTHER INFORMATION: Synthetic Construct

<400> SEQUENCE: 251
cctactgtgg tactgaagac ttctg 25

<210> SEQ ID NO 252
<211> LENGTH: 25
<212> TYPE: DNA
<213> ORGANISM: Artificial Sequence
<220> FEATURE:
<223> OTHER INFORMATION: Synthetic Construct

<400> SEQUENCE: 252
aaaaatttcc agctcaacca agata 25

<210> SEQ ID NO 253
<211> LENGTH: 25
<212> TYPE: DNA
<213> ORGANISM: Artificial Sequence
<220> FEATURE:
<223> OTHER INFORMATION: Synthetic Construct

<400> SEQUENCE: 253
agggttgcgc ttgcattgga cccta 25

<210> SEQ ID NO 254
<211> LENGTH: 25
<212> TYPE: DNA
<213> ORGANISM: Artificial Sequence
<220> FEATURE:
<223> OTHER INFORMATION: Synthetic Construct

<400> SEQUENCE: 254
acaatgtagc atatttgatt ttctt 25

<210> SEQ ID NO 255
<211> LENGTH: 25
<212> TYPE: DNA
<213> ORGANISM: Artificial Sequence
<220> FEATURE:
<223> OTHER INFORMATION: Synthetic Construct

<400> SEQUENCE: 255
cagtaataac tgcaggtcac ttgta 25

<210> SEQ ID NO 256
<211> LENGTH: 25
<212> TYPE: DNA
<213> ORGANISM: Artificial Sequence
<220> FEATURE:
<223> OTHER INFORMATION: Synthetic Construct

<400> SEQUENCE: 256
ggacatacag ctcgttgaag cactg 25

<210> SEQ ID NO 257
<211> LENGTH: 25
<212> TYPE: DNA
<213> ORGANISM: Artificial Sequence
<220> FEATURE:
<223> OTHER INFORMATION: Synthetic Construct

<400> SEQUENCE: 257
agacattgag ttcaaattgc cttca 25

<210> SEQ ID NO 258
<211> LENGTH: 25
<212> TYPE: DNA

<213> ORGANISM: Artificial Sequence
<220> FEATURE:
<223> OTHER INFORMATION: Synthetic Construct

<400> SEQUENCE: 258
gtattttcca caagttttga tcctg 25

<210> SEQ ID NO 259
<211> LENGTH: 25
<212> TYPE: DNA
<213> ORGANISM: Artificial Sequence
<220> FEATURE:
<223> OTHER INFORMATION: Synthetic Construct

<400> SEQUENCE: 259
aagagtcagc tgatgccaga aggaa 25

<210> SEQ ID NO 260
<211> LENGTH: 25
<212> TYPE: DNA
<213> ORGANISM: Artificial Sequence
<220> FEATURE:
<223> OTHER INFORMATION: Synthetic Construct

<400> SEQUENCE: 260
ggtcccacgt tcatcatagg tatat 25

<210> SEQ ID NO 261
<211> LENGTH: 25
<212> TYPE: DNA
<213> ORGANISM: Artificial Sequence
<220> FEATURE:
<223> OTHER INFORMATION: Synthetic Construct

<400> SEQUENCE: 261
ggcatattcg ggagcttctt agagg 25

<210> SEQ ID NO 262
<211> LENGTH: 25
<212> TYPE: DNA
<213> ORGANISM: Artificial Sequence
<220> FEATURE:
<223> OTHER INFORMATION: Synthetic Construct

<400> SEQUENCE: 262
tcagcaagct ccagtgctac gtgtc 25

<210> SEQ ID NO 263
<211> LENGTH: 25
<212> TYPE: DNA
<213> ORGANISM: Artificial Sequence
<220> FEATURE:
<223> OTHER INFORMATION: Synthetic Construct

<400> SEQUENCE: 263
gaactcttgg tacctggaaa tgtga 25

<210> SEQ ID NO 264
<211> LENGTH: 25
<212> TYPE: DNA
<213> ORGANISM: Artificial Sequence
<220> FEATURE:
<223> OTHER INFORMATION: Synthetic Construct

<400> SEQUENCE: 264
gcaatagcac agccatccag gagct 25

<210> SEQ ID NO 265
<211> LENGTH: 25
<212> TYPE: DNA
<213> ORGANISM: Artificial Sequence
<220> FEATURE:
<223> OTHER INFORMATION: Synthetic Construct

<400> SEQUENCE: 265
ttaaatcctc cagcttttga acctt 25

<210> SEQ ID NO 266
<211> LENGTH: 25
<212> TYPE: DNA
<213> ORGANISM: Artificial Sequence
<220> FEATURE:
<223> OTHER INFORMATION: Synthetic Construct

<400> SEQUENCE: 266
aatcccagcc actccagagg ctgag 25

<210> SEQ ID NO 267
<211> LENGTH: 25
<212> TYPE: DNA
<213> ORGANISM: Artificial Sequence
<220> FEATURE:
<223> OTHER INFORMATION: Synthetic Construct

<400> SEQUENCE: 267
tttcctgagg gatttctaac catgt 25

<210> SEQ ID NO 268
<211> LENGTH: 25
<212> TYPE: DNA
<213> ORGANISM: Artificial Sequence
<220> FEATURE:
<223> OTHER INFORMATION: Synthetic Construct

<400> SEQUENCE: 268
tatacacaga catgctcttt tttta 25

<210> SEQ ID NO 269
<211> LENGTH: 25
<212> TYPE: DNA
<213> ORGANISM: Artificial Sequence
<220> FEATURE:
<223> OTHER INFORMATION: Synthetic Construct

<400> SEQUENCE: 269
gcatgtgaac gttattttta ccgtg 25

<210> SEQ ID NO 270
<211> LENGTH: 25
<212> TYPE: DNA
<213> ORGANISM: Artificial Sequence
<220> FEATURE:
<223> OTHER INFORMATION: Synthetic Construct

<400> SEQUENCE: 270
aagatggagc ctgggtctca agccc 25

<210> SEQ ID NO 271
<211> LENGTH: 25
<212> TYPE: DNA
<213> ORGANISM: Artificial Sequence
<220> FEATURE:

<223> OTHER INFORMATION: Synthetic Construct

<400> SEQUENCE: 271
tcctgctctc atgtagctaa aaaga 25

<210> SEQ ID NO 272
<211> LENGTH: 25
<212> TYPE: DNA
<213> ORGANISM: Artificial Sequence
<220> FEATURE:
<223> OTHER INFORMATION: Synthetic Construct

<400> SEQUENCE: 272
gccagtcgga ctgcgacata gccca 25

<210> SEQ ID NO 273
<211> LENGTH: 25
<212> TYPE: DNA
<213> ORGANISM: Artificial Sequence
<220> FEATURE:
<223> OTHER INFORMATION: Synthetic Construct

<400> SEQUENCE: 273
accaagaagc tactggacct cgttc 25

<210> SEQ ID NO 274
<211> LENGTH: 25
<212> TYPE: DNA
<213> ORGANISM: Artificial Sequence
<220> FEATURE:
<223> OTHER INFORMATION: Synthetic Construct

<400> SEQUENCE: 274
ttttaccaaa gcatcaatac aacca 25

<210> SEQ ID NO 275
<211> LENGTH: 25
<212> TYPE: DNA
<213> ORGANISM: Artificial Sequence
<220> FEATURE:
<223> OTHER INFORMATION: Synthetic Construct

<400> SEQUENCE: 275
ggcatatgtt tctgctagct atata 25

<210> SEQ ID NO 276
<211> LENGTH: 25
<212> TYPE: DNA
<213> ORGANISM: Artificial Sequence
<220> FEATURE:
<223> OTHER INFORMATION: Synthetic Construct

<400> SEQUENCE: 276
gttactgtgg tatctatgag ttatc 25

<210> SEQ ID NO 277
<211> LENGTH: 25
<212> TYPE: DNA
<213> ORGANISM: Artificial Sequence
<220> FEATURE:
<223> OTHER INFORMATION: Synthetic Construct

<400> SEQUENCE: 277
tctaccttaa tatctcccca aaaat 25

<210> SEQ ID NO 278
<211> LENGTH: 25
<212> TYPE: DNA
<213> ORGANISM: Artificial Sequence
<220> FEATURE:
<223> OTHER INFORMATION: Synthetic Construct

<400> SEQUENCE: 278
gaaacaccaa gatgtctgtc tctga 25

<210> SEQ ID NO 279
<211> LENGTH: 25
<212> TYPE: DNA
<213> ORGANISM: Artificial Sequence
<220> FEATURE:
<223> OTHER INFORMATION: Synthetic Construct

<400> SEQUENCE: 279
ggtgccaatt tcaagttcca agttg 25

<210> SEQ ID NO 280
<211> LENGTH: 25
<212> TYPE: DNA
<213> ORGANISM: Artificial Sequence
<220> FEATURE:
<223> OTHER INFORMATION: Synthetic Construct

<400> SEQUENCE: 280
aggtgccatt attctttcta gcctc 25

<210> SEQ ID NO 281
<211> LENGTH: 25
<212> TYPE: DNA
<213> ORGANISM: Artificial Sequence
<220> FEATURE:
<223> OTHER INFORMATION: Synthetic Construct

<400> SEQUENCE: 281
atcctcattc ttatactgct tttcg 25

<210> SEQ ID NO 282
<211> LENGTH: 25
<212> TYPE: DNA
<213> ORGANISM: Artificial Sequence
<220> FEATURE:
<223> OTHER INFORMATION: Synthetic Construct

<400> SEQUENCE: 282
aaaacttccc cggtatgatg attgt 25

<210> SEQ ID NO 283
<211> LENGTH: 25
<212> TYPE: DNA
<213> ORGANISM: Artificial Sequence
<220> FEATURE:
<223> OTHER INFORMATION: Synthetic Construct

<400> SEQUENCE: 283
aaagcttgtt gactctagcg gctca 25

<210> SEQ ID NO 284
<211> LENGTH: 25
<212> TYPE: DNA
<213> ORGANISM: Artificial Sequence
<220> FEATURE:
<223> OTHER INFORMATION: Synthetic Construct

<400> SEQUENCE: 284
aggtgctctg gactacatgt ccttc 25

<210> SEQ ID NO 285
<211> LENGTH: 25
<212> TYPE: DNA
<213> ORGANISM: Artificial Sequence
<220> FEATURE:
<223> OTHER INFORMATION: Synthetic Construct

<400> SEQUENCE: 285
agtactggtt gaacctgacc acttc 25

<210> SEQ ID NO 286
<211> LENGTH: 25
<212> TYPE: DNA
<213> ORGANISM: Artificial Sequence
<220> FEATURE:
<223> OTHER INFORMATION: Synthetic Construct

<400> SEQUENCE: 286
gaataaatct tctgtatcct caaaa 25

<210> SEQ ID NO 287
<211> LENGTH: 25
<212> TYPE: DNA
<213> ORGANISM: Artificial Sequence
<220> FEATURE:
<223> OTHER INFORMATION: Synthetic Construct

<400> SEQUENCE: 287
atgatcaccg tgaatccggc ttcct 25

<210> SEQ ID NO 288
<211> LENGTH: 25
<212> TYPE: DNA
<213> ORGANISM: Artificial Sequence
<220> FEATURE:
<223> OTHER INFORMATION: Synthetic Construct

<400> SEQUENCE: 288
gatcagtctc aaatgggttt cttgg 25

<210> SEQ ID NO 289
<211> LENGTH: 25
<212> TYPE: DNA
<213> ORGANISM: Artificial Sequence
<220> FEATURE:
<223> OTHER INFORMATION: Synthetic Construct

<400> SEQUENCE: 289
ggtattgcac agttgtcact ttatc 25

<210> SEQ ID NO 290
<211> LENGTH: 25
<212> TYPE: DNA
<213> ORGANISM: Artificial Sequence
<220> FEATURE:
<223> OTHER INFORMATION: Synthetic Construct

<400> SEQUENCE: 290
aaaagtcacc attctgcatt tagct 25

<210> SEQ ID NO 291
<211> LENGTH: 25

<212> TYPE: DNA
<213> ORGANISM: Artificial Sequence
<220> FEATURE:
<223> OTHER INFORMATION: Synthetic Construct

<400> SEQUENCE: 291
caggctatct tccagattcc ttaag 25

<210> SEQ ID NO 292
<211> LENGTH: 25
<212> TYPE: DNA
<213> ORGANISM: Artificial Sequence
<220> FEATURE:
<223> OTHER INFORMATION: Synthetic Construct

<400> SEQUENCE: 292
agacttggcc gtgatgtggt gtcct 25

<210> SEQ ID NO 293
<211> LENGTH: 25
<212> TYPE: DNA
<213> ORGANISM: Artificial Sequence
<220> FEATURE:
<223> OTHER INFORMATION: Synthetic Construct

<400> SEQUENCE: 293
tgtcctctgt gctgtatttg ccaat 25

<210> SEQ ID NO 294
<211> LENGTH: 25
<212> TYPE: DNA
<213> ORGANISM: Artificial Sequence
<220> FEATURE:
<223> OTHER INFORMATION: Synthetic Construct

<400> SEQUENCE: 294
gttttctgca tacttttcat cacga 25

<210> SEQ ID NO 295
<211> LENGTH: 25
<212> TYPE: DNA
<213> ORGANISM: Artificial Sequence
<220> FEATURE:
<223> OTHER INFORMATION: Synthetic Construct

<400> SEQUENCE: 295
gactgagttt gattcttcct gtacc 25

<210> SEQ ID NO 296
<211> LENGTH: 25
<212> TYPE: DNA
<213> ORGANISM: Artificial Sequence
<220> FEATURE:
<223> OTHER INFORMATION: Synthetic Construct

<400> SEQUENCE: 296
cctgctgtgc ccagtagttc tgaag 25

<210> SEQ ID NO 297
<211> LENGTH: 25
<212> TYPE: DNA
<213> ORGANISM: Artificial Sequence
<220> FEATURE:
<223> OTHER INFORMATION: Synthetic Construct

<400> SEQUENCE: 297
gagttagcaa catgcctgac ttcct 25

<210> SEQ ID NO 298
<211> LENGTH: 25
<212> TYPE: DNA
<213> ORGANISM: Artificial Sequence
<220> FEATURE:
<223> OTHER INFORMATION: Synthetic Construct

<400> SEQUENCE: 298
gaaatgacca cgtgaaattt gcctc 25

<210> SEQ ID NO 299
<211> LENGTH: 25
<212> TYPE: DNA
<213> ORGANISM: Artificial Sequence
<220> FEATURE:
<223> OTHER INFORMATION: Synthetic Construct

<400> SEQUENCE: 299
acttcttgat tgtcagtctg tgtca 25

<210> SEQ ID NO 300
<211> LENGTH: 25
<212> TYPE: DNA
<213> ORGANISM: Artificial Sequence
<220> FEATURE:
<223> OTHER INFORMATION: Synthetic Construct

<400> SEQUENCE: 300
taacgtttcc ggtattactc tgcta 25

<210> SEQ ID NO 301
<211> LENGTH: 25
<212> TYPE: DNA
<213> ORGANISM: Artificial Sequence
<220> FEATURE:
<223> OTHER INFORMATION: Synthetic Construct

<400> SEQUENCE: 301
gatttctgca gtgacttgat gctct 25

<210> SEQ ID NO 302
<211> LENGTH: 25
<212> TYPE: DNA
<213> ORGANISM: Artificial Sequence
<220> FEATURE:
<223> OTHER INFORMATION: Synthetic Construct

<400> SEQUENCE: 302
atcatgttct agttgcttga ccctg 25

<210> SEQ ID NO 303
<211> LENGTH: 25
<212> TYPE: DNA
<213> ORGANISM: Artificial Sequence
<220> FEATURE:
<223> OTHER INFORMATION: Synthetic Construct

<400> SEQUENCE: 303
gtatgggacc tacacttaat ctata 25

<210> SEQ ID NO 304
<211> LENGTH: 25
<212> TYPE: DNA
<213> ORGANISM: Artificial Sequence
<220> FEATURE:
<223> OTHER INFORMATION: Synthetic Construct

<400> SEQUENCE: 304
tggctcctag gaatgcttgg tgctg 25

<210> SEQ ID NO 305
<211> LENGTH: 25
<212> TYPE: DNA
<213> ORGANISM: Artificial Sequence
<220> FEATURE:
<223> OTHER INFORMATION: Synthetic Construct

<400> SEQUENCE: 305
tattaagacg accatctctt ctatt 25

<210> SEQ ID NO 306
<211> LENGTH: 25
<212> TYPE: DNA
<213> ORGANISM: Artificial Sequence
<220> FEATURE:
<223> OTHER INFORMATION: Synthetic Construct

<400> SEQUENCE: 306
cttttatggg gccctgtcca ggtag 25

<210> SEQ ID NO 307
<211> LENGTH: 25
<212> TYPE: DNA
<213> ORGANISM: Artificial Sequence
<220> FEATURE:
<223> OTHER INFORMATION: Synthetic Construct

<400> SEQUENCE: 307
aaacttgctc tcaaacttca gggtt 25

<210> SEQ ID NO 308
<211> LENGTH: 25
<212> TYPE: DNA
<213> ORGANISM: Artificial Sequence
<220> FEATURE:
<223> OTHER INFORMATION: Synthetic Construct

<400> SEQUENCE: 308
cctattgtcc attacacacc gaatg 25

<210> SEQ ID NO 309
<211> LENGTH: 25
<212> TYPE: DNA
<213> ORGANISM: Artificial Sequence
<220> FEATURE:
<223> OTHER INFORMATION: Synthetic Construct

<400> SEQUENCE: 309
gtatgctcat acttggacag ttagg 25

<210> SEQ ID NO 310
<211> LENGTH: 25
<212> TYPE: DNA
<213> ORGANISM: Artificial Sequence
<220> FEATURE:
<223> OTHER INFORMATION: Synthetic Construct

<400> SEQUENCE: 310
tatggcgctg ttttgagttg gaccc 25

<210> SEQ ID NO 311
<211> LENGTH: 25
<212> TYPE: DNA
<213> ORGANISM: Artificial Sequence
<220> FEATURE:
<223> OTHER INFORMATION: Synthetic Construct

<400> SEQUENCE: 311
cgacgaacac tacgagtacc ggcat 25

<210> SEQ ID NO 312
<211> LENGTH: 24
<212> TYPE: DNA
<213> ORGANISM: Artificial Sequence
<220> FEATURE:
<223> OTHER INFORMATION: Synthetic Construct

<400> SEQUENCE: 312
ggagaagtat ccctgctagt ggct 24

<210> SEQ ID NO 313
<211> LENGTH: 25
<212> TYPE: DNA
<213> ORGANISM: Artificial Sequence
<220> FEATURE:
<223> OTHER INFORMATION: Synthetic Construct

<400> SEQUENCE: 313
gggatgataa cctgaggacc cccac 25

<210> SEQ ID NO 314
<211> LENGTH: 25
<212> TYPE: DNA
<213> ORGANISM: Artificial Sequence
<220> FEATURE:
<223> OTHER INFORMATION: Synthetic Construct

<400> SEQUENCE: 314
gaatggaatt tcctctctgt gacag 25

<210> SEQ ID NO 315
<211> LENGTH: 25
<212> TYPE: DNA
<213> ORGANISM: Artificial Sequence
<220> FEATURE:
<223> OTHER INFORMATION: Synthetic Construct

<400> SEQUENCE: 315
atgccagatg gtgtttatgg gctat 25

<210> SEQ ID NO 316
<211> LENGTH: 25
<212> TYPE: DNA
<213> ORGANISM: Artificial Sequence
<220> FEATURE:
<223> OTHER INFORMATION: Synthetic Construct

<400> SEQUENCE: 316
cccactcttc tctgggactt gtggg 25

<210> SEQ ID NO 317
<211> LENGTH: 25
<212> TYPE: DNA
<213> ORGANISM: Artificial Sequence
<220> FEATURE:
<223> OTHER INFORMATION: Synthetic Construct

```
<400> SEQUENCE: 317

ctgccttttc tgtctcagcg ggcag                                                25

<210> SEQ ID NO 318
<211> LENGTH: 25
<212> TYPE: DNA
<213> ORGANISM: Artificial Sequence
<220> FEATURE:
<223> OTHER INFORMATION: Synthetic Construct

<400> SEQUENCE: 318

tgtgctgttc cagtatatgc aatac                                                25

<210> SEQ ID NO 319
<211> LENGTH: 25
<212> TYPE: DNA
<213> ORGANISM: Artificial Sequence
<220> FEATURE:
<223> OTHER INFORMATION: Synthetic Construct

<400> SEQUENCE: 319

tttaagggct aatctcacac ctcct                                                25

<210> SEQ ID NO 320
<211> LENGTH: 25
<212> TYPE: DNA
<213> ORGANISM: Artificial Sequence
<220> FEATURE:
<223> OTHER INFORMATION: Synthetic Construct

<400> SEQUENCE: 320

acggatttag acgaggttcg aggct                                                25

<210> SEQ ID NO 321
<211> LENGTH: 25
<212> TYPE: DNA
<213> ORGANISM: Artificial Sequence
<220> FEATURE:
<223> OTHER INFORMATION: Synthetic Construct

<400> SEQUENCE: 321

gcttctgcag ctgtagattc tcact                                                25

<210> SEQ ID NO 322
<211> LENGTH: 25
<212> TYPE: DNA
<213> ORGANISM: Artificial Sequence
<220> FEATURE:
<223> OTHER INFORMATION: Synthetic Construct

<400> SEQUENCE: 322

gcagccagga tatgaccacc ttact                                                25

<210> SEQ ID NO 323
<211> LENGTH: 25
<212> TYPE: DNA
<213> ORGANISM: Artificial Sequence
<220> FEATURE:
<223> OTHER INFORMATION: Synthetic Construct

<400> SEQUENCE: 323

tgaaacgacc ccacaggtca ggtgg                                                25

<210> SEQ ID NO 324
```

<211> LENGTH: 25
<212> TYPE: DNA
<213> ORGANISM: Artificial Sequence
<220> FEATURE:
<223> OTHER INFORMATION: Synthetic Construct

<400> SEQUENCE: 324
gaaaaattgc cttacgtaca ttcct 25

<210> SEQ ID NO 325
<211> LENGTH: 25
<212> TYPE: DNA
<213> ORGANISM: Artificial Sequence
<220> FEATURE:
<223> OTHER INFORMATION: Synthetic Construct

<400> SEQUENCE: 325
taagctcatc atccaggcag gtata 25

<210> SEQ ID NO 326
<211> LENGTH: 25
<212> TYPE: DNA
<213> ORGANISM: Artificial Sequence
<220> FEATURE:
<223> OTHER INFORMATION: Synthetic Construct

<400> SEQUENCE: 326
aaggatgctt gtacataatg cgtgc 25

<210> SEQ ID NO 327
<211> LENGTH: 25
<212> TYPE: DNA
<213> ORGANISM: Artificial Sequence
<220> FEATURE:
<223> OTHER INFORMATION: Synthetic Construct

<400> SEQUENCE: 327
gtgtgagctg gtggacggtg atgag 25

<210> SEQ ID NO 328
<211> LENGTH: 25
<212> TYPE: DNA
<213> ORGANISM: Artificial Sequence
<220> FEATURE:
<223> OTHER INFORMATION: Synthetic Construct

<400> SEQUENCE: 328
gctaacctta acatctgaga gcagt 25

<210> SEQ ID NO 329
<211> LENGTH: 25
<212> TYPE: DNA
<213> ORGANISM: Artificial Sequence
<220> FEATURE:
<223> OTHER INFORMATION: Synthetic Construct

<400> SEQUENCE: 329
aaagccctgt ggtgtatcaa ctact 25

<210> SEQ ID NO 330
<211> LENGTH: 25
<212> TYPE: DNA
<213> ORGANISM: Artificial Sequence
<220> FEATURE:
<223> OTHER INFORMATION: Synthetic Construct

<400> SEQUENCE: 330
gcactctgaa ggcatccttg ctggt 25

<210> SEQ ID NO 331
<211> LENGTH: 25
<212> TYPE: DNA
<213> ORGANISM: Artificial Sequence
<220> FEATURE:
<223> OTHER INFORMATION: Synthetic Construct

<400> SEQUENCE: 331
gcttagtatt gacactctct accaa 25

<210> SEQ ID NO 332
<211> LENGTH: 25
<212> TYPE: DNA
<213> ORGANISM: Artificial Sequence
<220> FEATURE:
<223> OTHER INFORMATION: Synthetic Construct

<400> SEQUENCE: 332
tatttacagc tctgtaacct cccgt 25

<210> SEQ ID NO 333
<211> LENGTH: 25
<212> TYPE: DNA
<213> ORGANISM: Artificial Sequence
<220> FEATURE:
<223> OTHER INFORMATION: Synthetic Construct

<400> SEQUENCE: 333
gcaattgact tccctttttt aatgt 25

<210> SEQ ID NO 334
<211> LENGTH: 25
<212> TYPE: DNA
<213> ORGANISM: Artificial Sequence
<220> FEATURE:
<223> OTHER INFORMATION: Synthetic Construct

<400> SEQUENCE: 334
gaatccatcc ttaaagtcaa aaact 25

<210> SEQ ID NO 335
<211> LENGTH: 25
<212> TYPE: DNA
<213> ORGANISM: Artificial Sequence
<220> FEATURE:
<223> OTHER INFORMATION: Synthetic Construct

<400> SEQUENCE: 335
aaattgctta ttctaggtct gtaat 25

<210> SEQ ID NO 336
<211> LENGTH: 25
<212> TYPE: DNA
<213> ORGANISM: Artificial Sequence
<220> FEATURE:
<223> OTHER INFORMATION: Synthetic Construct

<400> SEQUENCE: 336
tacgtgcaat acttcaatac ttcat 25

<210> SEQ ID NO 337
<211> LENGTH: 25
<212> TYPE: DNA

<213> ORGANISM: Artificial Sequence
<220> FEATURE:
<223> OTHER INFORMATION: Synthetic Construct

<400> SEQUENCE: 337
catgaccatt ctgctcatcg tcatc 25

<210> SEQ ID NO 338
<211> LENGTH: 25
<212> TYPE: DNA
<213> ORGANISM: Artificial Sequence
<220> FEATURE:
<223> OTHER INFORMATION: Synthetic Construct

<400> SEQUENCE: 338
caaaccaacc gcacatgcag atggg 25

<210> SEQ ID NO 339
<211> LENGTH: 25
<212> TYPE: DNA
<213> ORGANISM: Artificial Sequence
<220> FEATURE:
<223> OTHER INFORMATION: Synthetic Construct

<400> SEQUENCE: 339
gtggatcccc aacaacgtga aggtg 25

<210> SEQ ID NO 340
<211> LENGTH: 25
<212> TYPE: DNA
<213> ORGANISM: Artificial Sequence
<220> FEATURE:
<223> OTHER INFORMATION: Synthetic Construct

<400> SEQUENCE: 340
gggcgagttc gaggaggagg ctgag 25

<210> SEQ ID NO 341
<211> LENGTH: 25
<212> TYPE: DNA
<213> ORGANISM: Artificial Sequence
<220> FEATURE:
<223> OTHER INFORMATION: Synthetic Construct

<400> SEQUENCE: 341
tggtgcactg agctgtaact tcttc 25

<210> SEQ ID NO 342
<211> LENGTH: 25
<212> TYPE: DNA
<213> ORGANISM: Artificial Sequence
<220> FEATURE:
<223> OTHER INFORMATION: Synthetic Construct

<400> SEQUENCE: 342
ttattgtttt gatgtctagc ccctc 25

<210> SEQ ID NO 343
<211> LENGTH: 25
<212> TYPE: DNA
<213> ORGANISM: Artificial Sequence
<220> FEATURE:
<223> OTHER INFORMATION: Synthetic Construct

<400> SEQUENCE: 343
agcccctgtg gagatctcct atgag 25

<210> SEQ ID NO 344
<211> LENGTH: 25
<212> TYPE: DNA
<213> ORGANISM: Artificial Sequence
<220> FEATURE:
<223> OTHER INFORMATION: Synthetic Construct

<400> SEQUENCE: 344
tactcatcct gctatcaatt tctta 25

<210> SEQ ID NO 345
<211> LENGTH: 25
<212> TYPE: DNA
<213> ORGANISM: Artificial Sequence
<220> FEATURE:
<223> OTHER INFORMATION: Synthetic Construct

<400> SEQUENCE: 345
aaatccacag ctatatcctg atgct 25

<210> SEQ ID NO 346
<211> LENGTH: 25
<212> TYPE: DNA
<213> ORGANISM: Artificial Sequence
<220> FEATURE:
<223> OTHER INFORMATION: Synthetic Construct

<400> SEQUENCE: 346
tctgcctttt ctgtctcagc ggcag 25

<210> SEQ ID NO 347
<211> LENGTH: 25
<212> TYPE: DNA
<213> ORGANISM: Artificial Sequence
<220> FEATURE:
<223> OTHER INFORMATION: Synthetic Construct

<400> SEQUENCE: 347
aatgaagctg gctgctcaga cggtc 25

<210> SEQ ID NO 348
<211> LENGTH: 25
<212> TYPE: DNA
<213> ORGANISM: Artificial Sequence
<220> FEATURE:
<223> OTHER INFORMATION: Synthetic Construct

<400> SEQUENCE: 348
gttaaggatt acttggctgc catag 25

<210> SEQ ID NO 349
<211> LENGTH: 25
<212> TYPE: DNA
<213> ORGANISM: Artificial Sequence
<220> FEATURE:
<223> OTHER INFORMATION: Synthetic Construct

<400> SEQUENCE: 349
aaaagtactc ttgtccatct gttct 25

<210> SEQ ID NO 350
<211> LENGTH: 25
<212> TYPE: DNA
<213> ORGANISM: Artificial Sequence
<220> FEATURE:

<223> OTHER INFORMATION: Synthetic Construct

<400> SEQUENCE: 350
catgtaccaa gacccttttc acagt 25

<210> SEQ ID NO 351
<211> LENGTH: 25
<212> TYPE: DNA
<213> ORGANISM: Artificial Sequence
<220> FEATURE:
<223> OTHER INFORMATION: Synthetic Construct

<400> SEQUENCE: 351
actcagagct ctggaccgaa agcag 25

<210> SEQ ID NO 352
<211> LENGTH: 25
<212> TYPE: DNA
<213> ORGANISM: Artificial Sequence
<220> FEATURE:
<223> OTHER INFORMATION: Synthetic Construct

<400> SEQUENCE: 352
gttctggacc agaatacctc aaacg 25

<210> SEQ ID NO 353
<211> LENGTH: 25
<212> TYPE: DNA
<213> ORGANISM: Artificial Sequence
<220> FEATURE:
<223> OTHER INFORMATION: Synthetic Construct

<400> SEQUENCE: 353
aaggagcttc gagacatgtc caaga 25

<210> SEQ ID NO 354
<211> LENGTH: 25
<212> TYPE: DNA
<213> ORGANISM: Artificial Sequence
<220> FEATURE:
<223> OTHER INFORMATION: Synthetic Construct

<400> SEQUENCE: 354
ctgtatatcg ccctgtactt ggata 25

<210> SEQ ID NO 355
<211> LENGTH: 25
<212> TYPE: DNA
<213> ORGANISM: Artificial Sequence
<220> FEATURE:
<223> OTHER INFORMATION: Synthetic Construct

<400> SEQUENCE: 355
gttatcactc ttaggtcaga cagcc 25

<210> SEQ ID NO 356
<211> LENGTH: 25
<212> TYPE: DNA
<213> ORGANISM: Artificial Sequence
<220> FEATURE:
<223> OTHER INFORMATION: Synthetic Construct

<400> SEQUENCE: 356
tgattctgtt cggactgggt tctca 25

<210> SEQ ID NO 357
<211> LENGTH: 25
<212> TYPE: DNA
<213> ORGANISM: Artificial Sequence
<220> FEATURE:
<223> OTHER INFORMATION: Synthetic Construct

<400> SEQUENCE: 357
gtcagaggac acgcgtgaga ccgac 25

<210> SEQ ID NO 358
<211> LENGTH: 25
<212> TYPE: DNA
<213> ORGANISM: Artificial Sequence
<220> FEATURE:
<223> OTHER INFORMATION: Synthetic Construct

<400> SEQUENCE: 358
attgaccttt tggacattcg aacag 25

<210> SEQ ID NO 359
<211> LENGTH: 25
<212> TYPE: DNA
<213> ORGANISM: Artificial Sequence
<220> FEATURE:
<223> OTHER INFORMATION: Synthetic Construct

<400> SEQUENCE: 359
ttatgtgtac attattgttg ctatt 25

<210> SEQ ID NO 360
<211> LENGTH: 25
<212> TYPE: DNA
<213> ORGANISM: Artificial Sequence
<220> FEATURE:
<223> OTHER INFORMATION: Synthetic Construct

<400> SEQUENCE: 360
gagcaacggc acctatttgg aactt 25

<210> SEQ ID NO 361
<211> LENGTH: 25
<212> TYPE: DNA
<213> ORGANISM: Artificial Sequence
<220> FEATURE:
<223> OTHER INFORMATION: Synthetic Construct

<400> SEQUENCE: 361
cccccagaac tgcagcatca tgtaa 25

<210> SEQ ID NO 362
<211> LENGTH: 25
<212> TYPE: DNA
<213> ORGANISM: Artificial Sequence
<220> FEATURE:
<223> OTHER INFORMATION: Synthetic Construct

<400> SEQUENCE: 362
tcaacagagt atttcccttg gccga 25

<210> SEQ ID NO 363
<211> LENGTH: 25
<212> TYPE: DNA
<213> ORGANISM: Artificial Sequence
<220> FEATURE:
<223> OTHER INFORMATION: Synthetic Construct

<400> SEQUENCE: 363
tgaaaacgag ctttctttcc catga 25

<210> SEQ ID NO 364
<211> LENGTH: 25
<212> TYPE: DNA
<213> ORGANISM: Artificial Sequence
<220> FEATURE:
<223> OTHER INFORMATION: Synthetic Construct

<400> SEQUENCE: 364
gttatttctt ttagtcatgt tgatt 25

<210> SEQ ID NO 365
<211> LENGTH: 25
<212> TYPE: DNA
<213> ORGANISM: Artificial Sequence
<220> FEATURE:
<223> OTHER INFORMATION: Synthetic Construct

<400> SEQUENCE: 365
aaccctgtat ttcccttatg atgtc 25

<210> SEQ ID NO 366
<211> LENGTH: 25
<212> TYPE: DNA
<213> ORGANISM: Artificial Sequence
<220> FEATURE:
<223> OTHER INFORMATION: Synthetic Construct

<400> SEQUENCE: 366
tatgcaaacc tgttccattc tttct 25

<210> SEQ ID NO 367
<211> LENGTH: 25
<212> TYPE: DNA
<213> ORGANISM: Artificial Sequence
<220> FEATURE:
<223> OTHER INFORMATION: Synthetic Construct

<400> SEQUENCE: 367
aatatttcat aaccttcttc attag 25

<210> SEQ ID NO 368
<211> LENGTH: 25
<212> TYPE: DNA
<213> ORGANISM: Artificial Sequence
<220> FEATURE:
<223> OTHER INFORMATION: Synthetic Construct

<400> SEQUENCE: 368
cgaagactct tcttccacat gatcc 25

<210> SEQ ID NO 369
<211> LENGTH: 25
<212> TYPE: DNA
<213> ORGANISM: Artificial Sequence
<220> FEATURE:
<223> OTHER INFORMATION: Synthetic Construct

<400> SEQUENCE: 369
aagttttcta cctgggctga cgttg 25

<210> SEQ ID NO 370
<211> LENGTH: 25

<212> TYPE: DNA
<213> ORGANISM: Artificial Sequence
<220> FEATURE:
<223> OTHER INFORMATION: Synthetic Construct

<400> SEQUENCE: 370
gcagctcttg gtcaaagcac tgttg 25

<210> SEQ ID NO 371
<211> LENGTH: 25
<212> TYPE: DNA
<213> ORGANISM: Artificial Sequence
<220> FEATURE:
<223> OTHER INFORMATION: Synthetic Construct

<400> SEQUENCE: 371
ggtcggatct cacaggctga gaact 25

<210> SEQ ID NO 372
<211> LENGTH: 25
<212> TYPE: DNA
<213> ORGANISM: Artificial Sequence
<220> FEATURE:
<223> OTHER INFORMATION: Synthetic Construct

<400> SEQUENCE: 372
agttctcaag agacgccagt gtggc 25

<210> SEQ ID NO 373
<211> LENGTH: 25
<212> TYPE: DNA
<213> ORGANISM: Artificial Sequence
<220> FEATURE:
<223> OTHER INFORMATION: Synthetic Construct

<400> SEQUENCE: 373
taagatcaaa ccccatggag cagcc 25

<210> SEQ ID NO 374
<211> LENGTH: 25
<212> TYPE: DNA
<213> ORGANISM: Artificial Sequence
<220> FEATURE:
<223> OTHER INFORMATION: Synthetic Construct

<400> SEQUENCE: 374
gggggatagg cacttggacc cccat 25

<210> SEQ ID NO 375
<211> LENGTH: 25
<212> TYPE: DNA
<213> ORGANISM: Artificial Sequence
<220> FEATURE:
<223> OTHER INFORMATION: Synthetic Construct

<400> SEQUENCE: 375
ggttgtactt ggaattctta gtcac 25

<210> SEQ ID NO 376
<211> LENGTH: 25
<212> TYPE: DNA
<213> ORGANISM: Artificial Sequence
<220> FEATURE:
<223> OTHER INFORMATION: Synthetic Construct

<400> SEQUENCE: 376

-continued tctcaatccc ctgctgtggt aggaa 25

<210> SEQ ID NO 377
<211> LENGTH: 25
<212> TYPE: DNA
<213> ORGANISM: Artificial Sequence
<220> FEATURE:
<223> OTHER INFORMATION: Synthetic Construct

<400> SEQUENCE: 377
aaaatccaga ctctttcgat accca 25

<210> SEQ ID NO 378
<211> LENGTH: 25
<212> TYPE: DNA
<213> ORGANISM: Artificial Sequence
<220> FEATURE:
<223> OTHER INFORMATION: Synthetic Construct

<400> SEQUENCE: 378
agctgccaat tagttttctt tgttt 25

<210> SEQ ID NO 379
<211> LENGTH: 25
<212> TYPE: DNA
<213> ORGANISM: Artificial Sequence
<220> FEATURE:
<223> OTHER INFORMATION: Synthetic Construct

<400> SEQUENCE: 379
cagggccaga agttcaggct gcccc 25

<210> SEQ ID NO 380
<211> LENGTH: 25
<212> TYPE: DNA
<213> ORGANISM: Artificial Sequence
<220> FEATURE:
<223> OTHER INFORMATION: Synthetic Construct

<400> SEQUENCE: 380
gtagtcacgg tgctctcaga aaata 25

<210> SEQ ID NO 381
<211> LENGTH: 25
<212> TYPE: DNA
<213> ORGANISM: Artificial Sequence
<220> FEATURE:
<223> OTHER INFORMATION: Synthetic Construct

<400> SEQUENCE: 381
gcattctgcc gtgtttatag gtgtt 25

<210> SEQ ID NO 382
<211> LENGTH: 25
<212> TYPE: DNA
<213> ORGANISM: Artificial Sequence
<220> FEATURE:
<223> OTHER INFORMATION: Synthetic Construct

<400> SEQUENCE: 382
gacttcagtg gatttcagct tctag 25

<210> SEQ ID NO 383
<211> LENGTH: 25
<212> TYPE: DNA
<213> ORGANISM: Artificial Sequence
<220> FEATURE:
<223> OTHER INFORMATION: Synthetic Construct

<400> SEQUENCE: 383
agctttgcct ctgtattgtg tacca 25

<210> SEQ ID NO 384
<211> LENGTH: 25
<212> TYPE: DNA
<213> ORGANISM: Artificial Sequence
<220> FEATURE:
<223> OTHER INFORMATION: Synthetic Construct

<400> SEQUENCE: 384
agggaccggt gctgcaggag tgtcc 25

<210> SEQ ID NO 385
<211> LENGTH: 25
<212> TYPE: DNA
<213> ORGANISM: Artificial Sequence
<220> FEATURE:
<223> OTHER INFORMATION: Synthetic Construct

<400> SEQUENCE: 385
cactaccatt gctgttctac ttttt 25

<210> SEQ ID NO 386
<211> LENGTH: 25
<212> TYPE: DNA
<213> ORGANISM: Artificial Sequence
<220> FEATURE:
<223> OTHER INFORMATION: Synthetic Construct

<400> SEQUENCE: 386
gccatgtgtt ccaaggcatt ttagc 25

<210> SEQ ID NO 387
<211> LENGTH: 25
<212> TYPE: DNA
<213> ORGANISM: Artificial Sequence
<220> FEATURE:
<223> OTHER INFORMATION: Synthetic Construct

<400> SEQUENCE: 387
gtagcatttc cctgcagatg gtaca 25

<210> SEQ ID NO 388
<211> LENGTH: 25
<212> TYPE: DNA
<213> ORGANISM: Artificial Sequence
<220> FEATURE:
<223> OTHER INFORMATION: Synthetic Construct

<400> SEQUENCE: 388
aagtactgga cattctaact cgcct 25

<210> SEQ ID NO 389
<211> LENGTH: 25
<212> TYPE: DNA
<213> ORGANISM: Artificial Sequence
<220> FEATURE:
<223> OTHER INFORMATION: Synthetic Construct

<400> SEQUENCE: 389
caacacgcaa gttccttctt gaacc 25

<210> SEQ ID NO 390
<211> LENGTH: 25
<212> TYPE: DNA
<213> ORGANISM: Artificial Sequence
<220> FEATURE:
<223> OTHER INFORMATION: Synthetic Construct

<400> SEQUENCE: 390
tcttgaaaga gccctgtttc ccagc 25

<210> SEQ ID NO 391
<211> LENGTH: 25
<212> TYPE: DNA
<213> ORGANISM: Artificial Sequence
<220> FEATURE:
<223> OTHER INFORMATION: Synthetic Construct

<400> SEQUENCE: 391
tataccaatg acttccatat tttaa 25

<210> SEQ ID NO 392
<211> LENGTH: 25
<212> TYPE: DNA
<213> ORGANISM: Artificial Sequence
<220> FEATURE:
<223> OTHER INFORMATION: Synthetic Construct

<400> SEQUENCE: 392
cgaacctgca agcccagatg taccg 25

<210> SEQ ID NO 393
<211> LENGTH: 25
<212> TYPE: DNA
<213> ORGANISM: Artificial Sequence
<220> FEATURE:
<223> OTHER INFORMATION: Synthetic Construct

<400> SEQUENCE: 393
gtaaccaccc agacctggat gtcca 25

<210> SEQ ID NO 394
<211> LENGTH: 25
<212> TYPE: DNA
<213> ORGANISM: Artificial Sequence
<220> FEATURE:
<223> OTHER INFORMATION: Synthetic Construct

<400> SEQUENCE: 394
ggactgcaaa ttgagtttct ttctc 25

<210> SEQ ID NO 395
<211> LENGTH: 25
<212> TYPE: DNA
<213> ORGANISM: Artificial Sequence
<220> FEATURE:
<223> OTHER INFORMATION: Synthetic Construct

<400> SEQUENCE: 395
gagagcctca tggattgtaa ctaaa 25

<210> SEQ ID NO 396
<211> LENGTH: 25
<212> TYPE: DNA
<213> ORGANISM: Artificial Sequence
<220> FEATURE:
<223> OTHER INFORMATION: Synthetic Construct

<400> SEQUENCE: 396
gaagaaccct gactttgttt ctgca 25

<210> SEQ ID NO 397
<211> LENGTH: 25
<212> TYPE: DNA
<213> ORGANISM: Artificial Sequence
<220> FEATURE:
<223> OTHER INFORMATION: Synthetic Construct

<400> SEQUENCE: 397
gtcctatctg tacttcacac agttc 25

<210> SEQ ID NO 398
<211> LENGTH: 25
<212> TYPE: DNA
<213> ORGANISM: Artificial Sequence
<220> FEATURE:
<223> OTHER INFORMATION: Synthetic Construct

<400> SEQUENCE: 398
gaactgttga gtttccgttg ctggc 25

<210> SEQ ID NO 399
<211> LENGTH: 25
<212> TYPE: DNA
<213> ORGANISM: Artificial Sequence
<220> FEATURE:
<223> OTHER INFORMATION: Synthetic Construct

<400> SEQUENCE: 399
tcctccagtg ttaagctata gccat 25

<210> SEQ ID NO 400
<211> LENGTH: 25
<212> TYPE: DNA
<213> ORGANISM: Artificial Sequence
<220> FEATURE:
<223> OTHER INFORMATION: Synthetic Construct

<400> SEQUENCE: 400
tggagtccgc agagcactcg gaacc 25

<210> SEQ ID NO 401
<211> LENGTH: 25
<212> TYPE: DNA
<213> ORGANISM: Artificial Sequence
<220> FEATURE:
<223> OTHER INFORMATION: Synthetic Construct

<400> SEQUENCE: 401
tgccagaccc taagaccttc aagca 25

<210> SEQ ID NO 402
<211> LENGTH: 25
<212> TYPE: DNA
<213> ORGANISM: Artificial Sequence
<220> FEATURE:
<223> OTHER INFORMATION: Synthetic Construct

<400> SEQUENCE: 402
ggttttcatt agtggaagct cttca 25

<210> SEQ ID NO 403

<211> LENGTH: 25
<212> TYPE: DNA
<213> ORGANISM: Artificial Sequence
<220> FEATURE:
<223> OTHER INFORMATION: Synthetic Construct

<400> SEQUENCE: 403
gattacttgt actcttctta tgcta 25

<210> SEQ ID NO 404
<211> LENGTH: 25
<212> TYPE: DNA
<213> ORGANISM: Artificial Sequence
<220> FEATURE:
<223> OTHER INFORMATION: Synthetic Construct

<400> SEQUENCE: 404
actttataat cgtcattgtt caatc 25

<210> SEQ ID NO 405
<211> LENGTH: 25
<212> TYPE: DNA
<213> ORGANISM: Artificial Sequence
<220> FEATURE:
<223> OTHER INFORMATION: Synthetic Construct

<400> SEQUENCE: 405
tgattgtttt catcctgata ctgta 25

<210> SEQ ID NO 406
<211> LENGTH: 25
<212> TYPE: DNA
<213> ORGANISM: Artificial Sequence
<220> FEATURE:
<223> OTHER INFORMATION: Synthetic Construct

<400> SEQUENCE: 406
gtcaccagct gtttgtgcca ttttt 25

<210> SEQ ID NO 407
<211> LENGTH: 25
<212> TYPE: DNA
<213> ORGANISM: Artificial Sequence
<220> FEATURE:
<223> OTHER INFORMATION: Synthetic Construct

<400> SEQUENCE: 407
agggagattt ctccattttc ctctt 25

<210> SEQ ID NO 408
<211> LENGTH: 25
<212> TYPE: DNA
<213> ORGANISM: Artificial Sequence
<220> FEATURE:
<223> OTHER INFORMATION: Synthetic Construct

<400> SEQUENCE: 408
gtggcacttt cacaatgtag aggaa 25

<210> SEQ ID NO 409
<211> LENGTH: 25
<212> TYPE: DNA
<213> ORGANISM: Artificial Sequence
<220> FEATURE:
<223> OTHER INFORMATION: Synthetic Construct

<400> SEQUENCE: 409
atgccagtcg ggcagcccag gatag 25

<210> SEQ ID NO 410
<211> LENGTH: 25
<212> TYPE: DNA
<213> ORGANISM: Artificial Sequence
<220> FEATURE:
<223> OTHER INFORMATION: Synthetic Construct

<400> SEQUENCE: 410
tatccagtac tcctggttcc taggt 25

<210> SEQ ID NO 411
<211> LENGTH: 25
<212> TYPE: DNA
<213> ORGANISM: Artificial Sequence
<220> FEATURE:
<223> OTHER INFORMATION: Synthetic Construct

<400> SEQUENCE: 411
agctggggct gcccaaagag cacgc 25

<210> SEQ ID NO 412
<211> LENGTH: 25
<212> TYPE: DNA
<213> ORGANISM: Artificial Sequence
<220> FEATURE:
<223> OTHER INFORMATION: Synthetic Construct

<400> SEQUENCE: 412
gatgatgacc tgtatggcta agtgg 25

<210> SEQ ID NO 413
<211> LENGTH: 25
<212> TYPE: DNA
<213> ORGANISM: Artificial Sequence
<220> FEATURE:
<223> OTHER INFORMATION: Synthetic Construct

<400> SEQUENCE: 413
gacatgtttt ctgacggcaa cttca 25

<210> SEQ ID NO 414
<211> LENGTH: 25
<212> TYPE: DNA
<213> ORGANISM: Artificial Sequence
<220> FEATURE:
<223> OTHER INFORMATION: Synthetic Construct

<400> SEQUENCE: 414
acatcatata agccccaact ttgtt 25

<210> SEQ ID NO 415
<211> LENGTH: 3070
<212> TYPE: DNA
<213> ORGANISM: Homo sapiens

<400> SEQUENCE: 415
ggcgccgtct tgatactttc agaaagaatg cattccctgt aaaaaaaaaa aaaaaatact 60
gagagaggga gagagagaga gaagaagaga gagagacgga gggagagcga gacagagcga 120
gcaacgcaat ctgaccgagc aggtcgtacg ccgccgcctc ctcctcctct ctgctcttcg 180
ctacccaggt gacccgagga gggactccgc ctccgagcgg ctgaggaccc cggtgcagag 240

-continued

```
gagcctggct cgcagaattg cagagtcgtc gccccttttt acaacctggt cccgttttat    300
tctgccgtac ccagtttttg gatttttgtc ttccccttct tctctttgct aaacgacccc    360
tccaagataa tttttaaaaa accttctcct ttgctcacct ttgcttccca gccttcccat    420
ccccccaccg aaagcaaatc attcaacgac ccccgaccct ccgacggcag gagccccccg    480
acctcccagg cggaccgccc tccctccccg cgcgcgggtt ccgggcccgg cgagagggcg    540
cgagcacagc cgaggccatg gaggtgacgg cggaccagcc gcgctgggtg agccaccacc    600
accccgccgt gctcaacggg cagcacccgg acacgcacca cccgggcctc agccactcct    660
acatggacgc ggcgcagtac ccgctgccgg aggaggtgga tgtgcttttt aacatcgacg    720
gtcaaggcaa ccacgtcccg ccctactacg gaaactcggt cagggccacg gtgcagaggt    780
accctccgac ccaccacggg agccaggtgt gccgcccgcc tctgcttcat ggatccctac    840
cctggctgga cggcggcaaa gccctgggca gccaccacac cgcctccccc tggaatctca    900
gccccttctc caagacgtcc atccaccacg gctccccggg gcccctctcc gtctaccccc    960
cggcctcgtc ctcctccttg tcgggggggcc acgccagccc gcacctcttc accttcccgc   1020
ccaccccgcc gaaggacgtc tccccggacc catcgctgtc caccccaggc tcggccggct   1080
cggcccggca ggacgagaaa gagtgcctca agtaccaggt gcccctgccc gacagcatga   1140
agctggagtc gtcccactcc cgtggcagca tgaccgccct gggtggagcc tcctcgtcga   1200
cccaccaccc catcaccacc tacccgccct acgtgcccga gtacagctcc ggactcttcc   1260
cccccagcag cctgctgggc ggctccccca ccggcttcgg atgcaagtcc aggcccaagg   1320
cccggtccag cacagaaggc agggagtgtg tgaactgtgg ggcaacctcg accccactgt   1380
ggcggcgaga tggcacggga cactacctgt gcaacgcctg cgggctctat cacaaaatga   1440
acggacagaa ccggcccctc attaagccca agcgaaggct gtctgcagcc aggagagcag   1500
ggacgtcctg tgcgaactgt cagaccacca caaccacact ctggaggagg aatgccaatg   1560
gggaccctgt ctgcaatgcc tgtgggctct actacaagct tcacaatatt aacagacccc   1620
tgactatgaa gaaggaaggc atccagacca gaaaccgaaa aatgtctagc aaatccaaaa   1680
agtgcaaaaa agtgcatgac tcactggagg acttccccaa gaacagctcg tttaacccgg   1740
ccgccctctc cagacacatg tcctccctga gccacatctc gcccttcagc cactccagcc   1800
acatgctgac cacgcccacg ccgatgcacc cgccatccag cctgtccttt ggaccacacc   1860
acccctccag catggtcacc gccatgggtt agagccctgc tcgatgctca cagggccccc   1920
agcgagagtc cctgcagtcc ctttcgactt gcatttttgc aggagcagta tcatgaagcc   1980
taaacgcgat ggatatatgt ttttgaaggc agaaagcaaa attatgtttg ccactttgca   2040
aaggagctca ctgtggtgtc tgtgttccaa ccactgaatc tggaccccat ctgtgaataa   2100
gccattctga ctcatatccc ctatttaaca gggtctctag tgctgtgaaa aaaaaaatgc   2160
tgaacattgc atataactta tattgtaaga aatactgtac aatgacttta ttgcatctgg   2220
gtagctgtaa ggcatgaagg atgccaagaa gtttaaggaa tatgggagaa atagtgtgga   2280
aattaagaag aaactaggtc tgatattcaa atggacaaac tgccagtttt gtttcctttc   2340
actggccaca gttgtttgat gcattaaaag aaaataaaaa aaagaaaaaa gagaaaagaa   2400
aaaaaaagaa aaaagttgta ggcgaatcat ttgttcaaag ctgttggcct ctgcaaagga   2460
aataccagtt ctgggcaatc agtgttaccg ttcaccagtt gccgttgagg gtttcagaga   2520
gcctttttct aggcctacat gctttgtgaa caagtccctg taattgttgt ttgtatgtat   2580
aattcaaagc accaaaataa gaaaagatgt agatttattt catcatatta tacagaccga   2640
```

actgttgtat aaatttattt actgctagtc ttaagaactg ctttctttcg tttgtttgtt 2700
tcaatatttt ccttctctct caatttttgg ttgaataaac tagattacat tcagttggcc 2760
taaggtggtt gtgctcggag ggtttcttgt ttcttttcca ttttgttttt ggatgatatt 2820
tattaaatag cttctaagag tccggcggca tctgtcttgt ccctattcct gcagcctgtg 2880
ctgagggtag cagtgtatga gctaccagcg tgcatgtcag cgaccctggc ccgacaggcc 2940
acgtcctgca atcggcccgg ctgcctcttc gccctgtcgt gttctgtgtt agtgatcact 3000
gcctttaata cagtctgttg gaataatatt ataagcataa taataaagtg aaaatatttt 3060
aaaactacaa 3070

<210> SEQ ID NO 416
<211> LENGTH: 4372
<212> TYPE: DNA
<213> ORGANISM: Homo sapiens

<400> SEQUENCE: 416
acagctggct gcctcacccg caggctgcag ggagaccttc cccagcctgc agccccaggc 60
ccgccccgcg tcacatgagc cccagggctc ccaccccctc cccagggcag aggacaccca 120
gttggtggcc gggagggcct cggctttcca gggacagagg cccaactcca ggacgcccca 180
gctggcccag cccctcctct ttccctcaag gctgcaggag gtcgggaaag gcagtcctgg 240
tagaggcctg tcctgggctc caggttggcc cctgagggtg gccctcctca tgccggcttc 300
aagactgagg gacagggcag ccagttcagc ctcgggatcc acctgtggct ccatgtccca 360
gacgcaccct gtgctggaga gcggcctcct ggcatctgcc ggctgctccg caccccgggg 420
tcccaggaag ggcggcccag ccccagtgga caggaaagct aaggcctcag cgatgccgga 480
ctccccagcg gaggtgaaga cgcagccccg gtccacaccc cccagcatgc cgcccccacc 540
gcctgccgca tcccaggggg ccacacgccc cccctccttc acgccacaca cacatcgaga 600
ggacgggcct gcgacgctgc cccacggccg ttttcatggc tgcttaaaat ggtctatggt 660
ctgtctcttg atgaacggca gcagccactc accaacagcc atcaatggtg caccgtgcac 720
acccaacggc ttcagcaatg gcccggccac ctcgtccaca gcctccttgt ccacacagca 780
cctgccccca gcctgcgggg cccggcagct cagcaagctc aagcgcttcc tcaccacact 840
gcagcagttt ggcagcgaca tctccccaga gattggggag cgcgtgcgca cactggtgct 900
gggcctggtg aactcgacat tgacgatcga ggagtttcat tccaagcttc aggaggccac 960
caacttccct ctgcggccgt ttgtcattcc cttcctgaag gcaaacctgc ccttgctgca 1020
gcgggagctc ctgcactgtg cacgcctggc caagcagacg cccgcccagt acttggccca 1080
gcatgagcag ctcctgctgg acgccagcgc ctcctccccc atcgactcct cagagctgct 1140
actggaagtc aacgagaacg gcaagaggag gacgcccgac aggaccaaag agaacgggtc 1200
agaccgcgac ccgctgcacc ccgagcacct cagcaaacgg ccatgcaccc tgaaccctgc 1260
ccagcgctac agccccagca acgggccacc gcagcccaca ccgccgccgc actaccgcct 1320
ggaggacata gccatggccc accacttccg agatgcctac cgccacccag acccccggga 1380
gctacgagag cgccatcggc cgcttgtggt gcctgggtcc cggcaggaag aagtgatcga 1440
ccacaagctc acagagcgtg agtgggcaga agagtggaag cacctcaaca acctcctgaa 1500
ctgcatcatg gacatggtgg agaagacgcg gcgctcgctc acggtgctgc gcaggtgcca 1560
ggaggccgac cgcgaggagc tcaaccactg ggcgcggcgc tacagcgacg ccgaggacac 1620

-continued aaagaagggc cccgctcccg ccgcggcccg gccccgcagc agctccgccg gtcccgaagg 1680
gcctcagcta gacgtgcctc gcgagttcct gccgaggacc ctcaccggct acgtgcctga 1740
ggacatctgg aggaaggctg aagaggccgt gaatgaggtg aagcggcagg ccatgtcgga 1800
gctgcagaaa gccgtgtcgg acgcggagcg caaagcgcac gagctcatca ccacggagcg 1860
tgccaagatg gagcgggccc tggccgaggc gaagcggcag gcctccgagg acgccctgac 1920
ggtcatcaac cagcaggagg actccagcga gagctgctgg aactgcgggc ggaaagccag 1980
tgagacgtgc agcggctgca acgcggcacg ctactgcggg tccttctgcc agcatcggga 2040
ctgggagaag catcaccacg tgtgtggcca gagcctgcag ggccccacag ccgtggtggc 2100
cgacccggtg cctggaccgc ccgaagccgc ccacagcctg ggcccctccc tgcctgtggg 2160
tgctgccagc cccagcgaag ccggctctgc ggggccttct cgccccggct cccccagccc 2220
acctggccca ctggacaccg tgccccgctg accccactgg cccctggcct gccggacaca 2280
gcaccgtgcc aaccccaccc agctccaggc ccaccggatg ctgtgcctgg cctccgatgc 2340
ctggcctgcc agacactgcg ccccgcctga cctgggggag ccgaccaatt agtcactgct 2400
gctactgccc ctctccgaaa gaagacacag aaccaacaaa accgcattca gtgcacctgc 2460
ctcagctacc taatgattcc gcgcggagac ctcctgacaa cgtctcttca agcatcctca 2520
gaagcctcga ctgagcttta gacagcagag cagatgccgc aggcgcggcg gctctgccca 2580
cctctctttt cctctctgtc tgtctctccc cctctgtctt ctctatcctc tctctctcta 2640
tgactatcac acactttctc ttcaatgaaa aaatcgaatt ggtggcttat attttcagca 2700 aagaatttg gggggtttg tgtgttggca aaagagctac tcagaaatgg acaaagaaaa 2760 cggggggtt ctcccctcc tgattaaaaa gggagaaaga aaactgcgat tttatagctg 2820
gagatctgaa cccagctgtg cccctccccc aggggcgtga ggctgatcag cgaagacggg 2880
aggaaagatt tcgatttctg actcaagatg catttttggt ttcagatttt tttttcctgt 2940
aatgttaaac tctttggctt taagtaaaaa tccaaaaagt ttttttaaaa aagcaaagga 3000
agcatacttg tgaactacct tgctagctag ccagccaagg ataccggaca cacctctgct 3060
ccaaaggaaa tccaaaaaag caaacacaag aaatcaaaat ccaaaatttg tttgtcactg 3120
ccaaagtatt tttttcactg tttcacttgc tcttgggttt gtttggatgt gggtcttttt 3180
ctcttctgtt ctgattttgt ttgtgggtgt cgggatattt gggtgcagag ggtttgtgcc 3240
cagttagaag cgacttttgt tctcttctgc gtaggcgttg gtgcgtccgc cgcgtgtgcg 3300
tggtccgtgt gccgttgctc cggcctgcgt ctccatatgt gtaggaaagg acacgccgtc 3360
tgtcctcacg ccccctgtga cttttcatat ttccgttttc cacttgtgga aaaaaagtgc 3420 taaagtttc ttcccagaga gagcataatt ccgaaacaaa actgtgacaa tcttttgggt 3480
tgattctcga ctgcttttcg agcatgcgga gccagcaggc ctccctgaaa cactgcttct 3540
cggccagccc gtcctcctct acctctctcc tctccgcgcc ctccgacctc tctcggcccc 3600
ctcaccccag ctccgacctc tctcagcccc atcgccccaa ctccaacctc tcggccccat 3660
cgccccaccg cagctactcc cctttcttcc aaacttttgc agaaaaaaca aaaaaactac 3720
aaacaaaagc agccctctgc ctcctcccca gggaagaccc tgaccgtgta catagccctg 3780
gtgctcctgc ccagccaccc ctcagatgcg ttcgcctctg gccctggggt gtgtctcggt 3840
gacgttttct atcagacgtg ctccctccca tcctccagcc ctgcccaccc tccctccact 3900
cctctcaact gcctcagcga tttcaagaag gaaataaagg gataaagaaa ttcatgcttg 3960
caccgagtac aaggacagac agcaggcacg gcccgcagcc tggcatctgt gcgtgtggcg 4020
tggcccgtgg cttggcatct gtgtgcgtgg tgtggcccgt ggcctggcat ctgtgtgcgt 4080
ggcgtggccc gtggcctggc atctgtgtgt gtggcgtggc ccgtggcctg gcatctgtgc 4140
gcgtggcgtg gcccgtggcc tggcatctgt gtgcgtggct atcaggagtt ctaggaactc 4200
agtgcaatac gggagtgacc cagctactga accagccacg aacagcccgc cagaggcctg 4260
aagctgagcg tgtacgttaa tgtgaatgta tatagtcttt gcagaggtcc aaatgatatt 4320
catgatggta ataaacgaga tgtttgccaa ataaaaaaca gaaaccgcag ga 4372

<210> SEQ ID NO 417
<211> LENGTH: 1914
<212> TYPE: DNA
<213> ORGANISM: Homo sapiens

<400> SEQUENCE: 417
aactcttcat ctcgcggctg tctgacttcc tcccagcaca ttcctgcact ctgccgtgtc 60
cacactgccc cacagaccca gtcctccaag cctgctgcca gctccctgca agcccctcag 120
gttgggcctt gccacggtgc cagcaggcag ccctgggctg ggggtagggg actccctaca 180
ggcacgcagc cctgagacct cagagggcca ccccttgagg gtggccaggc ccccagtggc 240
caacctgagt gctgcctctg ccaccagccc tgctggcccc tggttccgct ggccccccag 300
atgcctggct gagacacgcc agtggcctca gctgcccaca cctcttcccg gcccctgaag 360
ttggcactgc agcagacagc tccctgggca ccaggcagct aacagacaca gccgccagcc 420
caaacagcag cggcatgggc agcgccagcc cgggtctgag cagcgtatcc cccagccacc 480
tcctgctgcc ccccgacacg gtgtcgcgga caggcttgga gaaggcggca gcgggggcag 540
tgggtctcga gagacgggac tggagtccca gtccacccgc cacgcccgag cagggcctgt 600
ccgccttcta cctctcctac tttgacatgc tgtaccctga ggacagcagc tgggcagcca 660
aggcccctgg ggccagcagt cgggaggagc cacctgagga gcctgagcag tgcccggtca 720
ttgacagcca agccccagcg ggcagcctgg acttggtgcc cggcgggctg accttggagg 780
agcactcgct ggagcaggtg cagtccatgg tggtgggcga agtgctcaag gacatcgaga 840
cggcctgcaa gctgctcaac atcaccgcag atcccatgga ctggagcccc agcaatgtgc 900
agaagtggct cctgtggaca gagcaccaat accggctgcc ccccatgggc aaggccttcc 960
aggagctggc gggcaaggag ctgtgcgcca tgtcggagga gcagttccgc cagcgctcgc 1020
ccctgggtgg ggatgtgctg cacgcccacc tggacatctg gaagtcagcg gcctggatga 1080
aagagcggac ttcacctggg gcgattcact actgtgcctc gaccagtgag gagagctgga 1140
ccgacagcga ggtggactca tcatgctccg ggcagcccat ccacctgtgg cagttcctca 1200
aggagttgct actcaagccc cacagctatg gccgcttcat taggtggctc aacaaggaga 1260
agggcatctt caaaattgag gactcagccc aggtggcccg gctgtggggc atccgcaaga 1320
accgtcccgc catgaactac gacaagctga gccgctccat ccgccagtat tacaagaagg 1380
gcatcatccg gaagccagac atctcccagc gcctcgtcta ccagttcgtg caccccatct 1440
gagtgcctgg cccagggcct gaaacccgcc ctcaggggcc tctctcctgc ctgccctgcc 1500
tcagccaggc cctgagatgg gggaaaacgg gcagtctgct ctgctgctct gaccttccag 1560
agcccaaggt cagggagggg caaccaactg ccccaggggg atatgggtcc tctggggcct 1620
tcgggaccct ggggcagggg tgcttcctcc tcaggcccag ctgctcccct ggaggacaga 1680
gggagacagg gctgctcccc aacacctgcc tctgacccca gcatttccag agcagagcct 1740

-continued acagaagggc agtgactcga caaaggccac aggcagtcca ggcctctctc tgctccatcc 1800
ccctgcctcc cattctgcac cacacctggc atggtgcagg gagacatctg cacccctgag 1860
ttgggcagcc aggagtgccc ccgggaatgg ataataaaga tactagagaa ctga 1914

<210> SEQ ID NO 418
<211> LENGTH: 576
<212> TYPE: DNA
<213> ORGANISM: Homo sapiens

<400> SEQUENCE: 418
actcttctgg tccccacaga ctcagagaga acccaccatg gtgctgtctc ctgccgacaa 60
gaccaacgtc aaggccgcct ggggtaaggt cggcgcgcac gctggcgagt atggtgcgga 120
ggccctggag aggatgttcc tgtccttccc caccaccaag acctacttcc cgcacttcga 180
cctgagccac ggctctgccc aggttaaggg ccacggcaag aaggtggccg acgcgctgac 240
caacgccgtg gcgcacgtgg acgacatgcc caacgcgctg tccgccctga gcgacctgca 300
cgcgcacaag cttcgggtgg acccggtcaa cttcaagctc ctaagccact gcctgctggt 360
gaccctggcc gcccacctcc ccgccgagtt cacccctgcg gtgcacgcct ccctggacaa 420
gttcctggct tctgtgagca ccgtgctgac ctccaaatac cgttaagctg gagcctcggt 480
ggccatgctt cttgcccctt gggcctcccc ccagcccctc ctccccttcc tgcacccgta 540
cccccgtggt ctttgaataa agtctgagtg ggcggc 576

<210> SEQ ID NO 419
<211> LENGTH: 508
<212> TYPE: DNA
<213> ORGANISM: Homo sapiens

<400> SEQUENCE: 419
atccctgact cggggtcgcc tttggagcag agaggaggca atggccacca tggagaacaa 60
ggtgatctgc gccctggtcc tggtgtccat gctggccctc ggcaccctgg ccgaggccca 120
gacagagacg tgtacagtgg ccccccgtga aagacagaat tgtggttttc ctggtgtcac 180
gccctcccag tgtgcaaata agggctgctg tttcgacgac accgttcgtg gggtcccctg 240
gtgcttctat cctaatacca tcgacgtccc tccagaagag gagtgtgaat tttagacact 300
tctgcaggga tctgcctgca tcctgacgcg gtgccgtccc cagcacggtg attagtccca 360
gagctcggct gccacctcca ccggacacct cagacacgct tctgcagctg tgcctcggct 420
cacaacacag attgactgct ctgactttga ctactcaaaa ttggcctaaa aattaaaaga 480
gatcgatatt aaaaaaaaaa aaaaaaaa 508

<210> SEQ ID NO 420
<211> LENGTH: 1433
<212> TYPE: DNA
<213> ORGANISM: Homo sapiens

<400> SEQUENCE: 420
accccagccg cgactgtctc cgccgagccc ccggggccag gtgtcccggg cgcgccacga 60
tgcggccgcg gctgtggctc ctcttggccg cgcagctgac agttctccat ggcaactcag 120
tcctccagca gacccctgca tacataaagg tgcaaaccaa caagatggtg atgctgtcct 180
gcgaggctaa aatctccctc agtaacatgc gcatctactg gctgagacag cgccaggcac 240
cgagcagtga cagtcaccac gagttcctgg ccctctggga ttccgcaaaa gggactatcc 300
acggtgaaga ggtggaacag gagaagatag ctgtgtttcg ggatgcaagc cggttcattc 360

```
tcaatctcac aagcgtgaag ccggaagaca gtggcatcta cttctgcatg atcgtcggga    420
gccccgagct gaccttcggg aagggaactc agctgagtgt ggttgatttc cttcccacca    480
ctgcccagcc caccaagaag tccaccctca agaagagagt gtgccggtta cccaggccag    540
agacccagaa gggcccactt tgtagcccca tcacccttgg cctgctggtg gctggcgtcc    600
tggttctgct ggtttccctg ggagtggcca tccacctgtg ctgccggcgg aggagagccc    660
ggcttcgttt catgaaacaa ttttacaaat gagcagagaa tacggttttg gtgtcctgct    720
acaaaaagac atcggtcagt aacgagcacg atgtggaaaa atgagagaag ggacacattc    780
aaccctggag agttcaatgg ctgctgaagc tgcctgcttt tcactgctgc aaggcctttc    840
tgtgtgtgat gtgcatggga gcaacttgtt cgtgggtcat cgggaatact agggagaagg    900
tttcattgcc cccagggcac ttcacagagt gtgctggagg actgagtaag aaatgctgcc    960
catgccaccg cttccggctc ctgtgctttc cctgaactgg gacctttagt ggtggccatt   1020
tagccaccat ctttgcaggt tgctttgccc tggtagggca gtaacattgg gtcctgggtc   1080
tttcatgggg tgatgctggg ctggctccct cttggtcttc ccaggctggg gctgaccttc   1140
ctcgcagaga ggccaggtgc aggttgggaa tgaggcttgc tgagaggggc tgtccagttc   1200
ccagaaggca tatcagtctc tgagggcttc ctttggggcc gggaacttgc gggtttgagg   1260
ataggagttc acttcatctt ctcagctccc atttctactc ttaagtttct cagctcccat   1320
ttctactctc ccatggctta atgcttcttt cattttctgt ttgttttata caaatgtctt   1380
agttgtacaa ataaagtccc aggttaaaga taacaaacgg ctcctgtgac ata          1433
```

<210> SEQ ID NO 421
<211> LENGTH: 4701
<212> TYPE: DNA
<213> ORGANISM: Homo sapiens

<400> SEQUENCE: 421

```
gactgcctgc ttgcaggctg tgtcacagaa gagaacatgg cagaacagta tgctcaggag     60
ttgataccaa gttgaaattc actcttgagc catctttagg tcaaaatggt tttcagcagt    120
ggtacgatgc tctcaaggca gttgccaggc tatccacagg aataccaaag gaatggagga    180
gaaaggtttg gttgaccttg gcagatcatt atttgcacag tatagccatt gactgggaca    240
aaaccatgcg cttcactttc aatgaaagga gtaatcctga tgatgactcc atgggaattc    300
agatagtcaa ggaccttcac cgcacaggct gtagttctta ctgtggccag gaggctgagc    360
aggacagggt tgtgttgaag cgggtgctgc tggcctatgc ccgatggaac aaaactgttg    420
ggtactgcca aggctttaac atcctggctg cactaattct ggaagtgatg gaaggcaatg    480
aaggggatgc cctgaaaatt atgatttacc ttattgataa ggtacttccc gaaagctatt    540
tcgtcaataa tctccgggca ttgtctgtgg atatggctgt cttcagagac cttttaagaa    600
tgaagctgcc ggaattatct cagcacctgg atactcttca gagaactgca aacaaagaaa    660
gtggaggtgg atatgagccc ccacttacaa atgtcttcac gatgcagtgg tttctgactc    720
tctttgccac atgcctccct aatcagaccg ttttaaagat ctgggattca gtcttctttg    780
aaggttcaga aatcatccta agggtgtcgc tggctatctg ggcaaaatta ggagagcaga    840
tagaatgttg tgaaacagca gatgaattct acagcaccat ggggcgcctt acccaggaga    900
tgctagagaa tgatcttctg caaagccatg aactcatgca gactgtttat tccatggctc    960
cgttcccttt cccacaattg gcagagttga gggaaaaata cacctacaac attacaccgt   1020
```

-continued

```
tcccagccac agttaaaccc acctcagttt ctggacgaca tagtaaggcc agagacagtg   1080
atgaagagaa tgacccagac gatgaggatg ctgtcgttaa tgcagtgggg tgtcttggac   1140
cttttagtgg gttcctggct cctgaactgc agaagtacca aaaacaaatt aaagagccaa   1200
atgaggagca gagtctgaga tctaataaca ttgcagagct gagtccagga gcaatcaatt   1260
cctgtcgaag tgaataccat gcagctttta acagtatgat gatggaacgc atgaccacag   1320
atatcaatgc actgaagcgg cagtactctc gaattaaaaa gaagcaacag cagcaggttc   1380
atcaggtgta catcagggca gacaaagggc cagtgaccag cattctcccg tctcaggtaa   1440
acagttctcc agttataaac caccttcttt taggaaagaa gatgaaaatg actaacagag   1500
ctgccaagaa tgctgtcatc cacatccctg gtcacacagg agggaaaata tctcctgtcc   1560
cctacgaaga ccttaagacg aagctcaact ccccgtggcg aactcacatc cgagtccaca   1620
aaaagaacat gccaaggacc aagagtcatc cgggctgtgg ggacaccgta gggctgatag   1680
atgagcagaa cgaggccagc aagaccaatg ggctgggggc agcagaggca ttcccctctg   1740
gttgtacagc gacagctggg agagaaggca gcagccctga aggcagtacc aggaggacga   1800
tcgaggggca gtctccggag ccggtgttcg gagatgctga tgtggatgtg tctgcagttc   1860
aggcgaagtt gggagccctg gaactgaacc agagggatgc tgcagctgaa actgagctca   1920
gggtgcaccc accctgccag cggcactgcc cagagccgcc gagtgcaccc gaagaaaaca   1980
aagccaccag caaagctccc caaggcagca actcaaaaac ccccatcttt agccctttc    2040
ccagcgtcaa gcccctgcgg aaatctgcta ctgccaggaa cttgggatta tatggcccta   2100
cagaaagaac cccaactgtg cactttcctc aaatgagtag gagcttcagc aaacccggcg   2160
gtggaaacag tggcactaaa aaacgatgat gtctccccga aactttgtat ctggactcac   2220
cttttcacag tagtataagg gttgcagctg aatggctcta aaagagtttt atttgtccag   2280
tgaaaatgaa taggttcagg gatgagcaac agcccataaa aaatgggaac tggaagtttt   2340
ataataggag ttagaacagg gctgttttcc cagctacttg ctaactgacg aagtggattc   2400
ttgtggcaaa ataaatattg tggttttata gtgtgaagtt ttcccaattt ttcattgtga   2460
gctgtttaaa aaagactata tctagattgt taactctcgt ccatccttct gttctggggg   2520
ccttcagagt ccctgtgaca gcacccccaa accttccagt tctctgggtg ttactaatac   2580
tcaagcatgc acataccagc ttgctaggac agaaactgta aaaagaaagt aagtttcttc   2640
gttacaaaaa acttcctgat tttccttttc atgctttacg gaggggattg tgtcgtgtga   2700
gatttcccac agtaccagtt tcaaattttt ttttattctt atgctaaatc ataggagaaa   2760
aatctagatg gcctttcttt aactgtctat ttctacctgc aaaatgaaga aaacctttca   2820
tctgttgaaa tttcaatcga taacccagct gaagatctta tgcacaggac acacttggca   2880
tatgctttac gcagttgctc cggacagctt gctcgcgcca ctgagctttt cctgaggttt   2940
gtgttcgcct ctcaaggaga gctttgatcc tcagtggtac ggatgacttg atgggctcca   3000
tgcggagcct ggcctgcatc ccccaccaca cagctcactc acccaccagc tctagactgc   3060
agacgcacaa ggcctctgct cagaagccag aacacagcac ctgtgactct gttacttgaa   3120
ttttgtgctt tttgattgga gtcctttgtt gagtactttg ttaattgaac actgcctttc   3180
tctggagaag gccccagtgc tttctagctc cctctcactc ctgccctttc tagctctctc   3240
tcacccagcg ggtcagggat agcacctctt gtctccacta tgcagatggg aactctgagc   3300
cacacagagg tgaagtagca cttcagttac tcaaggtcag tactctcggt attccaagtg   3360
acttagccac atttccttca gtgcaatagg tgggtttaat gctctttgta cacagatgta   3420
```

ttggctacat agcgtgtaaa aaccaagact gggaagccat tcactaaaat ccctcctgac 3480
tcaaaggacc tgtctccaga tggtacagag tcccttgatg gcattttaca aaaccagctc 3540
tgacttcctt atcctgaaca gggagtttat tttaaaaatg cttcatgcac ctgttatttg 3600
gctgaacaga aggctcactc ctcaatcccc ttctcctcgc catcattaga ggaatagact 3660
cagccttcat gtttgtctct ggaagacgat tggcgatact tgcaggaata ttgttgatgc 3720
agccaatatt aatttgagct aatggattgt taattctgaa acgaaaactg taactgtaga 3780
gcaggctttt actatgagag gtactacttt ttataataga gaatgtggtt gtgtgggctt 3840
tttttgaaca gaaaacacaa caatgaccta taccgtgaga aaagccattt tatcttcttc 3900
gtggtatttt tacccccaaa ggaactgaag atggaaaata tgactaataa gttattgcag 3960
ttttggtctt gaattctgtg ccatctgaag ttagcatcca gcttcttaaa aagcagccac 4020
gcctacagcc tgtttttgg gaaggctgta ggtggagaga tgggcttatt ttgcatacca 4080
ccctcagggc ccagagaccc actgcatttt ccaaagttaa gcatgacacc attttcttcc 4140
atcagctaaa ctttacagat aatagtgttt ccacctcata tccttttctt tgccccttct 4200
caaatgagtc agaatagtca tgttcccctt gagggatgtc tgacttgaat ggagaattgt 4260
tctttcctct cttgaatcag ctcactagct ccctgatggt ctgggttcaa ggaaatggtt 4320
aatgaggtag aggccactta tacaagtcct tgggattgta ccattgctgt ccacaaactt 4380
agtatcaaca acacatgctg tgccctgtga acactctcct ctcacctatt tccagggttg 4440
gtcttcctga gaaggggatg gatgaggtaa cacacagttt gggatacgta tctgttgaat 4500
gaatgaataa gtgaaaggat aatagtcctc tgaggtaaaa atggccttgt cagaattttg 4560
aaaatccaac agattcctat taaagcactc tgtgtaccaa taacatgcat gcattgtacc 4620
aagtaatcac aatgtgaatt ggtcaattta tgagccttgc ctactttaga aaataaagaa 4680
acctgcagta gcctctacca c 4701

<210> SEQ ID NO 422
<211> LENGTH: 6492
<212> TYPE: DNA
<213> ORGANISM: Homo sapiens

<400> SEQUENCE: 422
tttctgtgaa gcagaagtct gggaatcgat ctggaaatcc tcctaatttt tactccctct 60
ccccgcgact cctgattcat tgggaagttt caaatcagct ataactggag agtgctgaag 120
attgatggga tcgttgcctt atgcatttgt tttggtttta caaaaaggaa acttgacaga 180
ggatcatgct gtacttaaaa aatacaacat cacagaggaa gtagactgat attaacaata 240
cttactaata ataacgtgcc tcatgaaata aagatccgaa aggaattgga ataaaaattt 300
cctgcatctc atgccaaggg ggaaacacca gaatcaagtg ttccgcgtga ttgaagacac 360
cccctcgtcc aagaatgcaa agcacatcca ataaaatagc tggattataa ctcctcttct 420
ttctctgggg gccgtggggt gggagctggg gcgagaggtg ccgttggccc ccgttgcttt 480
tcctctggga aggatggcgc acgctgggag aacagggtac gataaccggg agatagtgat 540
gaagtacatc cattataagc tgtcgcagag gggctacgag tgggatgcgg gagatgtggg 600
cgccgcgccc ccgggggccg cccccgcacc gggcatcttc tcctcccagc ccgggcacac 660
gccccatcca gccgcatccc gggacccggt cgccaggacc tcgccgctgc agaccccggc 720
tgcccccggc gccgccgcgg ggcctgcgct cagcccggtg ccacctgtgg tccacctgac 780

-continued

```
cctccgccag gccggcgacg acttctcccg ccgctaccgc cgcgacttcg ccgagatgtc    840
cagccagctg cacctgacgc ccttcaccgc gcggggacgc tttgccacgg tggtggagga    900
gctcttcagg gacggggtga actgggggag gattgtggcc ttctttgagt tcggtggggt    960
catgtgtgtg gagagcgtca accgggagat gtcgcccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca cacaacaatt   1380
aacagtcttc aggcaaaacg tcgaatcagc tatttactgc caaagggaaa tatcatttat   1440
tttttacatt attaagaaaa aaagatttat ttatttaaga cagtcccatc aaaactcctg   1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtgggggaa gtccatgcct ccctggcctg aagaagagac tctttgcata    1800
tgactcacat gatgcatacc tggtgggagg aaaagagttg ggaacttcag atggacctag   1860
tacccactga gatttccacg ccgaaggaca gcgatgggaa aaatgccctt aaatcatagg   1920
aaagtatttt tttaagctac caattgtgcc gagaaaagca ttttagcaat ttatacaata   1980
tcatccagta ccttaagccc tgattgtgta tattcatata ttttggatac gcacccccca   2040
actcccaata ctggctctgt ctgagtaaga aacagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaaagtt ccaggtgtgg   2760
aatatggggg ttatctgtac atcctggggc attaaaaaaa aaatcaatgg tggggaacta   2820
taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gtttttttgt ttttaattgt   3060
atttagttat ggcctataca ctatttgtga gcaaaggtga tcgttttctg tttgagattt   3120
ttatctcttg attcttcaaa agcattctga gaaggtgaga taagccctga gtctcagcta   3180
```

-continued

```
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
gtttcttgaa ggtttcctcg tccctgggca attccgcatt taattcatgg tattcaggat   3360
tacatgcatg tttggttaaa cccatgagat tcattcagtt aaaaatccag atggcaaatg   3420
accagcagat tcaaatctat ggtggtttga cctttagaga gttgctttac gtggcctgtt   3480
tcaacacaga cccacccaga gccctcctgc cctccttccg cgggggcttt ctcatggctg   3540
tccttcaggg tcttcctgaa atgcagtggt gcttacgctc caccaagaaa gcaggaaacc   3600
tgtggtatga agccagacct ccccggcggg cctcagggaa cagaatgatc agacctttga   3660
atgattctaa tttttaagca aaatattatt ttatgaaagg tttacattgt caaagtgatg   3720
aatatggaat atccaatcct gtgctgctat cctgccaaaa tcattttaat ggagtcagtt   3780
tgcagtatgc tccacgtggt aagatcctcc aagctgcttt agaagtaaca atgaagaacg   3840
tggacgtttt taatataaag cctgttttgt cttttgttgt tgttcaaacg ggattcacag   3900
agtatttgaa aaatgtatat atattaagag gtcacggggg ctaattgctg gctggctgcc   3960
ttttgctgtg gggttttgtt acctggtttt aataacagta aatgtgccca gcctcttggc   4020
cccagaactg tacagtattg tggctgcact tgctctaaga gtagttgatg ttgcattttc   4080
cttattgtta aaaacatgtt agaagcaatg aatgtatata aaagcctcaa ctagtcattt   4140
ttttctcctc ttcttttttt tcattatatc taattatttt gcagttgggc aacagagaac   4200
catccctatt ttgtattgaa gagggattca catctgcatc ttaactgctc tttatgaatg   4260
aaaaaacagt cctctgtatg tactcctctt tacactggcc agggtcagag ttaaatagag   4320
tatatgcact ttccaaattg gggacaaggg ctctaaaaaa agccccaaaa ggagaagaac   4380
atctgagaac ctcctcggcc ctcccagtcc ctcgctgcac aaatactccg caagagaggc   4440
cagaatgaca gctgacaggg tctatggcca tcgggtcgtc tccgaagatt tggcaggggc   4500
agaaaactct ggcaggctta agatttggaa taaagtcaca gaattaagga agcacctcaa   4560
tttagttcaa acaagacgcc aacattctct ccacagctca cttacctctc tgtgttcaga   4620
tgtggccttc catttatatg tgatctttgt tttattagta aatgcttatc atctaaagat   4680
gtagctctgg cccagtggga aaaattagga agtgattata aatcgagagg agttataata   4740
atcaagatta aatgtaaata atcagggcaa tcccaacaca tgtctagctt tcacctccag   4800
gatctattga gtgaacagaa ttgcaaatag tctctatttg taattgaact tatcctaaaa   4860
caaatagttt ataaatgtga acttaaactc taattaattc caactgtact tttaaggcag   4920
tggctgtttt tagactttct tatcacttat agttagtaat gtacacctac tctatcagag   4980
aaaaacagga aaggctcgaa atacaagcca ttctaaggaa attagggagt cagttgaaat   5040
tctattctga tcttattctg tggtgtcttt tgcagcccag acaaatgtgg ttacacactt   5100
tttaagaaat acaattctac attgtcaagc ttatgaaggt tccaatcaga tctttattgt   5160
tattcaattt ggatctttca gggatttttt ttttaaatta ttatgggaca aaggacattt   5220
gttggagggg tgggagggag gaagaatttt taaatgtaaa acattcccaa gtttggatca   5280
gggagttgga agttttcaga ataaccagaa ctaagggtat gaaggacctg tattggggtc   5340
gatgtgatgc ctctgcgaag aaccttgtgt gacaaatgag aaacattttg aagtttgtgg   5400
tacgaccttt agattccaga gacatcagca tggctcaaag tgcagctccg tttggcagtg   5460
caatggtata aatttcaagc tggatatgtc taatgggtat ttaaacaata aatgtgcagt   5520
```

tttaactaac aggatattta atgacaacct tctggttggt agggacatct gtttctaaat 5580
gtttattatg tacaatacag aaaaaaattt tataaaatta agcaatgtga aactgaattg 5640
gagagtgata atacaagtcc tttagtctta cccagtgaat cattctgttc catgtctttg 5700
gacaaccatg accttggaca atcatgaaat atgcatctca ctggatgcaa agaaaatcag 5760
atggagcatg aatggtactg taccggttca tctggactgc cccagaaaaa taacttcaag 5820
caaacatcct atcaacaaca aggttgttct gcataccaag ctgagcacag aagatgggaa 5880
cactggtgga ggatggaaag gctcgctcaa tcaagaaaat tctgagacta ttaataaata 5940
agactgtagt gtagatactg agtaaatcca tgcacctaaa ccttttggaa aatctgccgt 6000
gggccctcca gatagctcat ttcattaagt ttttccctcc aaggtagaat ttgcaagagt 6060
gacagtggat tgcatttctt ttggggaagc tttcttttgg tggttttgtt tattatacct 6120
tcttaagttt tcaaccaagg tttgcttttg ttttgagtta ctggggttat ttttgtttta 6180
aataaaaata agtgtacaat aagtgttttt gtattgaaag cttttgttat caagattttc 6240
atacttttac cttccatggc tctttttaag attgatactt ttaagaggtg gctgatattc 6300
tgcaacactg tacacataaa aaatacggta aggatacttt acatggttaa ggtaaagtaa 6360
gtctccagtt ggccaccatt agctataatg gcactttgtt tgtgttgttg gaaaaagtca 6420
cattgccatt aaactttcct tgtctgtcta gttaatattg tgaagaaaaa taaagtacag 6480
tgtgagatac tg 6492

<210> SEQ ID NO 423
<211> LENGTH: 2032
<212> TYPE: DNA
<213> ORGANISM: Homo sapiens

<400> SEQUENCE: 423
ggactctggg acgctcagac gccgcgcggg gcggggattg gtctgtggtc ctctctcggc 60
tcctcgcggc tcgcggcggc cgacggttcc tgggacacct gcttgcttgg cccgtccggc 120
ggctcagggc ttctctgctg cgctcccggt tcgctggacg ggaagaaggg ctgggccgtc 180
ccgtcccgtc cccatcggaa ccccaagtcg cgccgctgac ccgtcgcagg gcgagatgag 240
cgcggacgca gcggccgggg cgcccctgcc ccggctctgc tgcctggaga agggtccgaa 300
cggctacggc ttccacctgc acggggagaa gggcaagttg ggccagtaca tccggctggt 360
ggagcccggc tcgccggccg agaaggcggg gctgctggcg ggggaccggc tggtggaggt 420
gaacggcgaa aacgtggaga aggagaccca ccagcaggtg gtgagccgca tccgcgccgc 480
actcaacgcc gtgcgcctgc tggtggtcga ccccgagacg gacgagcagc tgcagaagct 540
cggcgtccag gtccgagagg agctgctgcg cgcccaggaa gcgccggggc aggccgagcc 600
gccggccgcc gccgaggtgc agggggctgg caacgaaaat gagcctcgcg aggccgacaa 660
gagccacccg gagcagcgcg agcttcggcc tcggctctgt accatgaaga agggccccag 720
tggctatggc ttcaacctgc acagcgacaa gtccaagcca ggccagttca tccggtcagt 780
ggacccagac tccccggctg aggcttcagg gctccgggcc caggatcgca ttgtggaggt 840
gaacggggtc tgcatggagg ggaagcagca tggggacgtg gtgtccgcca tcagggctgg 900
cggggacgag accaagctgc tggtggtgga cagggaaact gacgagttct tcaagaaatg 960
cagagtgatc ccatctcagg agcacctgaa tggtcccctg cctgtgccct tcaccaatgg 1020
ggagatacag aaggagaaca gtcgtgaagc cctggcagag gcagccttgg agagccccag 1080
gccagccctg gtgagatccg cctccagtga caccagcgag gagctgaatt cccaagacag 1140

```
cccccaaaa caggactcca cagcgccctc gtctacctcc tcctccgacc ccatcctaga   1200

cttcaacatc tccctggcca tggccaaaga gagggcccac cagaaacgca gcagcaaacg   1260

ggccccgcag atggactgga gcaagaaaaa cgaactcttc agcaacctct gagcgccctg   1320

ctgccaccca gtgactggca gggccgagcc agcattccac cccacctttt tccttctccc   1380

caattactcc cctgaatcaa tgtacaaatc agcacccaca tcccctttct tgacaaatga   1440

tttttctaga gaactatgtt cttccctgac tttagggaag gtgaatgtgt tcccgtcctc   1500

ccgcagtcag aaaggagact ctgcctccct cctcctcact gagtgcctca tcctaccggg   1560

tgtccctttg ccaccctgcc tgggacatcg ctggaacctg caccatgcca ggatcatggg   1620

accaggcgag agggcaccct cccttcctcc cccatgtgat aaatgggtcc agggctgatc   1680

aaagaactct gactgcagaa ctgccgctct cagtggacag ggcatctgtt accctgagac   1740

ctgtggcaga cacgtcttgt tttcatttga tttttgttaa gagtgcagta ttgcagagtc   1800

tagaggaatt tttgtttcct tgattaacat gattttcctg gttgttacat ccagggcatg   1860

gcagtggcct cagccttaaa cttttgttcc tactcccacc ctcagcgaac tgggcagcac   1920

ggggagggtt tggctacccc tgcccatccc tgagccaggt accaccattg taaggaaaca   1980

ctttcagaaa ttcagctggt tcctccaaac ccttcaaaaa aaaaaaaaaa aa           2032


<210> SEQ ID NO 424
<211> LENGTH: 1647
<212> TYPE: DNA
<213> ORGANISM: Homo sapiens

<400> SEQUENCE: 424

gaagatccaa gcaggcggag ccgcggtctg gtccgcgggg taggcggggc gcaagagtgt     60

tcccggggc ggggggccga cccgcgtcta aaggtttccg cgattcaccc gccggcgcct    120

ggcctggccc agttgcacca cgagcgctgc ggacactcgg ggcggcagtc ggtctgtcag    180

tcctcccgcc aggtcccgcg gcccgcacct gccgcccgca cctgcagctc cgcacctgcg    240

gccagtgcct actgccctct cttgccgccc gcacctgcag ccccgcacct gccgcttgca    300

cctgcagccc cgcgctctac ccggttcaag catggctgac caggcgccct tcgacacgga    360

cgtcaacacc ctgacccgct tcgtcatgga ggagggcagg aaggcccgcg gcacgggcga    420

gttgacccag ctgctcaact cgctctgcac agcagtcaaa gccatctctt cggcggtgcg    480

caaggcgggc atcgcgcacc tctatggcat tgctggttct accaacgtga caggtgatca    540

agttaagaag ctggacgtcc tctccaacga cctggttatg aacatgttaa agtcatcctt    600

tgccacgtgt gttctcgtgt cagaagaaga taaacacgcc atcatagtgg aaccggagaa    660

aaggggtaaa tatgtggtct gttttgatcc ccttgatgga tcttccaaca tcgattgcct    720

tgtgtccgtt ggaaccattt ttggcatcta tagaaagaaa tcaactgatg agccttctga    780

gaaggatgct ctgcaaccag gccggaacct ggtggcagcc ggctacgcac tgtatggcag    840

tgccaccatg ctggtccttg ccatggactg tggggtcaac tgcttcatgc tggacccggc    900

catcggggag ttcattttgg tggacaagga tgtgaagata aaaaagaaag gtaaaatcta    960

cagccttaac gagggctacg ccagggactt tgaccctgcc gtcactgagt acatccagag   1020

gaagaagttc cccccagata attcagctcc ttatggggcc cggtatgtgg gctccatggt   1080

ggctgatgtt catcgcactc tggtctacgg agggatattt ctgtaccccg ctaacaagaa   1140

gagccccaat ggaaagctga gactgctgta cgaatgcaac cccatggcct acgtcatgga   1200
```

gaaggctggg ggaatggcca ccactgggaa ggaggccgtg ttagacgtca ttcccacaga 1260
cattcaccag agggcgccgg tgatcttggg atcccccgac gacgtgctcg agttcctgaa 1320
ggtgtatgag aagcactctg cccagtgagc acctgccctg cctgcatccg gagaattgcc 1380
tctacctgga ccttttgtct cacacagcag taccctgacc tgctgtgcac cttacattcc 1440
tagagagcag aaataaaaag catgactatt tccaccatca aatgctgtag aatgcttggc 1500
actccctaac caaatgctgt ctccataatg ccactggtgt taagatatat tttgagtgga 1560
tggaggagaa ataaacttat tcctccttaa aaaaaaaaaa aaaaaaaaaa aaaaaaaaaa 1620
aaaaaaaaaa aaaaaaaaaa aaaaaaa 1647

<210> SEQ ID NO 425
<211> LENGTH: 2878
<212> TYPE: DNA
<213> ORGANISM: Homo sapiens

<400> SEQUENCE: 425
aaatcttccc caccctgggg agtgtcactt cctcctctgc cgtctcccag atcagtacac 60
aaaggctgct gctgccgcca gaggaaggac tgctctgcac gcacctatgt ggaaactaaa 120
gcccagagag aaagtctgac ttgccccaca gccagtgagt gactgcagca gcaccagaat 180
ctggtctgtt tcctgtttgg ctcttctacc actacggctt gggatctcgg gcatggtggc 240
tttgccaatg gtccttgttt tgctgctggt cctgagcaga ggtgagagtg aattggacgc 300
caagatccca tccacagggg atgccacaga atggcggaat cctcacctgt ccatgctggg 360
gtcctgccag ccagcccct cctgccagaa gtgcatcctc tcacacccca gctgtgcatg 420
gtgcaagcaa ctgaacttca ccgcgtcggg agaggcggag gcgcggcgct gcgcccgacg 480
agaggagctg ctggctcgag gctgcccgct ggaggagctg gaggagcccc gcggccagca 540
ggaggtgctg caggaccagc cgctcagcca gggcgcccgc ggagagggtg ccacccagct 600
ggcgccgcag cgggtccggg tcacgctgcg gcctggggag ccccagcagc tccaggtccg 660
cttccttcgt gctgagggat acccggtgga cctgtactac cttatggacc tgagctactc 720
catgaaggac gacctggaac gcgtgcgcca gctcgggcac gctctgctgg tccggctgca 780
ggaagtcacc cattctgtgc gcattggttt tggttccttt gtggacaaaa cggtgctgcc 840
ctttgtgagc acagtaccct ccaaactgcg ccacccctgc cccacccggc tggagcgctg 900
ccagtcacca ttcagctttc accatgtgct gtccctgacg gggacgcac aagccttcga 960 gcgggaggtg ggcgccaga gtgtgtccgg caatctggac tcgcctgaag gtggcttcga 1020
tgccattctg caggctgcac tctgccagga gcagattggc tggagaaatg tgtcccggct 1080
gctggtgttc acttcagacg acacattcca tacagctggg gacgggaagt tgggcggcat 1140
tttcatgccc agtgatgggc actgccactt ggacagcaat ggcctctaca gtcgcagcac 1200
agagtttgac taccctttctg tgggtcaggt agcccaggcc ctctctgcag caaatatcca 1260
gcccatcttt gctgtcacca gtgccgcact gcctgtctac caggagctga gtaaactgat 1320
tcctaagtct gcagttgggg agctgagtga ggactccagc aacgtggtac agctcatcat 1380
ggatgcttat aatagcctgt cttccaccgt gacccttgaa cactcttcac tccctcctgg 1440
ggtccacatt tcttacgaat cccagtgtga gggtcctgag aagagggagg gtaaggctga 1500
ggatcgagga cagtgcaacc acgtccgaat caaccagacg gtgactttct gggtttctct 1560
ccaagccacc cactgcctcc cagagcccca tctcctgagg ctccgggccc ttggcttctc 1620
agaggagctg attgtggagt tgcacacgct gtgtgactgt aattgcagtg acacccagcc 1680

-continued

```
ccaggctccc cactgcagtg atggccaggg acacctacaa tgtggtgtat gcagctgtgc   1740
ccctggccgc ctaggtcggc tctgtgagtg ctctgtggca gagctgtcct ccccagacct   1800
ggaatctggg tgccgggctc ccaatggcac agggcccctg tgcagtggaa agggtcactg   1860
tcaatgtgga cgctgcagct gcagtggaca gagctctggg catctgtgcg agtgtgacga   1920
tgccagctgt gagcgacatg agggcatcct ctgcggaggc tttggtcgct gccaatgtgg   1980
agtatgtcac tgtcatgcca accgcacggg cagagcatgc gaatgcagtg gggacatgga   2040
cagttgcatc agtcccgagg gagggctctg cagtgggcat ggacgctgca aatgcaaccg   2100
ctgccagtgc ttggacggct actatggtgc tctatgcgac caatgcccag gctgcaagac   2160
accatgcgag agacaccggg actgtgcaga gtgtggggcc ttcaggactg gcccactggc   2220
caccaactgc agtacagctt gtgcccatac caatgtgacc ctggccttgg cccctatctt   2280
ggatgatggc tggtgcaaag agcggaccct ggacaaccag ctgttcttct tcttggtgga   2340
ggatgacgcc agaggcacgg tcgtgctcag agtgagaccc caagaaaagg gagcagacca   2400
cacgcaggcc attgtgctgg gctgcgtagg gggcatcgtg gcagtggggc tggggctggt   2460
cctggcttac cggctctcgg tggaaatcta tgaccgccgg gaatacagtc gctttgagaa   2520
ggagcagcaa caactcaact ggaagcagga cagtaatcct ctctacaaaa gtgccatcac   2580
gaccaccatc aatcctcgct ttcaagaggc agacagtccc actctctgaa ggagggaggg   2640
acacttaccc aaggctcttc tccttggagg acagtgggaa ctggagggtg agaggaaggg   2700
tgggtctgta agaccttggt aggggactaa ttcactggcg aggtgcggcc accaccctac   2760
ttcattttca gagtgacacc caagagggct gcttcccatg cctgcaacct tgcatccatc   2820
tgggctaccc cacccaagta tacaataaag tcttacctca gaccacaaaa aaaaaaaa     2878
```

<210> SEQ ID NO 426
<211> LENGTH: 1227
<212> TYPE: DNA
<213> ORGANISM: Homo sapiens

<400> SEQUENCE: 426

```
atttggaaaa gtcagtgcca aaaagtgtaa aatacctaac aattttaatt tcgataacat     60
tgaaatatgt tggctatatt ggattaagca aaatattaaa aattaatttt tccttgtttt    120
gttacaatgt tctcctagat aagtgtaaat tacttatatt gctctcattt ccactggaaa    180
tcgctagtat agtgaacaac tgtatagcga aaatagaaaa taaaatatgg agaccatgaa    240
ctgctaagtc tgtcagagga ataggtgaac aacaaaaatt tgagtccttc gccaatccgg    300
ttactgttgg gtaggccttc agcatacttt tgtccaatca gcttcagact ctcactataa    360
ataagcggct agctttctct ttctcctgaa gtgaatctag ctctgaaggc atggcgcgta    420
cgaagcagac tgctcgcaag tccaccggcg gcaaggctcc gcgcaagcag ctggccacca    480
aggcggctcg gaagagcgct ccggccaccg gcggtgtcaa gaagccccat cgctatcggc    540
ctggtacagt ggctctccgc gagattcgcc gctaccagaa gtccaccgag ctgctgatca    600
gaaagctgcc ttttcagcgt ctggtgcgtg agatcgcgca ggacttcaag accgacttgc    660
gcttccagag ctccgcggtg atggcgctgc aagaggcatg cgaggcctac ctggtggggc    720
tctttgagga caccaacctg tgcgccatcc acgccaagcg ggtgactatc atgcccaagg    780
acatccagct cgcacgtcgt atccgcggcg agagggcttg agtctcaagg actcactgat    840
tacataccca aaggctcttt tcagagccac ccacatgcgc gctgaaaaga tctgtttctc    900
```

-continued

```
tcaggaattc ttcctggtac ttgttttgcc tgtagtagat agggcccatt tccagacgtt     960

atacaatctg tttcgtaaga ctcagcctat cccttttttga atgctaattt tgggagtctt   1020

aacatctaat aatgtccggc atttttccgt aagcattgag tgtagccaaa agttccttcg   1080

tgtattgctc tcccatctcc gcagcccggt tttgaccgga tggtgcttct aattttctgc   1140

taacctgtac tgtggtgtgt gtatatttct tgccaacacg ccagaaataa aactaaggtt   1200

gtactgaagt tggaaaaatt caggtta                                        1227
```

<210> SEQ ID NO 427
<211> LENGTH: 3728
<212> TYPE: DNA
<213> ORGANISM: Homo sapiens

<400> SEQUENCE: 427

```
cttttcctcc tcagctccgg ctccgccgcc acgattggcc agccgaccac ccggcctcgg     60

ccaataagcg ccgccctctc gcccccgtgt tactgggtag aagaaaacaa aaacaaacag    120

agcgagaagg gccagagact ctccgaggcg gcggcagaga cagaagagcg gggtcggggc    180

cggctgacca ggaacctggg cgagcagcgg cgggggcccg agggattctg aaggaagatt    240

tccattaggt aatttgttta atcagtgcaa gcgaaattaa gggaaaatgg atgtagaaaa    300

tgagcagata ctgaatgtaa accctgcagg gtattttccc taattctcca tggtgcttca    360

atagcatgtt attatcataa aaatgaacag ttttgtggaa tagatgacca aatatcctga    420

taacttaagt gactctctct tttccggtga tgaagaaaat gctgggactg aggaaataaa    480

gaatgaaata aatggaaatt ggatttcagc atcctccatt aacgaagcta gaattaatgc    540

caaggcaaaa aggcgactaa ggaaaaactc atcccgggac tctggcagag gcgattcggt    600

cagcgacagt gggagtgacg cccttagaag tggattaact gtgccaacca gtccaaaggg    660

aaggttgctg gataggcgat ccagatctgg gaaaggaagg ggactaccaa agaaaggtgg    720

tgcaggaggc aaaggtgtct ggggtacacc tggacaggtg tatgatgtgg aggaggtgga    780

tgtgaaagat cctaactatg atgatgacca ggagaactgt gtttatgaaa ctgtagtttt    840

gcctttggat gaaagggcat ttgagaagac tttaacacca atcatacagg aatattttga    900

gcatggagat actaatgaag ttgcggaaat gttaagagat ttaaatcttg gtgaaatgaa    960

aagtggagta ccagtgttgg cagtatcctt agcattggag gggaaggcta gtcatagaga   1020

gatgacatct aagcttcttt ctgacctttg tgggacagta atgagcacaa ctgatgtgga   1080

aaaatcattt gataaattgt tgaaagatct acctgaatta gcactggata ctcctagagc   1140

accacagttg gtgggccagt ttattgctag agctgttgga gatggaattt tatgtaatac   1200

ctatattgat agttacaaag gaactgtaga ttgtgtgcag gctagagctg ctctggataa   1260

ggctaccgtg cttctgagta tgtctaaagg tggaaagcgt aaagatagtg tgtggggctc   1320

tggaggtggg cagcaatctg tcaatcacct tgttaaagag attgatatgc tgctgaaaga   1380

atatttactc tctggagaca tatctgaagc tgaacattgc cttaaggaac tggaagtacc   1440

tcattttcac catgagcttg tatatgaagc tattataatg gttttagagt caactggaga   1500

aagtacattt aagatgattt tggatttatt aaagtccctt tggaagtctt ctaccattac   1560

tgtagaccaa atgaaaagag gttatgagag aatttacaat gaaattccgg acattaatct   1620

ggatgtccca cattcatact ctgtgctgga gcggtttgta gaagaatgtt ttcaggctgg   1680

aataatttcc aaacaactca gagatctttg tccttcaagg ggcagaaagc gttttgtaag   1740

cgaaggagat ggaggtcgtc ttaaaccaga gagctactga atataagaac tcttgcagtc   1800
```

ttagatgtta taaaaatata tatctgaatt gtaagagttg ttagcacaag ttttttttt 1860 ttttttttt aagcacttgt tttgggtaca aggcatttct gacattttat aaacctacat 1920
ttaaggggaa tttttaaagg aaatgttttt tcttttttt ttgtttttcg agggggcaag 1980
gagggacaga aaagtaacct cttcttaagt ggaatattct aataagctac cttttgtaag 2040
tgccatgttt attatctaat cattccaagt tttgcattga tgtctgactg ccactccttt 2100
ctttcaagga cagtgttttt tgtagtaaaa tcactggttt atacaaagct ttatttaggg 2160
ggtaaagtta agctgctaaa accccatgtt ggctgctgct gttgagatac tgtgctttgg 2220
gagtaaaaaa agaaagttat ttctttgtct taaagaattt ttaaaaaatt agtcatgaga 2280
cttattcatc tttccaggga acatactgat tggtcttaaa agactagaca gttaagtaaa 2340
aggtggctgg aacatctatt tttctacaaa actggaaaaa tgaacctggt tctagaagaa 2400
tgtacaccaa aataaaacat gtgaagcagt attgattctt tattgggagt acattttttt 2460
aggtctctta aactttaatt tcacacagta aattttgaat ctcataagga agcatatttg 2520
aacctagtca atttaatctt agtgttccct tgaaaacttt ttttccctac aaaattttaa 2580
gtgaaaaata caatagtaaa ttaagattac actggggaaa aaaatgcagg tatcacttta 2640
ctccattgtt atctgaccta gagcttaatt aagttttaga aatatgtaat accttccatc 2700
attccatcat ccttaaattc tgttaccaaa taatggctaa tgttacaaaa agttatactc 2760
cagagaccca aagcttgaca tttacctaat gtatgagaaa atattaccaa ttaacaataa 2820
agaatgatca tatttttaac ctcttttaca tagcctaata actcagcaag gcctcaacgt 2880
ctgtgctaat ttaaactgcc aaatattgac tgcagcaaac aagaattata ttcagaattt 2940
atgagggtac tgttaggagt atactgctta caggtttaga tatagtctgt tagaattaaa 3000
accaagttta gtgttcatat ttacctcatg ggctttatca agcccatatt acctcagctt 3060
atatatagtt accattttta ggtttttaat tgtttgacac ttggatgata aatgcagtca 3120
ttttattctc aagtgcttaa aattaatgta attaaaagct tagctgacta cagaataggt 3180
gagggtttct taaaaatgag atttaagggc tgggcacggt ggctcatgcc tgtaatccca 3240
gcactttggg aggccgaggt gggcggatca cttgaggttg ggagttcatg accagcttga 3300
ccaacatgaa gaaaccctgt ctctattaaa aatacaaaag tagccaggca tggtggcgca 3360
tgcgtgtaat cccagctact tgggaggctg aggcaggaga attgcttgaa cctgggaggc 3420
agaggttgca gtgagtcgag atggtgccat tgctctcgtt tgggcaacaa gagtgaaact 3480
cttgtctcaa aaaaaaaaaa aaatgaggtt taagacagtt ttgtcattac tggtgggatc 3540
tggtcacaca agatagcatt aaacgtgaca tggcacataa aattggttaa aaaattttgt 3600
tttttaatta cgtaatgtaa aagcccaaca aacactttat gcaagattgg aatgtatctt 3660
caaattcaga tttaataaac atgtaaagat cctctgtaaa aaaaaaaaaa aaaaaaaaaa 3720
aaaaaaaa 3728

<210> SEQ ID NO 428
<211> LENGTH: 622
<212> TYPE: DNA
<213> ORGANISM: Homo sapiens

<400> SEQUENCE: 428
cataaaccct ggcgcgctcg cgggccggca ctcttctggt ccccacagac tcagagagaa 60
cccaccatgg tgctgtctcc tgccgacaag accaacgtca aggccgcctg ggtaaggtc 120

-continued

```
ggcgcgcacg ctggcgagta tggtgcggag gccctggaga ggatgttcct gtccttcccc    180

accaccaaga cctacttccc gcacttcgac ctgagccacg gctctgccca ggttaagggc    240

cacggcaaga aggtggccga cgcgctgacc aacgccgtgg cgcacgtgga cgacatgccc    300

aacgcgctgt ccgccctgag cgacctgcac gcgcacaagc ttcgggtgga cccggtcaac    360

ttcaagctcc taagccactg cctgctggtg accctggccg cccacctccc cgccgagttc    420

acccctgcgg tgcacgcctc cctggacaag ttcctggctt ctgtgagcac cgtgctgacc    480

tccaaatacc gttaagctgg agcctcggta gccgttcctc ctgcccgctg ggcctcccaa    540

cgggccctcc tcccctcctt gcaccggccc ttcctggtct ttgaataaag tctgagtggg    600

cagcaaaaaa aaaaaaaaaa aa                                             622
```

<210> SEQ ID NO 429
<211> LENGTH: 1263
<212> TYPE: DNA
<213> ORGANISM: Homo sapiens

<400> SEQUENCE: 429

```
ttcctttctc tctcagctct ccgtctctct ttctctctca gcctctttct ttctccctgt     60

ctccccccact gtcagcacct cttctgtgtg gtgagtggac cgcttacccc actaggtgaa    120

gatgtcagcc caggagagct gcctcagcct catcaagtac ttcctcttcg ttttcaacct    180

cttcttcttc gtcctcggca gcctgatctt ctgcttcggc atctggatcc tcattgacaa    240

gaccagcttc gtgtcctttg tgggcttggc cttcgtgcct ctgcagatct ggtccaaagt    300

cctggccatc tcaggaatct tcaccatggg catcgccctc ctgggttgtg tgggggccct    360

caaggagctc cgctgcctcc tgggcctgta ttttgggatg ctgctgctcc tgtttgccac    420

acagatcacc ctgggaatcc tcatctccac tcagcgggcc cagctggagc gaagcttgcg    480

ggacgtcgta gagaaaacca tccaaaagta cggcaccaac cccgaggaga ccgcggccga    540

ggagagctgg gactatgtgc agttccagct gcgctgctgc ggctggcact acccgcagga    600

ctggttccaa gtcctcatcc tgagaggtaa cgggtcggag gcgcaccgcg tgccctgctc    660

ctgctacaac ttgtcggcga ccaacgactc cacaatccta gataaggtga tcttgcccca    720

gctcagcagg cttggacacc tggcgcggtc cagacacagt gcagacatct gcgctgtccc    780

tgcagagagc cacatctacc gcgagggctg cgcgcagggc ctccagaagt ggctgcacaa    840

caaccttatt tccatagtgg gcatttgcct gggcgtcggc ctactcgagc tcgggttcat    900

gacgctctcg atattcctgt gcagaaacct ggaccacgtc tacaaccggc tcgctcgata    960

ccgttaggcc ccgccctccc caaagtcccg ccccgccccc gtcacgtgcg ctgggcactt   1020

ccctgctgcc tgtaaatatt tgtttaatcc ccagttcgcc tggagccctc cgccttcaca   1080

ttcccctggg gacccacgtg gctgcgtgcc cctgctgctg tcacctctcc cacgggacct   1140

ggggctttcg tccacagctt cctgtcccca tctgtcggcc taccaccacc cacaagatta   1200

tttttcaccc aaacctcaaa taaatcccct gcgtttttgg taaaaaaaaa aaaaaaaaaa   1260

aaa                                                                 1263
```

<210> SEQ ID NO 430
<211> LENGTH: 1027
<212> TYPE: DNA
<213> ORGANISM: Homo sapiens

<400> SEQUENCE: 430

```
gggcaagagt tgggcaaaaa aatcaaggta tttggtcccg gaacaaagct tatcattaca     60
```

gataaacaac ttgatgcaga tgtttccccc aagcccacta tttttcttcc ttcaattgct 120
gaaacaaagc tccagaaggc tggaacatac ctttgtcttc ttgagaaatt tttccctgat 180
gttattaaga tacattggca agaaaagaag agcaacacga ttctgggatc ccaggagggg 240
aacaccatga agactaacga cacatacatg aaatttagct ggttaacggt gccagaaaag 300
tcactggaca aagaacacag atgtatcgtc agacatgaga ataataaaaa cggagttgat 360
caagaaatta tctttcctcc aataaagaca gatgtcatca caatggatcc caaagacaat 420
tgttcaaaag atgcaaatga tacactactg ctgcagctca caaacacctc tgcatattac 480
atgtacctcc tcctgctcct caagagtgtg gtctattttg ccatcatcac ctgctgtctg 540
cttagaagaa cggctttctg ctgcaatgga gagaaatcat aacagacggt ggcacaagga 600
ggccatcttt tcctcatcgg ttattgtccc tagaagcgtc ttctgaggat ctagttgggc 660
tttctttctg ggtttgggcc atttcagttc tcatgtgtgt actattctat cattattgta 720
taacggtttt caaaccagtg ggcacacaga gaacctcact ctgtaataac aatgaggaat 780
agccacggcg atctccagca ccaatctctc catgttttcc acagctcctc cagccaaccc 840
aaatagcgcc tgctatagtg tagacatcct gcggcttcta gccttgtccc tctcttagtg 900
ttctttaatc agataactgc ctggaagcct ttcattttac acgccctgaa gcagtcttct 960
ttgctagttg aattatgtgg tgtgtttttc cgtaataagc aaaataaatt taaaaaaatg 1020
aaaagtt 1027

<210> SEQ ID NO 431
<211> LENGTH: 1399
<212> TYPE: DNA
<213> ORGANISM: Homo sapiens

<400> SEQUENCE: 431
agtgtgaaat cttcagagaa gaatttctct ttagttcttt gcaagaaggt agagataaag 60
acactttttc aaaaatggca atggtatcag aattcctcaa gcaggcctgg tttattgaaa 120
atgaagagca ggaatatgtt caaactgtga agtcatccaa aggtggtccc ggatcagcgg 180
tgagccccta tcctaccttc aatccatcct cggatgtcgc tgccttgcat aaggccataa 240
tggttaaagg tgtggatgaa gcaaccatca ttgacattct aactaagcga aacaatgcac 300
agcgtcaaca gatcaaagca gcatatctcc aggaaacagg aaagcccctg gatgaaacac 360
ttaagaaagc ccttacaggt caccttgagg aggttgtttt agctctgcta aaaactccag 420
cgcaatttga tgctgatgaa cttcgtgctg ccatgaaggg ccttggaact gatgaagata 480
ctctaattga gattttggca tcaagaacta acaaagaaat cagagacatt aacagggtct 540
acagagagga actgaagaga gatctggcca aagacataac ctcagacaca tctggagatt 600
ttcggaacgc tttgctttct cttgctaagg gtgaccgatc tgaggacttt ggtgtgaatg 660
aagacttggc tgattcagat gccagggcct tgtatgaagc aggagaaagg agaaagggga 720
cagacgtaaa cgtgttcaat accatcctta ccaccagaag ctatccacaa cttcgcagag 780
tgtttcagaa atacaccaag tacagtaagc atgacatgaa caaagttctg gacctggagt 840
tgaaaggtga cattgagaaa tgcctcacag ctatcgtgaa gtgcgccaca agcaaaccag 900
ctttctttgc agagaagctt catcaagcca tgaaaggtgt tggaactcgc cataaggcat 960
tgatcaggat tatggtttcc cgttctgaaa ttgacatgaa tgatatcaaa gcattctatc 1020
agaagatgta tggtatctcc ctttgccaag ccatcctgga tgaaaccaaa ggagattatg 1080
agaaaatcct ggtggctctt tgtggaggaa actaaacatt cccttgatgg tctcaagcta 1140
tgatcagaag actttaatta tatattttca tcctataagc ttaaatagga aagtttcttc 1200
aacaggatta cagtgtagct acctacatgc tgaaaaatat agcctttaaa tcatttttat 1260
attataactc tgtataatag agataagtcc attttttaaa aatgttttcc ccaaaccata 1320
aaaccctata caagttgttc tagtaacaat acatgagaaa gatgtctatg tagctgaaaa 1380
taaaatgacg tcacaagac 1399

<210> SEQ ID NO 432
<211> LENGTH: 1200
<212> TYPE: DNA
<213> ORGANISM: Homo sapiens

<400> SEQUENCE: 432
cagttaaaag gaggcgcctg ctggcctccc cttacagtgc ttgttcgggg cgctccgctg 60
gcttcttgga caattgcgcc atgtgtgctg ctcggctagc ggcggcggcg gcggcggccc 120
agtcggtgta tgccttctcg gcgcgcccgc tggccggcgg ggagcctgtg agcctgggct 180
ccctgcgggg caaggtacta cttatcgaga atgtggcgtc cctctgaggc accacggtcc 240
gggactacac ccagatgaac gagctgcagc ggcgcctcgg accccggggc ctggtggtgc 300
tcggcttccc gtgcaaccag tttgggcatc aggtgcgccg ggcggagcgg ggcggggcgg 360
gggcggacgt gcagtagtgg ctgggggcgc cggcggtgtg ctggtgggtg ccgtcggctc 420
catgcgcgga gagtctggct actctctcgt ttcctttctg ttgctcgtag ctgctgaaat 480
tcctctccgc ccttgggatt gcgcatggag ggcaaaatcc cggtgactca tagaaaatct 540
cccttgtttg tggttagaac gtttctctcc tcctcttgac cccgggttct agctgccctt 600
ctctcctgta ggagaacgcc aagaacgaag agattctgaa ttccctcaag tacgtccggc 660
ctggtggtgg gttcgagccc aacttcatgc tcttcgagaa gtgcgaggtg aacggtgcgg 720
gggcgcaccc tctcttcgcc ttcctgcggg aggccctgcc agctcccagc gacgacgcca 780
ccgcgcttat gaccgacccc aagctcatca cctggtctcc ggtgtgtcgc aacgatgttg 840
cctggaactt tgagaagttc ctggtgggcc ctgacggtgt gcccctacgc aggtacagcc 900
gccgcttcca gaccattgac atcgagcctg acatcgaagc cctgctgtct caagggccca 960
gctgtgccta gggcgcccct cctaccccgg ctgcttggca gttgcagtgc tgctgtctcg 1020
ggggggtttt catctatgag ggtgtttcct ctaaacctac gagggaggaa cacctgatct 1080
tacagaaaat accacctcga gatgggtgct ggtcctgttg atcccagtct ctgccagacc 1140
aaggcgagtt tccccactaa taaagtgccg ggtgtcagca gaaaaaaaaa aaaaaaaaaa 1200

<210> SEQ ID NO 433
<211> LENGTH: 10238
<212> TYPE: DNA
<213> ORGANISM: Homo sapiens

<400> SEQUENCE: 433
ggattcctcc agtccctccc tcggccgcct ctcctcccgg agcgagcgcg cagccctgcg 60
cagcagcgcc cactggtccc gtcctgtgag ccccggcccc agccgcggac agacccgcgg 120
agtcgcctcc cggcccaccc gcccggccgc cgaggagcgg gaggaggacg ggaccccggc 180
gcccccaccc catccccggg agaactctaa gaaggagctg atgtggagga gcagctgaga 240
cagttcaaga tgacgaccac agtagccaca gactatgaca acattgagat ccagcagcag 300
tacagtgatg tcaacaaccg ctgggatgtc gacgactggg acaatgagaa cagctctgcg 360
cggctttttg agcggtcccg catcaaggct ctggcagatg agcgtgaagc cgtgcagaag 420
aagaccttca ccaagtgggt caattcccac cttgcccgtg tgtcctgccg gatcacagac 480
ctgtacactg accttcgaga tggacggatg ctcatcaagc tgctggaggt cctctctgga 540
gagaggctgc ctaaacccac caagggacga atgcgcatcc actgcttaga gaatgtggac 600
aaggcccttc agttcctgaa ggagcagaga gtccatcttg agaacatggg gtcccatgac 660
atcgtggatg gaaaccaccg gctgaccctt ggcctcatct ggaccatcat cctgcgcttc 720
cagatccagg atatcagtgt ggaaactgaa gacaacaaag agaagaaatc tgccaaggat 780
gcattgctgt tgtggtgcca gatgaagaca gctgggtacc ccaatgtcaa cattcacaat 840
ttcaccacta gctggaggga cggcatggcc ttcaatgcac tgatacacaa acaccggcct 900
gacctgatag attttgacaa actaaagaaa tctaacgcac actacaacct gcagaatgca 960
tttaatctgg cagaacagca cctcggcctc actaaactgt tggaccccga agacatcagc 1020
gtggaccatc ctgatgagaa gtccataatc acttatgtgg tgacttatta ccactacttc 1080
tctaagatga aggccttagc tgttgaagga aaacgaattg gaaaggtgct tgacaatgct 1140
attgaaacag aaaaaatgat tgaaaagtat gaatcacttg cctctgacct tctggaatgg 1200
attgaacaaa ccatcatcat tctgaacaat cgcaaatttg ccaattcact ggtcggggtt 1260
caacagcagc ttcaggcatt caacacttac cgcactgtgg agaaaccacc caaatttact 1320
gagaagggga acttggaagt gctgctcttc accattcaga gcaagatgag ggccaacaac 1380
cagaaggtct acatgccccg ggaggggaag ctcatctctg acatcaacaa ggcctgggaa 1440
agactggaaa aagcggaaca cgaaagagaa ctggctttgc ggaatgagct cataagacag 1500
gagaaactgg aacagctcgc ccgcagattt gatcgcaagg cagctatgag ggagacttgg 1560
ctgagcgaaa accagcgtct ggtgtctcag gacaactttg ggtttgacct tcctgcagtt 1620
gaggccgcca caaaaaagca cgaggccatt gagacagaca ttgccgcata cgaggagcgt 1680
gtgcaggctg tggtagccgt ggccagggag ctcgaggccg agaattacca cgacatcaag 1740
cgcatcacag cgaggaagga caatgtcatc cggctctggg aatacctact ggaactgctc 1800
agggcccgga gacagcggct cgagatgaac ctggggctgc agaagatatt ccaggaaatg 1860
ctctacatta tggactggat ggatgaaatg aaggtgctag tattgtctca agactatggc 1920
aaacacttac ttggtgtgga agacctgtta cagaagcaca ccctggttga agcagacatt 1980
ggcatccagg cagagcgggt gagaggtgtc aatgcctccg cccagaagtt cgcaacagac 2040
ggggaaggtt acaagccctg tgacccccag gtgatccgag accgcgtggc ccacatggag 2100
ttctgttatc aagagctttg ccagctggcg gctgagcgca gggcccgtct ggaagagtcc 2160
cgccgcctct ggaagttctt ctgggagatg gcagaagagg aaggctggat acgggagaag 2220
gagaagatcc tgtcctcgga cgattacggg aaagacctga ccagcgtcat gcgcctgctc 2280
agcaagcacc gggcgttcga ggacgagatg agcggccgca gtggccactt tgagcaggcc 2340
atcaaggaag gcgaagacat gatcgcggag gagcacttcg ggtcggagaa gatccgtgag 2400
aggatcattt acatccggga gcagtgggcc aacctagagc agctctcggc cattcggaag 2460
aagcgcctgg aggaggcctc cctgctgcac cagttccagg cagatgctga tgacattgat 2520
gcctggatgc tggacatcct caagattgtc tccagcagcg acgtgggcca cgatgagtat 2580
tccacacagt ctctggtcaa gaaacacaag gacgtggcgg aagagatcgc caattacagg 2640
cccacccttg acacgctgca cgaacaagcc agcgccctcc cccaggagca tgccgagtct 2700

```
ccagacgtga ggggcaggct gtcgggcatc gaggagcggt ataaggaggt ggcagagctg   2760
acgcggctgc ggaagcaggc actccaggac actctggccc tgtacaagat gttcagcgag   2820
gctgatgcct gtgagctctg gatcgacgag aaggagcagt ggctcaacaa catgcagatc   2880
ccagagaagc tggaggatct ggaggtcatc cagcacagat ttgagagcct agaaccagaa   2940
atgaacaacc aggcttcccg ggttgcagtg gtgaaccaga ttgcacgcca gctgatgcac   3000
agcggccacc caagtgagaa ggaaatcaaa gcccagcagg acaaactcaa cacaaggtgg   3060
agccagttca gagaactggt tgacaggaag aaggatgccc tcctgtctgc cctgagcatc   3120
cagaactacc acctcgagtg caatgaaacc aaatcctgga ttcgggaaaa gaccaaggtc   3180
atcgagtcca cccaggacct gggcaatgac ctggctggcg tcatggccct gcagcgcaag   3240
ctgaccggca tggagcggga cttggtggcc attgaggcaa agctgagtga cctgcagaag   3300
gaggcggaga agctggagtc cgagcacccc gaccaggccc aggccatcct gtctcggctg   3360
gccgagatca gcgacgtgtg ggaggagatg aagaccaccc tgaaaaaccg agaggcctcc   3420
ctgggagagg ccagcaagct gcagcagttc ctacgggact tggacgactt ccagtcctgg   3480
ctctctagga cccagacagc gatcgcctcg gaggacatgc caaacaccct gaccgaggct   3540
gagaagctgc tcacgcagca cgagaacatc aagaacgaga tcgacaacta cgaggaggac   3600
taccagaaga tgagggacat gggcgagatg gtcacccagg ggcagaccga tgcccagtac   3660
atgtttctgc ggcagcggct gcaggccctg gacactggat ggaacgagct ccacaagatg   3720
tgggagaaca gacaaaatct cctatcccag tcacatgcct accagcagtt cctcagagac   3780
acgaagcaag ccgaagcctt tcttaacaac caggagtatg ttctggctca cactgaaatg   3840
cctaccacct tggaaggagc tgaagcagca attaaaaagc aagaggactt catgaccacc   3900
atggacgcca atgaggagaa gatcaatgct gtggtggaga ctggccggag gctggtgagc   3960
gatgggaaca tcaactcaga tcgcatccag gagaaggtgg actctattga tgacagacat   4020
aggaagaatc gtgagacagc cagtgaactt ttgatgaggt tgaaggacaa cagggatcta   4080
cagaaattcc tgcaagattg tcaagagctg tctctctgga tcaatgagaa gatgctcaca   4140
gcccaggaca tgtcttacga tgaagccaga aatctgcaca gtaaatggtt gaagcatcaa   4200
gcatttatgg cagaacttgc atccaacaaa gaatggcttg acaaaatcga gaaggaagga   4260
atgcagctca tttcagaaaa gcctgagacg gaagctgtgg tgaaggagaa actcactggt   4320
ttacataaaa tgtgggaagt ccttgaatcc actacccaga caaaggccca gcggctcttt   4380
gatgcaaaca aggccgaact tttcacccag agctgtgcag atctagacaa atggctgcac   4440
ggcctggaga gtcagattca gtctgatgac tatggcaaag acctgaccag tgtcaatatc   4500
ctgctgaaaa agcaacagat gctggagaat cagatggaag tgcggaagaa ggagatcgaa   4560
gagctccaaa gccaagccca ggccctgagt caggaaggga agagcaccga cgaggtagac   4620
agcaagcgcc tcaccgtgca gaccaagttc atggagttgc tggagccctt gaacgagagg   4680
aagcataacc tgctggcctc caaagagatc catcagttca acagggatgt ggaggacgag   4740
atcttgtggg ttggagagag gatgcctttg gcaacttcca cggatcatgg ccacaacctc   4800
cagactgtgc agctgttaat aaagaaaaat cagaccctcc agaaagaaat ccaggggcac   4860
cagcctcgca ttgacgacat ctttgagagg agccaaaaca tcgtcactga cagcagcagc   4920
ctcagcgctg aggccatcag acagaggctt gccgacctga agcagctgtg ggtctcctc    4980
attgaggaga cagagaaacg ccacaggcgg ctggaggagg cgcacagggc ccagcagtac   5040
tactttgacg ctgctgaggc cgaagcctgg atgagcgagc aggagctgta catgatgtca   5100
```

```
gaggagaagg ccaaggatga gcagagtgct gtctccatgt tgaagaagca ccagatctta   5160
gaacaagctg tggaggacta tgcagagacc gtgcatcagc tctccaagac cagccgggcc   5220
ctggtggccg acagccatcc tgaaagtgag cgcattagca tgcggcagtc caaagtggat   5280
aaactgtacg ctggtctgaa agaccttgct gaagagagaa gaggcaagct ggatgagaga   5340
cacaggttat tccagctcaa ccgggaggtg gacgacctgg agcagtggat cgctgagagg   5400
gaggtggtcg cagggtccca tgaactggga caggactatg agcatgtcac gatgttacaa   5460
gaacgattcc gggagtttgc ccgagacacc gggaacattg ggcaggagcg cgtggacacg   5520
gtcaatcacc tggcagatga gctcatcaac tctggacatt cagatgccgc caccatcgct   5580
gaatggaagg atggcctcaa tgaagcctgg gccgacctcc tggagctcat tgacacaaga   5640
acacagattc ttgccgcttc ctatgaactg cacaagtttt accacgatgc caaggagatc   5700
tttgggcgta tacaggacaa acacaagaaa ctccctgagg agcttgggag agatcagaac   5760
acagtggaga ccttacagag aatgcacact acatttgagc atgacatcca ggctctgggc   5820
acacaggtga ggcagctgca ggaggatgca gcccgcctcc aggcggccta tgcgggtgac   5880
aaggccgacg atatccagaa gcgcgagaac gaggtcctgg aagcctggaa gtccctcctg   5940
gacgcctgtg agagccgcag ggtgcggctg gtggacacag gggacaagtt ccgcttcttc   6000
agcatggtgc gcgacctcat gctctggatg gaggatgtca tccggcagat cgaggcccag   6060
gagaagccaa gggatgtatc atctgttgaa ctcttaatga ataatcatca aggcatcaaa   6120
gctgaaattg atgcacgtaa tgacagtttc acaacctgca ttgaacttgg gaaatccctg   6180
ttggcgagaa aacactatgc atctgaggag atcaaggaaa aattactgca gttgacggaa   6240
aagaggaaag aaatgatcga caagtgggaa gaccgatggg aatggttaag actgattctg   6300
gaggtccatc agttctcaag agacgccagt gtggccgagg cctggctgct tggacaggag   6360
ccgtacctat ccagccgaga gataggccag agcgtggacg aggtggagaa gctcatcaag   6420
cgccacgagg catttgaaaa gtctgcagca acctgggatg agaggttctc tgccctggaa   6480
aggctgacta cattggagtt actggaagtg cgcagacagc aagaggaaga ggagaggaag   6540
aggcggccgc cttctcccga gccgagcacg aaggtttcag aggaagccga gtcccagcag   6600
cagtgggata cttcaaaagg agaacaagtt tcccaaaacg gtttgccagc tgaacaggga   6660
tctccacgga tggcagaaac ggtggacaca agcgaaatgg tcaacggcgc tacagaacaa   6720
aggacgagct ctaaagagtc cagccccatc cctccccga cctctgatcg taaagccaag    6780
actgccctcc cagcccagag tgccgccacc ttaccagcca gaacccagga gacaccttcg   6840
gcccagatgg aaggcttcct caatcggaaa cacgagtggg aggcccacaa taagaaagcc   6900
tcaagcaggt cctggcacaa tgtttattgt gtcataaata accaagaaat gggtttctac   6960
aaagatgcaa agactgctgc ttctggaatt ccctaccaca gcgaggtccc tgtgagtttg   7020
aaagaagctg tctgcgaagt ggcccttgat tacaaaaaga agaaacacgt attcaagcta   7080
agactaaatg atggcaatga gtacctcttc caagccaaag acgatgagga aatgaacaca   7140
tggatccagg ctatctcttc cgccatctcc tctgataaac acgaggtgtc tgccagcacc   7200
cagagcacgc cagcatccag ccgcgcgcag accctcccca ccagcgtcgt caccatcacc   7260
agcgagtcca gtcccggcaa gcgggaaaag gacaaagaga aagacaaaga gaagcggttc   7320
agcctttttg gcaaaaagaa atgaactcct ttccttcacc tcctgccctt ctcttacctt   7380
ttcagtgaaa ttccagcatg caagctcaga accaacacat tactctctgt gcctaatgtt   7440
```

-continued

```
cctcaatgtg gttgattttt tttttttttt aatttataga gcatttcggg gggggtgggg   7500
gaaacacacc taaacacttt atctccaagt tacaaaagtt tgaggtgcag agggaaggcc   7560
agattttttt tttaatgaaa ttatatagat tagatctcag tatttaaact gttcctcaat   7620
tttgtgaggc tgtgttggaa ataacccgcc tctagtgctg ttggtatgca aggcagcggt   7680
gcttaatcaa tatttcctgt gctcaccaga ggcaaaatgt accaatatcc tgacaccatt   7740
ctctctccat ttacttctgg tggttaccct gactcttgac tcttagaagt gcccgagatg   7800
gggctaacct ttattaaaca gatcgcatat tatgatcttg ctgcagccac agtgcagctc   7860
cacattaact ctacagacca aaccatttgt atctggcatc acttactaac acacgacatg   7920
cggcttttct gcatcaactg ctatgacggt taagaatgtc agtatacaag aaggaataga   7980
aaactgatac tgttttaaat aatctgtaat ttcaattttt ttttttgct gaaatacatt   8040
atattgtacg tttgagataa ttctagtaca aagtataata aaactagatg tataataaac   8100
cctttaaatc attggtaagt gtacaagtgg tggaactgaa gcatttactg gacaaagtaa   8160
tgttactcta atggttactt gctcgtgcgt tgccacactg tgttataatt tgcttcattt   8220
ccttgctatt tgatacatag tgtgcatttc tctgtcactg taactattgt aatgacaaat   8280
tttcatctta ctgcacaatc aaaatgacat tgataggaat gaactccaga ggctgggcct   8340
gaacagggag gtggtcgctc aggcctggtg ctcagtcgta cgacctgtac ctctcaactt   8400
ttgccctatc tgttaaatat atgctatgtc attaaatgct tttaaatcta gcacggtgac   8460
tagttgttgt tcttcctctg ctgcgtgtgc atgcccagta gggaaactgc aaagggagaa   8520
atgacaaaca agaaacattt tacaaccagt ctgggctcac ttttgcattt tttatgcatg   8580
tctggtgcac aagctttgaa aactacagca aacagtaata aatgtgactg ttttgtagtt   8640
atacattcag gctttatctt ttatttatga aaaagttacc agagcacttg tgaaacctga   8700
actctgagat aggggttggc aaatttgttc tgtaaaggga cagagatagt aaatatttta   8760
ggctttgtag gccgtaactg tctctgttgc tcaattctgc tgttgcgtaa tacaaaggca   8820
gccattgacg gtatgtgaat gcctgggcat ggctgtgttc cagtaaaact atttaaggac   8880
ataaatttga atttcatata actttgacat gccatacaat attttgattt tcttaatgat   8940
ttcaaaatgt aaagtctatt ttatacagat cagaccaaaa agaagaaaaa aaaaaaacag   9000
gcaagaggtt aggtttggcc catgggccat agtttgctga cttcagcata gagtcgtggg   9060
ttatttacaa gtgacatact tttcctgggt tatctgggta tgttgactcc atgccacttg   9120
cataaagcag caatggatat tagtattatg gatgtccagt aagttattcc acaaagacca   9180
tgcctaaggt ggcatcagcc ctgggctcca cagctgcgtg gcatcaaagc tttctcttaa   9240
ctctcttacc tctaggcaaa ctgagacctc accatcctct cccctgcttc ccacgacagt   9300
cctttgccct tgccatgctc agggttggaa tcaagttgtt ctattctcaa cagaccaaaa   9360
tgtttagtta aggcaaagta tcttggaaac aattgtgatt aattacagtc ttgtactctt   9420
gacaaagctg tgcagatggc aataagttca taccagcaat cctggagtcc cataataaat   9480
acgtacatgt ggaacatcgt gcacataatt tcaacagttc gcagatctgt agttatgaag   9540
ccagggtttg gtggtatttg ctctctcttg gtgcatttga taaggatcca ctgaggcctg   9600
aatgtggaag atgatgggca gcgagaggag cgtcagaaga ccccagtcaa gacgtgttcg   9660
ccatcagagg ttacaggccg cacagcctga tgagcttcaa gcctggcagg gtaaatagtt   9720
tttgggtttt ttgttttttt tttattcttc cactatcatg ttttttgagg attttgcata   9780
tttcttgttg ccataatgct gtgctatttt accctgattt tcagtgatac aatatgggtg   9840
```

```
acaatactgg cccctccata aatctgaaga gtaagaagta gtgaaaataa ggcttaggat   9900
atgaaatggc gttgtcactt gaatcaaggc cactttttgt cctacttgag catctcaagt   9960
tgggatgcat cttctgatgg cacttccgga actggctgtg gtttttttgg gtgtaccgag  10020
agtgccagtg actgtgcttc ttacaattcc tggcatcttg agtaggtgaa acactgtatc  10080
agactgggtg atgggcacat tgtcatttca ccaagttcct ggaactgtta gaattgcttg  10140
tgtatgggga tcctatgtta gttcccctgg atacattgtt ttatcagtcg gaattcttaa  10200
ataaagacat acttcccttc aaaaaaaaaa aaaaaaaa                          10238
```

<210> SEQ ID NO 434
<211> LENGTH: 1632
<212> TYPE: DNA
<213> ORGANISM: Homo sapiens

<400> SEQUENCE: 434

```
gctcagcatt tggggacgct ctcagctctc ggcgcacggc ccaggtaagc ggggcgcgcc     60
ctgcccgccc gcgatgggcc gccagctagc ggggtgtgga gacgctggga agaaggcttc    120
cttcaaaatg tctactgttc acgaaatcct gtgcaagctc agcttggagg gtgatcactc    180
tacacccccca agtgcatatg ggtctgtcaa agcctatact aactttgatg ctgagcggga    240
tgctttgaac attgaaacag ccatcaagac caaaggtgtg gatgaggtca ccattgtcaa    300
cattttgacc aaccgcagca atgcacagag acaggatatt gccttcgcct accagagaag    360
gaccaaaaag gaacttgcat cagcactgaa gtcagcctta tctggccacc tggagacggt    420
gattttgggc ctattgaaga cacctgctca gtatgacgct tctgagctaa aagcttccat    480
gaaggggctg ggaaccgacg aggactctct cattgagatc atctgctcca gaaccaacca    540
ggagctgcag gaaattaaca gagtctacaa ggaaatgtac aagactgatc tggagaagga    600
cattatttcg gacacatctg gtgacttccg caagctgatg gttgccctgg caaagggtag    660
aagagcagag gatggctctg tcattgatta tgaactgatt gaccaagatg ctcgggatct    720
ctatgacgct ggagtgaaga ggaaaggaac tgatgttccc aagtggatca gcatcatgac    780
cgagcggagc gtgccccacc tccagaaagt atttgatagg tacaagagtt acagccctta    840
tgacatgttg gaaagcatca ggaaagaggt taaaggagac ctggaaaatg ctttcctgaa    900
cctggttcag tgcattcaga acaagcccct gtattttgct gatcggctgt atgactccat    960
gaagggcaag ggggacgcgag ataaggtcct gatcagaatc atggtctccc gcagtgaagt   1020
ggacatgttg aaaattaggt ctgaattcaa gagaaagtac ggcaagtccc tgtactatta   1080
tatccagcaa gacactaagg gcgactacca gaaagcgctg ctgtacctgt gtggtggaga   1140
tgactgaagc ccgacacggc ctgagcgtcc agaaatggtg ctcaccatgc ttccagctaa   1200
caggtctaga aaaccagctt gcgaataaca gtccccgtgg ccatccctgt gagggtgacg   1260
ttagcattac ccccaacctc attttagttg cctaagcatt gcctggcctt cctgtctagt   1320
ctctcctgta agccaaagaa atgaacattc caaggagttg gaagtgaagt ctatgatgtg   1380
aaacactttg cctcctgtgt actgtgtcat aaacagatga ataaactgaa tttgtacttt   1440
agaaacacgt actttgtggc cctgctttca actgaattgt ttgaaaatta aacgtgcttg   1500
gggttcagct ggtgaggctg tccctgtagg aagaaagctc tgggactgag ctgtacagta   1560
tggttgcccc tatccaagtg tcgctattta agttaaattt aaatgaaata aaataaaata   1620
aaatcaaaaa aa                                                        1632
```

<210> SEQ ID NO 435
<211> LENGTH: 3492
<212> TYPE: DNA
<213> ORGANISM: Homo sapiens

<400> SEQUENCE: 435
caggccgcag gatggcctgg tcccgggccg ggagcccagc aggccgggag cggctgaggc 60
cacaccccgc gggccgggcc gcttccctcc ggtgaatcat cgctcgcagc ggcggcgccc 120
gcagtggccg cagcagcgcg ccgggccctg gccgcgcccc agccgagcgc agcgcggagt 180
cgccccgacc tttctctgcg cagtacggcc gccgggaccg cagcatggcg ggcatcgcgg 240
ccaagctggc gaaggaccgg gaggcggccg aggggctggg ctcccacgag agggccatca 300
agtacctcaa ccaggactac gaggcgctgc ggaacgagtg cctggaggcc gggacgctct 360
tccaggaccc gtccttcccg gccatcccct cggccctggg cttcaaggag ttggggccct 420
actccagcaa aacccggggc atcgagtgga agcgccccac ggagatctgc gctgaccccc 480
agtttatcat tggaggagcc acccgcacag acatctgcca aggagccctg ggtgactgct 540
ggctgctggc agccattgcc tccctcacct tgaatgaaga aatcctggct cgagtcgtcc 600
ccctaaacca gagcttccag gaaaactatg cagggatctt tcacttccag ttctggcaat 660
acggcgagtg ggtggaggtg gtggtggatg acaggctgcc caccaaggac ggggagctgc 720
tctttgtgca ttcagccgaa gggagcgagt tctggagcgc cctgctggag aaggcatacg 780
ccaagatcaa cggatgctat gaagcgctat caggggggtgc caccactgag ggcttcgaag 840
acttcaccgg aggcattgct gagtggtatg agttgaagaa gccccctccc aacctgttca 900
agatcatcca gaaagctctg caaaaaggct ctctccttgg ctgctccatc gacatcacca 960
gcgccgcgga ctcggaggcc atcacgtttc agaagctggt gaaggggcac gcgtactcgg 1020
tcaccggagc cgaggaggtt gaaagtaacg gaagcctaca gaaactgatc cgcatccgaa 1080
atccctgggg agaagtggag tggacagggc ggtggaatga caactgccca agctggaaca 1140
ctatagaccc agaggagagg gaaaggctga ccagacggca tgaagatgga gaattctgga 1200
tgtctttcag tgacttcctg aggcactatt cccgcctgga gatctgtaac ctgaccccag 1260
acactctcac cagcgatacc tacaagaagt ggaaactcac caaaatggat gggaactgga 1320
ggcggggctc caccgcggga ggttgcagga actacccgaa cacattctgg atgaaccctc 1380
agtacctgat caagctggag gaggaggatg aggacgagga ggatggggag agcggctgca 1440
ccttcctggt ggggctcatt cagaagcacc gacggcggca gaggaagatg ggcgaggaca 1500
tgcacaccat cggctttggc atctatgagg ttccagagga gttaagtggg cagaccaaca 1560
tccacctcag caaaaacttc ttcctgacga atcgcgccag ggagcgctca gacaccttca 1620
tcaacctccg ggaggtgctc aaccgcttca agctgccgcc aggagagtac attctcgtgc 1680
cttccacctt cgaacccaac aaggatgggg atttctgcat ccgggtcttt tctgaaaaga 1740
aagctgacta ccaagctgtc gatgatgaaa tcgaggccaa tcttgaagag ttcgacatca 1800
gcgaggatga cattgatgat ggattcagga gactgtttgc ccagttggca ggagaggatg 1860
cggagatctc tgcctttgag ctgcagacca tcctgagaag ggttctagca aagcgccaag 1920
atatcaagtc agatggcttc agcatcgaga catgcaaaat tatggttgac atgctagatt 1980
cggacgggag tggcaagctg gggctgaagg agttctacat tctctggacg aagattcaaa 2040
aataccaaaa aatttaccga gaaatcgacg ttgacaggtc tggtaccatg aattcctatg 2100
aaatgcggaa ggcattagaa gaagcaggtt tcaagatgcc ctgtcaactc caccaagtca 2160
tcgttgctcg gtttgcagat gaccagctca tcatcgattt tgataatttt gttcggtgtt 2220
tggttcggct ggaaacgcta ttcaagatat ttaagcagct ggatcccgag aatactggaa 2280
caatagagct cgaccttatc tcttggctct gtttctcagt actttgaagt tataactaat 2340
ctgcctgaag acttctcatg atggaaaatc agccaaggac taagcttcca tagaaataca 2400
ctttgtatct ggacctcaaa attatgggaa catttactta aacggatgat catagctgaa 2460
aataatgata ctgtcaattt gagatagcag aagtttcaca catcaaagta aaagatttgc 2520
atatcattat actaaatgca aatgagtcgc ttaacccttg acaaggtcaa agaaagcttt 2580
aaatctgtaa atagtataca ctttttactt ttacacactt tcctgttcat agcaatatta 2640
aatcaggaaa aaaaaatgca gggaggtatt taacagctga gcaaaaacat tgagtcgctc 2700
tcaaaggaca cgaggccctt ggcagggaat atttaaagca acttcaagtt taaaatgcag 2760
ctgttgattc taccaaacaa cagtccaaga ttaccatttc ccatgagcca actgggaaac 2820
atggtatatc atgaagtaat cttgtcaagg catctggaga gtccaggaga gaagactcac 2880
ctctgtcgct tgggttaaac aagagacagg ttttgtagaa tattgattgg taatagtaaa 2940
tcgttctcct tacaatcaag ttcttgaccc tattcggcct tatacatctg gtcttacaaa 3000
gaccaaaggg atcctgcgct tgatcaactg aaccagtatg ccaaaaccag gcatccaatt 3060
tgtaaaccaa ttatgataaa ggacaaaata agctgtttgc cacctcaaaa ctttatgaac 3120
ttcaccacca ctagtgtctg tccatggagt tagaggggac atcacttaga agttcttata 3180
gaaaggacac aagtttgttt cctggcttta ccttgggaaa atgctagcaa cattatagaa 3240
attttgcctt gttgccttat cttcttccaa atgtactgtt aaataaaaat aaagggttac 3300
cccatgcaat cacaccatgc catgttttcc ttcctggagg gcagccccac aggacggttt 3360
atgagcacac aattatagct tgtttctact ttaacaaggt atgctgcctc tgtaaattca 3420
tgtattcaaa ggaaaagaca ccttgcctat aattaaaatg tggaactata aaattttta 3480 aaatccaaaa aa 3492

<210> SEQ ID NO 436
<211> LENGTH: 5887
<212> TYPE: DNA
<213> ORGANISM: Homo sapiens

<400> SEQUENCE: 436
ctcttttccc tcacagcccg ggcgccgggc ggcgagtgcg ttagtcggcc gggacgcgga 60
gctgtgtgca tctcctacgc gggctcgctc gctcccggga gccgcgcagc ttccccggcg 120
gtggcaggag cggcgaagag cgccatcagc gggcccttac ggccccaggc ctcgcggcgc 180
gcggtccgct cgccctcctc gtccgcccaa cctgcggcct gtggaggcgt gaggcgacga 240
caggcgagcg cctcgagcag cgttagccgc tgcggccgcc ggtcctccct ccacctcctc 300
ctcggccccc cctcgcttcc ctcctcccac ttcccgagct ccggcgtgtc ccggccacgc 360
tcgacgctgc tgcaggaaca aaggaagacc ccgcggcggc ggcggcgcca cctccgcctg 420
ctgctccgac ccgctcccgg cccgcggcgg cggcaccagg gcgcccggct cagccttccc 480
ggaggcctcg gcccggcctc atcgtgccgg cttcgcgcgc gaacccggct ttcgcatttg 540
ggaccctgca gggccctgaa aaggagcctt taaaagtcaa ttctactcca tttggcaaag 600
agggaactga aatctggaaa gtaaggactt gcccaaggtc actgacttag tggcagacta 660
gagacttgaa ctcaggtctc cattcccagc agaaaaatat ggctcaggag actaaccaga 720

-continued

```
ccccggggcc catgctgtgt agcacaggat gtggctttta tggaaatcct aggacaaatg    780
gaatgtgttc agtttgctac aaagaacatc ttcagaggca gcaaaatagt ggcagaatga    840
gcccaatggg gacagctagt ggttccaaca gtcctacctc agattctgca tctgtacaga    900
gagcagacac tagcttaaac aactgtgaag gtgctgctgg cagcacatct gaaaaatcaa    960
gaaatgtgcc tgtggctgcc ttgcctgtaa ctcagcaaat gacagaaatg agcatttcaa   1020
gagaggacaa aataactacc ccgaaaacag aggtgtcaga gccagttgtc actcagccca   1080
gtccatcagt ttctcagccc agtacttctc agagtgaaga aaaagctcct gaattgccca   1140
aaccaaagaa aaacagatgt ttcatgtgca gaaagaaagt tggtcttaca gggtttgact   1200
gccgatgtgg aaatttgttt tgtggacttc accgttactc tgacaagcac aactgtccgt   1260
atgattacaa agcagaagct gcagcaaaaa tcagaaaaga gaatccagtt gttgtggctg   1320
aaaaaattca gagaatataa attacttctt gtgaagagac tgaaactttg tttttatttt   1380
aatatatcgt aggaaaacat taaagagcag atgcatggcc atttttcttt gatgttctcc   1440
agagttttac attacacttg tctgtcttat aattgatatt ttaggatgtt tgggtgtttg   1500
ttacaggcag aattggatag atacagccct acaaatgtat atgccctccc ctgaaaaaaa   1560
ttggatgaaa atctgcacag caaagtgaaa cacacagata ataggaacaa aatgtagttc   1620
ccatgtgcca aacaaaataa atgaaatctc tgcatgtttg cagcatatct gccttttggg   1680
aatgtaatca aggtataatc tttggctagt gttatgtgcc tgtatttttt taaaatggta   1740
caccagaaaa ggactggcag tctacttcta ccatagttaa acttcaccct ctttaatttc   1800
acaacatatt ctttggaagc aggaagaaat gctcataaag aggatcagac cttctttccc   1860
gtgaaaccag tatttggcgc catatataag cctggttaaa ttggtcatct aaagctgtca   1920
aataagacat tctgtgaaag gtaaacatcg aaactggtta taagtaaaac catcaagcca   1980
acaacagggt cttgagataa cctttgaagc ttattgtact ggcctgcacc agaagatgtc   2040
tgcattactc attgctaaaa atgtgtagca cagaactgca ctaggattaa tttgtttaca   2100
agaagaaatt taaactctac gtttggtttt cacatacagc agctctattg aataacatgc   2160
atctgaattt taagttgcaa aggtatctga ataatttttc atgtgcatct tttgtcgaat   2220
gttttggttc aagaaagaat gtttaaagct ttttaaaaga cttcagttct taatgtaact   2280
gtacccttct gcatggaaaa tcataaccaa catggctgca gtagacttct tagtggtatc   2340
cagcaccact tgcagagggc tgctttatca tattgtactt gggtgtagga ctctagtgtt   2400
cttgggtgta ttgcatgggc tgcattatct acagcattgt acaataacaa ctagaaaagg   2460
cagtatactt cactgatgct tgtctggtaa taatcacttc tgtgttataa tggaaggttt   2520
tttgtgatgt atgaaacttg tgttttttat atataaatga gtatagttag tgttgtggta   2580
atgcctgttt tcatctgtaa atagttaagt atgtacacga ggcactactt ctgatttatt   2640
gcaatgttca gtcctagttt ttacttttat tcttaaagca ttcagttttg ctttcaattt   2700
tatgtacctt agttctgagt tagacctgca gatgtgtaca gatagttcat atttatgtat   2760
tgcacataat catgctattc agcattgatg ctatattgta ttatgtaaat aataaaagcc   2820
atgtacagag ggaaacttca cttgttcatt gggtttttaa gccatagttg gagtcctaaa   2880
gggggaaaat tagaaaatgt tactttacat ggctatataa tttttttcc tttgccatcg    2940
ctgaacttgt tcaagtgata atcaagagat attagaagca tttgcaggta tgatacctga   3000
taggcagttt atttttgaag aattcaatag gcacctttgg gattaaaaca attttaaaat   3060
ttgagaaaga tgaaatttga acaattatgg cctacctcgc ttctccatgt tgtaaaagat   3120
```

-continued

```
gatgttttat gacaattctg aagaagaaag taggtatgac ttagtttaca aaaagagttc   3180
tgttttattt ctgttttggg tttggctcta atacagagat tcacccatgg acttggtctc   3240
tgtagcgttt atgccagatc ataaagaaca aggggtgaca ggtacatgtt gactttacct   3300
ggggtaaatg attaccagag tgcaactgtt gcttctctgt gatggagttt ggggtggaaa   3360
taccctagtt ttatctgtca gttctttgca tgctgctact tttgcttcaa gttagggagg   3420
tacatatgta tgtcaaagtt cctatactga catagggtag tatttctctg aatatgaaaa   3480
gtcacaattg agttgaaaat ttagaagttg aagatttaga agggcaactt aatttttcaa   3540
gttaaaaatg gaagtaagag tggtatagag aaggtaagat gagccctcgg actccatcac   3600
tctgaaggtc tgagtagtag caagagatag atttttgttt ggccaggctg cagtgcaatg   3660
gcgtaatctt ggctcactgc aacctctgcc tcctgggttc aagtgattct cctgcctctg   3720
cctcctaagt agctgggatc acaggcacca gccaccacgc ccagctaatt tttgtatttt   3780
taatagagac agtttctcca tgttggtcag gctggtcttg aactcctgac ctcaggtgag   3840
ctgcccgcct cggcctccca aagtgctggg attacaggcg tgaggcaccg cacccggcca   3900
atcagttttt tttgtttttt ttttgtttgt ttgttttaca agaaacatta aaccagatca   3960
gaacaaagat ttgtcagggt tgtccattga ctggggagaa agggaatcag tgtgtaaggc   4020
acctgagagg actcagttct acccaaattc ttgcattcaa acctgaatgc aaggccatga   4080
agtcctttga aatgtacaga tattaagcaa tttaataata taccatgttt cccttacata   4140
agcagacaaa tatttacacc cccatgacct gaagttttgt taggctgtga ccacatgaat   4200
tcgcagtata aatgggtgag tcctttttga aaacctcatc ttcagtgtgc ctgatctgta   4260
aaactagagc ctcaggtttg atcctaggta ggcttcccac aacgtgggga aaattagttt   4320
gtgagggaaa gctgtttctg agcattatgg catagtgatt aagatgaggg accctggaac   4380
cagcccgtga ttttgggcaa gttattttag gtccactttg gactgcttca tctcttaaat   4440
gaagacagca accaccttca ggagtgtgaa ggtgacaaca cttaaaactg tgcctggcac   4500
attgtatttg ctattgtctt aatgttctgg aataatggtt tccataactt gggaagaaaa   4560
ctttgagaac aggattggtt acatcaagtt gtatagtgaa aagataaaga tttgttattt   4620
aaacttgcag tttaaagtca ttagaatcat tcttttccgt aaggctttct ttgcaagaga   4680
tctgcattaa ataaagttgc taggaaataa ctaaaattgg ggaaataatc taataatagc   4740
aagatgttaa gcatactatt attgtatttt gggggttggt aataacattc acatggattt   4800
atcaatacac actgagaagc aaagcctctc aagctgtccc atatcctcca tttcaaaggc   4860
acacatacat tttaggtaac tcataattta gaaaggttat ttaatctttt ccacatgtaa   4920
atatttgaat atgtacaaag acttgatttg actcttgtct gtttttgttt tgttttgttt   4980
gtttgagaca gaggctccgt cgcccaggct ggagtaaaat ggcatggtct cagctcactg   5040
caagttccgc ctcccgggtt cacgccattc tcctggctca gcctccggag tagttgggac   5100
tacaggcacc cgtcaccaca cctggctaat gtttttttgtt ttttgggttt ttttgtattt   5160
ttagtagaga gagggtttca ccgtgttagc cagggtggtc tcgatctcct gacctcatga   5220
tccgcccacc ccggcctccc aaaatgctgg gattacaggt gtgagccact gcgcctggcc   5280
gactcttgtc tgtttgaatg caaagttctc aatagtggtt tttgtccata agtattaact   5340
tataattttg gagagtgata ggtatggttg ctggttgatt agcaataaga ttatgtagcc   5400
ttaaactagc tagaagagtt tgcatgggtg aggcaacagg ctgttaacaa aaagaaactg   5460
```

gaaatacagt ttcccctgtt tgtttctcct gtttgtacaa tctgctttaa aaacaagtga 5520
acatgcacca tgtcagtcat ggtgaatcgg ccaacagcca gcccttgcca gttgacatca 5580
cagtctaaga tgggaaactg gtacagatag acatgaagag agcttagcag tggttgaggt 5640
ggtgactaaa tatacagtca ttgaataaat accgtgtagc aaatgtaaaa aaaaaaaaaa 5700
aagtacaaca gaatacaaaa gtgccattta atattttata gctatttcta tgcacaagtg 5760
ctggttttaa atttatataa aagcaaagac tgtttctgtg ttttcttcca gagtatttct 5820
gttacagcca tagaagtaaa gttaataaat gtaagacttt ttttgtttaa aaaaaaaaaa 5880
aaaaaaa 5887

<210> SEQ ID NO 437
<211> LENGTH: 482
<212> TYPE: DNA
<213> ORGANISM: Homo sapiens

<400> SEQUENCE: 437
gcgggcgccg ctcttttgtt tcttgctgca gcaacgcgag tgggagcacc aggatctcgg 60
gctcggaacg agactgcacg gattgtttta agaaaatggc agacaaacca gacatggggg 120
aaatcgccag cttcgataag gccaagctga agaaaacgga gacgcaggag aagaacaccc 180
tgccgaccaa agagaccatt gagcaggaga agcggagtga aatttcctaa gatcctggag 240
gatttcctac ccccgtcctc ttcgagaccc cagtcgtgat gtggaggaag agccacctgc 300
aagatggaca cgagccacaa gctgcactgt gaacctgggc actccgcgcc gatgccaccg 360
gcctgtgggt ctctgaaggg accccccccc aatcggactg ccaaattctc cggtttgccc 420
cgggatatta tagaaaatta tttgtatgaa taatgaaaat aaaacacacc tcgtggcatg 480
gc 482

<210> SEQ ID NO 438
<211> LENGTH: 2755
<212> TYPE: DNA
<213> ORGANISM: Homo sapiens

<400> SEQUENCE: 438
attaaagatg atttttacag tcaatgagcc acgtcaggga gcgatggcac ccgcaggcgg 60
tatcaactga tgcaagtgtt caagcgaatc tcaactcgtt ttttccggtg actcattccc 120
ggccctgctt ggcagcgctg caccctttaa cttaaacctc ggccggccgc ccgccggggg 180
cacagagtgt gcgccgggcc gcgcggcaat tggtccccgc gccgacctcc gcccgcgagc 240
gccgccgctt cccttccccg ccccgcgtcc ctccccctcg gccccgcgcg tcgcctgtcc 300
tccgagccag tcgctgacag ccgcggcgcc gcgagcttct cctctcctca cgaccgaggc 360
agagcagtca ttatggcgaa ccttggctgc tggatgctgg ttctctttgt ggccacatgg 420
agtgacctgg gcctctgcaa gaagcgcccg aagcctggag gatggaacac tgggggcagc 480
cgatacccgg ggcagggcag ccctggaggc aaccgctacc cacctcaggg cggtggtggc 540
tgggggcagc ctcatggtgg tggctggggg cagcctcatg gtggtggctg gggggcagccc 600 catggtggtg gctggggaca gcctcatggt ggtggctggg gtcaaggagg tggcacccac 660
agtcagtgga acaagccgag taagccaaaa accaacatga agcacatggc tggtgctgca 720
gcagctgggg cagtggtggg gggccttggc ggctacatgc tgggaagtgc catgagcagg 780
cccatcatac atttcggcag tgactatgag gaccgttact atcgtgaaaa catgcaccgt 840
taccccaacc aagtgtacta caggcccatg gatgagtaca gcaaccagaa caactttgtg 900

```
cacgactgcg tcaatatcac aatcaagcag cacacggtca ccacaaccac caagggggag    960
aacttcaccg agaccgacgt taagatgatg gagcgcgtgg ttgagcagat gtgtatcacc   1020
cagtacgaga gggaatctca ggcctattac cagagaggat cgagcatggt cctcttctcc   1080
tctccacctg tgatcctcct gatctctttc ctcatcttcc tgatagtggg atgaggaagg   1140
tcttcctgtt ttcaccatct ttctaatctt tttccagctt gagggaggcg gtatccacct   1200
gcagcccttt tagtggtggt gtctcactct ttcttctctc tttgtcccgg ataggctaat   1260
caataccctt ggcactgatg ggcactggaa aacatagagt agacctgaga tgctggtcaa   1320
gcccccttg attgagttca tcatgagccg ttgctaatgc caggccagta aaagtataac   1380
agcaaataac cattggttaa tctggactta tttttggact tagtgcaaca ggttgaggct   1440
aaaacaaatc tcagaacagt ctgaaatacc tttgcctgga tacctctggc tccttcagca   1500
gctagagctc agtatactaa tgccctatct tagtagagat ttcatagcta tttagagata   1560
ttttccattt taagaaaacc cgacaacatt tctgccaggt ttgttaggag gccacatgat   1620
acttattcaa aaaaatccta gagattctta gctcttggga tgcaggctca gcccgctgga   1680
gcatgagctc tgtgtgtacc gagaactggg gtgatgtttt acttttcaca gtatgggcta   1740
cacagcagct gttcaacaag agtaaatatt gtcacaacac tgaacctctg gctagaggac   1800
atattcacag tgaacataac tgtaacatat atgaaaggct tctgggactt gaaatcaaat   1860
gtttgggaat ggtgcccttg gaggcaacct cccattttag atgtttaaag gaccctatat   1920
gtggcattcc tttctttaaa ctataggtaa ttaaggcagc tgaaaagtaa attgccttct   1980
agacactgaa ggcaaatctc ctttgtccat ttacctggaa accagaatga ttttgacata   2040
caggagagct gcagttgtga aagcaccatc atcatagagg atgatgtaat taaaaaatgg   2100
tcagtgtgca aagaaaagaa ctgcttgcat ttctttattt ctgtctcata attgtcaaaa   2160
accagaatta ggtcaagttc atagtttctg taattggctt ttgaatcaaa gaatagggag   2220
acaatctaaa aaatatctta ggttggagat gacagaaata tgattgattt gaagtggaaa   2280
aagaaattct gttaatgtta attaaagtaa aattattccc tgaattgttt gatattgtca   2340
cctagcagat atgtattact tttctgcaat gttattattg gcttgcactt tgtgagtatt   2400
ctatgtaaaa atatatatgt atataaaata tatattgcat aggacagact taggagtttt   2460
gtttagagca gttaacatct gaagtgtcta atgcattaac ttttgtaagg tactgaatac   2520
ttaatatgtg ggaaaccctt ttgcgtggtc cttaggctta caatgtgcac tgaatcgttt   2580
catgtaagaa tccaaagtgg acaccattaa caggtctttg aaatatgcat gtactttata   2640
ttttctatat ttgtaacttt gcatgttctt gttttgttat ataaaaaaat tgtaaatgtt   2700
taatatctga ctgaaattaa acgagcgaag atgagcacca aaaaaaaaaa aaaaa        2755
```

<210> SEQ ID NO 439
<211> LENGTH: 931
<212> TYPE: DNA
<213> ORGANISM: Homo sapiens

<400> SEQUENCE: 439

```
tttcgtcggc ccgccccttg gcttctgcac tgatggtggg tggatgagta atgcatccag     60
gaagcctgga ggcctgtggt ttccgcaccc gctgccaccc ccgcccctag cgtggacatt    120
tatcctctag cgctcaggcc ctgccgccat cgccgcagat ccagcgccca gagagacacc    180
agagaaccca ccatggcccc ctttgagccc ctggcttctg gcatcctgtt gttgctgtgg    240
```

ctgatagccc ccagcagggc ctgcacctgt gtcccacccc acccacagac ggccttctgc 300
aattccgacc tcgtcatcag ggccaagttc gtggggacac cagaagtcaa ccagaccacc 360
ttataccagc gttatgagat caagatgacc aagatgtata aagggttcca agccttaggg 420
gatgccgctg acatccggtt cgtctacacc cccgccatgg agagtgtctg cggatacttc 480
cacaggtccc acaaccgcag cgaggagttt ctcattgctg gaaaactgca ggatggactc 540
ttgcacatca ctacctgcag ttttgtggct ccctggaaca gcctgagctt agctcagcgc 600
cggggcttca ccaagaccta cactgttggc tgtgaggaat gcacagtgtt tccctgttta 660
tccatcccct gcaaactgca gagtggcact cattgcttgt ggacggacca gctcctccaa 720
ggctctgaaa agggcttcca gtcccgtcac cttgcctgcc tgcctcggga gccagggctg 780
tgcacctggc agtccctgcg gtcccagata gcctgaatcc tgcccggagt ggaagctgaa 840
gcctgcacag tgtccaccct gttcccactc ccatctttct tccggacaat gaaataaaga 900
gttaccaccc agcagaaaaa aaaaaaaaaa a 931

<210> SEQ ID NO 440
<211> LENGTH: 1498
<212> TYPE: DNA
<213> ORGANISM: Homo sapiens

<400> SEQUENCE: 440
cggccgccca acagggacgc gagccgggac cacgccgacc cagcgtgccc aggccgagga 60
aagcgcggcg gcggcagtcc gaagacccac cgggactgaa agagaaggac gaggtcatct 120
tcggacggga ggggcaagcc agccatcctg ggaccccagg cgtgcaggtt ctctttgagg 180
gtattccacc ctgcaaaaag catgtattca tggtcagctc tcagcaaggc cagtagcaga 240
gtggtaaagg ccttggccct ccaaggctgg gaaaagacaa tgacaagtca aatccagacc 300
tatgttgtat gttggtctac taggtgactg tctcctggaa atgttatgca gctcagcaag 360
gtgaagtttc gaaatcagta tgacaatgat gtcactgttt ggagccccca gggcaggatt 420
catcaaattg aatatgcaat ggaagctgtt aaacaaggtt cagccacagt tggtctgaaa 480
tcaaaaactc atgcagtttt ggttgcattg aaaagggcgc aatcagagct tgcagctcat 540
cagaaaaaaa ttctccatgt tgacaaccat attggtatct caattgcggg gcttactgct 600
gatgctagac tgttatgtaa ttttatgcgt caggagtgtt tggattccag atttgtattc 660
gatagaccac tgcctgtgtc tcgtcttgta tctctaattg gaagcaagac ccagatacca 720
acacaacgat atggccggag accatatggt gttggtctcc ttattgctgg ttatgatgat 780
atgggccctc acattttcca aacctgtcca tctgctaact attttgactg cagagccatg 840
tccattggag cccgttccca atcagctcgt acttacttgg agagacatat gtctgaattt 900
atggagtgta atttaaatga actagttaaa catggtctgc gtgccttaag agagacgctt 960
cctgcagaac aggacctgac tacaaagaat gtttccattg gaattgttgg taaagacttg 1020
gagtttacaa tctatgatga tgatgatgtg tctccattcc tggaaggtct tgaagaaaga 1080
ccacagagaa aggcacagcc tgctcaacct gctgatgaac ctgcagaaaa ggctgatgaa 1140
ccaatggaac attaagtgat aagccagtct atatatgtat tatcaaatat gtaagaatac 1200
aggcaccaca tactgatgac aataatctat actttgaacc aaaagttgca gagtggtgga 1260
atgctatgtt ttaggaatca gtccagatgt gagttttttc caagcaacct cactgaaacc 1320
tatataatgg aatacatttt tctttgaaag ggtctgtata atcattttct agaaagtatg 1380
ggtatctata ctaatgtttt tatatgaaga acataggtgt ctttgtggtt ttaaagacaa 1440
ctgtgaaata aaattgtttc accgcctggt aaaaaaaaaa aaaaaaaaaa aaaaaaa 1498

<210> SEQ ID NO 441
<211> LENGTH: 4759
<212> TYPE: DNA
<213> ORGANISM: Homo sapiens

<400> SEQUENCE: 441
ggggagattt taccgagcaa cgtagggaaa cggctgcctg gctacctacc cctttttgac 60
acccacacgt gctcggcacc ttacatacac tgcgtgattt tatcctaaag ccacttttaa 120
aatcttagtg tgtaaacaga gaaactgggc gtcacataag gcaagtgacc tgcacagcct 180
gctccggagg agacccgtac gatcccagag acaagcactg aacataaggc acccggcgcc 240
gcgcccgctt tgcaacctct cgcgacagtt gtacgtcatc cgagagcgcc gtggaagtcg 300
tgctgcaggc gtcgcgccaa tcttcgctct gaggtgctgt ctcaccggtg agacctggaa 360
gcgggcgagt ctcgtgctgt gtcggacctg cagcccctgg ccttccgcca ccatggagta 420
cctcatcggt atccaaggcc ccgactatgt tcttgtcgcc tccgaccggg tggccgccag 480
caatattgtc cagatgaagg acgatcatga caagatgttt aagatgagtg aaaagatatt 540
actcctgtgt gttggagagg ctggagacac tgtacagttt gcagaatata ttcagaaaaa 600
cgtgcaactt tataagatgc gaaatggata tgaattgtct cccacggcag cagctaactt 660
cacacgccga aacctggctg actgtcttcg gagtcggacc ccatatcatg tgaacctcct 720
cctggctggc tatgatgagc atgaagggcc agcgctgtat tacatggact acctggcagc 780
cttggccaag gccccttttg cagcccacgg ctatggtgcc ttcctgactc tcagtatcct 840
cgaccgatac tacacaccga ctatctcacg tgagagggca gtggaactcc ttaggaaatg 900
tctggaggag ctccagaaac gcttcatcct gaatctgcca accttcagtg ttcgaatcat 960
tgacaaaaat ggcatccatg acctggataa catttccttc cccaaacagg gctcctaaca 1020
tcatgtcctc cctcccactt gccagggaac tttttttttga tgggctcctt tattttttttc 1080
tactcttttc aggcgcactc ttgataaatg gttaattcag aataaaggtg actatggata 1140
taattgagcc ctctggtcca ggtctcagtt tacctaatat tacctcagaa aggatatgga 1200
gggaagatga tctttttgcc aggtctgact tttcttcctg ctccgccctc cattaacgct 1260
cagtaccctt tagcagctga cggccccacg ttctactcca tgcttggctt cctttccaac 1320
tagctctttc atatatttta cttgctagta tctccattct ctctaaagta gtggttcttt 1380
ttgcccttaa acttaaattt ttaaattaat taacctgaat taataataca tgcacttaat 1440
gtaacatgca aacagtacaa aaacatgtag tgaaaaatat ttcttccaga gctgggtgtg 1500
gtggctcata cctgtaatcc cagcactttg ggaggccgag gcgggcggat cacgaggtca 1560
agagagcgag accatcctga ccaacatggt aaaaccccgt ctctactaaa aatacaaaaa 1620
ttagctgggc gtggtggcac gcacccctag tcccagctac tggggaggct gagacaggag 1680
aatcggtcga acccgggagg cagaggttgc agtgagccta gatcgcgcca ctgtactcca 1740
gcctggcaac agagtgagac tccgtctcaa aaaaagaagg aaaaatgttt cttccatccc 1800
tataatccag tcatctgctt cctgcttccc ttcctggagg aaacttcagc tactaatttc 1860
ttatgttttt taagagatat tctgttactg tgtaaagtat acatacatac agacacatgc 1920
cccctttaaa ttttttagat ttatttattt atttagagac agggtctcac tctagcccag 1980
gctggagtgc tgtggcgtaa tcttggctca ctgcaacctc cgcctcccgg gcccaagtga 2040
tcctcccatc tcagcctcct gagtagctag gattacaggc gcacaccacc aatgcccagc 2100
tagtttttgt gtttttcata gagacagggt ctcaccatgt cattcaggtt ggtcttgaac 2160
tcctgggctc aagcagtctg cctgccttgg cttcccagtg ctgggattac aggcgtgagc 2220
caccgtgccc ggctaaaaag tatttttaag ttctgcatat tgcttatttc acttaacact 2280
atattagaga ttgttttata tcaatacata tagatatgct tattcttgtt gacagttgca 2340
taattttcca ttaaattgat gtatcatggg cagttaacca gttactcgtt ttactcttag 2400
cataacttta gggaacaatg tggatgtttt gtggttaaag ctattaaaac agtggttctt 2460
gaccagatgt gtgtttcaga atgttcatct cacatttcca gttgctactg atgctgctgg 2520
tctaggaacc acatatcaaa accatttggt ctccgactaa gataaaccct actttatcca 2580
attctgtgct cctcttaata tcatatacag ataggttttt gttttgtctg tgattaaatg 2640
tatcatctaa gatactacct actgatcata acgttcatat taaagtattg ggttaacatt 2700
agatttgggt gtcttataca ctatttaata cgccaatgat aaatgcctta caccataaga 2760
agaaagctaa tcattgagta aatgggagaa aagagatgat tcacgtcact acagttgatt 2820
caacctccaa caccaccatg aatatgcata ggtttgagct tttagctaga ttcctgagtg 2880
taaggcatct attttaaaag tgccacaggt tggccgggtg cggtggctca tgcctgtaat 2940
cccagcactt tggccgcccg ccgaggcggg cggatcacct gaggtcagga gttcaagacc 3000
agcctggcca acatggtgaa accccatctc tactaaaaaa atatataaca attagccagg 3060
cgtggtggca cacgcctgta aacccaacta cttgggaggc tgaggcagga gaattgcttg 3120
agcccgggag agggaggttg cagtgagccg agatcatgcc actgcactcc agcctggctg 3180
acagagcaag actctgtctc aaaaaaaaaa aaaaaaaaaa aaaaaaagcg ccacagatga 3240
ttctgacgcc ctacccagtg gagtgctgct actaaagcac agactatcct gctacatgat 3300
tttcccatct gtacaatgac tgaaatagca cctattctat gtggtagata tgagaattcc 3360
atgaagtaat ataggtaaac atttagttca gggcttggca tgtggtaagt gctcagtaag 3420
tgtataatga ttggtaaact tgttattctg cattcaggcc tcaccaggga tgacatacgg 3480
ttctctgcct ttgaatgtaa gtgtccccag ggcaatctca ggcaagcctg caaacccatc 3540
ctgactctca gtgttttttt gccaatctgg atctctttcc tgagctccaa atcaactcat 3600
tcctagatag ctcaccctcc agatttaggg acatcgaact cagtatgtct aaagctgagc 3660
cttaccatct gcccctctcc aaaccgcctc tatgacattc tgtcttagag aattagagct 3720
acctggtttc ccaagtgccc aagtcagaaa cccaggcatc atttattttt aataaatgtt 3780
ttattttgga ataaatttgg ttttacagaa aagttgcaaa gataatatgg tgtccttata 3840
ccccttattc agtttctgta atgttaacat cttctatata ccacagtatg tttgtcaaaa 3900
ctgagaaacc aacattggtt ggtgtattag tattactaag ctccaggctt tattcagatt 3960
ttaccagttt ttccactaat tttcttctgt tctaggatat aatccaagat acaacattgc 4020
atttagctgg gcatcatttt tatgccattc tttatctcct gtctctacat ggccaccaag 4080
ttctggcatt tctacatcct aaatctttta attttattat aattttttat tgttgttttt 4140
cagagacagg gtcttgctcc atcacctagg ctggagtaca gtggcacgat cgtagcttac 4200
tgcagtaagt tcacttgaac tcctgggctc aagtgaacct cttaccccag cctcccaact 4260
agctgggact agaggggtgc accactgcac ccagctaatt ttgtcaaaat tttttgtaga 4320
gacagggtct cgccatgttg cctaggctgg tctcgaactc ttggcctcaa gtgatcctcc 4380
caccttggtc tgccaaagca ctgggattac agatgtgagc cactgcaccc agcctaatct 4440
ttataaatct ccatccccat tactctggtt cacccctat cgtttcttag actatttaac 4500
agcctcctaa cttcactcta cttttaatct cttccctctc caggtctttc tccatatttt 4560
aaaaaactag tttcaccatc cattcctctc tgcccttaaa actttctggt ggttttccat 4620
ggcttaagag aataaagccc aattctttga tttgacatgc taggcattcc ataatcctct 4680
ccgaacctaa ctccccactt cctttccctc ctttacacct cataaagcct gtgttccaac 4740
taaaaaaaaa aaaaaaaaa 4759

<210> SEQ ID NO 442
<211> LENGTH: 2185
<212> TYPE: DNA
<213> ORGANISM: Homo sapiens

<400> SEQUENCE: 442
tggttttacc ttttccggga gtctccagct ggccctcatt tgtgtccgga gctcaggagt 60
tcccaaaccg actcagtcgc accaagtttc cgtcttttgg aattggggaa ggagtttctt 120
tctttctttt ctttttcttt gagccagttt taatcgcttt gaataaatac tcccttaagt 180
agttaaatat aggaggagaa agaatacatc ggttgttaaa gcaggagagg aagagagacc 240
tgccctgtag cgtgactcct ctagaaaaaa aaaaaaaaag ccggagtatt ttactaagcc 300
cctaaaatgt cgagatttgt acaagatctt agcaaagcaa tgtctcaaga tggtgcttct 360
cagttccaag aagtcattcg gcaagagcta gaattatctg tgaagaagga actagaaaaa 420
atactcacca cagcatcatc acatgaattt gagcacacca aaaaagacct ggatggattt 480
cggaagctat ttcatagatt tttgcaagaa aaggggcctt ctgtggattg ggaaaaaatc 540
cagagacccc ctgaagattc gattcaaccc tatgaaaaga taaaggccag ggcttgcct 600 gataatatat cttccgtgtt gaacaaacta gtggtggtga aactcaatgg tggtttggga 660
accagcatgg gctgcaaagg ccctaaaagt ctgattggtg tgaggaatga gaataccttt 720
ctggatctga ctgttcagca aattgaacat ttgaataaaa cctacaatac agatgttcct 780
cttgttttaa tgaactcttt taacacggat gaagatacca aaaaaatact acagaagtac 840
aatcattgtc gtgtgaaaat ctacactttc aatcaaagca ggtacccgag gattaataaa 900
gaatctttac ttcctgtagc aaaggacgtg tcttactcag gggaaaatac agaagcttgg 960
taccctccag gtcatggtga tatttacgcc agtttctaca actctggatt gcttgatacc 1020
tttataggag aaggcaaaga gtatattttt gtgtctaaca tagataatct gggtgccaca 1080
gtggatctgt atattcttaa tcatctaatg aacccaccca atggaaaacg ctgtgaattt 1140
gtcatggaag tcacaaataa aacacgtgca gatgtaaagg gcgggacact cactcaatat 1200
gaaggcaaac tgagactggt ggaaattgct caagtgccaa aagcacatgt agacgagttc 1260
aagtctgtat caaagttcaa aatatttaat acaaacaacc tatggatttc tcttgcagca 1320
gttaaaagac tgcaggagca aaatgccatt gacatggaaa tcattgtgaa tgcaaagact 1380
ttggatggag gcctgaatgt cattcaatta gaaactgcag taggggctgc catcaaaagt 1440
tttgagaatt ctctaggtat taatgtgcca aggagccgtt ttctgcctgt caaaaccaca 1500
tcagatctct tgctggtgat gtcaaacctc tatagtctta atgcaggatc tctgacaatg 1560
agtgaaaagc gggaatttcc tacagtgccc ttggttaaat taggcagttc ttttacgaag 1620
gttcaagatt atctaagaag atttgaaagt ataccagata tgcttgaatt ggatcacctc 1680
acagtttcag gagatgtgac atttggaaaa aatgtttcat taaagggaac ggttatcatc 1740
attgcaaatc atggtgacag aattgatatc ccacctggag cagtattaga gaacaagatt 1800
gtgtctggaa accttcgcat cttggaccac tgaaatgaaa aatactgtgg acacttaaat 1860
aatgggctag tttcttacaa tgaaatgttc tctaggattc taaaataggc aggtacttta 1920
ctatgttact gtaccctgca gtgttgattt ttaaaataga gttttctgca gtatgctttt 1980
agtctaagaa aagcacagat ggagcaatac tttccttctt tgaagagaat cccaaaagtt 2040
agttcatctt aaagtgcaat attgtttaat cttaaaactg ggcaactttg gaagaacttt 2100
taacagaagc ctcaatgatg atcactttga attgcttgtg atttcaaaaa taaagcagtg 2160
aagcaataaa aaaaaaaaaa aaaaa 2185

<210> SEQ ID NO 443
<211> LENGTH: 5748
<212> TYPE: DNA
<213> ORGANISM: Homo sapiens

<400> SEQUENCE: 443
gagaagaaag ccagtgcgtc tctgggcgca ggggccagtg gggctcggag gcacaggcac 60
cccgcgacac tccaggttcc ccgacccacg tccctggcag ccccgattat ttacagcctc 120
agcagagcac ggggcggggg cagaggggcc cgcccgggag ggctgctact tcttaaaacc 180
tctgcgggct gcttagtcac agcccccctt gcttgggtgt gtccttcgct cgctccctcc 240
ctccgtctta ggtcactgtt ttcaacctcg aataaaaact gcagccaact tccgaggcag 300
cctcattgcc cagcggaccc cagcctctgc caggttcggt ccgccatcct cgtcccgtcc 360
tccgccggcc cctgccccgc gcccagggat cctccagctc ctttcgcccg cgccctccgt 420
tcgctccgga caccatggac aagttttggt ggcacgcagc ctggggactc tgcctcgtgc 480
cgctgagcct ggcgcagatc gatttgaata taacctgccg ctttgcaggt gtattccacg 540
tggagaaaaa tggtcgctac agcatctctc ggacggaggc cgctgacctc tgcaaggctt 600
tcaatagcac cttgcccaca atggcccaga tggagaaagc tctgagcatc ggatttgaga 660
cctgcaggta tgggttcata gaagggcacg tggtgattcc ccggatccac cccaactcca 720
tctgtgcagc aaacaacaca ggggtgtaca tcctcacatc caacacctcc cagtatgaca 780
catattgctt caatgcttca gctccacctg aagaagattg tacatcagtc acagacctgc 840
ccaatgcctt tgatggacca attaccataa ctattgttaa ccgtgatggc acccgctatg 900
tccagaaagg agaatacaga acgaatcctg aagacatcta ccccagcaac cctactgatg 960
atgacgtgag cagcggctcc tccagtgaaa ggagcagcac ttcaggaggt tacatctttt 1020 acacctttc tactgtacac cccatcccag acgaagacag tccctggatc accgacagca 1080
cagacagaat ccctgctacc actttgatga gcactagtgc tacagcaact gagacagcaa 1140
ccaagaggca agaaacctgg gattggtttt catggttgtt tctaccatca gagtcaaaga 1200
atcatcttca cacaacaaca caaatggctg gtacgtcttc aaataccatc tcagcaggct 1260
gggagccaaa tgaagaaaat gaagatgaaa gagacagaca cctcagtttt tctggatcag 1320
gcattgatga tgatgaagat tttatctcca gcaccatttc aaccacacca cgggcttttg 1380
accacacaaa acagaaccag gactggaccc agtggaaccc aagccattca aatccggaag 1440
tgctacttca gacaaccaca aggatgactg atgtagacag aaatggcacc actgcttatg 1500
aaggaaactg gaacccagaa gcacaccctc ccctcattca ccatgagcat catgaggaag 1560
aagagacccc acattctaca agcacaatcc aggcaactcc tagtagtaca acggaagaaa 1620
cagctaccca gaaggaacag tggtttggca acagatggca tgagggatat cgccaaacac 1680

```
ccaaagaaga ctcccattcg acaacaggga cagctgcagc ctcagctcat accagccatc   1740
caatgcaagg aaggacaaca ccaagcccag aggacagttc ctggactgat ttcttcaacc   1800
caatctcaca ccccatggga cgaggtcatc aagcaggaag aaggatggat atggactcca   1860
gtcatagtat aacgcttcag cctactgcaa atccaaacac aggtttggtg gaagatttgg   1920
acaggacagg acctctttca atgacaacgc agcagagtaa ttctcagagc ttctctacat   1980
cacatgaagg cttggaagaa gataaagacc atccaacaac ttctactctg acatcaagca   2040
ataggaatga tgtcacaggt ggaagaagag acccaaatca ttctgaaggc tcaactactt   2100
tactggaagg ttatacctct cattacccac acacgaagga aagcaggacc ttcatcccag   2160
tgacctcagc taagactggg tcctttggag ttactgcagt tactgttgga gattccaact   2220
ctaatgtcaa tcgttcctta tcaggagacc aagacacatt ccaccccagt ggggggtccc   2280
ataccactca tggatctgaa tcagatggac actcacatgg gagtcaagaa ggtggagcaa   2340
acacaacctc tggtcctata aggacacccc aaattccaga atggctgatc atcttggcat   2400
ccctcttggc cttggctttg attcttgcag tttgcattgc agtcaacagt cgaagaaggt   2460
gtgggcagaa gaaaaagcta gtgatcaaca gtggcaatgg agctgtggag gacagaaagc   2520
caagtggact caacggagag gccagcaagt ctcaggaaat ggtgcatttg gtgaacaagg   2580
agtcgtcaga aactccagac cagtttatga cagctgatga gacaaggaac ctgcagaatg   2640
tggacatgaa gattggggtg taacacctac accattatct tggaaagaaa caaccgttgg   2700
aaacataacc attacaggga gctgggacac ttaacagatg caatgtgcta ctgattgttt   2760
cattgcgaat ctttttagc ataaaatttt ctactctttt tgttttttgt gttttgttct    2820
ttaaagtcag gtccaatttg taaaaacagc attgctttct gaaattaggg cccaattaat   2880
aatcagcaag aatttgatcg ttccagttcc cacttggagg cctttcatcc ctcgggtgtg   2940
ctatggatgg cttctaacaa aaactacaca tatgtattcc tgatcgccaa cctttccccc   3000
accagctaag gacatttccc agggttaata gggcctggtc cctgggagga aatttgaatg   3060
ggtccatttt gcccttccat agcctaatcc ctgggcattg ctttccactg aggttggggg   3120
ttggggtgta ctagttacac atcttcaaca gacccccctct agaaattttt cagatgcttc  3180
tgggagacac ccaaagggtg aagctattta tctgtagtaa actatttatc tgtgtttttg   3240
aaatattaaa ccctggatca gtcctttgat cagtataatt ttttaaagtt actttgtcag   3300
aggcacaaaa gggtttaaac tgattcataa taaatatctg tacttcttcg atcttcacct   3360
tttgtgctgt gattcttcag tttctaaacc agcactgtct gggtccctac aatgtatcag   3420
gaagagctga gaatggtaag gagactcttc taagtcttca tctcagagac cctgagttcc   3480
cactcagacc cactcagcca aatctcatgg aagaccaagg agggcagcac tgtttttgtt   3540
ttttgttttt tgtttttttt ttttgacact gtccaaaggt tttccatcct gtcctggaat   3600
cagagttgga agctgaggag cttcagcctc ttttatggtt taatggccac ctgttctctc   3660
ctgtgaaagg ctttgcaaag tcacattaag tttgcatgac ctgttatccc tggggcccta   3720
tttcatagag gctggcccta ttagtgattt ccaaaaacaa tatggaagtg ccttttgatg   3780
tcttacaata agagaagaag ccaatggaaa tgaaagagat tggcaaaggg gaaggatgat   3840
gccatgtaga tcctgtttga catttttatg gctgtatttg taaacttaaa cacaccagtg   3900
tctgttcttg atgcagttgc tatttaggat gagttaagtg cctggggagt ccctcaaaag   3960
gttaaaggga ttcccatcat tggaatctta tcaccagata ggcaagttta tgaccaaaca   4020
```

agagagtact ggctttatcc tctaacctca tattttctcc cacttggcaa gtcctttgtg 4080
gcatttattc atcagtcagg gtgtccgatt ggtcctagaa cttccaaagg ctgcttgtca 4140
tagaagccat tgcatctata aagcaacggc tcctgttaaa tggtatctcc tttctgaggc 4200
tcctactaaa agtcatttgt tacctaaact tatgtgctta acaggcaatg cttctcagac 4260
cacaaagcag aaagaagaag aaaagctcct gactaaatca gggctgggct tagacagagt 4320
tgatctgtag aatatcttta aaggagagat gtcaactttc tgcactattc ccagcctctg 4380
ctcctccctg tctaccctct cccctccctc tctccctcca cttcacccca caatcttgaa 4440
aaacttcctt tctcttctgt gaacatcatt ggccagatcc attttcagtg gtctggattt 4500
ctttttattt tcttttcaac ttgaaagaaa ctggacatta ggccactatg tgttgttact 4560
gccactagtg ttcaagtgcc tcttgttttc ccagagattt cctgggtctg ccagaggccc 4620
agacaggctc actcaagctc tttaactgaa aagcaacaag ccactccagg acaaggttca 4680
aaatggttac aacagcctct acctgtcgcc ccagggagaa aggggtagtg atacaagtct 4740
catagccaga gatggttttc cactccttct agatattccc aaaaagaggc tgagacagga 4800
ggttattttc aattttattt tggaattaaa tactttttc cctttattac tgttgtagtc 4860
cctcacttgg atatacctct gttttcacga tagaaataag ggaggtctag agcttctatt 4920
ccttggccat tgtcaacgga gagctggcca agtcttcaca aacccttgca acattgcctg 4980
aagtttatgg aataagatgt attctcactc ccttgatctc aagggcgtaa ctctggaagc 5040
acagcttgac tacacgtcat ttttaccaat gattttcagg tgacctgggc taagtcattt 5100
aaactgggtc tttataaaag taaaaggcca acatttaatt attttgcaaa gcaacctaag 5160
agctaaagat gtaattttc ttgcaattgt aaatcttttg tgtctcctga agacttccct 5220
taaaattagc tctgagtgaa aaatcaaaag agacaaaaga catcttcgaa tccatatttc 5280
aagcctggta gaattggctt ttctagcaga acctttccaa aagttttata ttgagattca 5340
taacaacacc aagaattgat tttgtagcca acattcattc aatactgtta tatcagagga 5400
gtaggagaga ggaaacattt gacttatctg gaaaagcaaa atgtacttaa gaataagaat 5460
aacatggtcc attcaccttt atgttataga tatgtctttg tgtaaatcat ttgttttgag 5520
ttttcaaaga atagcccatt gttcattctt gtgctgtaca atgaccactg ttattgttac 5580
tttgactttt cagagcacac ccttcctctg gtttttgtat atttattgat ggatcaataa 5640
taatgaggaa agcatgatat gtatattgct gagttgaaag cacttattgg aaaatattaa 5700
aaggctaaca ttaaaagact aaaggaaaca gaaaaaaaaa aaaaaaaa 5748

<210> SEQ ID NO 444
<211> LENGTH: 1712
<212> TYPE: DNA
<213> ORGANISM: Homo sapiens

<400> SEQUENCE: 444
aagggcggga cattccccct gcctcttcgc accacagcca gagcctgcca ttaggaccaa 60
tgaaagcaaa gtacctcatc ccctcagtga ctaagaatcg cagtatttaa gaggtagcag 120
gaatgggctg agagtggtgt ttgctttctc caccagaagg gcacactttc atctaatttg 180
gggtatcact gagctgaaga caaagagaag ggggagaaaa cctagcagac caccatgtgc 240
tatgggaagt gtgcacgatg catcggacat tctctggtgg ggctcgccct cctgtgcatc 300
gcggctaata ttttgcttta ctttcccaat ggggaaacaa agtatgcctc cgaaaaccac 360
ctcagccgct tcgtgtggtt cttttctggc atcgtaggag gtggcctgct gatgctcctg 420

```
ccagcatttg tcttcattgg gctggaacag gatgactgct gtggctgctg tggccatgaa    480

aactgtggca aacgatgtgc gatgctttct tctgtattgg ctgctctcat tggaattgca    540

ggatctggct actgtgtcat tgtggcagcc cttggcttag cagaaggacc actatgtctt    600

gattccctcg gccagtggaa ctacaccttt gccagcactg agggccagta ccttctggat    660

acctccacat ggtccgagtg cactgaaccc aagcacattg tggaatggaa tgtatctctg    720

ttttctatcc tcttggctct tggtggaatt gaattcatct tgtgtcttat tcaagtaata    780

aatggagtgc ttggaggcat atgtggcttt tgctgctctc accaacagca atatgactgc    840

taaaagaacc aacccaggac agagccacaa tcttcctcta tttcattgta atttatatat    900

ttcacttgta ttcatttgta aaactttgta ttagtgtaac atactcccca cagtctactt    960

ttacaaacgc ctgtaaagac tggcatcttc acaggatgtc agtgtttaaa tttagtaaac   1020

ttcttttttg tttgtttatt tgtttttgtt ttttttaag gaatgaggaa acaaaccacc   1080

ctctggggggt aatttacaga ctgagtgaca gtactcagta tatctgagat aaactctata   1140

atgttttgga taaaaataac attccaatca ctattgtata tatgtgcatg tattttttaa   1200

attaaagatg tctagttgct ttttataaga ccaagaagga gaaaatccga caacctggaa   1260

agatttttgt tttcactgct tgtatgatgt ttcccattca tacacctata aatctctaac   1320

aagaggccct ttgaactgcc ttgtgttctg tgagaaacaa atatttactt agagtggaag   1380

gactgattga gaatgttcca atccaaatga atgcatcaca acttacaatg ctgctcattg   1440

ttgtgagtac tatgagattc aaatttttct aacatatgga aagccttttg tcctccaaag   1500

atgagtacta gggatcatgt gtttaaaaaa agaaaggcta cgatgactgg gcaagaagaa   1560

agatgggaaa ctgaataaag cagttgatca gcatcattgg aacatgggga cgagtgacgg   1620

caggaggacc acgaggaaat accctcaaaa ctaacttgtt tacaacaaaa taaagtattc   1680

actaccatgt taaaaaaaaa aaaaaaaaaa aa                                 1712
```

<210> SEQ ID NO 445
<211> LENGTH: 3966
<212> TYPE: DNA
<213> ORGANISM: Homo sapiens

<400> SEQUENCE: 445

```
aggcgcgggc ggagggcggg ctgaagcagc tgaagcggcg gtagcggcgg cggctcgggc     60

agaggggcgg gagctgaggc gggagcggac aggctggtgg gcgagcgaga ggcggcggaa    120

tggtggacta ccacgcggcg aaccagtcgt accagtacgg ccccagcagc gcgggcaatg    180

gcgctggcgg cgggggcagc atgggcgact acatggccca ggaggacgac tgggaccggg    240

acctgctgct ggacccggcc tgggagaagc agcagcgcaa gaccttcacg gcatggtgca    300

actcccacct gcggaaggca ggcacacaga tcgagaacat tgatgaggac ttccgagacg    360

ggctcaagct catgctgctc ctggaggtca tatcagggga gcggttacct aagccggagc    420

gggggaagat gagagtgcac aaaatcaaca atgtgaacaa agcgctggac tttattgcca    480

gcaaaggcgt caagctggtc tccatcgggg cagaagagat tgtggacggc aacgcaaaga    540

tgaccctggg aatgatctgg accatcatcc ttaggttcgc catccaggac atctccgtgg    600

aagagacctc ggccaaggaa gggctccttc tctggtgcca gagaaagaca gccccgtata    660

agaacgtcaa tgtgcagaac ttccacatca gctggaagga tggtcttgcc ttcaatgccc    720

tgatccaccg gcacagacca gagctgattg agtatgacaa gctgaggaag gacgaccctg    780
```

-continued

```
tcaccaacct gaacaatgcc ttcgaagtgg ctgagaaata cctcgacatc cccaagatgc    840
tggatgcaga ggacatcgtg aacacggccc ggcccgacga gaaggccata atgacctatg    900
tgtccagctt ctaccatgcc ttttcaggag cgcagaaggc tgaaactgcc gccaaccgga    960
tctgtaaggt gctggctgtc aaccaagaga acgagcacct gatggaggac tacgagaagc   1020
tggccagcga cctcctggag tggatccggc gcaccatccc ctggctggag gaccgtgtgc   1080
cccaaaagac tatccaggag atgcagcaga agctggagga cttccgcgac taccggcgtg   1140
tgcacaagcc gcccaaggtg caggagaagt gccagctgga gatcaacttc aacacgctgc   1200
agaccaagct gcgcctcagc aaccggcccg ccttcatgcc ctccgagggc aagatggtct   1260
cggacatcaa caatggctgg cagcacttgg agcaggctga gaagggctac gaggagtggc   1320
tgctgaatga gatccgcagg ctggagcggc tcgaccacct ggcagagaag ttccggcaga   1380
aggcctccat ccacgaggcc tggactgacg ggaaggaagc catgctgaag caccgggact   1440
acgagacggc cacactatcg gacatcaaag ccctcattcg caagcacgag gccttcgaga   1500
gcgacctggc tgcgcaccag gaccgcgtgg agcagatcgc cgccattgcc caggagctca   1560
acgagctgga ttactacgac tcccacaatg tcaacacccg gtgccagaag atctgtgacc   1620
agtgggacgc cctcggctct ctgacacata gtcgcaggga agccctggag aaaacagaga   1680
agcagctgga ggccatcgac cagctgcacc tggaatacgc caagcgcgcg gccccccttca   1740
acaactggat ggagagcgcc atggaggacc tccaggacat gttcatcgtc cataccatcg   1800
aggagattga gggcctgatc tcagcccatg accagttcaa gtccaccctg ccggacgccg   1860
atagggagcg cgaggccatc ctggccatcc acaaggaggc ccagaggatc gctgagagca   1920
accacatcaa gctgtcgggc agcaacccct acaccaccgt caccccgcaa atcatcaact   1980
ccaagtggga gaaggtgcag cagctggtgc caaaacggga ccatgccctc ctggaggagc   2040
agagcaagca gcagtccaac gagcacctgc gccgccagtt cgccagccag gccaatgttg   2100
tggggccctg gatccagacc aagatggagg agatcgggcg catctccatt gagatgaacg   2160
ggaccctgga ggaccagctg agccacctga agcagtatga acgcagcatc gtggactaca   2220
agcccaacct ggacctgctg gagcagcagc accagctcat ccaggaggcc ctcatcttcg   2280
acaacaagca caccaactat accatggagc acatccgcgt gggctgggag cagctgctca   2340
ccaccattgc ccgcaccatc aacgaggtgg agaaccagat cctcacccgc gacgccaagg   2400
gcatcagcca ggagcagatg caggagttcc gggcgtcctt caaccacttc gacaaggatc   2460
atggcggggc gctggggccc gaggagttca aggcctgcct catcagcctg ggctacgacg   2520
tggagaacga ccggcagggt gaggccgagt tcaaccgcat catgagcctg gtcgacccca   2580
accatagcgg ccttgtgacc ttccaagcct tcatcgactt catgtcgcgg gagaccaccg   2640
acacggacac ggctgaccag gtcatcgctt ccttcaaggt cttagcaggg gacaagaact   2700
tcatcacagc tgaggagctg cggagagagc tgccccccga ccaggccgag tactgcatcg   2760
cccgcatggc gccataccag ggccctgacg ccgtgcccgg tgccctcgac tacaagtcct   2820
tctccacggc cttgtatggc gagagcgacc tgtgaggccc cagagacctg acccaacacc   2880
cccgacggcc tccaggaggg gcctgggcag ccccacagtc ccattcctcc actctgtatc   2940
tatgcaaagc actctctgca gtcctccggg gtgggtgggt gggcagggag gggctggggc   3000
aggctctctc ctctctctct ttgtgggttg gccaggaggt tcccccgacc aggttgggga   3060
gacttggggc cagcgcttct ggtctggtaa atatgtatga tgtgttgtgc ttttttaacc   3120
aaggaggggc cagtggattc ccacagcaca accggtccct tccatgccct gggatgcctc   3180
```

-continued

```
accacaccca ggtctcttcc tttgctctga ggtcccttca aggcctcccc aatccaggcc   3240

aaagccccat gtgccttgtc caggaactgc ctgggccatg cgaggggcca gcagagggcg   3300

ccaccaccac ctgacggctg gggacccacc cagcccctct cccctctctg ctccagactc   3360

acttgccatt gccaggagat ggccccaaca agcaccccgc ttttgcagca gaggagctga   3420

gttggcagac cgggcccccc tgaaccgcac cccatcccac cagccccggc cttgctttgt   3480

ctggcctcac gtgtctcaga ttttctaaga accaaaaaaa aaaaaggaaa aaaaacacaa   3540

aacaacaaaa accaaaaaaa aaaaaaatca caaaaacaaa aaaactataa aaaagaaaga   3600

attaaaaact ttcagagaat tactatttac tttattaact tacggattta ttatataaat   3660

atatattcac ctagcaacat atctctgccg tctctcctgc tctcataatg aagacatagc   3720

cgattctctg cccgggcccc ttgctgatgc tcctccgggt ctgcgtcggg cgtgggtctc   3780

tggggaccct ccagaggtgg aggtgggctg atggcctggc tgcctggtgg ttgatggttt   3840

tgctccccct acctttttt tttgagttta ttctgattga ttttttttct tggtttctgg    3900

ataaaccacc ctctggggac aggataataa aacatgtaat atttttaaga aggaaaaaaa   3960

aaaaaa                                                              3966
```

METHODS AND DEVICES FOR PREDICTING TREATMENT EFFICACY OF FULVESTRANT IN CANCER PATIENTS

FIELD OF THE INVENTION

The invention features the use of biomarkers in methods and devices to predict the sensitivity of a patient to a medical treatment, e.g. fulvestrant.

BACKGROUND

DNA microarrays have been used to measure gene expression in tumor samples from patients and to facilitate diagnosis. Gene expression can reveal the presence of cancer in a patient, its type, stage, and origin, and whether genetic mutations are involved. Gene expression may even have a role in predicting the efficacy of chemotherapy. Over recent decades, the National Cancer Institute (NCI) has tested compounds, including chemotherapy agents, for their effect in limiting the growth of 60 human cancer cell lines. The NCI has also measured gene expression in those 60 cancer cell lines using DNA microarrays. Various studies have explored the relationship between gene expression and compound effect using the NCI datasets.

During chemotherapy for cancers critical time is often lost due to a trial and error approach to finding an effective therapy. In addition, cancer cells often develop resistance to a previously effective therapy. In such situations, patient outcome would be greatly improved by early detection of such resistance.

There remains a need for proven methods and devices that predict the sensitivity or resistance of cancer patients to a medical treatment.

SUMMARY OF THE INVENTION

The invention features methods and devices for predicting the sensitivity or resistance of a patient, e.g., a cancer patient, to a treatment, e.g., treatment with a compound, such as an anticancer agent (e.g., a chemotherapeutic agent), such as fulvestrant. The devices and methods of the invention have been used to accurately predict treatment efficacy in cancer patients. In an embodiment, the methods include assaying for the level of expression of at least the gene GATA3 (alone or in combination with one or more (e.g., two, three, four, five, ten, twenty, thirty, forty, or fifty or more) additional biomarkers from Table 1, Table 2, or both. For example, the method includes assaying the level of expression of at least the first 5 biomarkers from Table 1, Table 2, or both (e.g., at least the first 10 biomarkers (e.g., the first 13 biomarkers) from Table 1, Table 2, or both, such as at least the first 15 biomarkers from Table 1, Table 2, or both) in a sample from the patient (e.g., a cell, tissue, or organ sample from a patient). In an embodiment, the method can be used to determine the sensitivity of a patient to at least one treatment for cancer (e.g., an anti-cancer agent (e.g., a chemotherapy drug), such as fulvestrant (FASLODEX®)). In other embodiments, the method can be used to determine the sensitivity of a patient to two or more (e.g., three, four, five, ten, twenty, or more) treatments for cancer.

Devices employing one or more of the biomarkers of the invention (e.g., one or more of the biomarkers listed in Table 1, Table 2, or both) for the anti-cancer agent fulvestrant are also provided. In an embodiment, the device includes at least one nucleic acid molecule that is complementary to or identical to at least 5 (e.g., at least 6, at least 7, at least 8, at least 9, at least 10, at least 11, at least 12, at least 13, at least 14, at least 15, or at least 20) consecutive nucleotides of GATA3 (SEQ ID NO: 415). In another embodiment, the device includes are least one nucleic acid molecule that is complementary to or identical to at least 5 (e.g., at least 6, at least 7, at least 8, at least 9, at least 10, at least 11, at least 12, at least 13, at least 14, at least 15, or at least 20) consecutive nucleotides of any one of SEQ ID NOs: 415-430. In yet another embodiment, the device includes are least five nucleic acid molecules, each of which is complementary to or identical to at least 5 (e.g., at least 6, at least 7, at least 8, at least 9, at least 10, at least 11, at least 12, at least 13, at least 14, at least 15, or at least 20) consecutive nucleotides of any one of SEQ ID NOs: 415-430.

The methods and devices can be used to predict the sensitivity or resistance of a subject (e.g., a cancer patient) diagnosed with a disease condition, e.g., cancer (e.g., a cancer of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, or gastrointestines, as well as any form of cancer including, e.g., chronic myeloid leukemia, acute lymphocytic leukemia, non-Hodgkin lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin lymphoma, carcinoid tumors, acute tumor, or soft tissue sarcoma) to a treatment, e.g., treatment with a compound or drug, e.g., an anti-cancer agent (e.g., a chemotherapeutic agent), such as fulvestrant listed above.

In the first aspect, the invention features a method of predicting sensitivity of a cancer patient to a treatment for cancer (e.g., an anti-cancer agent, such as fulvestrant, gefitinib, erlotiniv, trastuzumab, cisplatin, vincristine, belinostat, or tamoxifen; preferably, the anti-cancer agent is fulvestrant) by determining the expression level of at least one gene or noncoding RNA (e.g. microRNA (miRNA) in a cell (e.g., a cancer cell) of the patient in which the level of expression of the gene and/or RNA (e.g., miRNA)) indicates the patient is sensitive or resistant to at least one treatment for cancer (e.g., an anti-cancer agent). In an embodiment, the method involves assaying for the level of expression of one or more (e.g., two, three, four, five, ten, twenty, thirty, forty, or fifty or more) biomarkers from Table 1, Table 2, or both) in a patient. For example, the method includes assaying the level of expression of GATA3 in a sample from the patient (e.g., a cell, tissue, or organ sample from a patient). In another embodiment, the method includes assaying the level of expression of at least GATA3 (alone or in combination with one or more (e.g., two, three, four, or more) of the biomarkers listed in Table 1, Table 2, or both). In an embodiment, the method includes determining the expression level of two of the biomarkers listed in Table 1, Table 2, or both, more preferably three, four, five, six, seven, eight, nine, or ten of the listed biomarkers, and most preferably twenty, thirty, forty, fifty, sixty, seventy, eighty, ninety, or one hundred or more of the biomarkers listed in Table 1, Table 2, or both. In another embodiment, the level of biomarker expression is determined relative to the level of biomarker expression in a cell or tissue known to be sensitive to the treatment, such that a similar level of biomarker expression exhibited by a cell or tissue of the patient indicates the patient is sensitive to the treatment. In another embodiment, the level of biomarker expression is determined relative to the level of biomarker expression in a cell or tissue known to be resistant to the treatment, such that a similar level of biomarker expression exhibited by a cell or tissue of the patient indicates the patient is resistant to the treatment.

The method may be performed one or more times (e.g., at least 2, 3, 4, 5, or 6 times or more) over time (e.g., over the course of a week, two weeks, a month, three months, six months, nine months, a year, one year and a half, two years, three years, or four years).

A second aspect of the invention features a method for determining the development of resistance by a patient (i.e., a cell, such as a cancer cell, in the patient) to a treatment to which the patient was previously sensitive. The method includes determining the level of expression of one or more of the biomarkers set forth in the first aspect of the invention (e.g., GATA3), such that the expression level of a biomarker(s) which is decreased in a cell or tissue known to be sensitive to the treatment indicates that the patient is resistant to or has a propensity to become resistant to the treatment. Alternatively, a decrease in the expression level of a biomarker(s) which is increased in a cell or tissue known to be sensitive to the treatment indicates that the patient is resistant to or has a propensity to become resistant to the treatment.

A third aspect of the invention features a kit that includes a device having at least one or more single-stranded nucleic acid molecules (e.g., deoxyribonucleic acid (DNA) or ribonucleic acid (RNA) molecules) that are complementary to or identical to at least 5 consecutive nucleotides (e.g., at least 6, at least 7, at least 8, at least 9, at least 10, at least 11, at least 12, at least 13, at least 14, at least 15, or at least 20; more preferably at least 10, 15, 20, 25, 30, 35, 40, 45, 50, 55, 60, 65, 70, 75, 80, 85, 90, 95, 100, 150, 200, 250, 300, or more consecutive nucleotides; the nucleic acid molecule can also be 5-20, 25, 5-50, 50-100, or over 100 consecutive nucleotides long) of at least one of the biomarkers set forth in the first aspect of the invention, such that the single stranded nucleic acid molecules are sufficient for the detection of expression of the biomarkers (e.g., GATA3) in, e.g., a sample from a patient, by allowing specific hybridization between the single stranded nucleic acid molecules and one or more of the nucleic acid molecules corresponding to the biomarker, or a complement thereof. The kit further includes instructions for applying nucleic acid molecules collected from a sample from a cancer patient (e.g., from a cell, tissue, or organ of the patient), determining the level of expression of the biomarkers in the sample that hybridize to the single stranded nucleic acid molecule(s), and predicting the patient's sensitivity to at least one or more treatments for cancer when use of the kit establishes that the expression level of the biomarkers is changed (i.e., increased or decreased relative to a control sample (i.e., a cell, tissue, and/or organ) known to be sensitive or resistant to the treatment(s), as is discussed above in connection with the first aspect of the invention). In an embodiment, the instructions further indicate that an alteration in the expression level of the biomarker(s) relative to the expression of the biomarker(s) in a control sample (e.g., a cell, tissue, and/or organ known to be sensitive or resistant to the treatment(s)) indicates a change in sensitivity of the patient to the treatment(s) (i.e., a decrease in the level of expression of a biomarker (e.g., a gene and/or RNA (e.g., a miRNA)) known to be expressed in cells sensitive to the treatment(s) indicates that the patient is becoming resistant to the treatment(s) or is likely to become resistant to the treatment(s), and vice versa).

In an embodiment, the kit can be utilized to determine a patient's resistance or sensitivity to at least one anti-cancer agent, such as fulvestrant, by determining the expression level of one or more of the biomarkers set forth in the first aspect of the invention and known to be increased in a patient sensitive to treatment with one or more of these agents (i.e., a patient is determined to be sensitive, or is likely to be sensitive, to the indicated treatment if the level of expression of one or more of the biomarkers increases relative to the level of expression of the biomarkers in a control sample (i.e., a cell, tissue, or organ) in which increased expression of the biomarkers indicates sensitivity to the treatment, and vice versa).

In an embodiment, the nucleic acid molecules of the methods and/or devices are characterized by their ability to specifically identify (e.g., by hybridization) nucleic acid molecules complementary to or identical to the biomarkers in a sample collected from a cancer patient.

A fourth aspect of the invention features a method of identifying biomarkers indicative of sensitivity of a cancer patient to a treatment for cancer by obtaining pluralities of measurements of the expression level of one or more gene(s) and/or RNA(s) (e.g., a miRNA)). For example, the measurements can be obtained by detecting the expression of one or more genes and/or RNAs using a single probe or by using multiple probes directed to a single gene or RNA. The methods can include assaying the expression levels of the gene(s) and/or RNA(s) in one or more different cell types and/or measuring the growth of those cell types in the presence of a treatment for cancer relative to the growth of the cell types in the absence of the treatment for cancer. The method further includes correlating each plurality of measurements of the expression level of the gene and/or RNAs in cells with the growth of the cells to obtain a correlation coefficient; selecting the median correlation coefficient calculated for the gene(s) and/or RNA(s); and identifying the gene(s) and/or RNA(s) as a biomarker for use in determining the sensitivity of a cancer patient to one or more treatments for cancer if said median correlation coefficient exceeds 0.25 (preferably the gene and/or RNA is identified as a biomarker for a patient's sensitivity to a treatment if the correlation coefficient exceeds 0.3, 0.4, 0.5, 0.6, 0.7, 0.8. 0.9, 0.95, or 0.99 or more; preferably the correlation coefficient exceeds 0.3). In an embodiment, the method is performed in the presence of a second treatment.

A fifth aspect of the invention features a method of predicting sensitivity of a patient (e.g., a cancer patient) to a treatment for cancer by obtaining a measurement of the expression of a biomarker gene or RNA (e.g., a miRNA) from a sample (e.g., a cell or tissue) from the patient; applying a model predictive of sensitivity to a treatment for cancer to the measurement, in which the model is developed using an algorithm selected from the group consisting of linear sums, nearest neighbor, nearest centroid, linear discriminant analysis, support vector machines, and neural networks; and predicting whether or not the patient will be responsive to the treatment for cancer. In an embodiment, the measurement is obtained by assaying expression of the gene and/or RNA biomarker in a cell known to be sensitive or resistant to the treatment. In another embodiment, the model combines the outcomes of linear sums, linear discriminant analysis, support vector machines, neural networks, k-nearest neighbors, and nearest centroids, or the model is cross-validated using a random sample of multiple measurements. In another embodiment, treatment, e.g., a compound, such as an anti-cancer agent, has previously failed to show efficacy in a patient. In several embodiments, the linear sum is compared to a sum of a reference population with known sensitivity; the sum of a reference population is the median of the sums derived from the population members' biomarker gene and/or RNA expression. In another embodiment, the model is derived from the components of a data set obtained by independent component analysis or is derived from the components of a data set obtained by principal component analysis.

A sixth aspect of the invention features a kit, apparatus, and software used to implement the method of the fifth aspect of the invention.

In several embodiments of all aspects of the invention, the expression level of the gene(s) is determined by detecting the level of mRNA transcribed from the gene(s), by detecting the level of RNA(s) (e.g., miRNA(s)) expressed from noncoding regions, by detecting the level of a protein product of the gene(s), and/or by detecting the level of the biological activity of a protein product of the gene(s). In further embodiments of all aspects of the invention, an increase or decrease in the expression level of the gene(s) and/or RNA(s), relative to the expression level of the gene(s) and/or RNA(s) in a cell, tissue, or organ sensitive to the treatment(s), indicates increased sensitivity of the cancer patient to the treatment(s). Alternatively, an increase or decrease in the expression level of the gene(s) and/or RNA(s), relative to the expression level of the gene(s) and/or RNA(s) in a cell, tissue, or organ resistant to the treatment(s), indicates increased resistance of the cancer patient to the treatment(s). In another embodiment of all aspects of the invention, the cell is a cancer cell. In another embodiment of all aspects of the invention, the expression level of one or more of the biomarkers described herein is measured using a quantitative reverse transcription-polymerase chain reaction (qRT-PCR). In yet another embodiment of all aspects of the invention, the expression level of one or more of the biomarkers described herein is measured using a quantitative loop-mediated isothermal amplification reaction (q-LAMP). In an embodiment of all aspects of the invention, the level of expression of two or more of the biomarkers described herein (e.g., two of more of the biomarkers in Table 1, Table 2, or both) is measured, more preferably the level of expression of three, four, five, six, seven, eight, nine, or ten of the biomarkers described herein is measured, and most preferably twenty, thirty, forty, fifty, sixty, seventy, eighty, ninety, or one hundred or more of the biomarkers described herein is measured (e.g., any combination of two or more of the biomarkers (e.g., the combination of GATA3 with one or more of the other biomarkers described herein). In another embodiment of all aspects of the invention, the expression level of the biomarker(s) is determined using the kit of the third aspect of the invention.

In another embodiment of all aspects of the invention, the treatment is a compound, such as an anti-cancer agent (e.g., chemotherapeutic agent), such as fulvestrant. In another embodiment of all aspects of the invention, one or more of the treatments has previously failed to show effect in a subject (e.g., a subject selected from a subpopulation predicted to be sensitive to the treatment(s), a subject selected from a subpopulation predicted to die without treatment(s), a subject selected from a subpopulation predicted to have disease symptoms without treatment(s), a subject selected from a subpopulation predicted to be cured without treatment(s).

In another embodiment of all aspects of the invention, the treatment is, e.g., administration of a compound, a protein, an antibody, an oligonucleotide, a chemotherapeutic agent, or radiation to a patient. In an embodiment of all aspects of the invention, the treatment is, e.g., an anti-cancer agent, such as fulvestrant. In another embodiment of all aspects of the invention, a second treatment is utilized to determine gene expression in a sample from the patient.

A seventh aspect of the invention features a device (e.g., a microarray) having at least one or more single-stranded nucleic acid molecules (e.g., deoxyribonucleic acid (DNA) or ribonucleic acid (RNA) molecules) that are complementary to or identical to at least 5 consecutive nucleotides (e.g., at least 6, at least 7, at least 8, at least 9, at least 10, at least 11, at least 12, at least 13, at least 14, at least 15, or at least 20; more preferably at least 10, 15, 20, 25, 30, 35, 40, 45, 50, 55, 60, 65, 70, 75, 80, 85, 90, 95, 100, 150, 200, 250, 300, or more consecutive nucleotides; the nucleic acid molecule can also be 5-20, 25, 5-50, 50-100, or over 100 consecutive nucleotides long) of at least one of the biomarkers set forth in the first aspect of the invention, such that the single stranded nucleic acid molecules are sufficient for the detection of expression of the biomarkers (e.g., in a sample from a patient) by allowing specific hybridization between the single stranded nucleic acid molecules and one or more of the nucleic acid molecules corresponding to the biomarker, or a complement thereof.

In an embodiment, the device can be utilized to determine a patient's resistance or sensitivity to at least one anti-cancer agent (e.g., a chemotherapeutic agent), such as fulvestrant, by determining the expression level of one or more of the biomarkers set forth in the first aspect of the invention and known to be increased in a patient sensitive to treatment with one or more of these agents (i.e., a patient is determined to be sensitive, or is likely to be sensitive, to the indicated treatment if the level of expression of one or more of the biomarkers increases relative to the level of expression of the biomarkers in a control sample (i.e., a cell, tissue, or organ) in which increased expression of the biomarkers indicates sensitivity to the treatment, and vice versa).

An eighth aspect of the invention features a method of predicting the responsiveness of a patient having a cancer to an anti-cancer agent by:

i) determining a level of expression of at least one biomarker of sensitivity in a first sample from the patient, the biomarker of sensitivity selected from one or more of the biomarkers of Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); or ii) determining a level of expression of at least one biomarker of resistance in a second sample from the patient, the biomarker of resistance selected from one or more of the biomarkers of Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements). The level of expression of the biomarker of sensitivity in the first sample or the biomarker of resistance in the second sample indicates whether the patient is responsive to the anti-cancer agent.

In some embodiments, the method may involve:

i) determining a level of expression of at least one biomarker of sensitivity in a first sample from the patient, the biomarker of sensitivity selected from Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); and ii) determining a level of expression of at least one biomarker of resistance in a second sample from the patient, the biomarker of resistance selected from Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements). The level of expression of the biomarker of sensitivity in the first sample and the biomarker of resistance in the second sample indicates whether the patient is responsive to the anti-cancer agent.

A ninth aspect of the invention features a method of treating a patient having a cancer. The method may involve:

(i) (a) determining a level of expression of at least one biomarker of sensitivity in a first sample from the cancer patient, the biomarker of sensitivity selected from one or more of the biomarkers of Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); or (b) determining a level of expression of at least one biomarker of resistance in a second sample from the cancer patient, the biomarker of resistance selected from one or more of the biomarkers of Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements); and (ii) administering the anti-cancer agent to the patient, if the level of expression of the biomarker of sensitivity in the first sample or the biomarker of resistance in the second sample indicates that the patient is responsive to the anti-cancer agent.

In other embodiments, the method may involve:

(i) (a) determining a level of expression of at least one biomarker of sensitivity in a first sample from the patient, the biomarker of sensitivity selected from one or more of the biomarkers of Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); and (b) determining a level of expression of at least one biomarker of resistance in a second sample from the patient, the biomarker of resistance selected from one or more of the biomarkers of Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements); and (ii) administering the anti-cancer agent to the patient, if the levels of expression of the biomarker of sensitivity in the first sample and the biomarker of resistance in the second sample indicate that the patient is responsive to the anti-cancer agent.

A tenth aspect of the invention features a method of inhibiting growth of a cancer cell of a patient. The method may involve:

(i) (a) determining a level of expression of at least one biomarker of sensitivity in a first sample from the patient, the biomarker of sensitivity selected from one or more of the biomarkers of Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); or (b) determining a level of expression of at least one biomarker of resistance in a second sample from the patient, the biomarker of resistance selected from one or more of the biomarkers of Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements); and (ii) contacting the anti-cancer agent with the cancer cell, if the level of expression of the biomarker of sensitivity in the first sample or the biomarker of resistance in the second sample indicates that the patient is responsive to an anti-cancer agent.

In certain embodiments, the method may involve:

(i) (a) determining a level of expression of at least one biomarker of sensitivity in a first sample from the cancer patient, the biomarker of sensitivity selected from one or more of the biomarkers of Table 1 (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements); and (b) determining a level of expression of at least one biomarker of resistance in a second sample from the cancer patient, the biomarker of resistance selected from one or more of the biomarkers of Table 2 (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements); and (ii) contacting the anti-cancer agent with the cancer cell, if the levels of expression of the biomarker of sensitivity in the first sample and the biomarker of resistance in the second sample indicate that the patient is responsive to the anti-cancer agent.

In some embodiments of any aspect of the invention, one of the at least one biomarker of sensitivity may be GATA3 (e.g., as measured using an oligonucleotide or its complement having at least 85% (e.g., at least 90%, at least 95%, or 100%) sequence identity to SEQ ID NO: 1, 2, or 3). One of the at least one biomarker of sensitivity may be CBFA2T3 (e.g., as measured using an oligonucleotide or its complement having at least 85% (e.g., at least 90%, at least 95%, or 100%) sequence identity to SEQ ID NO: 4). One of the at least one biomarker of sensitivity may be SPDEF (e.g., as measured using an oligonucleotide or its complement having at least 85% (e.g., at least 90%, at least 95%, or 100%) sequence identity to SEQ ID NO: 5). One of the at least one biomarker of sensitivity may be HBA1 (e.g., as measured using an oligonucleotide or its complement having at least 85% (e.g., at least 90%, at least 95%, or 100%) sequence identity to SEQ ID NO: 6 or 17). One of the at least one biomarker of sensitivity may be TFF1 (e.g., as measured using an oligonucleotide or its complement having at least 85% (e.g., at least 90%, at least 95%, or 100%) sequence identity to SEQ ID NO: 7). One of the at least one biomarker of sensitivity may be CD8B1 (e.g., as measured using an oligonucleotide or its complement having at least 85% (e.g., at least 90%, at least 95%, or 100%) sequence identity to SEQ ID NO: 8). One of the at least one biomarker of sensitivity may be KIAA0984 (e.g., as measured using an oligonucleotide or its complement having at least 85% (e.g., at least 90%, at least 95%, or 100%) sequence identity to SEQ ID NO: 9). One of the at least one biomarker of sensitivity may be BCL2 (e.g., as measured using an oligonucleotide or its complement having at least 85% (e.g., at least 90%, at least 95%, or 100%) sequence identity to SEQ ID NO: 10). One of the at least one biomarker of sensitivity may be SLC9A3R1 (e.g., as measured using an oligonucleotide or its complement having at least 85% (e.g., at least 90%, at least 95%, or 100%) sequence identity to SEQ ID NO: 12). One of the at least one biomarker of sensitivity may be FBP1 (e.g., as measured using an oligonucleotide or its complement having at least 85% (e.g., at least 90%, at least 95%, or 100%) sequence identity to SEQ ID NO: 13). One of the at least one biomarker of sensitivity may be ITGB7 (e.g., as measured using an oligonucleotide or its complement having at least 85% (e.g., at least 90%, at least 95%, or 100%) sequence identity to SEQ ID NO: 14). One of the at least one biomarker of sensitivity may be HIST1H3H (e.g., as measured using an oligonucleotide or its complement having at least 85% (e.g., at least 90%, at least 95%, or 100%) sequence identity to SEQ ID NO: 16). One of the at least one biomarker of sensitivity may be PDCD4 (e.g., as measured using an oligonucleotide or its complement having at least 85% (e.g., at least 90%, at least 95%, or 100%) sequence identity to SEQ ID NO: 18). One of the at least one biomarker of sensitivity may be HBA2 (e.g., as measured using an oligonucleotide or its complement having at least 85% (e.g., at least 90%, at least 95%, or 100%) sequence identity to SEQ ID NO: 19). One of the at least one biomarker of sensitivity may be CD37 (e.g., as measured using an oligonucleotide or its complement having at least 85% (e.g., at least 90%, at least 95%, or 100%) sequence identity to SEQ ID NO: 20). One of the at least one biomarker of sensitivity may be TARP (e.g., as measured using an oligonucleotide or its complement having at least 85% (e.g., at least 90%, at least 95%, or 100%) sequence identity to SEQ ID NO: 21 or 22). One of the at least one biomarker of sensitivity may be SPI1 (e.g., as measured using an oligonucleotide or its complement having at least 85% (e.g., at least 90%, at least 95%, or 100%) sequence identity to SEQ ID NO: 23). One of the at least one biomarker of sensitivity may be KIAA0182 (e.g., as measured using an oligonucleotide or its complement having at least 85% (e.g., at least 90%, at least 95%, or 100%) sequence identity to SEQ ID NO: 24 or 27). One of the at least one biomarker of sensitivity may be PTP4A3 (e.g., as measured using an oligonucleotide or its complement having at least 85% (e.g., at least 90%, at least 95%, or 100%) sequence identity to SEQ ID NO: 26).

In certain embodiments of any aspect of the invention, one of the at least one biomarker of resistance may be ANXA1 (e.g., as measured using an oligonucleotide or its complement having at least 85% (e.g., at least 90%, at least 95%, or 100%) sequence identity to SEQ ID NO: 104). One of the at least one biomarker of resistance may be GPX1 (e.g., as measured using an oligonucleotide or its complement having at least 85% (e.g., at least 90%, at least 95%, or 100%) sequence identity to SEQ ID NO: 105). One of the at least one biomarker of resistance may be SPTBN1 (e.g., as measured using an oligonucleotide or its complement having at least 85% (e.g., at least 90%, at least 95%, or 100%) sequence identity to SEQ ID NO: 106). One of the at least one biomarker of resistance may be ANXA2 (e.g., as measured using an oligonucleotide or its complement having at least 85% (e.g., at least 90%, at least 95%, or 100%) sequence identity to SEQ ID NO: 107, 110, or 114). One of the at least one biomarker of resistance may be CAPN2 (e.g., as measured using an oligonucleotide or its complement having at least 85% (e.g., at least 90%, at least 95%, or 100%) sequence identity to SEQ ID NO: 108). One of the at least one biomarker of resistance may be ZA20D2 (e.g., as measured using an oligonucleotide or its complement having at least 85% (e.g., at least 90%, at least 95%, or 100%) sequence identity to SEQ ID NO: 109). One of the at least one biomarker of resistance may be TMSB10 (e.g., as measured using an oligonucleotide or its complement having at least 85% (e.g., at least 90%, at least 95%, or 100%) sequence identity to SEQ ID NO: 111). One of the at least one biomarker of resistance may be PRNP (e.g., as measured using an oligonucleotide or its complement having at least 85% (e.g., at least 90%, at least 95%, or 100%) sequence identity to SEQ ID NO: 112). One of the at least one biomarker of resistance may be TIMP1 (e.g., as measured using an oligonucleotide or its complement having at least 85% (e.g., at least 90%, at least 95%, or 100%) sequence identity to SEQ ID NO113). One of the at least one biomarker of resistance may be PSMA1 (e.g., as measured using an oligonucleotide or its complement having at least 85% (e.g., at least 90%, at least 95%, or 100%) sequence identity to SEQ ID NO: 115, 118, or 123). One of the at least one biomarker of resistance may be PSMB2 (e.g., as measured using an oligonucleotide or its complement having at least 85% (e.g., at least 90%, at least 95%, or 100%) sequence identity to SEQ ID NO: 116). One of the at least one biomarker of resistance may be UGP2 (e.g., as measured using an oligonucleotide or its complement having at least 85% (e.g., at least 90%, at least 95%, or 100%) sequence identity to SEQ ID NO: 117). One of the at least one biomarker of resistance may be CD44 (e.g., as measured using an oligonucleotide or its complement having at least 85% (e.g., at least 90%, at least 95%, or 100%) sequence identity to SEQ ID NO: 119 or 135). One of the at least one biomarker of resistance may be TM4SF1 (e.g., as measured using an oligonucleotide or its complement having at least 85% (e.g., at least 90%, at least 95%, or 100%) sequence identity to SEQ ID NO: 120 or 124). One of the at least one biomarker of resistance may be ANXA2P2 (e.g., as measured using an oligonucleotide or its complement having at least 85% (e.g., at least 90%, at least 95%, or 100%) sequence identity to SEQ ID NO: 122). One of the at least one biomarker of resistance may be MCF2L2 (e.g., as measured using an oligonucleotide or its complement having at least 85% (e.g., at least 90%, at least 95%, or 100%) sequence identity to SEQ ID NO: 125). One of the at least one biomarker of resistance may be DNAPTP6 (e.g., as measured using an oligonucleotide or its complement having at least 85% (e.g., at least 90%, at least 95%, or 100%) sequence identity to SEQ ID NO: 126). One of the at least one biomarker of resistance may be WDR1 (e.g., as measured using an oligonucleotide or its complement having at least 85% (e.g., at least 90%, at least 95%, or 100%) sequence identity to SEQ ID NO: 127). One of the at least one biomarker of resistance may be PSMD1 (e.g., as measured using an oligonucleotide or its complement having at least 85% (e.g., at least 90%, at least 95%, or 100%) sequence identity to SEQ ID NO: 128 or 133). One of the at least one biomarker of resistance may be VIM (e.g., as measured using an oligonucleotide or its complement having at least 85% (e.g., at least 90%, at least 95%, or 100%) sequence identity to SEQ ID NO: 129). One of the at least one biomarker of resistance may be RPS6KA3 (e.g., as measured using an oligonucleotide or its complement having at least 85% (e.g., at least 90%, at least 95%, or 100%) sequence identity to SEQ ID NO: 130). One of the at least one biomarker of resistance may be MSN (e.g., as measured using an oligonucleotide or its complement having at least 85% (e.g., at least 90%, at least 95%, or 100%) sequence identity to SEQ ID NO: 131). One of the at least one biomarker of resistance may be PFN1 (e.g., as measured using an oligonucleotide or its complement having at least 85% (e.g., at least 90%, at least 95%, or 100%) sequence identity to SEQ ID NO: 132). One of the at least one biomarker of resistance may be ASPH (e.g., as measured using an oligonucleotide or its complement having at least 85% (e.g., at least 90%, at least 95%, or 100%) sequence identity to SEQ ID NO: 134). One of the at least one biomarker of resistance may be YWHAB (e.g., as measured using an oligonucleotide or its complement having at least 85% (e.g., at least 90%, at least 95%, or 100%) sequence identity to SEQ ID NO: 136). One of the at least one biomarker of resistance may be LGALS3BP (e.g., as measured using an oligonucleotide or its complement having at least 85% (e.g., at least 90%, at least 95%, or 100%) sequence identity to SEQ ID NO: 137). One of the at least one biomarker of resistance may be ETF1 (e.g., as measured using an oligonucleotide or its complement having at least 85% (e.g., at least 90%, at least 95%, or 100%) sequence identity to SEQ ID NO: 138). One of the at least one biomarker of resistance may be MARCKS (e.g., as measured using an oligonucleotide or its complement having at least 85% (e.g., at least 90%, at least 95%, or 100%) sequence identity to SEQ ID NO: 139). One of the at least one biomarker of resistance may be CAV2 (e.g., as measured using an oligonucleotide or its complement having at least 85% (e.g., at least 90%, at least 95%, or 100%) sequence identity to SEQ ID NO: 140). One of the at least one biomarker of resistance may be ACTG1 (e.g., as measured using an oligonucleotide or its complement having at least 85% (e.g., at least 90%, at least 95%, or 100%) sequence identity to SEQ ID NO: 141). One of the at least one biomarker of resistance may be SEPT10 (e.g., as measured using an oligonucleotide or its complement having at least 85% (e.g., at least 90%, at least 95%, or 100%) sequence identity to SEQ ID NO: 142). One of the at least one biomarker of resistance may be M-RIP (e.g., as measured using an oligonucleotide or its complement having at least 85% (e.g., at least 90%, at least 95%, or 100%) sequence identity to SEQ ID NO: 143).

In some embodiments of any aspect of the invention, at least five biomarkers of sensitivity selected from the biomarkers of Table 1 may be measured according to the methods of the invention (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements). Alternatively, at least five oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 1, may be present in devices and kits of the invention. For example, the biomarkers of Table 1 may be those having a correlation coefficient of at least 0.3 (e.g., at least 0.35, at least 0.4, or at least 0.45). For example, the biomarkers of Table 1 may be GATA3 (SEQ ID NO: 415), CBFA2T3 (SEQ ID NO: 416), SPDEF (SEQ ID NO: 417), HBA1 (SEQ ID NO: 418), and TFF1 (SEQ ID NO: 419).

In some embodiments of any aspect of the invention, at least ten biomarkers of sensitivity selected from the biomarkers of Table 1 may be measured according to the methods of the invention (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements). Alternatively, at least ten oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 1, may be present in devices and kits of the invention. For example, the biomarkers of Table 1 may be those having a correlation coefficient of at least 0.3 (e.g., at least 0.35, at least 0.4, or at least 0.45). For example, the biomarkers of Table 1 may be GATA3 (SEQ ID NO: 415), CBFA2T3 (SEQ ID NO: 416), SPDEF (SEQ ID NO: 417), HBA1 (SEQ ID NO: 418), TFF1 (SEQ ID NO: 419), CD8B1 (SEQ ID NO: 420), KIAA0984 (SEQ ID NO: 421), BCL2 (SEQ ID NO: 422), SLC9A3R1 (SEQ ID NO: 423), FBP1 (SEQ ID NO: 424), and ITGB7 (SEQ ID NO: 425).

In some embodiments of any aspect of the invention, at least fifteen biomarkers of sensitivity selected from the biomarkers of Table 1 may be measured according to the methods of the invention (e.g., GATA3 biomarker (e.g., by hybridizing to any one of oligonucleotides of SEQ ID NOs: 1-3 or their complements), such as the biomarkers of any one of SEQ ID NOs: 415-430, which may be measured by hybridizing to any one of the oligonucleotides of SEQ ID NOs: 1-14 and 16-22 or their complements). Alternatively, at least fifteen oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 1, may be present in devices and kits of the invention. For example, the biomarkers of Table 1 may be those having a correlation coefficient of at least 0.3 (e.g., at least 0.35, or at least 0.4). For example, the biomarkers of Table 1 may be GATA3 (SEQ ID NO: 415), CBFA2T3 (SEQ ID NO: 416), SPDEF (SEQ ID NO: 417), HBA1 (SEQ ID NO: 418), TFF1 (SEQ ID NO: 419), CD8B1 (SEQ ID NO: 420), KIAA0984 (SEQ ID NO: 421), BCL2 (SEQ ID NO:

422), SLC9A3R1 (SEQ ID NO: 423), FBP1 (SEQ ID NO: 424), ITGB7 (SEQ ID NO: 425), HIST1H3H (SEQ ID NO: 426), PDCD4 (SEQ ID NO: 427), HBA2 (SEQ ID NO: 428), CD37 (SEQ ID NO: 429), and TARP (SEQ ID NO: 430).

In some embodiments of any aspect of the invention, at least five biomarkers of resistance selected from the biomarkers of Table 2 may be measured according to the methods of the invention (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements). Alternatively, at least five oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 2, may be present in devices and kits of the invention. For example, the biomarkers of Table 2 may be those having an absolute value of the correlation coefficient of at least 0.3 (e.g., at least 0.35, at least 0.4, or at least 0.45). For example, the biomarkers of Table 2 may be ANXA1 (SEQ ID NO: 431), GPX1 (SEQ ID NO: 432), SPTBN1 (SEQ ID NO: 433), ANXA2 (SEQ ID NO: 434), and CAPN2 (SEQ ID NO: 435).

In some embodiments of any aspect of the invention, at least ten biomarkers of resistance selected from the biomarkers of Table 2 may be measured according to the methods of the invention (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements). Alternatively, at least ten oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 2, may be present in devices and kits of the invention. For example, the biomarkers of Table 2 may be those having an absolute value of the correlation coefficient of at least 0.3 (e.g., at least 0.35, at least 0.4, or at least 0.45). For example, the biomarkers of Table 2 may be ANXA1 (SEQ ID NO: 431), GPX1 (SEQ ID NO: 432), SPTBN1 (SEQ ID NO: 433), ANXA2 (SEQ ID NO: 434), CAPN2 (SEQ ID NO: 435), ZA20D2 (SEQ ID NO: 436), TMSB10 (SEQ ID NO: 437), PRNP (SEQ ID NO: 438), TIMP1 (SEQ ID NO: 439), and PSMA1 (SEQ ID NO: 440).

In some embodiments of any aspect of the invention, at least fifteen biomarkers of resistance selected from the biomarkers of Table 2 may be measured according to the methods of the invention (e.g., ANXA1 biomarker (e.g., by hybridizing to an oligonucleotide of SEQ ID NO: 104 or its complement), such as the biomarkers of any one of SEQ ID NOs: 431-445, which may be measured by hybridizing to any one of oligonucleotides of SEQ ID NOs: 104-121 or their complements). Alternatively, at least fifteen oligonucleotides, each of which is complementary to or identical to at least 5 consecutive nucleotides (e.g., at least 6, at least 7, at least 8, at least 9, at least 10, at least 11, at least 12, at least 13, at least 14, at least 15, or at least 20; the oligonucleotide can also be 5-20, 25, 5-50, 50-100, or over 100 consecutive nucleotides long) of a biomarker of Table 2, may be present in devices and kits of the invention. For example, the biomarkers of Table 2 may be those having an absolute value of the correlation coefficient of at least 0.3 (e.g., at least 0.35, or at least 0.4). For example, the biomarkers of Table 2 may be ANXA1 (SEQ ID NO: 431), GPX1 (SEQ ID NO: 432), SPTBN1 (SEQ ID NO: 433), ANXA2 (SEQ ID NO: 434), CAPN2 (SEQ ID NO: 435), ZA20D2 (SEQ ID NO: 436), TMSB10 (SEQ ID NO: 437), PRNP (SEQ ID NO: 438), TIMP1 (SEQ ID NO: 439), PSMA1 (SEQ ID NO: 440), PSMB2 (SEQ ID NO: 441), UGP2 (SEQ ID NO: 442), CD44 (SEQ ID NO: 443), TM4SF1 (SEQ ID NO: 444), and ACTN4 (SEQ ID NO: 445).

In other embodiments of any aspect of the invention, the cancer is a cancer of the breast, prostate, lung and bronchus, colon and rectum, urinary bladder, skin, kidney, pancreas, oral cavity and pharynx, ovary, thyroid, parathyroid, stomach, brain, esophagus, liver and intrahepatic bile duct, cervix larynx, heart, testis, small and large intestine, anus, anal canal and anorectum, vulva, gallbladder, pleura, bones and joints, hypopharynx, eye and orbit, nose, nasal cavity and middle ear, nasopharynx, ureter, peritoneum, omentum and mesentery, or gastrointestines. In yet other embodiments of any aspect of the invention, the cancer may be chronic myeloid leukemia, acute lymphocytic leukemia, non-Hodgkin lymphoma, melanoma, carcinoma, basal cell carcinoma, malignant mesothelioma, neuroblastoma, multiple myeloma, leukemia, retinoblastoma, acute myeloid leukemia, chronic lymphocytic leukemia, Hodgkin lymphoma, carcinoid tumors, acute tumor, or soft tissue sarcoma.

In some embodiments of any aspect of the invention, the cancer is a hormone positive cancer. In certain embodiments of any aspect of the invention, the cancer is metastatic. In particular embodiments of any aspect of the invention, the cancer is a breast cancer (e.g., hormone receptor positive breast cancer).

In particular embodiments of any aspect of the invention, the anti-cancer agent is fulvestrant. In certain embodiments any aspect of the invention, the patient is a female (e.g., a postmenopausal female). In some embodiments of any aspect of the invention, the cancer has progressed following antiestrogen therapy.

In certain embodiments of any aspect of the invention, the anti-cancer agent is gefitinib. In particular embodiments of any aspect of the invention, the cancer is lung cancer (e.g., non-small cell lung cancer).

In other embodiments of any aspect of the invention, the anti-cancer agent is cisplatin. In some embodiments of any aspect of the invention, the cancer is a testicular tumor (e.g., metastatic testicular tumor), an ovarian tumor (e.g., a metastatic ovarian tumor), or a bladder cancer (e.g., advanced bladder cancer).

In some embodiments of any aspect of the invention, the anti-cancer agent is erlotinib. In certain embodiments of any aspect of the invention, the cancer is a non-small cell lung cancer (e.g., locally advanced or metastatic non-small cell lung cancer) or pancreatic cancer (e.g., locally advanced, unresectable, or metastatic pancreatic cancer).

In certain embodiments of any aspect of the invention, the anti-cancer agent is vincristine. In particular embodiments of any aspect of the invention, the cancer is leukemia (e.g., acute lymphocytic leukemia).

In some embodiments of any aspect of the invention, the anti-cancer agent is trastuzumab. In certain embodiments of any aspect of the invention, the cancer is breast cancer (e.g., adjuvant breast cancer or metastatic breast cancer) or gastric cancer (e.g., metastatic gastric cancer).

In other embodiments of any aspect of the invention, the first sample is a biopsy. In particular embodiments of any aspect of the invention, the second sample is a biopsy. In some embodiments any aspect of the invention, the first sample and the second sample are the same sample. In other embodiments of any aspect of the invention, the first sample and the second sample are not the same sample.

In certain embodiments of any aspect of the invention, the expression level of the biomarker of sensitivity is measured using qRT-PCR or q-LAMP. In particular embodiments of any aspect of the invention, the expression level of the biomarker of resistance is measured using qRT-PCR or q-LAMP.

In certain other embodiments of any one of eighth to tenth aspects of the invention, the step of determining a level of expression of at least one biomarker of sensitivity comprises contacting the first sample with an oligonucleotide or its complement having at least 85% (e.g., at least 90%, at least 95%, or 100%) sequence identity to a sequence that is complimentary or identical to the at least one biomarker of sensitivity, in which the contacting is performed under conditions allowing for hybridization of the oligonucleotide to the at least one biomarker of sensitivity. For example, the oligonucleotide may have at least 85% (e.g., at least 90%, at least 95%, or 100%) sequence identity to any one of SEQ ID NOs: 1-103, preferably the oligonucleotide may have at least 85% sequence identity to any one of SEQ ID NOs: 1-27.

In certain embodiments of any one of eighth to tenth aspects of the invention, the step of determining a level of expression of at least one biomarker of resistance comprises contacting the first sample with an oligonucleotide or its complement having at least 85% (e.g., at least 90%, at least 95%, or 100%) sequence identity to a sequence of an oligonucleotide that is complimentary or identical to the at least one biomarker of resistance, in which the contacting is performed under conditions allowing for hybridization of the oligonucleotide to the at least one biomarker of resistance. For example, the oligonucleotide may have at least 85% (e.g., at least 90%, at least 95%, or 100%) sequence identity to any one of SEQ ID NOs: 104-414, preferably the oligonucleotide may have at least 85% (e.g., at least 90%, at least 95%, or 100%) sequence identity to any one of SEQ ID NOs: 104-143.

In some embodiments of any one of eighth to tenth aspects of the invention, the level of expression of the one or more biomarkers of sensitivity is determined by detecting the level of mRNA transcribed from the one or more genes listed in Table 1.

In other embodiments of any one of eighth to tenth aspects of the invention, the level of expression of the one or more biomarkers of sensitivity is determined by measuring the level of a protein product of the one or more genes listed in Table 1.

In particular embodiments of any one of eighth to tenth aspects of the invention, the level of expression of the one or more biomarkers of sensitivity is determined by detecting the level of the biological activity of a protein product of the one or more genes listed in Table 1.

In certain embodiments of any one of eighth to tenth aspects of the invention, the level of expression of the one or more biomarkers of resistance is determined by detecting the level of mRNA transcribed from the one or more genes listed in Table 2.

In other embodiments of any one of eighth to tenth aspects of the invention, the level of expression of the one or more biomarkers of resistance is determined by measuring the level of a protein product of the one or more genes listed in Table 2.

In some embodiments of any one of eighth to tenth aspects of the invention, the level of expression of the one or more biomarkers of resistance is determined by detecting the level of the biological activity of a protein product of the one or more genes listed in Table 2.

In particular embodiments of any one of eighth to tenth aspects of the invention, an increase in the level of expression of the one or more biomarkers of sensitivity indicates increased responsiveness of the patient to the anti-cancer agent.

In some embodiments of any one of eighth to tenth aspects of the invention, a decrease in the level of expression of the one or more biomarkers of resistance indicates increased responsiveness of the patient to the anti-cancer agent.

In other embodiments of any one of eighth to tenth aspects of the invention, the method involves converting the level of expression of the one or more biomarkers of sensitivity into a mean score for the anti-cancer agent, where the mean score identifies the responsiveness of the patient to the anti-cancer agent.

In particular embodiments of any one of eighth to tenth aspects of the invention, the value of the mean score for the one or more biomarkers of sensitivity that is greater than or equal to 0.25 (e.g., greater than or equal to 0.3, greater than or equal to 0.4, greater than or equal to 0.5, greater than or equal to 0.6, or greater than or equal to 0.7; preferably greater than or equal to 0.3) indicates the patient is responsive to the anti-cancer agent.

In certain embodiments of any one of eighth to tenth aspects of the invention, the method involves converting the level of expression of the one or more biomarkers of resistance into a mean score for the anti-cancer agent, where the mean score identifies the responsiveness of the patient to the anti-cancer agent.

In some embodiments of any one of eighth to tenth aspects of the invention, the absolute value of the mean score for the one or more biomarkers of resistance that is greater than or equal to 0.25 (e.g., greater than or equal to 0.3, greater than or equal to 0.4, greater than or equal to 0.5, greater than or equal to 0.6, or greater than or equal to 0.7; preferably, greater than or equal to 0.3) indicates the patient is responsive to the anti-cancer agent.

In particular embodiments of any one of eighth to tenth aspects of the invention, the method involves:

(i) converting the level of expression of the one or more biomarkers of sensitivity into a first mean score for the anti-cancer agent;

(ii) converting the level of expression of the one or more biomarkers of resistance into a second mean score for the anti-cancer agent;

(iii) subtracting the second mean score from the first mean score to obtain a difference score for the anti-cancer agent, where the difference score identifies the responsiveness of the patient to the anti-cancer agent.

In some embodiments of any one of eighth to tenth aspects of the invention, the value of the difference score that is greater than or equal to 0.25 (e.g., greater than or equal to 0.3, greater than or equal to 0.4, greater than or equal to 0.5, greater than or equal to 0.6, or greater than or equal to 0.7) indicates the patient is responsive to the anti-cancer agent.

In some embodiments of any aspect of the invention, the biomarker of Table 1 is not ZNF165. In some embodiments of any aspect of the invention, the biomarker of Table 1 is not ZNF394. In some embodiments of any aspect of the invention, the biomarker of Table 2 is not ZFP36L1. In some embodiments of any aspect of the invention, the biomarker of Table 2 is not ZNF258. In some embodiments of any aspect of the invention, the biomarker of Table 2 is not ZNF238. In certain embodiments of any aspect of the invention, in particular, the methods, devices, and kits of the invention, the biomarker of Table 1 is not a zinc-finger gene. In certain embodiments of any aspect of the invention, in particular, the methods, devices, and kits of the invention, the biomarker of Table 2 is not a zinc-finger gene. In some embodiments of any aspect of the invention, the oligonucleotide may not be identical or complementary to SEQ ID NO: 89. In some embodiments of any aspect of the invention, the oligonucleotide may not be identical or complementary to SEQ ID NO: 101. In some embodiments of any aspect of the invention, the oligonucleotide may not be identical or complementary to SEQ ID NO: 394. In some embodiments of any aspect of the invention, the oligonucleotide may not be identical or complementary to SEQ ID NO: 215. In some embodiments of any aspect of the invention, the oligonucleotide may not be identical or complementary to SEQ ID NO: 232.

DEFINITIONS

"Resistant" or "resistance" as used herein means that a cell, a tumor, a person, or a living organism is able to withstand treatment, e.g., with a compound, such as an anti-cancer agent (e.g., a chemotherapeutic agent) or radiation treatment, in that the treatment inhibits the growth of a cell, e.g., a cancer cell, in vitro or in a tumor, person, or living organism by less than 10%, 20%, 30%, 40%, 50%, 60%, or 70% relative to the growth of a cell not exposed to the treatment. Resistance to treatment may be determined by a cell-based assay that measures the growth of treated cells as a function of the cells' absorbance of an incident light beam as used to perform the NCI60 assays described herein. In this example, greater absorbance indicates greater cell growth, and thus, resistance to the treatment. A smaller reduction in growth indicates more resistance to a treatment. By "chemoresistant" or "chemoresistance" is meant resistance to a compound.

"Sensitive," "sensitivity," "responsive," or "responsiveness" as used herein means that a cell, a tumor, a person, or a living organism is responsive to treatment, e.g., with a compound, such as an anti-cancer agent (e.g., a chemotherapeutic agent) or radiation treatment, in that the treatment inhibits the growth of a cell, e.g., a cancer cell, in vitro or in a tumor, person, or living organism by 70%, 80%, 90%, 95%, 99% or 100%. Sensitivity to treatment may be determined by a cell-based assay that measures the growth of treated cells as a function of the cells' absorbance of an incident light beam as used to perform the NCI60 assays described herein. In this example, lesser absorbance indicates lesser cell growth, and thus, sensitivity to the treatment. A greater reduction in growth indicates more sensitivity to the treatment. By "chemosensitive" or "chemosensitivity" is meant sensitivity to a compound.

"Complement" of a nucleic acid sequence or a "complementary" nucleic acid sequence as used herein refers to an oligonucleotide which is in "antiparallel association" when it is aligned with the nucleic acid sequence such that the 5' end of one sequence is paired with the 3' end of the other. Nucleotides and other bases may have complements and may be present in complementary nucleic acids. Bases not commonly found in natural nucleic acids that may be included in the nucleic acids of the present invention include, for example, inosine and 7-deazaguanine. "Complementarity" may not be perfect; stable duplexes of complementary nucleic acids may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

When complementary nucleic acid sequences form a stable duplex, they are said to be "hybridized" or to "hybridize" to each other or it is said that "hybridization" has occurred. Nucleic acids are referred to as being "complementary" if they contain nucleotides or nucleotide homologues that can form hydrogen bonds according to Watson-Crick base-pairing rules (e.g., G with C, A with T or A with U) or other hydrogen bonding motifs such as for example diaminopurine with T, 5-methyl C with G, 2-thiothymidine with A, inosine with C, pseudoisocytosine with G, etc. Anti-sense RNA may be complementary to other oligonucleotides, e.g., mRNA.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

"Biomarker" as used herein indicates a gene or RNA (e.g., a miRNA) whose expression indicates sensitivity or resistance to a treatment.

"Compound" as used herein means a chemical or biological substance, e.g., a drug, a protein, an antibody, or an oligonucleotide, which may be used to treat a disease or which has biological activity in vivo or in vitro. Preferred compounds may or may not be approved by the U.S. Food and Drug Administration (FDA). Preferred compounds include, e.g., anti-cancer agents (chemotherapy agents) that may inhibit cancer growth. Preferred anti-cancer agents (chemotherapy agents) include fulvestrant (also known under the name FASLODEX®), gefitinib (IRESSA®), ERLOTINIB (TARCEVA®), tamoxifen, trastuzumab (HERCEPTIN®), cisplatin, belinostat, and vincristine. Preferably, the anti-cancer agent is fulvestrant.

To "inhibit growth" as used herein means causing a reduction in cell growth in vivo or in vitro by, e.g., 10%, 20%, 30%, 40%, 50%, 60%, 70%, 80%, 90%, 95%, or 99% or more, as evident by a reduction in the size or number of cells exposed to a treatment (e.g., exposure to a compound), relative to the size or number of cells in the absence of the treatment. Growth inhibition may be the result of a treatment that induces apoptosis in a cell, induces necrosis in a cell, slows cell cycle progression, disrupts cellular metabolism, induces cell lysis, or induces some other mechanism that reduces the size or number of cells.

"Marker gene" or "biomarker gene" as used herein means a gene in a cell the expression of which correlates to sensitivity or resistance of the cell (and thus the patient from which the cell was obtained) to a treatment (e.g., exposure to a compound).

"Microarray" as used herein means a device employed by any method that quantifies one or more subject oligonucleotides, e.g., DNA or RNA, or analogues thereof, at a time. One exemplary class of microarrays consists of DNA probes attached to a glass or quartz surface. For example, many microarrays, including those made by Affymetrix, use several probes for determining the expression of a single gene. The DNA microarray may contain oligonucleotide probes that may be, e.g., full-length cDNAs complementary to an RNA or cDNA fragments that hybridize to part of an RNA. Exemplary RNAs include mRNA, miRNA, and miRNA precursors. Exemplary microarrays also include a "nucleic acid microarray" having a substrate-bound plurality of nucleic acids, hybridization to each of the plurality of bound nucleic acids being separately detectable. The substrate may be solid or porous, planar or non-planar, unitary or distributed. Exemplary nucleic acid microarrays include all of the devices so called in Schena (ed.), DNA Microarrays: A Practical Approach (Practical Approach Series), Oxford University Press (1999); Nature Genet. 21(1)(suppl.):1-60 (1999); Schena (ed.), Microarray Biochip: Tools and Technology, Eaton Publishing Company/BioTechniques Books Division (2000). Additionally, exemplary nucleic acid microarrays include substrate-bound plurality of nucleic acids in which the plurality of nucleic acids are disposed on a plurality of beads, rather than on a unitary planar substrate, as is described, inter alia, in Brenner et al., Proc. Natl. Acad. Sci. USA 97(4):1665-1670 (2000). Examples of nucleic acid microarrays may be found in U.S. Pat. Nos. 6,391,623, 6,383,754, 6,383,749, 6,380,377, 6,379,897, 6,376,191, 6,372,431, 6,351,712 6,344,316, 6,316,193, 6,312,906, 6,309,828, 6,309,824, 6,306,643, 6,300,063, 6,287,850, 6,284,497, 6,284,465, 6,280,954, 6,262,216, 6,251,601, 6,245,518, 6,263,287, 6,251,601, 6,238,866, 6,228,575, 6,214,587, 6,203,989, 6,171,797, 6,103,474, 6,083,726, 6,054,274, 6,040,138, 6,083,726, 6,004,755, 6,001,309, 5,958,342, 5,952,180, 5,936,731, 5,843,655, 5,814,454, 5,837,196, 5,436,327, 5,412,087, 5,405,783, the disclosures of which are incorporated herein by reference in their entireties.

Exemplary microarrays may also include "peptide microarrays" or "protein microarrays" having a substrate-bound plurality of polypeptides, the binding of a oligonucleotide, a peptide, or a protein to each of the plurality of bound polypeptides being separately detectable. Alternatively, the peptide microarray, may have a plurality of binders, including but not limited to monoclonal antibodies, polyclonal antibodies, phage display binders, yeast 2 hybrid binders, aptamers, which can specifically detect the binding of specific oligonucleotides, peptides, or proteins. Examples of peptide arrays may be found in WO 02/31463, WO 02/25288, WO 01/94946, WO 01/88162, WO 01/68671, WO 01/57259, WO 00/61806, WO 00/54046, WO 00/47774, WO 99/40434, WO 99/39210, WO 97/42507 and U.S. Pat. Nos. 6,268,210, 5,766,960, 5,143,854, the disclosures of which are incorporated herein by reference in their entireties.

"Gene expression" as used herein means the amount of a gene product in a cell, tissue, organism, or subject, e.g., amounts of DNA, RNA, or proteins, amounts of modifications of DNA, RNA, or protein, such as splicing, phosphorylation, acetylation, or methylation, or amounts of activity of DNA, RNA, or proteins associated with a given gene.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COLO205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The term "sample," as used herein, refers to any specimen (e.g., tissue and cells (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy). Biopsy (e.g., breast cancer biopsy) may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve amplification, e.g., using PCR (RT-PCR). The standard methods of sample purification, such as removal of unwanted molecules, are known in the art.

The terms "effective amount," "amount effective to," and "therapeutically effective amount," as used interchangeably herein, refer to an amount of an anti-cancer agent (e.g., fulvestrant) sufficient to produce a desired result, such as complete response (CR) of the patient having a cancer, partial response (PR) of the patient having a cancer, or stable disease (SD) in the patient having a cancer. The desirable response criteria (CR, PR, or SD) are well-known in the art, see, e.g., Response Evaluation Criteria in Solid Tumors (RECIST).

The terms "patient" and "subject," as used interchangeably herein, refer to any animal (e.g., a mammal, e.g., a human). A subject to be treated or tested for responsiveness to an anti-cancer agent according to the methods described herein may be one who has been diagnosed with a cancer (e.g., breast cancer). Diagnosis may be performed by any method or technique known in the art, such as self-exam, x-ray (e.g., mammogram), MRI, or biopsy. A non-limiting example of a patient includes a female (e.g., a postmenopausal female) having a breast cancer (e.g., a hormone receptor positive breast cancer). This patient may have been identified using techniques and methods known in the art. To minimize exposure of this patient to drugs that may not be useful, the patient may be determined as either responsive or non-responsive to a specific anti-cancer agent (e.g., fulvestrant) according to the methods of the invention.

"Treatment" or "medical treatment" means administering to a subject or living organism or exposing to a cell or tumor a compound, such as an anti-cancer agent (e.g., a drug, a protein, an antibody, an oligonucleotide, a chemotherapeutic agent, and a radioactive agent) or some other form of medical intervention used to treat or prevent cancer or the symptoms of cancer (e.g., cryotherapy and radiation therapy). Radiation therapy includes the administration to a patient of radiation generated from sources such as particle accelerators and related medical devices that emit X-radiation, gamma radiation, or electron (Beta radiation) beams. A treatment may further include surgery, e.g., to remove a tumor from a subject or living organism.

Other features and advantages of the invention will be apparent from the following Detailed Description, the drawings, and the claims.

DETAILED DESCRIPTION

Figure 1:
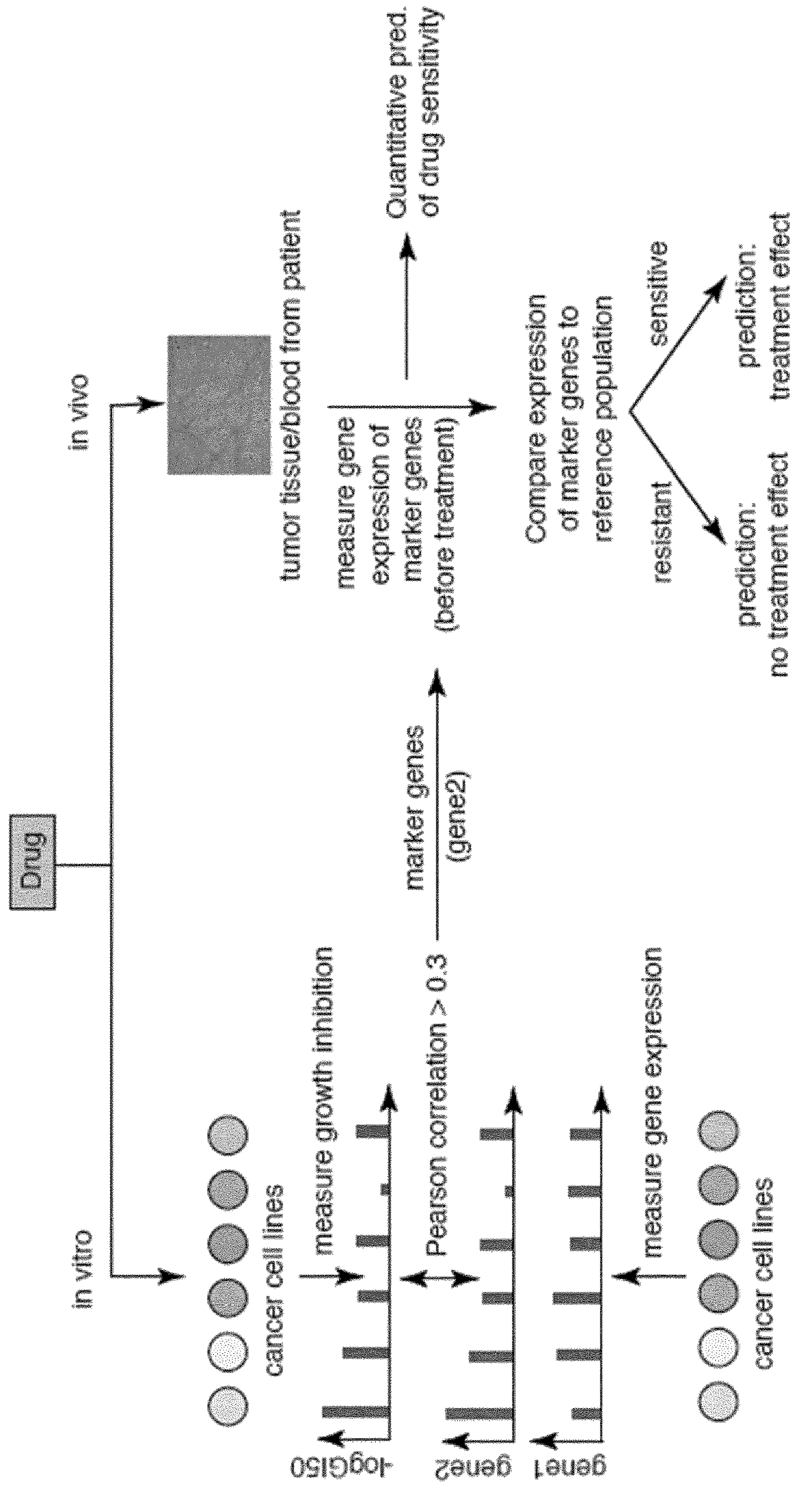
FIG. 1 depicts an illustration of the method of identifying biomarkers and predicting patient sensitivity to a medical treatment. The method has an in vitro component where the growth inhibition of a compound or medical treatment is measured on cell lines (6 of the 60 cell lines tested are shown). The gene expression is measured on the same cell lines without compound treatment. Those genes that have a correlation above a certain cutoff (e.g., a preferred cutoff of 0.25, in which a correlation coefficient equal to or greater than the cutoff of 0.25 is deemed statistcally significant by, e.g., cross-validation) to the growth inhibition are termed marker genes and the expression of those genes in vivo, e.g., may predict the sensitivity or resistance of a patient's cancer to a compound or other medical treatment. The in vivo component is applied to a patient to determine whether or not the treatment will be effective in treating disease in the patient. Here, the gene expression in cells of a sample of the suspected disease tissue (e.g., a tumor) in the patient is measured before or after treatment. The activity of the marker genes in the sample is compared to a reference population of patients known to be sensitive or resistant to the treatment. The expression of marker genes in the cells of the patient known to be expressed in the cells of reference patients sensitive to the treatment indicates that the patient to be treated is sensitive to the treatment and vice versa. Based on this comparison the patient is predicted to be sensitive or resistant to treatment with the compound.

The invention features methods for identifying and using one or more biomarkers of treatment sensitivity or resistance, e.g., sensitivity or resistance to one or more treatments for cancer (e.g., a chemothereutic agent such as fulvestrant), to predict treatment efficacy in a patient (e.g., a patient diagnosed with cancer), devices (e.g., a microarray) that include nucleic acid molecules that can detect the level of expression of the biomarkers, and kits that include the devices and instructions for use. The kits of the invention include an array (e.g., a microarray) with one or more single-stranded oligonucleotide probes that have at least 85% (e.g., at least 90%, 95%, 99%, or 100%) sequence identity to a target nucleic acid molecule having a sequence that is complementary or identical to the nucleic acid sequence of one or more biomarkers of sensitivity or resistance to treatment (e.g., treatment with an anti-cancer agent, such as a chemotherapeutic agent) described herein. For example, the probes can be used to detect one or more (e.g., two, three, four, five, ten, twenty, thirty, fifty, or all) of the biomarkers listed in one or more of Tables 1-2, such as GATA3. The oligonucleotide probes of the array can be used detect nucleic acid molecules present in sample applied to the array (e.g., nucleic acid molecules from a sample obtained, derived, or prepared from a subject (e.g., a cell, tissue, or organ sample from a subject)). The kits can also include instructions for using the device to predict the sensitivity or resistance of the subject to the treatment.

A beneficial aspect of the invention is that the methods, devices, and kits can be used to determine the sensitivity and/or resistance of a patient to one or more treatments for cancer (e.g., two, three, four, five, ten, twenty, thirty, or more treatments for cancer, and even all of the treatments for cancer described herein) at the same time by assaying for the level of expression of one or more biomarkers, the expression of which has been correlated with a patient's sensitivity or resistance to a specific treatment for cancer. For example, the methods, devices, and kits can utilize oligonucleotide probes capable of detecting the level of expression of at least one cancer therapy-sensitive biomarker associated with each of the cancer therapies described herein (e.g., the methods, devices, and kits can utilize oligonucleotide probes to detect at least one (e.g., two, three, or more, e.g. all) of the cancer therapy-specific sensitivity biomarkers listed in Table 1, or a subset thereof, e.g., the first 14 of the biomarkers listed in Table 1). Alternatively, or in addition to the cancer therapy-sensitive biomarkers, the methods, devices, and kits can utilize oligonucleotide probes capable of detecting the level of expression of at least one cancer therapy-resistant biomarker associated with each of the cancer therapies described herein (e.g., the methods, devices, and kits can utilize oligonucleotide probes to detect at least one (e.g., two, three, or more, e.g. all) of the cancer therapy-resistant sensitivity biomarkers listed in Table 2, or a subset thereof, e.g., the first 14 of the biomarkers listed in Table 2).

In other examples, the methods, devices, and kits can utilize oligonucleotide probes capable of detecting the level of expression of the cancer therapy-sensitive biomarkers of Table 1 (or a subset thereof) having the first and/or second and/or third highest correlation coefficient (positive correlation). Alternatively, or in addition to the cancer therapy-sensitive biomarkers, the methods, devices, and kits can utilize oligonucleotide probes capable of detecting the level of expression of the cancer therapy-resistant biomarkers of Table 2 (or a subset thereof) having the first and/or second and/or third highest correlation coefficient (negative correlation).

The invention also features methods of using the microarrays to determine whether a subject, e.g., a cancer patient (such as, a breast cancer patient), will be sensitive or resistant to treatment with, e.g., an anti-cancer agent, such as a chemotherapy agent. Also featured are methods of identifying biomarkers of sensitivity or resistance to a medical treatment based on the correlation of biomarker expression to treatment efficacy, e.g., the growth inhibition of cancer cells. Biomarkers that identify subjects as sensitive or resistant to a treatment may also be identified within patient populations already thought to be sensitive or resistant to that treatment. Thus, the methods, devices, and kits of the invention can be used to identify patient subpopulations that are responsive to one or more treatments thought to be ineffective for treating disease (e.g., cancer) in the general population. More generally, cancer patient sensitivity to one or more compounds or other medical treatments may be predicted using biomarker expression regardless of prior knowledge about patient responsiveness to treatment. The method according to the present invention can be implemented using software that is run on an apparatus for measuring gene expression in connection with a microarray. Devices of the invention (e.g., a microarray, such as a DNA and/or RNA microarray) can be included in a kit for processing a tumor sample from a subject (e.g., a cell, tissue, or organ sample containing a tumor or a cell thereof), and the apparatus for reading the device and turning the result into a chemosensitivity profile for the subject may be used to implement the methods of the invention.

Devices Containing Oligonucleotide Probes of the Invention

The devices (e.g., microarrays) of the invention can include one or more (e.g., two, three, four, five, ten, twenty, thirty, fifty, or all) oligonucleotide probes that have nucleotide sequences that are identical (or share at least 85%, 90%, 95%, or 99% identity) to or complementary to, e.g., at least 5, 8, 12, 20, 30, 40, 60, 80, 100, 150, or 200 consecutive nucleotides (or nucleotide analogues) of one or more of the biomarkers listed in Table 1, Table 2, or both. For example, a biomarker may be a biomarker of sensitivity, such as GATA3 (SEQ ID NO: 415), CBFA2T3 (SEQ ID NO: 416), SPDEF (SEQ ID NO: 417), HBA1 (SEQ ID NO: 418), TFF1 (SEQ ID NO: 419), CD8B1 (SEQ ID NO: 420), KIAA0984 (SEQ ID NO: 421), BCL2 (SEQ ID NO: 422), SLC9A3R1 (SEQ ID NO: 423), FBP1 (SEQ ID NO: 424), ITGB7 (SEQ ID NO: 425), HIST1H3H (SEQ ID NO: 426), PDCD4 (SEQ ID NO: 427), HBA2 (SEQ ID NO: 428), CD37 (SEQ ID NO: 429), or TARP (SEQ ID NO: 430). For example, a biomarker may be a biomarker of resistance, such as ANXA1 (SEQ ID NO: 431), GPX1 (SEQ ID NO: 432), SPTBN1 (SEQ ID NO: 433), ANXA2 (SEQ ID NO: 434), CAPN2 (SEQ ID NO: 435), ZA20D2 (SEQ ID NO: 436), TMSB10 (SEQ ID NO: 437), PRNP (SEQ ID NO: 438), TIMP1 (SEQ ID NO: 439), PSMA1 (SEQ ID NO: 440), PSMB2 (SEQ ID NO: 441), UGP2 (SEQ ID NO: 442), CD44 (SEQ ID NO: 443), TM4SF1 (SEQ ID NO: 444), or ACTN4 (SEQ ID NO: 445). The oligonucleotide probes may be, e.g., 5-20, 25, 5-50, 50-100, or over 100 nucleotides long (e.g., at least 15 nucleotides long). The oligonucleotide probes may be deoxyribonucleic acids (DNA) or ribonucleic acids (RNA). Consecutive nucleotides within the oligonucleotide probes (e.g., 5-20, 25, 5-50, 50-100, or over 100 consecutive nucleotides), which are used as biomarkers of chemosensitivity, may also appear as consecutive nucleotides in one or more of the genes and/or RNAs (e.g., miRNA(s)) described herein beginning at or near, e.g., the first, tenth, twentieth, thirtieth, fortieth, fiftieth, sixtieth, seventieth, eightieth, ninetieth, hundredth, hundred-fiftieth, two-hundredth, five-hundredth, or one-thousandth nucleotide of one or more of the biomarkers listed in one or more of Tables 1-2 below.

Probes that may be employed on devices (e.g., microarrays) of the invention include oligonucleotide probes having sequences complementary to or identical to (or sharing at least 85%, 90%, 95%, or 99% identity to) any of the target biomarker sequences described herein. Additionally, probes employed on devices (e.g., microarrays) of the invention may also include proteins, peptides, or antibodies that selectively bind any of the oligonucleotide probe sequences or their complementary sequences. Exemplary probes of treatment sensitivity are listed in Tables 1-2, wherein for each treatment listed, the biomarkers indicative of treatment sensitivity or resistance, respectively, the correlation of biomarker expression to growth inhibition and the sequence of an exemplary probe are shown.

Identification of Biomarkers

The gene expression measurements of the NCI60 cancer cell lines were obtained from the National Cancer Institute and the Massachusetts Institute of Technology (MIT). Each dataset was normalized so that sample expression measured by different chips could be compared. The preferred method of normalization is the log it transformation, which is performed for each gene y on each chip:

$$\log it(y)=\log [(y\text{-background})/(\text{saturation}-y)],$$

where background is calculated as the minimum intensity measured on the chip minus 0.1% of the signal intensity range: min-0.001*(max-min), and saturation is calculated as the maximum intensity measured on the chip plus 0.1% of the signal intensity range: max+0.001*(max-min). The resulting log it transformed data is then z-transformed to mean zero and standard deviation 1.

Next, gene expression is correlated to cancer cell growth inhibition. Growth inhibition data (GI50) of the NCI60 cell lines in the presence of any one of thousands of tested compounds was obtained from the NCI. The correlation between the log it-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given compound may be correlated to the patient's gene expression. Since a plurality of measurements may be available for a single gene, the most accurate determination of correlation coefficient was found to be the median of the correlation coefficients calculated for all probes measuring expression of the same gene.

The median correlation coefficient of gene expression measured on a probe to growth inhibition or patient sensitivity is calculated for all genes, and genes that have a median correlation above 0.3, 0.4, 0.5, 0.6, 0.7, 0.8, 0.9, 0.95, or 0.99 are retained as biomarker genes. Preferably, the correlation coefficient of biomarker genes will exceed 0.25. This is repeated for all the compounds to be tested. The result is a list of marker genes that correlates to sensitivity for each compound tested.

Predicting Patient Sensitivity or Resistance to Medical Treatments

For a given medical treatment (e.g., a compound, such as an anti-cancer agent (a chemotherapy agent)), the expression of one or more biomarkers has been shown to correlate to chemosensitivity and/or chemoresistance. This correlation can be used to classify a patient, e.g., a cancer patient, or a subpopulation of patients, as sensitive or resistant to one or more medical treatments, e.g., one or more of the anti-cancer agents (e.g., chemotherapeutic agents) or radiation therapies described herein. Using a tumor sample or a blood sample (e.g., in case of leukemia or lymphoma) from a patient, expression of the biomarkers in the cells of the patient in the presence of the treatment agent is determined (using, for example, an RNA extraction kit, a DNA microarray and a DNA microarray scanner). Measurements of biomarker expression are then log it transformed as described above. The sum of the expression measurements of the biomarkers is then compared to the median of the sums derived from a training set population of patients having the same tumor. If the sum of biomarker expression in the patient is closest to the median of the sums of expression in the surviving members of the training set, the patient is predicted to be sensitive to the compound or other medical treatment. If the sum of biomarker expression in the patient is closest to the median of the sums of expression in the non-surviving members of the training set, the patient is predicted to be resistant to the compound.

Machine learning techniques such as Neural Networks, Support Vector Machines, K Nearest Neighbor, and Nearest Centroids may also be employed to develop models that discriminate patients sensitive to treatment from those resistant to treatment using biomarker expression as model variables which assign each patient a classification as resistant or sensitive. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes", in Hanson S. J. et al. (Eds.), Computational Learning Theory and Natural Learning Systems 2, MIT Press, 1994, each of which are hereby incorporated by reference in their entirety.

A more compact microarray may be designed using only the oligonucleotide biomarker probes having measurements yielding the median correlation coefficients with cancer cell growth inhibition. Thus, in this embodiment, only one probe needs to be used to measure expression of each biomarker. For example, a microarray according to the invention includes one, two, or three (or more, e.g., all) of the biomarker probes provided in Table 1 having the highest correlation coefficients (positive correlation) from among those biomarkers listed and/or one, two, or three (or more, e.g., all) of the biomarker probes provided in Table 2 having the highest correlation coefficients (negative correlation) from among those biomarkers listed. The device can also include one or more probes directed to GATA3 along with one or more probes directed to one or more of the biomarker probes provided in one or more of Tables 1-2.

As an example, Table 1-2 provides exemplary biomarker probes for determining a patient's sensitivity to fulvestrant. A device of the invention can be prepared for assaying a patient's sensitivity to fulvestrant by incorporating one or more probes directed to the biomarker GATA3, which has the highest correlation coefficient of 0.59 for this group. In other embodiments, a device of the invention can be prepared for assaying a patient's sensitivity to fulvestrant by incorporating one or more probes directed to the two biomarkers associated with fulvestrant having the highest correlation coefficients (e.g., CBFA2T3 (0.54) and SPDEF (0.54)). Other devices of the invention can include one or more biomarker probes directed to those biomarkers having the first, second, and/or third, etc., highest correlation coefficients (positive correlatin) for fulvestrant in Table 1 and/or one or more biomarker probes directed to those biomarkers having the first, second, and/or third, etc., highest correlation coefficients (negative correlation) for fulvestrant in Table 2.

Identifying a Subpopulation of Patients Sensitive to One or More Treatments for Cancer The invention may also be used to identify a subpopulation of patients, e.g., cancer patients, that are sensitive to a compound or other medical treatment previously thought to be ineffective for the treatment of cancer. To this end, biomarkers, the expression of which correlates to sensitivity to a compound or other treatment, may be identified so that patients sensitive to a compound or other treatment may be identified. To identify such biomarkers, expression within cell lines may be correlated to the growth of those cell lines in the presence of the same compound or other treatment. Preferably, biomarkers (such as genes or RNAs) whose expression correlates to cell growth with a correlation coefficient exceeding 0.25 may be considered possible biomarkers.

Alternatively, genes or RNAs (e.g., miRNAs) may be identified as biomarkers according to their ability to discriminate patients known to be sensitive to a treatment from those known to be resistant. The significance of the differences in expression of biomarkers between the sensitive and resistant patients may be measured using, e.g., t-tests. Alternatively, naïve Bayesian classifiers may be used to identify biomarkers that discriminate sensitive and resistant patient subpopulations given the biomarker expressions of the sensitive and resistant subpopulations within a treated patient population.

The patient subpopulations considered may be further divided into patients predicted to survive without treatment, patients predicted to die without treatment, and patients predicted to have symptoms without treatment. The above methodology may be similarly applied to any of these further defined patient subpopulations to identify biomarkers able to predict a subject's sensitivity to compounds or other treatments for the treatment of cancer.

Patients with elevated expression of biomarkers correlated to sensitivity to a compound or other medical treatment would be predicted to be sensitive to that compound or other medical treatment.

The invention is particularly useful for recovering compounds or other treatments that failed in clinical trials by identifying sensitive patient subpopulations using the gene expression methodology disclosed herein to identify gene or NRA (e.g., miRNA) biomarkers that can be used to predict clinical outcome.

Kit, Apparatus, and Software for Clinical Use

This invention may also be used to predict patients who are resistant or sensitive to a particular treatment by using a kit that includes one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker expression (e.g., HG-U133_Plus2 or miRNA-1.0 from Affymetrix Inc), a microarray hybridization station and scanner (e.g., GeneChip System 3000Dx from Affymetrix Inc), and/or software for analyzing the expression of biomarker genes or RNAs (e.g., miRNAs) as described in herein (e.g., implemented in R from R-Project or S-Plus from Insightful Corp.). The predicted sensitivity is either given by the meanscore or diffscore as defined in Example 2 below.

Methodology of the In Vitro Cancer Growth Inhibition Screen

The human tumor cell lines of the cancer screening panel are grown in RPMI 1640 medium containing 5% fetal bovine serum and 2 mM L-glutamine. Cells are inoculated into 96 well microtiter plates in 100 μL at plating densities ranging from 5,000 to 40,000 cells/well depending on the doubling time of individual cell lines. After cell inoculation, the microtiter plates are incubated at 37° C., 5% CO2, 95% air and 100% relative humidity for 24 hours prior to addition of experimental compounds.

After 24 hours, two plates of each cell line are fixed in situ with TCA, to represent a measurement of the cell population for each cell line at the time of compound addition (Tz). Experimental compounds are solubilized in dimethyl sulfoxide at 400-fold the desired final maximum test concentration and stored frozen prior to use. At the time of compound addition, an aliquot of frozen concentrate is thawed and diluted to twice the desired final maximum test concentration with complete medium containing 50 μg/ml Gentamicin. Additional four, 10-fold or ½ log serial dilutions are made to provide a total of five compound concentrations plus control. Aliquots of 100 μl of these different compound dilutions are added to the appropriate microtiter wells already containing 100 μl of medium, resulting in the required final compound concentrations.

Following compound addition, the plates are incubated for an additional 48 h at 37° C., 5% CO2, 95% air, and 100% relative humidity. For adherent cells, the assay is terminated by the addition of cold TCA. Cells are fixed in situ by the gentle addition of 50 μl of cold 50% (w/v) TCA (final concentration, 10% TCA) and incubated for 60 minutes at 4° C. The supernatant is discarded, and the plates are washed five times with tap water and air-dried. Sulforhodamine B (SRB) solution (100 μl) at 0.4% (w/v) in 1% acetic acid is added to each well, and plates are incubated for 10 minutes at room temperature. After staining, unbound dye is removed by washing five times with 1% acetic acid and the plates are air-dried. Bound stain is subsequently solubilized with 10 mM trizma base, and the absorbance is read on an automated plate reader at a wavelength of 515 nm. For suspension cells, the methodology is the same except that the assay is terminated by fixing settled cells at the bottom of the wells by gently adding 50 μl of 80% TCA (final concentration, 16% TCA). Using the seven absorbance measurements [time zero, (Tz), control growth, (C), and test growth in the presence of compound at the five concentration levels (Ti)], the percentage growth is calculated at each of the compound concentrations levels. Percentage growth inhibition is calculated as:

$$[(Ti-Tz)/(C-Tz)]\times 100 \text{ for concentrations for which } Ti>/=Tz$$

$$[(Ti-Tz)/Tz]\times 100 \text{ for concentrations for which } Ti<Tz$$

Three dose response parameters are calculated for each experimental agent. Growth inhibition of 50% (GI50) is calculated from [(Ti−Tz)/(C−Tz)]×100=50, which is the compound concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from [(Ti−Tz)/Tz]×100=−50. Values are calculated for each of these three parameters if the level of activity is reached; however, if the effect is not reached or is exceeded, the value for that parameter is expressed as greater or less than the maximum or minimum concentration tested.

RNA Extraction and Biomarker Expression Measurement

Cell/tissue samples are snap frozen in liquid nitrogen until processing. RNA is extracted using, e.g., Trizol Reagent from Invitrogen following manufacturer's instructions. RNA is amplified using, e.g., MessageAmp kit from Ambion following manufacturer's instructions. Amplified RNA is quantified using, e.g., HG-U133A or HG-U133_Plus2 GeneChip from Affymetrix Inc and compatible apparatus e.g. GCS3000Dx from Affymetrix, using manufacturer's instructions.

The resulting biomarker expression measurements are further processed as described in this document. The procedures described can be implemented using R software available from R-Project and supplemented with packages available from Bioconductor.

For many drugs, 1-30 (e.g., 5-30 or 10-30, preferably, at least the first 14 of the biomarkers listed in Table 1, Table 2, or both) biomarkers are sufficient to give an adequate response. Thus, given the relatively small number of biomarkers required, procedures, such as quantitative reverse transcriptase polymerase chain reaction (qRT-PCR) or quantitative loop-mediated isothermal amplification (q-LAMP), may be performed to measure, with greater precision, the amount of one or more biomarker genes or RNAs (e.g., miRNAs) expressed in a sample. This will provide an alternative to or a complement to microarrays so that a single companion test, perhaps more quantitative than microarrays alone, employing one or more of the biomarkers of the invention (e.g., GATA3 alone or in combination with one or more of biomarkers recited in Tables 1 and 2) can be used to predict sensitivity to a new drug. qRT-PCR may be performed alone or in combination with a microarray described herein. Procedures for performing qRT-PCR are described in, e.g., U.S. Pat. No. 7,101,663 and U.S. Patent Application Publication Nos. 2006/0177837 and 2006/0088856. Procedures for performing q-LAMP are described in, e.g., U.S. Pat. No. 8,632,998 and U.S. Patent Application Publication No. 2007/0287157. The methods of the invention are readily applicable to newly discovered drugs as well as drugs described herein.

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, an anti-cancer agent can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers comprising excipients and auxiliaries that facilitate processing of an anti-cancer agent (e.g., fulvestrant) into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in *Remington: The Science and Practice of Pharmacy,* $21^{st}$ Ed., Gennaro, Ed., Lippencott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in *Handbook of Pharmaceutical Excipients,* $6^{th}$ Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in *Remington: The Science and Practice of Pharmacy,* $21^{st}$ Ed., Gennaro, Ed., Lippencott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of an anti-cancer agent (e.g., fulvestrant) will be that amount of the compound that is the lowest dose effective to produce a therapeutic effect. Such an effective dose will generally depend upon the factors described above.

An anti-cancer agent (e.g., fulvestrant) may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every $2^{nd}$, $3^{rd}$, $4^{th}$, $5^{th}$, or $6^{th}$ day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted over time according to the individual need and the professional judgment of the person administering or supervising the administration of the compositions. In a non-limiting example, fulvestrant may be administered to a patient (identified as responsive to fulvestrant according to the methods of the invention) three times (one or two doses each time) within about two weeks of each other, and once monthly thereafter.

While the attending physician ultimately will decide the appropriate amount and dosage regimen, an effective amount of an anti-cancer agent (e.g., fulvestrant) may be, for example, a total daily dosage of, e.g., from about 1 mg to about 5000 mg of any of the compounds described herein. Alternatively, the dosage amount can be calculated using the body weight of the patient. Such dose ranges may include, for example, from about 1 mg to about 3000 mg (e.g., from about 10 mg to about 1000 mg). In some embodiments, about 1, 5, 10, 25, 30, 50, 70, 100, 150, 200, 250, 300, 350, 400, 450, 500, 550, 600, 650, 700, 750, 800, 850, 900, 950, or 1000 mg of the compound is administered. In certain embodiments, from about 100 mg to about 1000 mg of fulvestrant are administered (e.g., from about 200 mg to about 600 mg, such as about 250 mg or about 500 mg).

In the methods of the invention, the time period during which multiple doses of an anti-cancer agent (e.g., fulvestrant) are administered to a patient can vary. For example, in some embodiments doses of an anti-cancer agent (e.g., fulvestrant) are administered to a patient over a time period that is 1-7 days; 1-12 weeks; or 1-3 months. In other embodiments, the compounds are administered to the patient over a time period that is, for example, 4-11 months or 1-30 years. In other embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease in which necrosis occurs. Administration may begin before the patient is symptomatic.

Exemplary routes of administration of the compounds (e.g., fulvestrant)), or pharmaceutical compositions thereof, used in the present invention include enteral, parenteral, and topical. Enteral routes of administration include oral, buccal, sublabial, sublingual, or by inhalation routes of administration. Parenteral routes of administration include transdermal, intradermal, intramuscular, intravenous, intra-arterial, intracranial, subcutaneous, intraorbital, intraventricular, intraspinal, intraperitoneal, or intranasal. The preferred route for administration of fulvestrant may be intramuscular. The compounds desirably are administered with a pharmaceutically acceptable carrier. Pharmaceutical formulations of the anti-cancer agents described herein are formulated for treatment of cancer in a patient identified as responsive to the anti-cancer agent.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In certain embodiments, compositions include biodegradable, pH, and/or temperature-sensitive polymer coatings.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Buccal, Sublingual, or Sublabial Administration

Dosages for buccal, sublingual, or sublabial administration may be 1 μg to 500 mg per single dose as required. In practice, the physician determines the actual dosing regimen which is most suitable for an individual patient, and the dosage varies with the age, weight, and response of the particular patient. The above dosages are exemplary of the average case, but individual instances exist wherein higher or lower dosages are merited, and such are within the scope of this invention. Exemplary formulations for buccal, sublingual, and/or sublabial administration may be found in U.S. Pre-grant Publication No. 2012/0058962, U.S. Pre-grant Publication No. 2013/0225626, U.S. Pre-grant Publication No. 2009/0117054, and U.S. Pat. No. 8,252,329; the disclosure of each of which is incorporated herein by reference.

For buccal, sublingual, or sublabial administration, the compositions may take the form of tablets, lozenges, etc. formulated in a conventional manner, as described for oral dosage forms. In some embodiments, the formulation for buccal, sublingual, or sublabial administration includes one or more of taste masking agents, enhancers, complexing agents, and other described above pharmaceutically acceptable excipients and carriers.

Taste masking agents include, for example, taste receptor blockers, compounds which mask the chalkiness, grittiness, dryness, and/or astringent taste properties of an active compound, compounds which reduce throat catch as well as compounds which add a flavor.

Enhancers are the agents that increase membrane permeability and/or increase the solubility of a particular active compound. An enhancer may be a chelator, a surfactant, a membrane-disrupting compound, a fatty or other acid; a non-surfactant, such as an unsaturated cyclic urea. A chelator may be, e.g., EDTA, citric acid, sodium salicylate, or a methoxysalicylate. A surfactant may be, e.g., sodium lauryl sulphate, polyoxyethylene, POE-9-laurylether, POE-20-cetylether, benzalkonium chloride, 23-lauryl ether, cetylpyridinium chloride, cetyltrimethyl ammonium bromide, or an amphoteric or a cationic surfactant. A membrane-disrupting compound may be, e.g., a powdered alcohol (such as, menthol) or a compound used as lipophilic enhancer. Fatty and other acids include, e.g., oleic acid, capric acid, lauric acid, lauric acid/propylene glycol, methyloleate, yso-phosphatidylcholine, and phosphatidylcholine. Other enhancers that may be used in buccal, sublingual, and sublabial formulations of the invention include, e.g., lysalbinic acid, glycosaminoglycans, aprotinin, azone, cyclodextrin, dextran sulfate, curcumin, menthol, polysorbate 80, sulfoxides, various alkyl glycosides, chitosan-4-thiobutylamide, chitosan-4-thiobutylamide/GSH, chitosan-cysteine, chitosan-(85% degree N-deacetylation), poly(acrylic acid)-homocysteine, polycarbophil-cysteine, polycarbophil-cysteine/GSH, chitosan-4-thioethylamide/GSH, chitosan-4-thioglycholic acid, hyaluronic acid, propanolol hydrochloride, bile salts, sodium glycocholate, sodium deoxycholate, sodium taurocholate, sodium glycodeoxycholate, and sodium taurodeoxycholate. Buffering materials can be both used to increase solubility and enhance adsorption of active compounds. The selection of the other excipients, such as permeation enhancers, disintegrants, masking agents, binders, flavors, sweeteners and taste-masking agents, is specifically matched to the active depending on the predetermined pharmacokinetic profile and/or organoleptic outcome.

Liquid drug formulations suitable for use with nebulizers and liquid spray devices and electrohydrodynamic (EHD) aerosol devices will typically include an anti-cancer agent with a pharmaceutically acceptable carrier. Preferably, the pharmaceutically acceptable carrier is a liquid, e.g., alcohol, water, polyethylene glycol, or a perfluorocarbon. Optionally, another material may be added to alter the aerosol properties of the solution or suspension of an anti-cancer agent. Desirably, this material is liquid, e.g., an alcohol, glycol, polyglycol, or a fatty acid. Other methods of formulating liquid drug solutions or suspension suitable for use in aerosol devices are known to those of skill in the art (see, e.g., U.S. Pat. No. 5,112,598 and U.S. Pat. No. 5,556,611, each of which is herein incorporated by reference).

Formulations for Nasal or Inhalation Administration

The compounds may also be formulated for nasal administration. Compositions for nasal administration also may conveniently be formulated as aerosols, drops, gels, and powders. The formulations may be provided in a single or multidose form. In the case of a dropper or pipette, dosing may be achieved by the patient administering an appropriate, predetermined volume of the solution or suspension. In the case of a spray, this may be achieved, for example, by means of a metering atomizing spray pump.

The compounds may further be formulated for aerosol administration, particularly to the respiratory tract by inhalation and including intranasal administration. The compound will generally have a small particle size for example on the order of five (5) microns or less. Such a particle size may be obtained by means known in the art, for example by micronization. The active ingredient is provided in a pressurized pack with a suitable propellant, e.g., a chlorofluorocarbon (CFC), for example, dichlorodifluoromethane, trichlorofluoromethane, or dichlorotetrafluoroethane, or carbon dioxide, or other suitable gas. The aerosol may conveniently also contain a surfactant, e.g., lecithin. The dose of drug may be controlled by a metered valve. Alternatively, the active ingredients may be provided in a form of a dry powder, e.g., a powder mix of the compound in a suitable powder base, e.g., lactose, starch, and starch derivatives, e.g., hydroxypropylmethyl cellulose, and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, e.g., a single dose nasal inhaler or an aerosol dispenser fitted with a metering valve which is intended for disposal after use. Where the dosage form comprises an aerosol dispenser, it will contain a propellant, which can be a compressed gas, e.g., compressed air or an organic propellant, e.g., fluorochlorohydrocarbon. The aerosol dosage forms can also take the form of a pump-atomizer.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of formula (I) may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (an anti-cancer agent), or a solution thereof;
(2) "Drug for Injection:" the drug substance (an anti-cancer agent) as a dry solid that will be combined with the appropriate sterile vehicle for parenteral administration as a drug injection;
(3) "Drug Injectable Emulsion:" a liquid preparation of the drug substance (an anti-cancer agent) that is dissolved or dispersed in a suitable emulsion medium;
(4) "Drug Injectable Suspension:" a liquid preparation of the drug substance (an anti-cancer agent) suspended in a suitable liquid medium; and
(5) "Drug for Injectable Suspension:" the drug substance (an anti-cancer agent) as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in *Remington: The Science and Practice of Pharmacy,* $21^{st}$ Ed., Gennaro, Ed., Lippencott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

A non-limiting example of a parenteral formulation (for intramuscular injection) of fulvestrant is described in detail in U.S. Pat. No. 8,466,139, the disclosure of which is incorporated herein by reference. In this example, the formulation contains about 50 mg/mL of fulvestrant, a mixture of from 17-23% w/v of ethanol and benzyl alcohol, 12-18% w/v of benzyl benzoate, and a sufficient amount of castor oil vehicle.

The following examples are provided so that those of ordinary skill in the art can see how to use the methods and kits of the invention. The examples are not intended to limit the scope of what the inventor regards as their invention.

EXAMPLES

Example 1

Identification of Gene Biomarkers for Chemosensitivity to Fulvestrant

DNA chip measurements of the 60 cancer cell lines of the NCI60 data set were performed using Affymetrix HG-U133A arrays and log it normalized that is, for each array the log it transformation was carried out followed by a Z-transformation to mean zero and SD 1, and correlated to growth inhibition (−log(GI50)). Growth inhibition data of fulvestrant against the same cell lines were downloaded from the National Cancer Institute. Each gene's expression in each cell line was correlated to its growth (−log(GI50)) in those cell lines in the presence of a given compound. The median Pearson correlation coefficient was used when multiple expression measurements were available for a given gene, and genes having a median correlation coefficient greater than 0.25 were identified as biomarkers for fulvestrant. Table 1 lists biomarkers for fulvestrant.

They can be used to predict the response of a human tumor sample to treatment by the drug in question by following the procedure described in "Kit, Apparatus, and Software for Clinical Use."

Example 2

Difference Between Positive and Negative Correlated Genes

In Example 1 a procedure for identifying microRNA biomarkers with a positive correlation to drug sensitivity is described. Sensitivity to a drug can then be predicted based on the mean expression of those microRNA biomarkers. This is called mean score. But there is also information in those biomakers that correlate negatively with drug sensitivity. They could be called biomarkers of resistance.

Table 2 (see appendix) lists the negatively correlated biomarkers for a number of drugs used to treat cancer. An even better accuracy of predicted response to a drug can be obtained when both negatively and positively correlated markers are used. One way of combining them is to subtract the mean expression of the negatively correlated biomarkers from the mean expression of the positively correlated biomarkers. This is called a difference score, or diffscore.

Table 3 shows how mean score and difference score compare in their ability to predict the GI50 values of cell lines treated with a drug. As the method would be applied to a human tumor sample in the same manner as it is here applied to a human cell line sample, the diffscore can also be used (e.g., as an alternative to the mean score, which is based on the correleation coefficient alone) to predict the response of human tumors (and thus, the patient) to treatment with one or more drugs (e.g., one or more of the anti-cancer agents (e.g., chemotherapy drugs) or radiation described herein).

TABLE 3 comparison of diff score and mean score in predicting human cell line response to a number of drugs (correlation coefficient between prediction and measurement is shown, a higher CC means more accurate prediction)

| Drug | Diff score CC | Mean score CC |
|---|---|---|
| Vincristine | 0.56 | 0.35 |
| Trastuzumab (HERCEPTIN ®) | 0.50 | 0.41 |
| Gefitinib (IRESSA ®) | 0.60 | 0.53 |
| Fulvestrant | 0.76 | 0.74 |
| Erlotinib (TARCEVA ®) | 0.62 | 0.59 |
| Belinostat (PXD101) | 0.61 | 0.60 |
| Cisplatin | 0.66 | 0.67 |

Example 3

Use of the Methods of the Invention to Predict Responsiveness of Cancer Patients to Treatment with Fulvestrant Materials and Methods Patients NEWEST (Neoadjuvant Endocrine Therapy for Women with Estrogen-Sensitive Tumors; 9238IL/0065) was a randomized, open-label, multicenter, Phase II study involving postmenopausal women with newly diagnosed, ER-positive, locally advanced breast cancer who had received no prior breast cancer treatment (NCT0093002). Eligible patients were randomized 1:1 to receive either fulvestrant 500 mg or 250 mg for 16 weeks preceding surgery. Fulvestrant 500 mg was given as two 5 ml intramuscular injections on days 0, 14, 28 and every 28 days thereafter for 16 weeks. Fulvestrant 250 mg was given as one 5 ml injection on days 0, 28 and every 28 days thereafter for 16 weeks (Kuter et al., *Breast Cancer Res. Treat.,* 133:237-246, 2012).

A total of 211 patients were enrolled in NEWEST. Of these, 173 completed the study and 121 met all protocol criteria. Fresh frozen pre-treatment samples with sufficient RNA (100 ng) was available from 44 patients. Two samples were discarded due to array quality, leaving 42 patients. Of these 42 patients, 22 were in the 500 mg treatment group and 20 were in the 250 mg treatment group.

During the 16-week treatment phase, patients underwent clinical breast examination every 4 weeks. Tumor volume was measured by 3D ultrasound at baseline, week 4, and after 16 weeks of treatment before definitive surgery. Tumor response was defined as complete response (CR, disappearance of all lesions), partial response (PR, at least 65% reduction in tumor volume by 3D ultrasound), disease progression (PD, at least 73% increase in tumor volume), or stable disease (SD, neither partial response nor disease progression). The reduction for partial response was in relation to baseline but for progressive disease was in relation to the smallest tumor volume at any preceding assessment. Objective responders were those patients with a complete response or partial response.

Of the 42 patients available for array analysis, 15 patients had partial responses, 22 patients had stable disease, 2 patients had progressive disease and 3 patients were not evaluable.

ER H score was derived by immunohistochemical staining using the 1 D5 anti-ER antibody (Dako) followed by microscopic assessment of the percentage of tumor cells in each of five staining categories (negative, very weak, weak, moderate and strong) to give an H score ranging from 0 to 300.

Trial 223 (Smith et al., *J. Clin. Oncol.,* 25:3816-3822, 2007) was a placebo-controlled trial of neoadjuvant anastrozole alone or with gefitinib in early breast cancer. We used pre-treatment samples from patients from arm B and C: anastrozole 1 mg/d for the duration of the 16 week period plus placebo 1 tablet/d orally for 2 weeks. Patients in arm B were followed by gefitinib 250 mg/d orally for 14 weeks whereas patients in arm C continued with placebo for 14 weeks. We received pre-treatment biopsy material from 21 patients in arms B and C with Ki67 measurements after 2 weeks. We received pre-treatment biopsy material from 16 patients in arm C with outcome information according to guidelines set forth in Response Evaluation Criteria in Solid Tumors (RECIST).

Microarray Analysis

44 RNA samples from NEWEST and 21 samples from 223 were run on Affymetrix HG-U133_Plus_2 arrays after amplification using Ambion MessageAmp Premier following the manufacturer's instructions. The quality criteria used for accepting RNA was a minimum of 100 ng of total RNA which amplified into a minimum of 5 μg aRNA. 42 arrays from NEWEST and 21 samples from 223 passed quality criteria and a visual inspection of array images for spatial artefacts. All array data have been deposited at GEO under accession numbers GSE48905 and GSE48906.

Predictor Development Based on In Vitro Assays

The in vitro based method of developing a predictor of drug response is described in Example 1.

Pathway Analysis

The probesets that correlated to fulvestrant sensitivity were converted to gene symbols and submitted to g:Profiler for association to pathways and gene ontologies (GO). In addition, the probesets that had a correlation to fulvestrant sensitivity above 0.4 or below −0.4 were manually searched in PubMed and NCBI Gene (http://www.ncbi.nlm.nih.gov/) for reported associations to pathways.

Prediction of Fulvestrant Sensitivity in Clinical Samples

After robust multi-array average (RMA; the method is described in detail in Irizarry et al., *Biostatistics,* 4:249-264, 2003) normalization of array data from the clinical samples, the expression of each gene in the response profile was used to predict sensitivity: Prediction score=mean(positively correlated genes)−mean(negatively correlated genes). That means that each gene in the profile is given equal weight. Next, the prediction score was normalized to a scale from 0 to 100 by a linear transformation of the prediction score of all patient samples.

Statistical Analysis

The statistical analysis of predicted and observed sensitivity to fulvestrant in patients was performed according to a Statistical Analysis Plan with a pre-specified cutoff equal to the population median and success criteria that were agreed upon before unblinding of the clinical data. The primary analysis was one-sided Wilcoxon test for difference in prediction score between objective responders (PR) and non-responders (SD+PD) and a Pearson correlation between prediction score and reduction in Ki67 at 4 weeks compared to baseline. Clinical covariates specified in the statistical analysis plan were combined with the prediction score without bias by giving equal weight to the prediction score and each of the clinical covariates available: Combination score=Prediction score+30*tumor grade+ER Hscore/3. Cutoff between predicted sensitive and predicted resistant to fulvestrant was pre-defined as the population median of the prediction score. The population median is taken over all samples, from both dose groups. Areas under the curve (AUC) in a receiver-operating characteristic (ROC) were calculated with the pROC package from www.r-project.org with confidence intervals calculated using the Delong method (Robin et al., *BMC Bioinformatics,* 12:77, 2011).

Response Predictor Genes and their Biological Interpretation.

A total of 103 probesets correlated to fulvestrant sensitivity in the NCI60 cell lines. That means that they are higher expressed in cell lines that are sensitive to fulvestrant than in cell lines that are resistant. The 103 probesets mapped to 83 unique genes shown in Table 1. Some of these sensitivity genes (higher expression in fulvestrant sensitive cell lines) sense the signaling through estrogen receptor alpha, either because they have Estrogen Responsive Elements (ERE) in their promoters, and/or through microRNA regulation, or though direct interaction with the estrogen-ER complex [14-18]. Other genes are associated to broader gene ontology definitions of cell activation and response to stimulus. A number of genes have associations to immune system and cell adhesion (not shown). Note that groups may be overlapping.

A total of 311 probesets correlated to fulvestrant resistance, meaning that they are higher expressed in cell lines resistant to fulvestrant. They are all higher expressed in ER positive breast cancer cell lines that are resistant to fulvestrant than in ER positive cell lines that are sensitive to fulvestrant (p=0.01 in a one-sided Wilcoxon rank test), and thus provide a potential hypothesis to explain why some ER positive cell lines are resistant to fulvestrant. Indeed, the expression of the 11-gene PI3K profile is correlated to resistance to fulvestrant in ER positive cell lines (CC=0.76, p=0.03).

Prediction of Fulvestrant Sensitivity in Breast Cancer Cell Lines

To verify that the predictor developed based on the NCI60 cell line panel is indeed able to predict the sensitivity of cell lines derived from breast cancer, we blind predicted the sensitivity of 20 breast cancer cell lines based on their baseline gene expression value measured in another lab. After unblinding, the prediction score was compared to the measured GI50 values for fulvestrant for the 20 cell lines (FIG. 2). The Pearson correlation was negative 0.63, because a higher predicted sensitivity is reflected as a lower GI50 (P=0.003). This was well beyond the pre-specified definition of success, a correlation of −0.30.

Figure 2A:
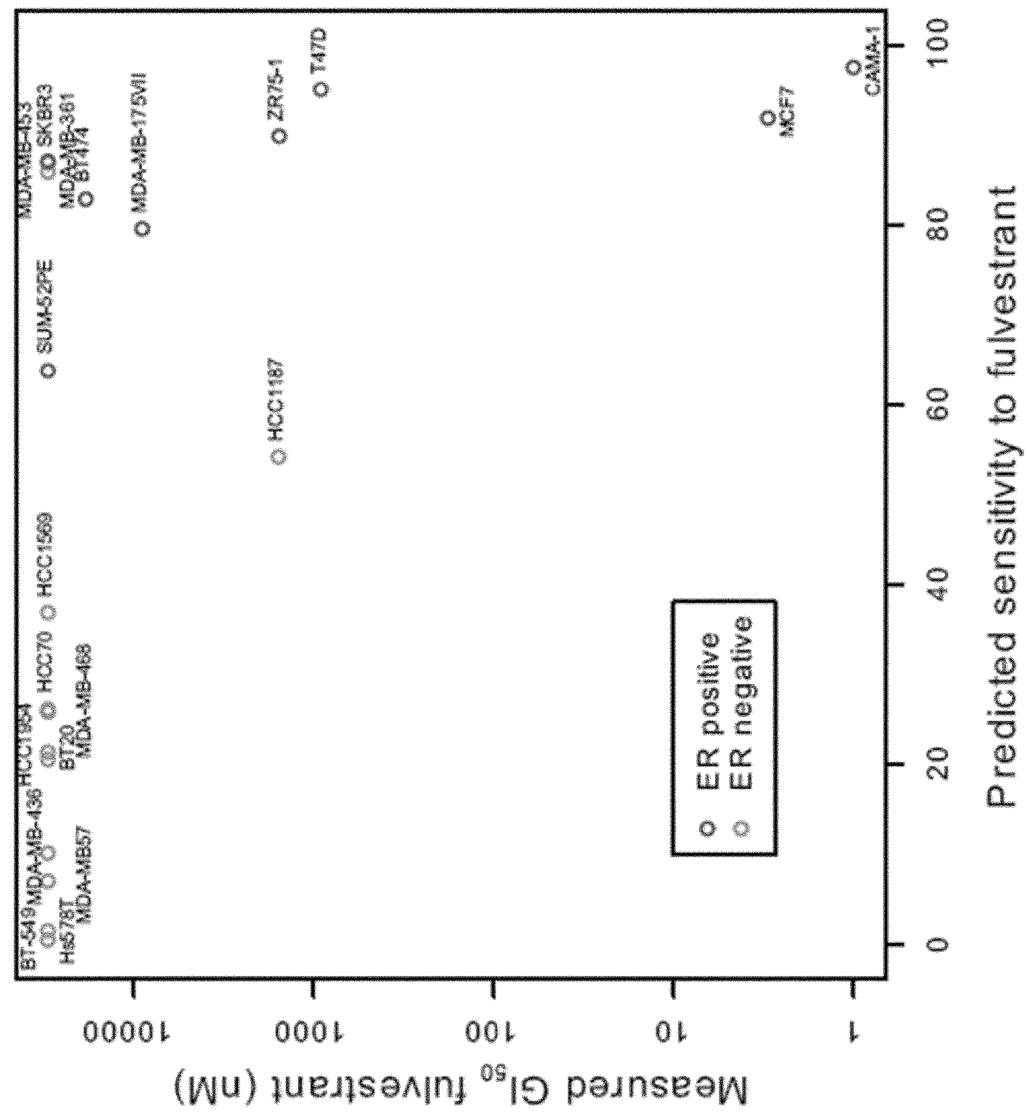
FIG. 2A is a graph comparing predicted and measured sensitivity to fulvestrant for 20 breast cancer cell lines. ERα status was determined using an immune assay or gene expression and are shown in color code (green, ERα negative; red, ERα positive; Neve et al., *Cancer Cell,* 10:515-527, 2006). SUM-52PE is positive for ERα gene expression but negative for ERα in western blotting. The prediction score is calculated from the gene expression measurements and has been normalized to a scale of 0 to 100 (no units). If a cutoff of 50 is applied to this score, then 9 out 15 cell lines are correctly predicted as resistant (GI50 5 μM or more), and 5 out of 5 cell lines are correctly predicted as sensitive. ER negative cell lines are: BT20, BT-549, HCC70, HCC1187, HCC1569, HCC1954, Hs578T, MDA-MB57, MDA-MB-436, MDA-MD-453, MDA-MB-468. ER positive cell lines are: BT474, CAMA-1, MCF7, MDA-MB-175VII, MDA-MB-361, SKBR3, SUM-52PE, T47D, and ZR75-1.
Figure 2B:
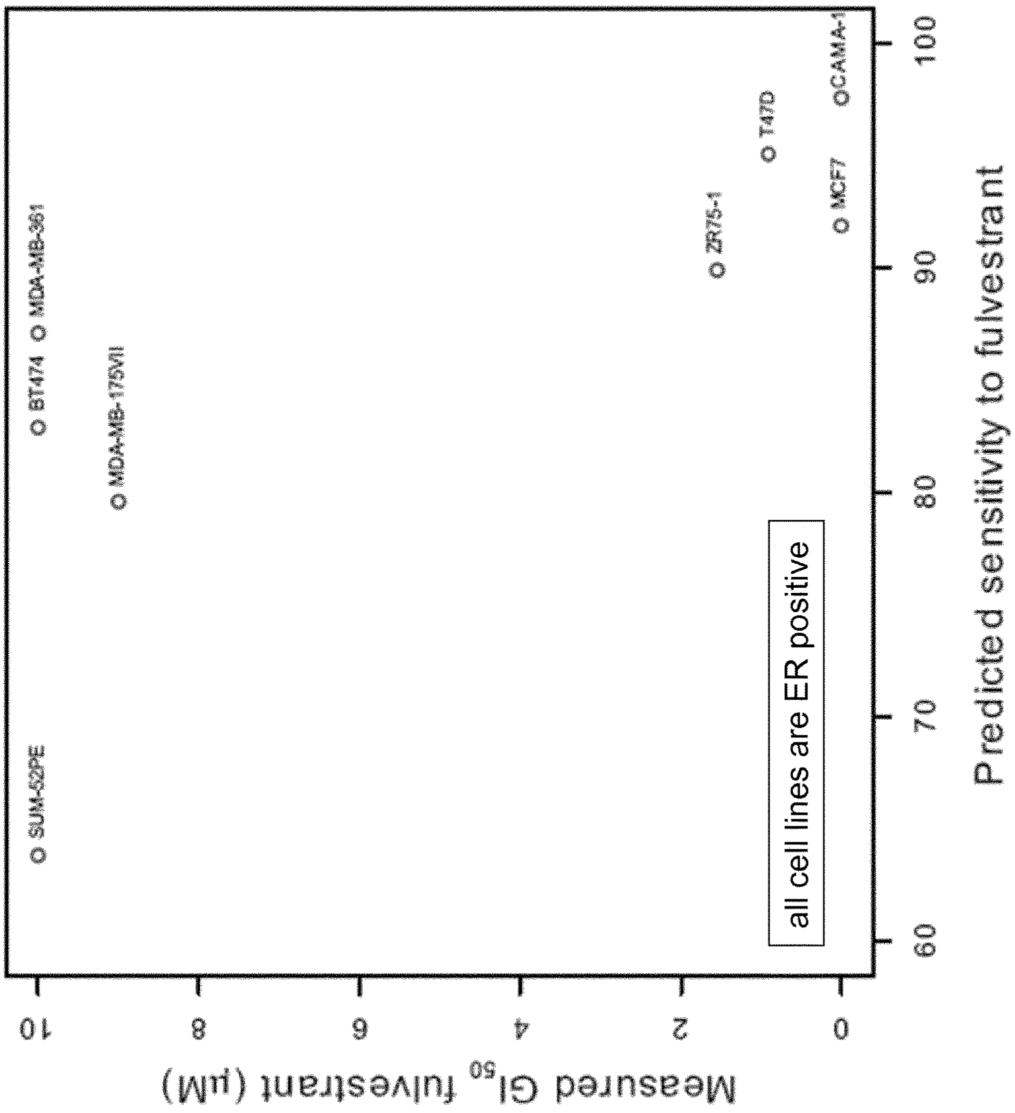
FIG. 2B is a graph showing the subgroup of ERα positive cell lines from FIG. 2A on a linear scale. GI50 values above 10 μM are shown as 10 μM.

FIG. 2A shows that all but one of the ER positive cell lines are in the 80 to 100 range for predicted senstivity, regardless of whether they are sensitive or resistant to fulvestrant. A subgroup analysis of ER positive cell lines only, however, reveals that even within ER positive cell lines, the predictor is able to differentiate cell lines based on their sensitivity to fulvestrant (CC=−0.74, P=0.037, FIG. 2B). This cannot be explained by ESR1 or PGR expression alone (CC=0.34 and CC=−0.23, respectively, meaning that their expression is anticorrelated and weakly correlated, respectively, to fulvestrant sensitivity (GI50) when analyzed separately in this subgroup).

Thus, it is possible that also within ER positive breast cancer patients, the predictor may be able to distinguish between responders and non-responders to fulvestrant treatment.

Prediction of Fulvestrant Sensitivity in Clinical Samples

Figure 3:
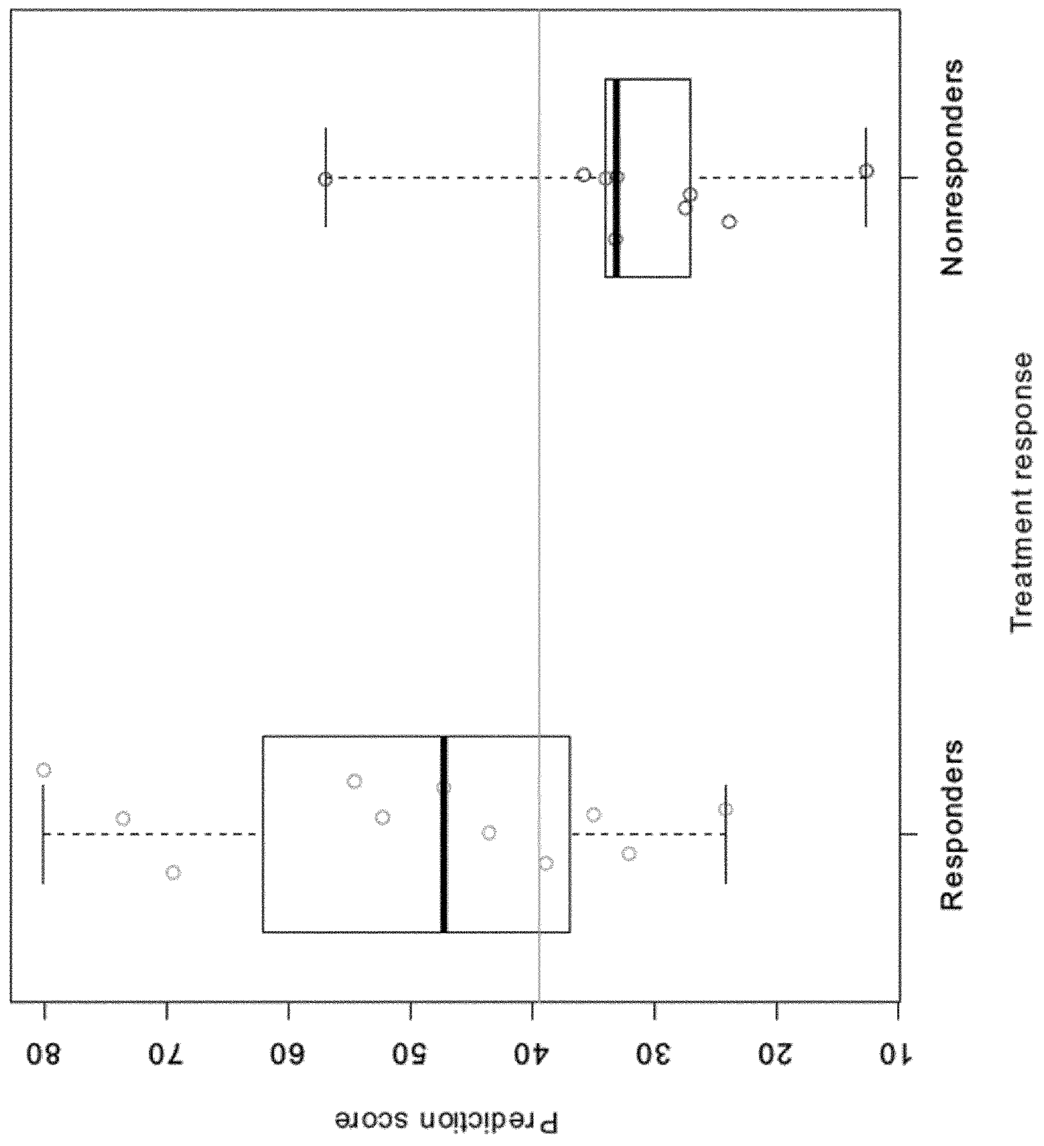
FIG. 3 is a graph showing prediction score and treatment response for the 500 mg fulvestrant cohort of the NEWEST trial. Responders are those patients that experienced a reduction in tumour size according to RECIST criteria (PR, n=11) following treatment with 500 mg fulvestrant for 16 weeks. Non-responders were defined as those with either stable or progressive disease after 16 weeks treatment (SD+PD, n=9). A one-sided Wilcoxon test for difference between predicted sensitivity of responders and non-responders yields a P-value of 0.01. The pre-specified cutoff (median of the prediction scores) is shown as an orange line. Boxes represent upper quartile, median and lower quartile.

The fulvestrant prediction score was calculated for 22 patients treated with the 500 mg-dose of fulvestrant, for whom we had pre-treatment gene expression measurements. The prediction was performed in a blinded manner and without knowledge of the clinical results. After unblinding, the predicted sensitivity of responders (PR, see Methods) was compared to the predicted sensitivity of nonresponders (SD+PD) (FIG. 3). Two patients were unevaluable for response.

The correlation between predicted sensitivity and absolute reduction in Ki67 from baseline to 4 weeks was calculated as 0.32 (both 500 and 250 mg doses, one-sided p-value 0.02). This is largely a reflection of a negative correlation between the predicted sensitivity and Ki67 at 4 weeks (CC=−0.32, p=0.02). Only tumors predicted resistant to fulvestrant had high values of Ki67 at 4 weeks. The prediction score was not significantly correlated to relative reduction in Ki67 from baseline to 4 weeks (CC=0.15). In the clinical trial, both relative and absolute changes in Ki67 were significant after 4 weeks of treatment (47% average reduction at 250 mg dose and 79% average reduction at 500 mg dose).

Standard clinicopathological features are already known for breast cancer: in particular, ER content by immunohistochemistry (H score), tumor grade, tumor size, and patient age. For this reason it was planned before unblinding that the prediction score would be compared to these covariates and the performance of the combination would be assessed as well.

When ER H score was added to absolute reduction in Ki67 the correlation of the combined score to predicted sensitivity increased to 0.41.

Figure 4:
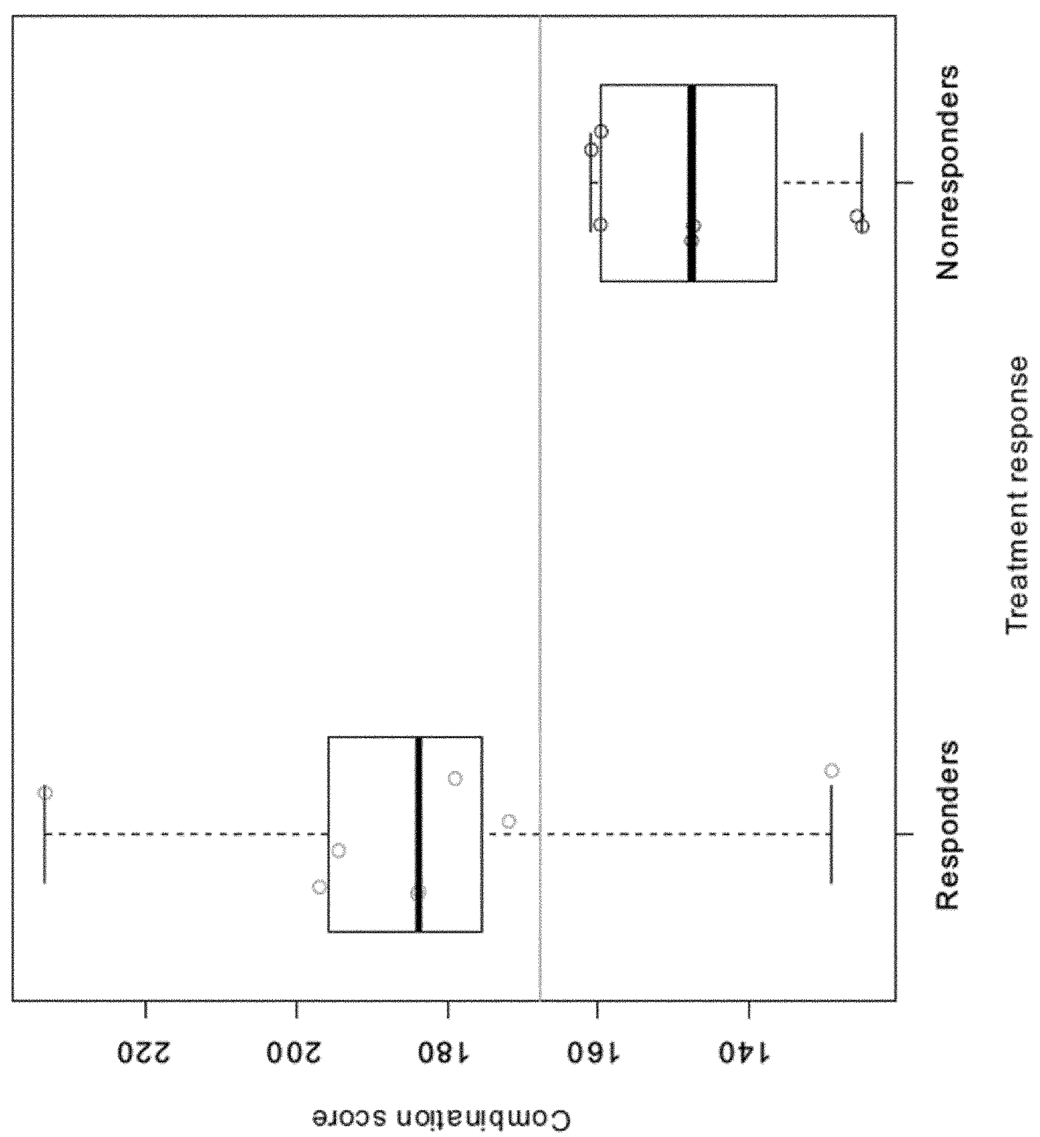
FIG. 4 is a graph showing a combination score of fulvestrant sensitivity and clinical covariates: tumor grade and ER H score. Responders (PR, n=8) were compared to non-responders (SD, n=7). Five patients including the two with progressive disease from FIG. 3 had grade information "Not done" or "unassessable" and were excluded from the analysis. A one-sided Wilcoxon test for difference between predicted sensitivity of responders and non-responders yields a P-value of 0.003. The pre-specified cutoff at the population median of the combination score is shown with an orange line. If this cutoff is used to divide this very limited sample of patients into predicted sensitive and predicted resistant to fulvestrant, the PPV of the prediction is 88% and the NPV of this prediction is 100%

The predicted sensitivity was combined with other covariates as described in the methods section. FIG. 4 shows the score obtained by combining the prediction score with tumor grade and ER H score for the 500 mg dose patients (the combination score). It is evident that this combination score gives a better separation between responders and non-responders than that obtained by comparing the individual values with response. Although all patients were selected for inclusion based on a categorization as ER positive, a more quantitative determination of ER receptor status in the H score obviously contains information that differentiates between fulvestrant responsive and unresponsive patients. The same holds true for tumor grade.

Figure 5:
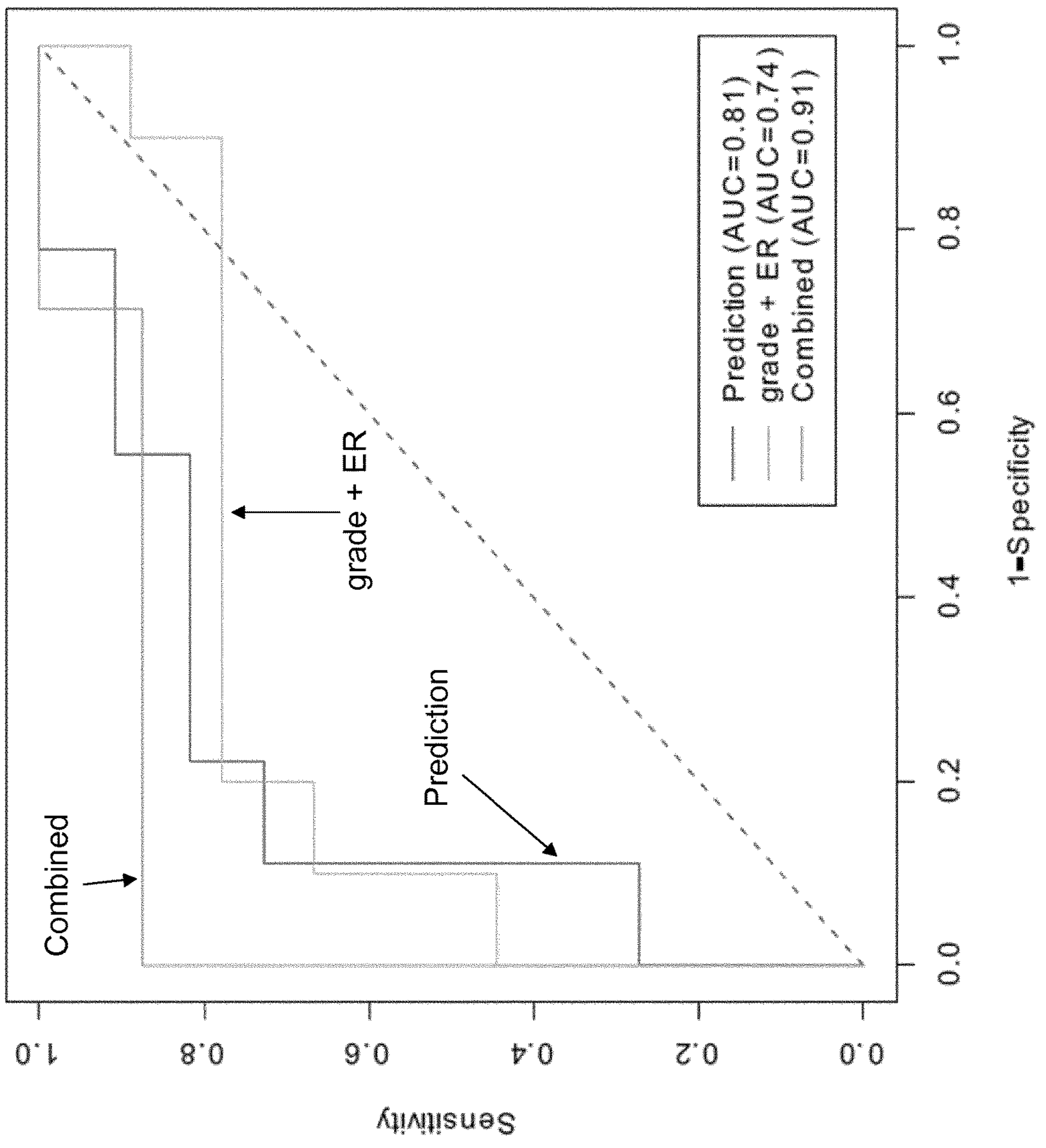
FIG. 5 is a graph showing a receiver operating characteristic comparing three prediction scores: grade+ER, prediction score and combination score. The dashed line shows an AUC of 0.5. Along x-axis is false positive score (1-specificity) and along y-axis is a true positive score (sensitivity).

The different predictors were compared by measuring the Area Under the Curve (AUC) in a Receiver-Operating Characteristic (ROC). FIG. 5 shows how the tradeoff between sensitivity and specificity varies with all possible cutoffs used. It can be seen that the prediction score appears to be a more accurate predictor (AUC 0.81, 95% CI 0.6-1.0) than the combination of clinical covariates ER H score and tumor grade (AUC 0.74, 95% CI 0.47-1.0), but the combination of prediction score and covariates is superior (AUC 0.91, 95% CI 0.73-1.0). The difference in AUC between combination score and grade+ER score was not statistically significant in this limited sample size.

Figure 6:
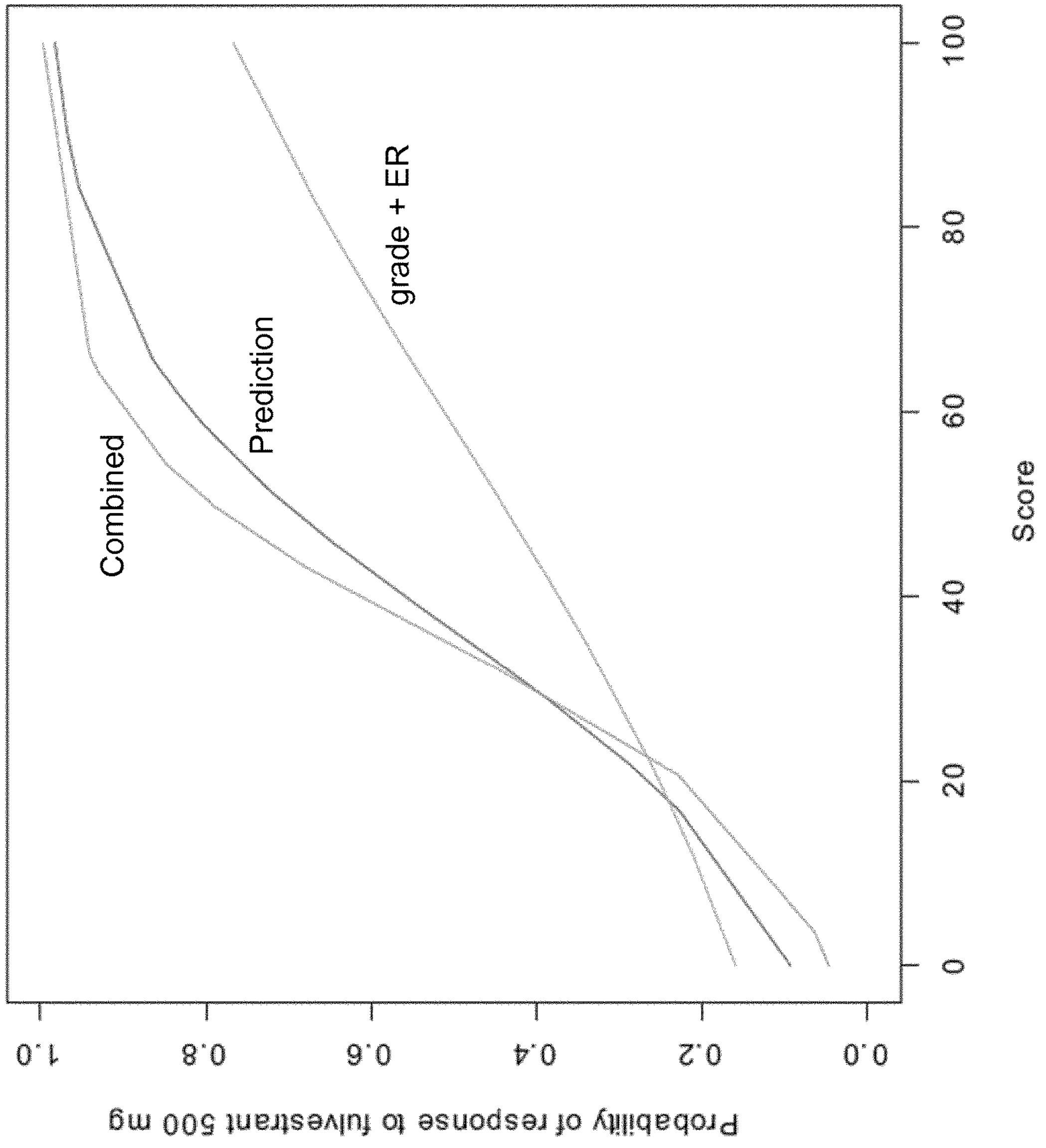
FIG. 6 is a graph showing a logistic regression of the relationship between fulvestrant prediction score and probability of response. Three predictors are shown: grade+ER, prediction score and combination score. The 95% confidence intervals are quite high (not shown) due to the limited sample size but a Wald test on the logistic regression of the prediction score is borderline statistically significant (P=0.0499), as is the combination score (P=0.0475). All scores have been normalized to a scale from 0 to 100 for comparison.
Figure 7:
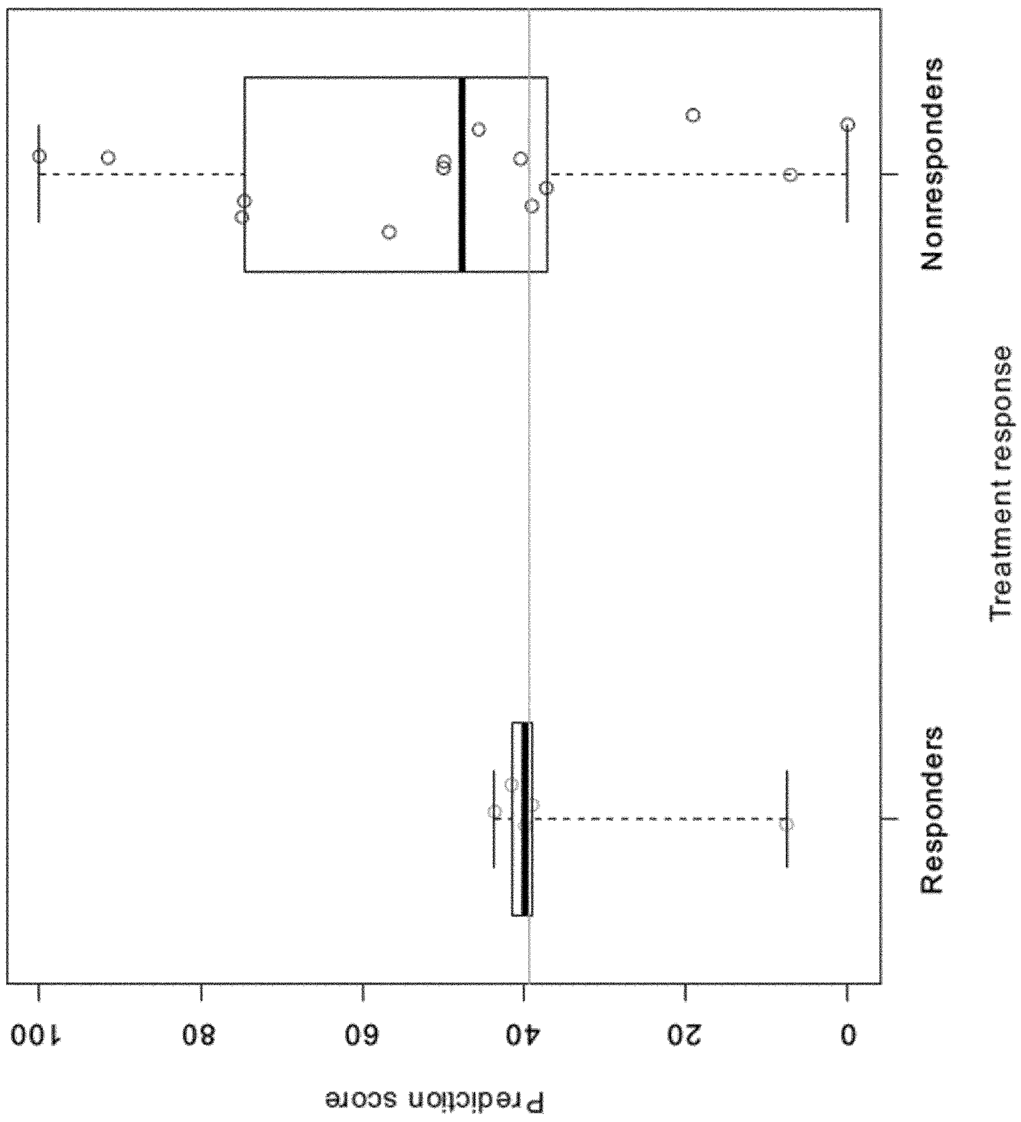
FIG. 7 is a graph showing the prediction score for patients treated with 250 mg fulvestrant. There are 5 partial responders, 13 patients with stable disease and 1 progressive disease patient. The median prediction score, as shown in FIG. 2, is represented by the yellow line in the graph. Most patients predicted to be sensitive (above cutoff indicated by a line, population median as shown in FIG. 2) exhibited stable disease at this dose, whereas they exhibited partial response at the 500 mg dose (FIG. 3).

The quantitative prediction score is more informative than a simple division of patients into those predicted to be responsive and those predicted to be resistant. A patient with a prediction score of 100 has a higher probability of responding to treatment than a patient with a prediction score of 60 even though they are both classified as responsive to fulvestrant. This information can be visualized in a logistic regression which converts the prediction score into a probability of response to treatment. FIG. 6 shows such logistic regression curves for the three prediction scores: grade+ER, prediction score and combination score. Again, the combination score is superior by giving a higher range of probabilities (from 5% to 99.66%) of response to fulvestrant treatment. It is only marginally better than the prediction score, however (ranging from 9% to 98% probability of response)

Analysis of 250 mg Fulvestrant Regimen

Array data and outcome information was available for 19 patients who received the lower dose of 250 mg fulvestrant in the NEWEST trial. FIG. 5 shows the predicted sensitivity score for responders and non-responders treated with 250 mg fulvestrant. Among these 19 patients, the overall response rate (CR+PR) was only half of that observed in those treated with the 500 mg dose, 26% vs. 50%. There is a wide range of prediction scores in the nonresponding group, and the average score of this group is not significantly different from the responders. Although the reasons behind the lack of difference in prediction score between the two groups is not clear, it is possible that it is due to the small group size and the fact that a lower dose of fulvestrant was given, which produced a smaller drop in tumour Ki67 levels in this trial.

Example 4

Comparison to Other Gene Expression Signatures

A number of prognostic and predictive signatures have been developed specifically for breast cancer. These prognostic and predictive signatures have either demonstrated inferior or equivalent predictive abilities to that of the methods of the invention. Among these are the PAM50 gene list that divides patients into the intrinsic subtypes of luminal A, luminal B, Her2, basal and normal. Applying the PAM50 matrix from Parker et al. (*J. Clin. Oncol.,* 27:1160-1167, 2009) to the baseline samples from the 500 mg group indicated that there were 7 luminal A-like, 12 luminal B-like, and one normal-like (this is a consequence of the PAM50 training set containing normal breast samples). The luminal subtypes did not correlate significantly with clinical response (Fisher P=0.07), nor did they contribute in a multivariate regression model including tumor grade and ER score. When subtypes were used to create a Risk-of-Relapse (ROR) score, as described by Parker et al. (*J. Clin. Oncol.,* 27:1160-1167, 2009), there was no correlation of the ROR score with post-treatment change in Ki67 (P=0.94).

Parker et al. (*J. Clin. Oncol.,* 27:1160-1167, 2009) observed that patients with a higher ROR score had a higher probability of clinical response to neoadjuvant treatment with chemotherapy T/FAC. Similarly, the ROR score is associated with a higher probability of response to treatment with fulvestrant in our cohort (AUC 0.74, 95% CI 0.54-0.94). Combining the ROR score with clinical covariates grade and ER H score did not improve the association within the NEWEST dataset (AUC 0.73, 95% CI: 0.48-0.99). This suggests that the predictive information in the ROR score is already present in the clinical covariates (AUC 0.74, 95% CI 0.47-1.0).

The Oncotype DX signature is used to predict the risk of recurrence in early breast cancer. The recurrence score was significantly correlated to absolute Ki67 measurements before ($P=3\times10^{-5}$) and 4 weeks after treatment (P=0.03), but was not correlated to absolute (P=0.86) or relative (P=1.0) change in Ki67 during treatment. The recurrence score did not contribute to prediction of response to treatment in a multivariate model.

A published signature (Lee et al., *PLoS One,* 6:e21112, 2011) of zinc-finger transcription factor induced fulvestrant resistance had minimal overlap to our signature. Only 5 out of 95 probesets in the published fulvestrant resistance signature were among the probesets used in our fulvestrant prediction score, and the published 95 probesets could not predict response in our fulvestrant treated cohort (P=0.29 in a one-sided Wilcoxon test between responder scores and nonresponder scores).

Example 5

Prediction of Response to Other Endocrine Agents

The prediction score of the invention (e.g., prediction score for fulvestrant) was tested for the ability to predict response to aromatase inhibition in a small cohort of 21 patients treated with neoadjuvant anastrozole in a similar protocol to that used to test fulvestrant. Nine responders had an average predicted sensitivity of 52 (95% CI 20-84). Seven nonresponders had an average predicted sensitivity of 51 (95% CI 4-97). In addition there was no correlation between prediction score and change in Ki67 produced after 2 weeks of anastrozole treatment (N=21, P=0.9).

Figure 8:
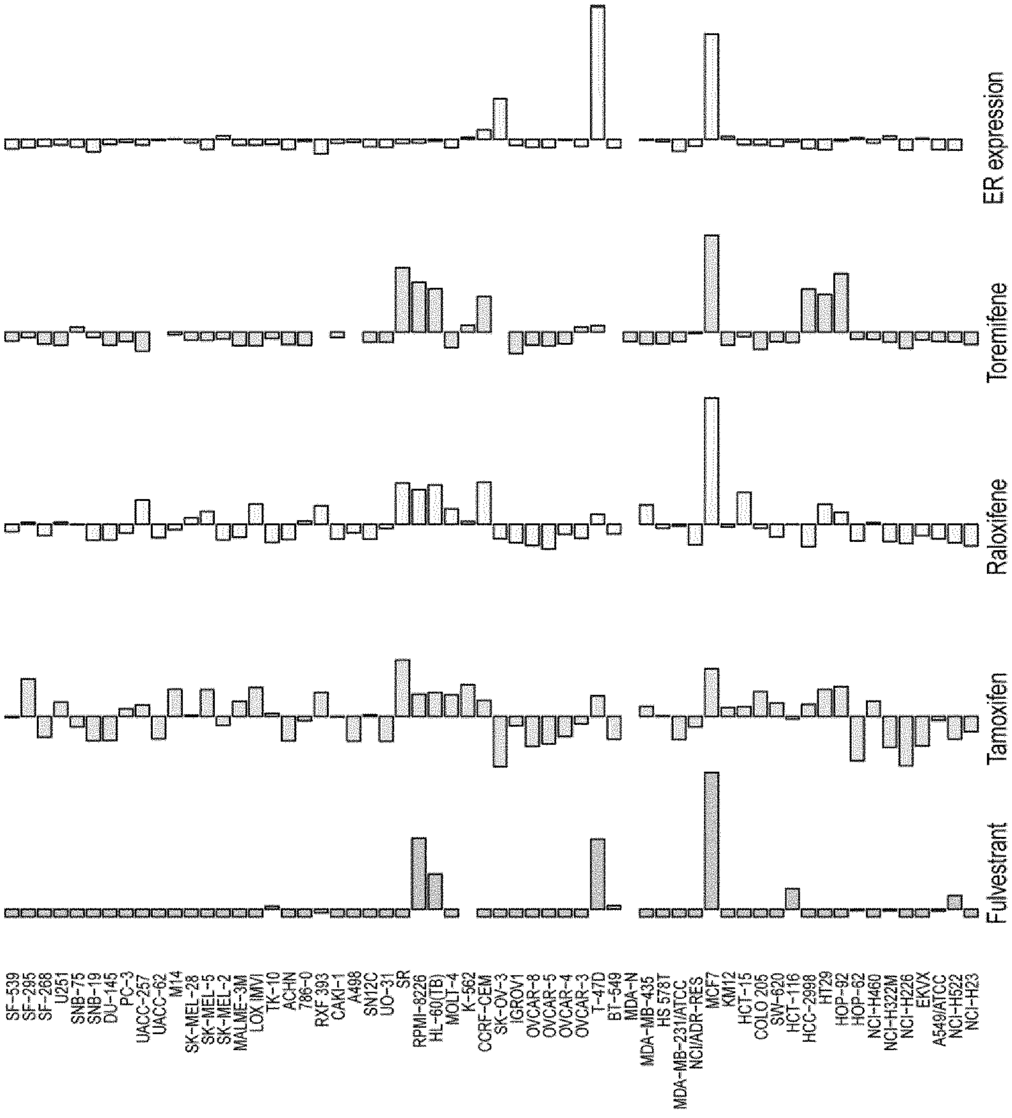
FIG. 8 is a graph showing differences in the sensitivity (GI50) of NCI60 cell lines to drugs targeting the ER pathway. For each drug, and each cell line, the GI50 is shown as a bar on a logarithmic scale relative to the mean GI50 of all cell lines (63 μM for fulvestrant, 4.3 μM for tamoxifen, 8.4 μM for raloxifene, 13 μM for toremifene). Bars to the right of the mean indicate above average sensitivity cell lines, whereas bars to the left of the mean indicate below average sensitivity cell lines. ER expression is measured with an Affymetrix array on all cell lines and shown on a logarithmic scale relative to the mean expression. MCF7 and T-47D are well known ER positive cell lines.

FIG. 8 shows how fulvestrant, tamoxifen and other agents targeting ER differ in their in vitro effects on the same NCI60 cell line panel. For fulvestrant, cell lines with a GI50 of less than 5 μM are considered sensitive. It is evident from FIG. 8 that fulvestrant differs in sensitivity profile from tamoxifen, raloxifene and toremifene. Indeed, the fulvestrant prediction score is better than the other in vitro based prediction scores at predicting the 500 mg dose fulvestrant clinical data of FIG. 3: fulvestrant score: P=0.010, tamoxifen score: P=0.012, anastrozole score: P=0.56, ER expression (ESR1 gene): P=0.10.

APPENDIX

TABLE 1 mRNA biomarkers of sensitivity to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| GATA3 | 209602_s_at | 0.59 | GCTTTGTGAACAAGTCCCTGTAATT | 1 |
| GATA3 | 209603_at | 0.59 | TCCCTGTAATTGTTGTTTGTATGTA | 2 |
| GATA3 | 209604_s_at | 0.59 | AGGAGCTCACTGTGGTGTCTGTGTT | 3 |
| CBFA2T3 | 208056_s_at | 0.54 | CATCTGTGTGCGTGGCTATCAGGAG | 4 |
| SPDEF | 220192_x_at | 0.53 | TGAACTACGACAAGCTGAGCCGCTC | 5 |
| HBA1 | 204018_x_at | 0.51 | CACGGCTCTGCCCAGGTTAAGGGCC | 6 |
| TFF1 | 205009_at | 0.51 | GACGTCCCTCCAGAAGAGGAGTGTG | 7 |
| CD8B1 | 207979_s_at | 0.51 | GTCCAGTTCCCAGAAGGCATATCAG | 8 |
| KIAA0984 | 213913_s_at | 0.51 | AGCAATGTCAGCCTGTGGACTGCAG | 9 |
| BCL2 | 203685_at | 0.48 | ACTTTCCTTGTCTGTCTAGTTAATA | 10 |
| HBA1 | 211745_x_at | 0.48 | CTGACCTCCAAATACCGTTAAGCTG | 11 |
| SLC9A3R1 | 201349_at | 0.47 | CTGCCGCTCTCAGTGGACAGGGCAT | 12 |
| FBP1 | 209696_at | 0.47 | ATCGCACTCTGGTCTACGGAGGGAT | 13 |
| ITGB7 | 205718_at | 0.45 | GGCACGGTCGTGCTCAGAGTGAGAC | 14 |
| — | 205922_at | 0.44 | AATGAAGATCAAACTCCAGCTCCAG | 15 |
| HIST1H3H | 206110_at | 0.44 | TATATTTCTTGCCAACACGCCAGAA | 16 |
| HBA1 | 211699_x_at | 0.44 | CTGACCTCCAAATACCGTTAAGCTG | 17 |
| PDCD4 | 212593_s_at | 0.44 | AGGGAACATACTGATTGGTCTTAAA | 18 |
| HBA2 | 217414_x_at | 0.44 | TCAAGGCCGCCTGGGGTAAGGTCGG | 19 |
| CD37 | 204192_at | 0.43 | CAACGACTCCACAATCCTAGATAAG | 20 |
| TARP | 215806_x_at | 0.43 | GGCTTTCTTTCTGGGTTTGGGCCAT | 21 |
| TARP | 216920_s_at | 0.43 | GTGTGGTCTATTTTGCCATCATCAC | 22 |
| SPI1 | 205312_at | 0.42 | GTCCGTATGTAAATCAGATCTCCCC | 23 |
| KIAA0182 | 212057_at | 0.42 | GTTGCCATGTTACTATGCCTCAAGC | 24 |
| — | 214857_at | 0.42 | TGAAAGACTTAACCAGCCATCACCG | 25 |
| PTP4A3 | 206574_s_at | 0.41 | GAAGGATGGCATCACCGTTGTGGAC | 26 |
| KIAA0182 | 212056_at | 0.41 | GAGCCACATGTTTCACACAAGTGTA | 27 |
| JUP | 201015_s_at | 0.39 | CCAGGGTGCTTAGTTGGCTTTGCCC | 28 |
| ORM1 | 205040_at | 0.39 | TGCTGATCCTCAGGGACACCAAGAC | 29 |
| DGKZ | 207556_s_at | 0.38 | GGCTCACAGGGAACAAGACACGGCT | 30 |
| HBA1 | 209458_x_at | 0.38 | CTGGAGAGGATGTTCCTGTCCTTCC | 31 |
| PSCD4 | 219183_s_at | 0.38 | TGTCAGCCTGTGAACTAGGCCCTGC | 32 |
| HEM1 | 209734_at | 0.37 | GTGGAAGCTGTGGTCACTTTCGCAG | 33 |
| TARP | 209813_x_at | 0.37 | TGGAAGCCTTTCATTTTACACGCCC | 34 |
| SELPLG | 209879_at | 0.37 | CAAGGAAGATGGAGCTCCCCCATCC | 35 |

TABLE 1-continued mRNA biomarkers of sensitivity to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| GIMAP4 | 219243_at | 0.37 | TCTTCTAGATTCTCTCTATGTTGGC | 36 |
| HAB1 | 215778_x_at | 0.36 | GGGCACAGGACAGAGAAGAGGAAGC | 37 |
| SIRPB2 | 220485_s_at | 0.36 | GTTGAGGTTCTCTATTGCCTCTTGA | 38 |
| ICOS | 210439_at | 0.35 | GAATCTAGTATGGTGTTCTGTTTTC | 39 |
| FLT3LG | 210607_at | 0.35 | GACACAGAGGAAGTTGGCTAGAGGC | 40 |
| HCLS1 | 202957_at | 0.34 | CTGTCTACTGCAACTGTGATTTCCC | 41 |
| — | 204057_at | 0.34 | AACCTCCCAGTGAAAGGGCAGCCTT | 42 |
| TARP | 211144_x_at | 0.34 | TGGGTTTGGGCCATTTCAGTTCTCA | 43 |
| PNAS-4 | 215900_at | 0.34 | CAACAGTGGACTTACCAGTTTGCCA | 44 |
| TRDD3 | 216191_s_at | 0.34 | AACAGAGTTTGATCCTGCTATTGTC | 45 |
| PTGER3 | 210375_at | 0.33 | TGCAGCTAAGGGCATCCTTGGAGTG | 46 |
| CIZ1 | 211358_s_at | 0.33 | GAAGAAGAGATCGAGGTTGAGGAGG | 47 |
| CLDN3 | 203954_x_at | 0.32 | GCTACGACCGCAAGGACTACGTCTA | 48 |
| CD28 | 206545_at | 0.32 | GATGAATCACACTTGAGATGTTTCT | 49 |
| — | 207672_at | 0.32 | CTAAGCATTTTGACCACGTTGAGCA | 50 |
| HIST1H2BG | 210387_at | 0.32 | TTGGGTCCCTAAAGATCACCTGATA | 51 |
| BIN2 | 219191_s_at | 0.32 | CCAAACCTCGCCAGAGAAGCTCTTC | 52 |
| SLC39A6 | 202088_at | 0.31 | GTACTTTGATATCTCTCAGTGCTTC | 53 |
| TOB1 | 202704_at | 0.31 | TTGAGTCAGTGTCTTACATGTTAAG | 54 |
| FMO5 | 205776_at | 0.31 | GGGAGCTCAGGTACTCTTTTAGTCA | 55 |
| ASS | 207076_s_at | 0.31 | CCCACTGTCTCTCTACAATGAGGAG | 56 |
| ATP2A3 | 207522_s_at | 0.31 | AATGGGCTCCATGTTCTGTAGCCCC | 57 |
| — | 208200_at | 0.31 | GGTCACATTCATCCTAATTCACAAA | 58 |
| — | 217608_at | 0.31 | AACACCAGAGGTAGAACAAGCTGTG | 59 |
| MFNG | 204153_s_at | 0.3 | GGTCCCAGCCAATTGTGATGATCCT | 60 |
| LRMP | 204674_at | 0.3 | TCCAGAAGTCTGTGGATGCCGCTCC | 61 |
| MCCC2 | 209624_s_at | 0.3 | CAAGATTTCTCTACATTTGGCCAAA | 62 |
| MAGEA9 | 210437_at | 0.3 | CATGTATACCTGGATTTGCTTGGCT | 63 |
| TNFRSF25 | 211282_x_at | 0.3 | GTCCTGGGACCAGTTGCCCAGCAGA | 64 |
| — | 215133_s_at | 0.3 | GAGGCCATTTGGACTTCAGTGTGAA | 65 |
| MYLIP | 220319_s_at | 0.3 | GGAGGTGTATGACCATGCCAGGAGG | 66 |
| IGLL1 | 206660_at | 0.29 | ACGCATGTGTTTGGCAGCGGGACCC | 67 |
| SIPA1L3 | 210922_at | 0.29 | ACAGCTTTCCCAGTGATGAAATCCA | 68 |
| NUP210 | 213947_s_at | 0.29 | CAAAGACCCAGTGTCATTTGCTCCT | 69 |
| CABC1 | 218168_s_at | 0.29 | GGCGCTGTGAATTTTTGTACAAGTC | 70 |
| MDS028 | 220589_s_at | 0.29 | CCTGCCAACACCAAGGTCATGCTGA | 71 |
| CISH | 221223_x_at | 0.29 | AGAAAATGCAGCCGGAGCCTCAGTC | 72 |

TABLE 1-continued mRNA biomarkers of sensitivity to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| LOC81558 | 221249_s_at | 0.29 | GCCCTAACGGGCCATAACACTTGAC | 73 |
| IFI30 | 201422_at | 0.28 | TGCCCTGGGTCACCGTCAATGGGAA | 74 |
| CTSS | 202902_s_at | 0.28 | ACAGCTGGGGCCACAACTTTGGTGA | 75 |
| CD48 | 204118_at | 0.28 | AAGCTGCAAGTGCTTGACCCTGTAC | 76 |
| IGFBP5 | 211958_at | 0.28 | TCCAGGGAGGCCCTTTTCTGATCAT | 77 |
| RNASE6 | 213566_at | 0.28 | TAAGGCATCCACTGCATTTCCTTTC | 78 |
| CLIC3 | 219529_at | 0.28 | ACACGCTGCAGATCGAGGACTTTCT | 79 |
| GALNT6 | 219956_at | 0.28 | TCATCCAAAGCACCTGCAGAGTCCA | 80 |
| FOXO1A | 202723_s_at | 0.27 | CGCCTGACCCAAGTGAAGACACCTG | 81 |
| DOK2 | 214054_at | 0.27 | GCACCTTTCAGATTTCTTGGTGGCA | 82 |
| GLUL | 200648_s_at | 0.26 | CAATGAAACCGGCGATGAGCCCTTC | 83 |
| DHCR7 | 201790_s_at | 0.26 | TTCTACATCATCTACATGGCCATCC | 84 |
| SSBP2 | 203787_at | 0.26 | ACATTGACCCACAGGACATTGTAAA | 85 |
| ICAM3 | 204949_at | 0.26 | TGGTACTTATCAGTGCCAAGCGTCC | 86 |
| ITGAM | 205786_s_at | 0.26 | GATATTCAAGTCACCTCCTTAAAGG | 87 |
| BG1 | 206465_at | 0.26 | CAAATGAGATCAGCTCTCCTTCCAG | 88 |
| ZNF165 | 206683_at | 0.26 | GCTCAGATCTTACTAGACATCGGCG | 89 |
| C1orf38 | 207571_x_at | 0.26 | GCTTCCTTCAGGTTCTAGATTCTTG | 90 |
| TETRAN | 209215_at | 0.26 | AAGGGCACGGTCATGGGTACACTGC | 91 |
| C1orf38 | 210785_s_at | 0.26 | GTAGCACCAAGCCTGATAGATCTGT | 92 |
| IGJ | 212592_at | 0.26 | GCTCACCTGAAAGAGGTATGCTCTC | 93 |
| SPDEF | 213441_x_at | 0.26 | GGGCAGTGACTCGACAAAGGCCACA | 94 |
| TRA@ | 215796_at | 0.26 | CAACTCTATTATCAACTGTGCTTAT | 95 |
| PSTPIP2 | 219938_s_at | 0.26 | ACTTGCATCAGTTGGATATCCTTTT | 96 |
| PIM2 | 204269_at | 0.25 | GAGGGGAGTTCCAAGTGTGCCCTCC | 97 |
| ICAM2 | 204683_at | 0.25 | CAAACACTCAGCCCCGAAGATGTTG | 98 |
| DMBT1 | 208250_s_at | 0.25 | GATTGAGCCCTACATTGTGCTGCAC | 99 |
| HSPA6 | 213418_at | 0.25 | GGCCTTCTAGACTGTCTTCTATGAT | 100 |
| ZNF394 | 214714_at | 0.25 | GAGCTTCAAACAGCGCTCTGACCTC | 101 |
| ABCA7 | 219577_s_at | 0.25 | GCACTGCCGAGACTGTGCTCTGAGC | 102 |
| PACAP | 221286_s_at | 0.25 | AGGCTCTCCAGGACATGTTTGCACT | 103 |

TABLE 2 mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| ANXA1 | 201012_at | -0.54 | GCTATCGTGAAGTGCGCCACAAGCA | 104 |
| GPX1 | 200736_s_at | -0.53 | ACATCGAGCCTGACATCGAAGCCCT | 105 |
| SPTBN1 | 212071_s_at | -0.53 | TAGGAATGAACTCCAGAGGCTGGGC | 106 |
| ANXA2 | 201590_x_at | -0.5 | CAGAAAGCGCTGCTGTACCTGTGTG | 107 |
| CAPN2 | 208683_at | -0.5 | ACCACTAGTGTCTGTCCATGGAGTT | 108 |
| ZA20D2 | 210275_s_at | -0.5 | GTGGTAATGCCTGTTTTCATCTGTA | 109 |
| ANXA2 | 213503_x_at | -0.5 | CAGAAAGCGCTGCTGTACCTGTGTG | 110 |
| TMSB10 | 217733_s_at | -0.5 | TTCGAGACCCCAGTCGTGATGTGGA | 111 |
| PRNP | 201300_s_at | -0.49 | AATGTGCACTGAATCGTTTCATGTA | 112 |
| TIMP1 | 201666_at | -0.49 | GGTTCCAAGCCTTAGGGGATGCCGC | 113 |
| ANXA2 | 210427_x_at | -0.49 | CAGAAAGCGCTGCTGTACCTGTGTG | 114 |
| PSMA1 | 201676_x_at | -0.48 | GTCCAGATGTGAGTTTTTTCCAAGC | 115 |
| PSMB2 | 200039_s_at | -0.47 | TGACCTGGATAACATTTCCTTCCCC | 116 |
| UGP2 | 205480_s_at | -0.47 | AAAACCACATCAGATCTCTTGCTGG | 117 |
| PSMA1 | 211746_x_at | -0.45 | TTCCAAGCAACCTCACTGAAACCTA | 118 |
| CD44 | 212063_at | -0.45 | GATTTTGTAGCCAACATTCATTCAA | 119 |
| TM4SF1 | 209386_at | -0.44 | TCATACACCTATAAATCTCTAACAA | 120 |
| ACTN4 | 200601_at | -0.43 | AGCGCTTCTGGTCTGGTAAATATGT | 121 |
| ANXA2P2 | 208816_x_at | -0.43 | AAGCCCTTGTATTTTGCTGATCAGC | 122 |
| PSMA1 | 210759_s_at | -0.43 | CATATGGTGTTGGTCTCCTTATTGC | 123 |
| TM4SF1 | 215034_s_at | -0.43 | GACTGGCATCTTCACAGGATGTCAG | 124 |
| MCF2L2 | 215112_x_at | -0.43 | GGAGTTACAGATGTTCAAATTAATT | 125 |
| DNAPTP6 | 222154_s_at | -0.43 | GGGTTTCACAGTGCAATCTCTGCCC | 126 |
| WDR1 | 200609_s_at | -0.42 | GACACACAACCCCTGGATATGTTTC | 127 |
| PSMD1 | 201199_s_at | -0.42 | GACTGTTGAGTGTGCTCTTTCACAG | 128 |
| VIM | 201426_s_at | -0.42 | GTCACCTTCGTGAATACCAAGACCT | 129 |
| RPS6KA3 | 203843_at | -0.42 | GTATACATGCCTTGTTTAACTTGGA | 130 |
| MSN | 200600_at | -0.41 | CAGTAACTTACCCTTAGGGAGGCTG | 131 |
| PFN1 | 200634_at | -0.41 | GTGTCCACGGTGGTTTGATCAACAA | 132 |
| PSMD1 | 201198_s_at | -0.41 | TGGTTGGCGTCCTTGTATTTACCCA | 133 |
| ASPH | 209135_at | -0.41 | AAAGCTGTGCTGTCGGTGATACAGA | 134 |
| CD44 | 209835_x_at | -0.41 | TGTAACACCTACACCATTATCTTGG | 135 |
| YWHAB | 217717_s_at | -0.41 | GTGCTCATATAACACACCACACTGA | 136 |
| LGALS3BP | 200923_at | -0.4 | TCACCAAGTCTGGCGGCTCAGATCG | 137 |
| ETF1 | 201574_at | -0.4 | ATTTAGGGTATGCAGCTCCTTTTGT | 138 |
| MARCKS | 201669_s_at | -0.4 | AAATCTTGATATCCAGAAGCACATG | 139 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| CAV2 | 203324_s_at | -0.4 | ATGTAGCTCCCACAAGGTAAACTTC | 140 |
| ACTG1 | 211995_x_at | -0.4 | CTCATGCTAGCCTCACGAAACTGGA | 141 |
| SEPT10 | 212698_s_at | -0.4 | TTCAGGTGGTATTTGCATTCAGTGC | 142 |
| M-RIP | 214771_x_at | -0.4 | GGAGGGCATCTGTGTTAGTCCTTTC | 143 |
| WDR1 | 200611_s_at | -0.39 | AACTGCAGCGGAACATGTCATTTCT | 144 |
| S100A10 | 200872_at | -0.39 | GGACCTGGACCAGTGTAGAGATGGC | 145 |
| RCN1 | 201063_at | -0.39 | TTTCTTTTCGACTTTATACTCTGAG | 146 |
| FAT | 201579_at | -0.39 | TGCCATTTCCCAACGTCTTTTGGGA | 147 |
| PTTG1 | 203554_x_at | -0.39 | TGCAGTCTCCTTCAAGCATTCTGTC | 148 |
| GARS | 208693_s_at | -0.39 | GATCTCTGAGCTGCCCAGCATAGTC | 149 |
| TM4SF1 | 209387_s_at | -0.39 | ATTCATCTTGTGTCTTATTCAAGTA | 150 |
| FLJ10350 | 217943_s_at | -0.39 | AAATAGCTTGTGCTCAGACTCCTCT | 151 |
| ACTG1 | 221607_x_at | -0.39 | AGAACACCGTGGGCTGTTACTTGCT | 152 |
| YWHAZ | 200640_at | -0.38 | ATACTCTTATAGCCTGCCTTCAATT | 153 |
| PPP2CB | 201375_s_at | -0.38 | GCTAACTTCCACTAATCCATTATCC | 154 |
| MET | 203510_at | -0.38 | ATCCCATCAACAGGACTACACACTT | 155 |
| ACTN1 | 208636_at | -0.38 | AACTATTTGCACCGAAATGTCTTGT | 156 |
| CLIC1 | 208659_at | -0.38 | GCAAAGGCCCTCAAATAAGCCCCTC | 157 |
| TPM4 | 209344_at | -0.38 | ACTCTCCACCATGCAGGACAAACAT | 158 |
| ASPH | 210896_s_at | -0.38 | ATTATTCTGCCTTTGGCTAATTGAG | 159 |
| CARS | 212971_at | -0.38 | TATCATGTTTACAGTCACCCTTGGG | 160 |
| FKBP1A | 200709_at | -0.37 | ACCTCTGAAGCCTTCTTTGTGGCCT | 161 |
| MAPRE1 | 200713_s_at | -0.37 | CACAGCCTATTCAGTTCCTTTGTTT | 162 |
| RHEB | 201453_x_at | -0.37 | TGAAGAAGCAAACTGCCCGTTCTCC | 163 |
| FOSL1 | 204420_at | -0.37 | GATCCTTAGAGGTCCTCTGGAGCCC | 164 |
| — | 208944_at | -0.37 | GTAGTGTCAGAGGATACTGTGGCTT | 165 |
| TNFRSF10B | 209295_at | -0.37 | TGCCCTGTCAAAGGTCCCTATTTGA | 166 |
| FTL | 212788xat | -0.37 | CTCTGTGACTTCCTGGAGACTCACT | 167 |
| TPI1 | 213011_s_at | -0.37 | ACTGTATCTTCCTTTACTGTTTATA | 168 |
| ELK3 | 221773_at | -0.37 | TATAGATCTGATTCTTTCTTTTCCT | 169 |
| TPI1 | 200822_x_at | -0.36 | CTCATCCAAACTGTATCTTCCTTTA | 170 |
| RHOC | 200885_at | -0.36 | GGACATGGCGAACCGGATCAGTGCC | 171 |
| PKM2 | 201251_at | -0.36 | AACGCCTCACTGAAACATGGCTGTG | 172 |
| TXNRD1 | 201266_at | -0.36 | GCAATTGAGGCAGTTGACCATATTC | 173 |
| MARCKS | 201670_s_at | -0.36 | AACCACCATTCCAACAGGTCGAGGA | 174 |
| RANBP1 | 202483_s_at | -0.36 | ATTTGCCTCTGAGAACGATCTCCCA | 175 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| F2R | 203989_x_at | -0.36 | GGTTGAAACATATCTCTTATCTTAC | 176 |
| FLNA | 214752_x_at | -0.36 | GGGGGAGTACACACTGGTGGTCAAA | 177 |
| TNPO1 | 221829_s_at | -0.36 | GTTGCCGTCACTGTATTAAGTCGAT | 178 |
| CALU | 200755_s_at | -0.35 | GAGAACACTTAGTCTTGCCTGTCAA | 179 |
| FLNA | 200859_x_at | -0.35 | GGGGGAGTACACACTGGTGGTCAAA | 180 |
| STRAP | 200870_at | -0.35 | GTACACTGCCTCTGAACATCTAATT | 181 |
| NUDC | 201173_x_at | -0.35 | TCCCACTCTTCTCTGGGACTTGTGG | 182 |
| GSTO1 | 201470_at | -0.35 | GAGCTCTACTTACAGAACAGCCCTG | 183 |
| LDLR | 202068_s_at | -0.35 | AGAATGATGTCCCCGTTGTATGTAT | 184 |
| UPP1 | 203234_at | -0.35 | CGGCTGGTGAGCTACTTCATCAAGA | 185 |
| ETV5 | 203349_s_at | -0.35 | CAAAGGACTCTTTCTAAACCATATT | 186 |
| CD44 | 204489_s_at | -0.35 | TTGAATGGGTCCATTTTGCCCTTCC | 187 |
| CD44 | 204490_s_at | -0.35 | GAATCAGATGGACACTCACATGGGA | 188 |
| AAK1 | 205434_s_at | -0.35 | GCCGTCTCAAGTTTAAACTTACACG | 189 |
| MAP4K4 | 206571_s_at | -0.35 | GGAATTCCTTGTAACTGGAGCTCGG | 190 |
| TXN | 208864_s_at | -0.35 | GACTGCTTTTCAGGAAGCCTTGGAC | 191 |
| PLAUR | 210845_s_at | -0.35 | ATTAATATTGTTGCCGCTGTTGTGT | 192 |
| CD44 | 212014_x_at | -0.35 | TGGAGATTCCAACTCTAATGTCAAT | 193 |
| CAV1 | 212097_at | -0.35 | AATTTTTTATCATGCATGTCCTGTA | 194 |
| FTL | 213187_x_at | -0.35 | GACGTGGAGGCAGCCGTCAACAGCC | 195 |
| FLNA | 213746_s_at | -0.35 | GCTTCACAGTAGACTGCAGCAAAGC | 196 |
| SPTAN1 | 215235_at | -0.35 | GTCACAATCATCATGTCACTGTGGG | 197 |
| GALNT2 | 217788_s_at | -0.35 | AGCTCAGATGATGGTATCTGTGAGT | 198 |
| EFHD2 | 217992_s_at | -0.35 | CTGTGACCATCACTCAGTCCAAACA | 199 |
| TNFRSF12A | 218368_s_at | -0.35 | AGAAAGGGAGCCTCACGCTGGCTCA | 200 |
| IMP-2 | 218847_at | -0.35 | TCAGCAAAATGATTCCTTTCTTTAA | 201 |
| COTL1 | 221059_s_at | -0.35 | GGGCTCCCAAAGCGACAAGATCGTT | 202 |
| UBA52 | 221700_s_at | -0.35 | GGTTCTTTCCTTGAAGGGCAGCCTC | 203 |
| MSF | 41220_at | -0.35 | TGCCAAAACCAAGATTTTGAAGGAA | 204 |
| NCL | 200610_s_at | -0.34 | TGGGGTTTTTACTGTTACCTGATCA | 205 |
| GNB1 | 200746_s_at | -0.34 | CCTTGCGGTAGGCCTGGATCTGGCA | 206 |
| ZYX | 200808_s_at | -0.34 | AGTGGTCGCCCTGGACAAGAACTTC | 207 |
| TM4SF8 | 200972_at | -0.34 | TAATGTACCCATGTAGACTAGCAAA | 208 |
| CD59 | 200985_s_at | -0.34 | CTGCTAACTCCTAGCTGACTCAGCA | 209 |
| SMS | 202043_s_at | -0.34 | AGCGAAGACTGCTAAATGCACTGAC | 210 |
| BIN1 | 202931_x_at | -0.34 | CGCAGACGGTCTGTGTGCTGTTTGA | 211 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| RABAC1 | 203136_at | -0.34 | GTACTACCAGAGCAACTATGTGTTC | 212 |
| BIN1 | 210201_x_at | -0.34 | AGCTGCTGTGTCCTCTAGTTGAGTT | 213 |
| TPM4 | 212481_s_at | -0.34 | CTGAAATCTCTGGAGGCTGCATCTG | 214 |
| ZNF258 | 213698_at | -0.34 | AAAGAGTCACTAAGCACCTGTATCC | 215 |
| BIN1 | 214439_x_at | -0.34 | AGCTGCTGTGTCCTCTAGTTGAGTT | 216 |
| MAFF | 36711_at | -0.34 | TTGCACGGATCTAAGTTATTCTCCC | 217 |
| TACC1 | 200911_s_at | -0.33 | TCCTTCTCAGCCGTCGGGATAGGAT | 218 |
| MLF2 | 200948_at | -0.33 | TGGTTTACCATTGATGACTTCGCCT | 219 |
| CD59 | 200983_x_at | -0.33 | TCCATTTCTGGCAGCAGCCTGGAGC | 220 |
| CCT6A | 201326_at | -0.33 | GAGAGCTGCAACTGTAAAGGGCAAG | 221 |
| CTSC | 201487_at | -0.33 | AATTGGTATATTCACAGACTGTAGA | 222 |
| EPB41L2 | 201719_s_at | -0.33 | GATTCACACAGGTTTGAGGATGCTG | 223 |
| — | 202028_s_at | -0.33 | GTCCTTGATTTCCTCAATTTTCCGA | 224 |
| LPP | 202822_at | -0.33 | TCACCATTCCTCTTGGCTTGGAAAG | 225 |
| CAV2 | 203323_at | -0.33 | AAGTAACATGACTTCCTTATTTCTG | 226 |
| UGDH | 203343_at | -0.33 | ATTTTTGCTTGTGTTAGATCATTAT | 227 |
| AATF | 209165_at | -0.33 | GCCCCTGCTAATGCTCATCTGAAGG | 228 |
| CD44 | 210916_s_at | -0.33 | TTTCAATAGCACCTTGCCCACAATG | 229 |
| SLC39A14 | 212110_at | -0.33 | GGCTTCTCTGTTTGGGTAGCGTAAG | 230 |
| MYO1B | 212364_at | -0.33 | GGGTGCCTATTTTAGTCATGGATCA | 231 |
| ZNF238 | 212774_at | -0.33 | AAATTTGATCGCCTTAACTACTGTA | 232 |
| TMEM2 | 218113_at | -0.33 | ACAGATAATTTCACTTTCCTCTTCC | 233 |
| CDC14B | 221556_at | -0.33 | GTCAGCAGACATGTTCATCCGATGA | 234 |
| CORO1C | 221676_s_at | -0.33 | CCACCGCTCTCATTTCATGGAGTCT | 235 |
| TAF10 | 200055_at | -0.32 | AGCAAGGACCGCAAGTACACTCTAA | 236 |
| CD63 | 200663_at | -0.32 | TGTCTTATGATCACGTTTGCCATCT | 237 |
| CALU | 200757_s_at | -0.32 | TTGAGGTGGGCTCCCTGGTATGGTA | 238 |
| SNRPD2 | 200826_at | -0.32 | GAACAATACCCAAGTGCTCATCAAC | 239 |
| PRSS23 | 202458_at | -0.32 | GCAGCAATTAAGGGTCTTCATGTTC | 240 |
| CTNNAL1 | 202468_s_at | -0.32 | AGTATGGCCTATTCTCTGTATTTAT | 241 |
| — | 202625_at | -0.32 | AAAGTGCCACATTCGGGGCTATTTT | 242 |
| UBE2S | 202779_s_at | -0.32 | GCCAATGGCGAGATCTGCGTCAACG | 243 |
| TCEB1 | 202824_s_at | -0.32 | AGATTCCTGAATTCCCAATTGCACC | 244 |
| PRPS2 | 203401_at | -0.32 | ATACTCATATGATCACTTTTCTTTT | 245 |
| GCLM | 203925_at | -0.32 | CATGAACCTCTGTATTGCTTTCCTT | 246 |
| OK/SW-cl.56 | 211714_x_at | -0.32 | CCACCTCGTGGCCTCAAGATGGCAG | 247 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| PNAS-4 | 212371_at | -0.32 | GAAACACATTCACTGCTTCAGGGTT | 248 |
| KIAA1033 | 212794_s_at | -0.32 | AATGCTATGGGCTATGTACGAATGA | 249 |
| TIMM17A | 215171_s_at | -0.32 | CTCTCTTCCTTTAGGGCTACTGAGT | 250 |
| PP1201 | 217730_at | -0.32 | CCTACTGTGGTACTGAAGACTTCTG | 251 |
| C13orf12 | 217769_s_at | -0.32 | AAAAATTTCCAGCTCAACCAAGATA | 252 |
| LRP12 | 219631_at | -0.32 | AGGGTTGCGCTTGCATTGGACCCTA | 253 |
| GLS | 221510_s_at | -0.32 | ACAATGTAGCATATTTGATTTTCTT | 254 |
| FNTA | 200090_at | -0.31 | CAGTAATAACTGCAGGTCACTTGTA | 255 |
| DNAJA1 | 200881_s_at | -0.31 | GGACATACAGCTCGTTGAAGCACTG | 256 |
| EBNA1BP2 | 201323_at | -0.31 | AGACATTGAGTTCAAATTGCCTTCA | 257 |
| PLEKHB2 | 201410_at | -0.31 | GTATTTTCCACAAGTTTTGATCCTG | 258 |
| LAMB1 | 201505_at | -0.31 | AAGAGTCAGCTGATGCCAGAAGGAA | 259 |
| GRSF1 | 201520_s_at | -0.31 | GGTCCCACGTTCATCATAGGTATAT | 260 |
| SLC20A1 | 201920_at | -0.31 | GGCATATTCGGGAGCTTCTTAGAGG | 261 |
| SEC61G | 203484_at | -0.31 | TCAGCAAGCTCCAGTGCTACGTGTC | 262 |
| PTP4A2 | 208616_s_at | -0.31 | GAACTCTTGGTACCTGGAAATGTGA | 263 |
| OK/SW-cl.56 | 209026_x_at | -0.31 | GCAATAGCACAGCCATCCAGGAGCT | 264 |
| SLC16A1 | 209900_s_at | -0.31 | TTAAATCCTCCAGCTTTTGAACCTT | 265 |
| — | 211452_x_at | -0.31 | AATCCCAGCCACTCCAGAGGCTGAG | 266 |
| CAST | 212586_at | -0.31 | TTTCCTGAGGGATTTCTAACCATGT | 267 |
| RRAS2 | 212590_at | -0.31 | TATACACAGACATGCTCTTTTTTTA | 268 |
| TFPI | 213258_at | -0.31 | GCATGTGAACGTTATTTTTACCGTG | 269 |
| KPNB1 | 213507_s_at | -0.31 | AAGATGGAGCCTGGGTCTCAAGCCC | 270 |
| ZCCHC11 | 217594_at | -0.31 | TCCTGCTCTCATGTAGCTAAAAAGA | 271 |
| S100A6 | 217728_at | -0.31 | GCCAGTCGGACTGCGACATAGCCCA | 272 |
| NHP2L1 | 201077_s_at | -0.3 | ACCAAGAAGCTACTGGACCTCGTTC | 273 |
| TNC | 201645_at | -0.3 | TTTTACCAAAGCATCAATACAACCA | 274 |
| SLC16A1 | 202236_s_at | -0.3 | GGCATATGTTTCTGCTAGCTATATA | 275 |
| ADAM9 | 202381_at | -0.3 | GTTACTGTGGTATCTATGAGTTATC | 276 |
| SVIL | 202565_s_at | -0.3 | TCTACCTTAATATCTCCCCAAAAAT | 277 |
| CTPS | 202613_at | -0.3 | GAAACACCAAGATGTCTGTCTCTGA | 278 |
| CAV1 | 203065_s_at | -0.3 | GGTGCCAATTTCAAGTTCCAAGTTG | 279 |
| KIAA0020 | 203712_at | -0.3 | AGGTGCCATTATTCTTTCTAGCCTC | 280 |
| EMP3 | 203729_at | -0.3 | ATCCTCATTCTTATACTGCTTTTCG | 281 |
| AKAP7 | 205771_s_at | -0.3 | AAAACTTCCCCGGTATGATGATTGT | 282 |
| C20orf3 | 206656_s_at | -0.3 | AAAGCTTGTTGACTCTAGCGGCTCA | 283 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| ACTN1 | 208637xat | -0.3 | AGGTGCTCTGGACTACATGTCCTTC | 284 |
| GALIG | 208949_s_at | -0.3 | AGTACTGGTTGAACCTGACCACTTC | 285 |
| PTBP1 | 211270_x_at | -0.3 | GAATAAATCTTCTGTATCCTCAAAA | 286 |
| NIPA2 | 212129_at | -0.3 | ATGATCACCGTGAATCCGGCTTCCT | 287 |
| FLJ46603 | 212509_s_at | -0.3 | GATCAGTCTCAAATGGGTTTCTTGG | 288 |
| RRAS2 | 212589_at | -0.3 | GGTATTGCACAGTTGTCACTTTATC | 289 |
| CDC10 | 213151_s_at | -0.3 | AAAAGTCACCATTCTGCATTTAGCT | 290 |
| FTH1 | 214211_at | -0.3 | CAGGCTATCTTCCAGATTCCTTAAG | 291 |
| CAB39 | 217873_at | -0.3 | AGACTTGGCCGTGATGTGGTGTCCT | 292 |
| KCMF1 | 217938_s_at | -0.3 | TGTCCTCTGTGCTGTATTTGCCAAT | 293 |
| PHLDA1 | 217996_at | -0.3 | GTTTTCTGCATACTTTTCATCACGA | 294 |
| GLT25D1 | 218473_s_at | -0.3 | GACTGAGTTTGATTCTTCCTGTACC | 295 |
| CDCA8 | 221520_s_at | -0.3 | CCTGCTGTGCCCAGTAGTTCTGAAG | 296 |
| TRAF3 | 221571_at | -0.3 | GAGTTAGCAACATGCCTGACTTCCT | 297 |
| LASP1 | 200618_at | -0.29 | GAAATGACCACGTGAAATTTGCCTC | 298 |
| GABARAP | 200645_at | -0.29 | ACTTCTTGATTGTCAGTCTGTGTCA | 299 |
| CD81 | 200675_at | -0.29 | TAACGTTTCCGGTATTACTCTGCTA | 300 |
| DPYSL2 | 200762_at | -0.29 | GATTTCTGCAGTGACTTGATGCTCT | 301 |
| PGAM1 | 200886_s_at | -0.29 | ATCATGTTCTAGTTGCTTGACCCTG | 302 |
| ATP1B1 | 201242_s_at | -0.29 | GTATGGGACCTACACTTAATCTATA | 303 |
| TOP2A | 201291_s_at | -0.29 | TGGCTCCTAGGAATGCTTGGTGCTG | 304 |
| CUL3 | 201371_s_at | -0.29 | TATTAAGACGACCATCTCTTCTATT | 305 |
| TGFBI | 201506_at | -0.29 | CTTTTATGGGGCCCTGTCCAGGTAG | 306 |
| PTBP1 | 202189_x_at | -0.29 | AAACTTGCTCTCAAACTTCAGGGTT | 307 |
| ARL7 | 202206_at | -0.29 | CCTATTGTCCATTACACACCGAATG | 308 |
| GFPT1 | 202722_s_at | -0.29 | GTATGCTCATACTTGGACAGTTAGG | 309 |
| CDC20 | 202870_s_at | -0.29 | TATGGCGCTGTTTTGAGTTGGACCC | 310 |
| CKS2 | 204170_s_at | -0.29 | CGACGAACACTACGAGTACCGGCAT | 311 |
| RAB32 | 204214_s_at | -0.29 | GGAGAAGTATCCCTGCTAGTGGCTC | 312 |
| KPNB1 | 208974_x_at | -0.29 | GGGATGATAACCTGAGGACCCCCAC | 313 |
| HDGFRP3 | 209526_s_at | -0.29 | GAATGGAATTTCCTCTCTGTGACAG | 314 |
| NUDC | 210574_s_at | -0.29 | CCCACTCTTCTCTGGGACTTGTGGG | 316 |
| ARHGDIA | 211716_x_at | -0.29 | CTGCCTTTTCTGTCTCAGCGGGCAG | 317 |
| DOCK9 | 212538_at | -0.29 | TGTGCTGTTCCAGTATATGCAATAC | 318 |
| LHFPL2 | 212658_at | -0.29 | TTTAAGGGCTAATCTCACACCTCCT | 319 |
| TAXIBP3 | 215464_s_at | -0.29 | ACGGATTTAGACGAGGTTCGAGGCT | 320 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| RAP1B | 200833_s_at | -0.28 | GCTTCTGCAGCTGTAGATTCTCACT | 321 |
| AKR1B1 | 201272_at | -0.28 | GCAGCCAGGATATGACCACCTTACT | 322 |
| TPD52L2 | 201379_s_at | -0.28 | TGAAACGACCCCACAGGTCAGGTGG | 323 |
| CNN3 | 201445_at | -0.28 | GAAAAATTGCCTTACGTACATTCCT | 324 |
| DCTD | 201571_s_at | -0.28 | TAAGCTCATCATCCAGGCAGGTATA | 325 |
| TJP1 | 202011_at | -0.28 | AAGGATGCTTGTACATAATGCGTGC | 326 |
| CTSL | 202087_s_at | -0.28 | GTGTGAGCTGGTGGACGGTGATGAG | 327 |
| IFRD1 | 202146_at | -0.28 | GCTAACCTTAACATCTGAGAGCAGT | 328 |
| ARL7 | 202207_at | -0.28 | AAAGCCCTGTGGTGTATCAACTACT | 329 |
| GFPT1 | 202721_s_at | -0.28 | GCACTCTGAAGGCATCCTTGCTGGT | 330 |
| YES1 | 202932_at | -0.28 | GCTTAGTATTGACACTCTCTACCAA | 331 |
| FHL2 | 202949_s_at | -0.28 | TATTTACAGCTCTGTAACCTCCCGT | 332 |
| FZD6 | 203987_at | -0.28 | GCAATTGACTTCCCTTTTTTAATGT | 333 |
| SNAPC1 | 205443_at | -0.28 | GAATCCATCCTTAAAGTCAAAAACT | 334 |
| TFPI | 209676_at | -0.28 | AAATTGCTTATTCTAGGTCTGTAAT | 335 |
| CD69 | 209795_at | -0.28 | TACGTGCAATACTTCAATACTTCAT | 336 |
| IFITM3 | 212203_x_at | -0.28 | CATGACCATTCTGCTCATCGTCATC | 337 |
| CEBPB | 212501_at | -0.28 | CAAACCAACCGCACATGCAGATGGG | 338 |
| TUBB4 | 213476_x_at | -0.28 | GTGGATCCCCAACAACGTGAAGGTG | 339 |
| TUBB2 | 213726_x_at | -0.28 | GGGCGAGTTCGAGGAGGAGGCTGAG | 340 |
| HLA-A | 213932_x_at | -0.28 | TGGTGCACTGAGCTGTAACTTCTTC | 341 |
| ZYX | 215706_x_at | -0.28 | TTATTGTTTTGATGTCTAGCCCCTC | 342 |
| PTP4A2 | 216988_s_at | -0.28 | AGCCCCTGTGGAGATCTCCTATGAG | 343 |
| C1orf24 | 217966_s_at | -0.28 | TACTCATCCTGCTATCAATTTCTTA | 344 |
| LDHA | 200650_s_at | -0.27 | AAATCCACAGCTATATCCTGATGCT | 345 |
| ARHGDIA | 201168_x_at | -0.27 | TCTGCCTTTTCTGTCTCAGCGGCAG | 346 |
| PSMD13 | 201232_s_at | -0.27 | AATGAAGCTGGCTGCTCAGACGGTC | 347 |
| PSMA2 | 201317_s_at | -0.27 | GTTAAGGATTACTTGGCTGCCATAG | 348 |
| UBE2D2 | 201345_s_at | -0.27 | AAAAGTACTCTTGTCCATCTGTTCT | 349 |
| COPB | 201358_s_at | -0.27 | CATGTACCAAGACCCTTTTCACAGT | 350 |
| — | 201952_at | -0.27 | ACTCAGAGCTCTGGACCGAAAGCAG | 351 |
| M96 | 203345_s_at | -0.27 | GTTCTGGACCAGAATACCTCAAACG | 352 |
| SGCE | 204688_at | -0.27 | AAGGAGCTTCGAGACATGTCCAAGA | 353 |
| CSRP2 | 207030_s_at | -0.27 | CTGTATATCGCCCTGTACTTGGATA | 354 |
| MAP1LC3B | 208786_s_at | -0.27 | GTTATCACTCTTAGGTCAGACAGCC | 355 |
| PTRF | 208789_at | -0.27 | TGATTCTGTTCGGACTGGGTTCTCA | 356 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| EIF354 | 208887_at | -0.27 | GTCAGAGGACACGCGTGAGACCGAC | 357 |
| ANXA3 | 209369_at | -0.27 | ATTGACCTTTTGGACATTCGAACAG | 358 |
| HDGFRP3 | 209524_at | -0.27 | TTATGTGTACATTATTGTTGCTATT | 359 |
| OSBPL3 | 209626_s_at | -0.27 | GAGCAACGGCACCTATTTGGAACTT | 360 |
| LMNA | 212086_x_at | -0.27 | CCCCCAGAACTGCAGCATCATGTAA | 361 |
| FKBP9 | 212169_at | -0.27 | TCAACAGAGTATTTCCCTTGGCCGA | 362 |
| ARHE | 212724_at | -0.27 | TGAAAACGAGCTTTCTTTCCCATGA | 363 |
| — | 213156_at | -0.27 | GTTATTTCTTTTAGTCATGTTGATT | 364 |
| EPLIN | 217892_s_at | -0.27 | AACCCTGTATTTCCCTTATGATGTC | 365 |
| MRPL15 | 218027_at | -0.27 | TATGCAAACCTGTTCCATTCTTTCT | 366 |
| C2orf33 | 219137_s_at | -0.27 | AATATTTCATAACCTTCTTCATTAG | 367 |
| BRIX | 219177_at | -0.27 | CGAAGACTCTTCTTCCACATGATCC | 368 |
| C19orf10 | 221739_at | -0.27 | AAGTTTTCTACCTGGGCTGACGTTG | 369 |
| MICAL-L1 | 55081_at | -0.27 | GCAGCTCTTGGTCAAAGCACTGTTG | 370 |
| SPARC | 200665_s_at | -0.26 | GGTCGGATCTCACAGGCTGAGAACT | 371 |
| SPTBN1 | 200671_s_at | -0.26 | AGTTCTCAAGAGACGCCAGTGTGGC | 372 |
| PEA15 | 200787_s_at | -0.26 | TAAGATCAAACCCCATGGAGCAGCC | 373 |
| CD99 | 201029_s_at | -0.26 | GGGGGATAGGCACTTGGACCCCCAT | 374 |
| ITGA6 | 201656_at | -0.26 | GGTTGTACTTGGAATTCTTAGTCAC | 375 |
| RYBP | 201844_s_at | -0.26 | TCTCAATCCCCTGCTGTGGTAGGAA | 376 |
| EGFR | 201983_s_at | -0.26 | AAAATCCAGACTCTTTCGATACCCA | 377 |
| HNRPDL | 201993_x_at | -0.26 | AGCTGCCAATTAGTTTTCTTTGTTT | 378 |
| ARL7 | 202208_s_at | -0.26 | CAGGGCCAGAAGTTCAGGCTGCCCC | 379 |
| OBRGRP | 202378_s_at | -0.26 | GTAGTCACGGTGCTCTCAGAAAATA | 380 |
| PALM2-AKAP2 | 202759_s_at | -0.26 | GCATTCTGCCGTGTTTATAGGTGTT | 381 |
| TGIF | 203313_s_at | -0.26 | GACTTCAGTGGATTTCAGCTTCTAG | 382 |
| CDH2 | 203440_at | -0.26 | AGCTTTGCCTCTGTATTGTGTACCA | 383 |
| EPHA2 | 203499_at | -0.26 | AGGGACCGGTGCTGCAGGAGTGTCC | 384 |
| BUB1B | 203755_at | -0.26 | CACTACCATTGCTGTTCTACTTTTT | 385 |
| GRK5 | 204396_s_at | -0.26 | GCCATGTGTTCCAAGGCATTTTAGC | 386 |
| LIF | 205266_at | -0.26 | GTAGCATTTCCCTGCAGATGGTACA | 387 |
| FLOT1 | 208749_x_at | -0.26 | AAGTACTGGACATTCTAACTCGCCT | 388 |
| MGC4083 | 209191_at | -0.26 | CAACACGCAAGTTCCTTCTTGAACC | 389 |
| HABP4 | 209818_s_at | -0.26 | TCTTGAAAGAGCCCTGTTTCCCAGC | 390 |
| PDE4D | 210837_s_at | -0.26 | TATACCAATGACTTCCATATTTTAA | 391 |
| AP2A2 | 211779_x_at | -0.26 | CGAACCTGCAAGCCCAGATGTACCG | 392 |

TABLE 2-continued mRNA biomarkers of resistance to fulvestrant. Dashes mean that the Affymetrix probeset has not been mapped to a specific gene.

| Gene | Affymetrix ID | Correlation | Affymetrix Probe Sequence | Affymetrix Probe SEQ ID NO: |
|---|---|---|---|---|
| PLAUR | 211924_s_at | -0.26 | GTAACCACCCAGACCTGGATGTCCA | 393 |
| ZFP36L1 | 211962_s_at | -0.26 | GGACTGCAAATTGAGTTTCTTTCTC | 394 |
| LOC130074 | 212017_at | -0.26 | GAGAGCCTCATGGATTGTAACTAAA | 395 |
| HLA-A | 215313_x_at | -0.26 | GAAGAACCCTGACTTTGTTTCTGCA | 396 |
| C19orf10 | 216483_s_at | -0.26 | GTCCTATCTGTACTTCACACAGTTC | 397 |
| SNX6 | 217789_at | -0.26 | GAACTGTTGAGTTTCCGTTGCTGGC | 398 |
| TENS1 | 217853_at | -0.26 | TCCTCCAGTGTTAAGCTATAGCCAT | 399 |
| C20orf149 | 218010_x_at | -0.26 | TGGAGTCCGCAGAGCACTCGGAACC | 400 |
| L0051123 | 218059_at | -0.26 | TGCCAGACCCTAAGACCTTCAAGCA | 401 |
| ERO1L | 218498_s_at | -0.26 | GGTTTTCATTAGTGGAAGCTCTTCA | 402 |
| TNFRSF21 | 218856_at | -0.26 | GATTACTTGTACTCTTCTTATGCTA | 403 |
| FLJ23548 | 219973_at | -0.26 | ACTTTATAATCGTCATTGTTCAATC | 404 |
| LRP12 | 220253_s_at | -0.26 | TGATTGTTTTCATCCTGATACTGTA | 405 |
| TRAM1 | 201398_s_at | -0.25 | GTCACCAGCTGTTTGTGCCATTTTT | 406 |
| MARCKS | 201668_x_at | -0.25 | AGGGAGATTTCTCCATTTTCCTCTT | 407 |
| TCTEL1 | 201999_s_at | -0.25 | GTGGCACTTTCACAATGTAGAGGAA | 408 |
| DUSP11 | 202703_at | -0.25 | ATGCCAGTCGGGCAGCCCAGGATAG | 409 |
| IFNGR1 | 202727_s_at | -0.25 | TATCCAGTACTCCTGGTTCCTAGGT | 410 |
| COMMD4 | 206441_s_at | -0.25 | AGCTGGGGCTGCCCAAAGAGCACGC | 411 |
| VCP | 208649_s_at | -0.25 | GATGATGACCTGTATGGCTAAGTGG | 412 |
| BAX | 211833_s_at | -0.25 | GACATGTTTTCTGACGGCAACTTCA | 413 |
| PRKCA | 213093_at | -0.25 | ACATCATATAAGCCCCAACTTTGTT | 414 |

OTHER EMBODIMENTS

Danish Patent application PA 2013 00348 is incorporated herein by reference in its entirety.

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining chemosensitivity.

The invention claimed is:

1. A method of predicting the responsiveness of breast cancer in a patient to treatment with fulvestrant comprising:

a) contacting a tumor sample from the patient comprising one or more nucleic acid molecules with a device comprising:

i) single-stranded nucleic acid molecules capable of specifically hybridizing with nucleotides of a GATA3 biomarker; and ii) single-stranded nucleic acid molecules capable of specifically hybridizing with nucleotides of an ANXA1 biomarker; and b) quantifying a level of expression of the GATA3 biomarker and the ANXA1 biomarker by performing microarray analysis, quantitative reverse transcriptase polymerase chain reaction (qRT-PCR), or qRT-loop-mediated isothermal amplification (LAMP), c) predicting the cancer in the patient to be responsive to the treatment with fulvestrant if the level of expression of the GATA3 and ANXA1 biomarkers in the tumor sample is equal to or above a cutoff difference level of expression of the GATA3 and ANXA1 biomarkers in a cell or tissue known to be sensitive to the treatment with fulvestrant and predicting the cancer in the patient to be non-responsive to the treatment with fulvestrant if the level of expression of the GATA3 and ANXA1 biomarkers in the tumor sample is below the cutoff difference level of expression of the GATA3 and ANXA1 biomarkers in a cell or tissue known to be resistant to the treatment with fulvestrant, wherein the cutoff difference level is obtained by subtracting the level of the ANXA1 biomarker from the level of the GATA3 biomarker, and (d) administering an effective amount of fulvestrant to said patient, wherein the patient has been determined to be responsive to fulvestrant.

2. The method of claim 1, wherein said method further comprises quantifying a level of a biomarker of sensitivity selected from the group consisting of CBFA2T3, SPDEF, HBA1, TFF1, CD8B1, KIAA0984, BCL2, SLC9A3R1, FBP1, ITGB7, HIST1 H3H, PDCD4, CD37, HBA2, TARP, SPI1, KIAA0182, PTP4A3, ANXA1, GPX1, SPTBN1, ANXA2, CAPN2, ZA20D2, TMSB10, PRNP, TIMP1, PSMA1, PSMB2, UGP2, CD44, TM4SF1, MCF2L2, DNAPTP6, WDR1, PSMD1, VIM, RPS6KA3, MSN, PFN1, ASPH, YWHAB, LGALS3BP, ETF1, MARCKS, CAV2, ACTG1, SEPT10, and M-RIP.

3. The method of claim 1, wherein said cancer is a hormone positive cancer.

4. The method of claim 1, wherein said cancer is metastatic.

5. The method of claim 1, wherein said patient is a female.

6. The method of claim 5, wherein said female is a postmenopausal female.

7. The method of claim 6, wherein said cancer has progressed following anti-estrogen therapy.

8. The method of claim 1, wherein said sample is a biopsy.

9. The method of claim 1, wherein the expression level of said GATA3 biomarker or said ANXA1 biomarker is measured using qRT-PCR.

10. The method of claim 1, wherein the GATA3 biomarker is an mRNA.

11. The method of claim 1, wherein the ANXA1 biomarker is an mRNA.

12. The method of claim 1, wherein said method comprises converting the level of expression of the GATA3 biomarker or the ANXA1 biomarker into a mean score, wherein said mean score identifies the responsiveness of said patient to fulvestrant.

13. The method of claim 1, wherein said method comprises:

(i) converting the level of expression of said GATA3 biomarker into a first mean score;

(ii) converting the level of expression of said ANXA1 biomarker into a second mean score;

(iii) subtracting said second mean score from said first mean score to obtain a difference score, wherein a value of said difference score that is greater than or equal to a cutoff indicates said patient is responsive to fulvestrant.

14. The method of claim 1, wherein said GATA3 biomarker has the sequence set forth in SEQ ID NO: 415; or wherein said ANXA1 biomarker has the sequence set forth in SEQ ID NO: 431.

15. The method of claim 1, wherein said breast cancer is hormone receptor positive breast cancer.

16. The method of claim 1, wherein:

i) the single-stranded nucleic acid molecules capable of specifically hybridizing with nucleotides of the GATA3 biomarker have the sequence of any one of SEQ ID NO: 1-3 and 415, or a complement thereof; or ii) the single-stranded nucleic acid molecules capable of specifically hybridizing with nucleotides of the ANXA1 biomarker have the sequence of any one of SEQ ID NO: 104 and 431, or a complement thereof.

17. The method of claim 16, wherein said device comprises two or more of said single-stranded nucleic acid molecules of i) and ii).

18. The method of claim 1, wherein said one or more single-stranded nucleic acid molecules have a length in the range of 10-100 nucleotides in length.

19. The method of claim 1, wherein said device allowing, when contacted with a diverse population of nucleic acid molecules prepared from a sample under conditions allowing hybridization to occur, the quantification of the level of expression of the GATA3 and ANXA1 biomarkers.

20. The method of claim 1, wherein said method further comprises quantifying a level of a biomarker of resistance selected from the group consisting of GPX1, SPTBN1, ANXA2, CAPN2, ZA20D2, TMSB10, PRNP, TIMP1, PSMA1, PSMB2, UGP2, CD44, TM4SF1, and ACTN4.

21. The method of claim 1, wherein the expression level of said GATA3 biomarker or said ANXA1 biomarker is measured using microarray analysis.

22. The method of claim 1, wherein the expression level of said GATA3 biomarker or said ANXA1 biomarker is measured using qRT-LAMP.

23. A method comprising administering an effective amount of fulvestrant to a patient with breast cancer, wherein the patient has a level of a GATA3 biomarker and an ANXA1 biomarker in a tumor sample that is equal to or above a cutoff difference level of a GATA3 biomarker and an ANXA1 biomarker in a cell or tissue known to be sensitive to treatment with fulvestrant, wherein the cutoff difference level is obtained by subtracting the level of the ANXA1 biomarker from the level of the GATA3 biomarker, thereby identifying the patient as responsive to fulvestrant.

24. The method of claim 23, wherein the level of the GATA3 biomarker and the ANXA1 biomarker is determined by a) contacting a tumor sample from the patient comprising one or more nucleic acid molecules with a device comprising:

i) single-stranded nucleic acid molecules capable of specifically hybridizing with nucleotides of the GATA3 biomarker; and ii) single-stranded nucleic acid molecules capable of specifically hybridizing with nucleotides of the ANXA1 biomarker; and b) quantifying the level of the GATA3 biomarker and the ANXA1 biomarker by performing microarray analysis, quantitative reverse transcriptase polymerase chain reaction (qRT-PCR), or qRT-loop-mediated isothermal amplification (LAMP).

25. A method of treating a patient with breast cancer, said method comprising:

a) contacting a tumor sample from the patient comprising one or more nucleic acid molecules with a device comprising:

i) single-stranded nucleic acid molecules capable of specifically hybridizing with nucleotides of a GATA3 biomarker; and ii) single-stranded nucleic acid molecules capable of specifically hybridizing with nucleotides of an ANXA1 biomarker; and b) quantifying a level of expression of the GATA3 biomarker and the ANXA1 biomarker by performing microarray analysis, quantitative reverse transcriptase polymerase chain reaction (qRT-PCR), or qRT-loop-mediated isothermal amplification (LAMP), and c) administering an effective amount of fulvestrant to said patient having a level of expression of the GATA3 and ANXA1 biomarkers in the tumor sample that is equal to or above a cutoff difference level of expression of the GATA3 and ANXA1 biomarkers in a cell or tissue known to be sensitive to treatment with fulvestrant, wherein the cutoff difference level is obtained by subtracting the level of the ANXA1 biomarker from the level of the GATA3 biomarker, thereby identifying the patient as responsive to fulvestrant.

* * * * *